US010072089B2

(12) United States Patent
Jespers et al.

(10) Patent No.: US 10,072,089 B2
(45) Date of Patent: Sep. 11, 2018

(54) POLYPEPTIDES, ANTIBODY VARIABLE DOMAINS AND ANTAGONISTS

(71) Applicant: Domantis Limited, Brentford, Middlesex (GB)

(72) Inventors: Laurent Jespers, Cambridge (GB); Malgorzata Pupecka-Swider, Cambridge (GB); Carolyn Enever, Cambridge (GB); Ian Tomlinson, Cambridge (GB)

(73) Assignee: Domantis Limited, Brentford (GB)

( * ) Notice: Subject to any disclaimer, the term of this patent is extended or adjusted under 35 U.S.C. 154(b) by 0 days.

(21) Appl. No.: 15/386,141

(22) Filed: Dec. 21, 2016

(65) Prior Publication Data

US 2017/0174775 A1     Jun. 22, 2017

Related U.S. Application Data

(60) Division of application No. 13/763,768, filed on Feb. 11, 2013, now Pat. No. 9,562,090, which is a continuation of application No. 12/663,502, filed as application No. PCT/GB2008/050405 on Jun. 4, 2008, now Pat. No. 8,398,979.

(60) Provisional application No. 60/933,632, filed on Jun. 6, 2007.

(30) Foreign Application Priority Data

Dec. 13, 2007   (GB) .................................. 0724331.4

(51) Int. Cl.
| | |
|---|---|
| *A61K 39/395* | (2006.01) |
| *C07K 16/28* | (2006.01) |
| *A61K 9/16* | (2006.01) |
| *A61K 9/00* | (2006.01) |
| *C07K 16/00* | (2006.01) |
| *C07K 16/22* | (2006.01) |
| *A61M 11/00* | (2006.01) |
| *A61M 15/08* | (2006.01) |

(52) U.S. Cl.
CPC .......... *C07K 16/2878* (2013.01); *A61K 9/007* (2013.01); *A61K 9/1623* (2013.01); *A61K 9/1641* (2013.01); *A61K 39/3955* (2013.01); *A61M 11/005* (2013.01); *A61M 15/08* (2013.01); *C07K 16/005* (2013.01); *C07K 16/22* (2013.01); *C07K 16/2866* (2013.01); *C07K 2317/569* (2013.01); *C07K 2317/64* (2013.01); *C07K 2317/92* (2013.01); *C07K 2317/94* (2013.01)

(58) Field of Classification Search
None
See application file for complete search history.

(56) References Cited

U.S. PATENT DOCUMENTS 5,055,289 A   10/1991   Frincke et al.

| | | | |
|---|---|---|---|
| 8,129,503 B2 | 3/2012 | De Wildt et al. | |
| 2009/0191217 A1 | 7/2009 | de Wildt et al. | |

FOREIGN PATENT DOCUMENTS

| | | |
|---|---|---|
| WO | WO 1990/005144 | 5/1990 |
| WO | WO 1990/014430 | 11/1990 |
| WO | WO 1992/001047 | 1/1992 |
| WO | WO 1992/020791 | 11/1992 |
| WO | WO 1993/011236 | 6/1993 |
| WO | WO 2002/043660 | 6/2002 |
| WO | WO2003/011251 | 2/2003 |
| WO | WO 2004/003019 | 1/2004 |
| WO | WO 2004/022096 | 3/2004 |
| WO | WO 2004/022718 | 3/2004 |
| WO | WO 2004/058820 A | 7/2004 |
| WO | WO 2004/058821 | 7/2004 |
| WO | WO 2005/035572 | 4/2005 |
| WO | WO 2006/038027 | 4/2006 |
| WO | WO 2006/059108 | 6/2006 |
| WO | WO 2007/049017 | 5/2007 |
| WO | WO 2007/049017 A | 5/2007 |
| WO | WO 2007/049017 A2 | 5/2007 |
| WO | WO 2007/063308 | 6/2007 |
| WO | WO 2007/063311 | 6/2007 |
| WO | WO 2008/021237 | 2/2008 |
| WO | WO2008/049897 | 5/2008 |
| WO | WO 2008/149147 | 12/2008 |
| WO | WO 2008/149149 | 12/2008 |
| WO | WO 2008/149150 | 12/2008 |

OTHER PUBLICATIONS

Mehrad et al. (J Immunol 1999; 162:1633-1640).*
Paulussen et al. (J Clin Oncol. Sep. 1998;16(9):3044-52).*
Rube et al. (Int. J. Radiation Oncology Biol. Phys., vol. 56, No. 5, pp. 1414-1425, 2003).*
Visser et al. (Lung (2012) 190:579-581).*
Kieszko et al. (Respiratory Medicine (2007) 101, 645-654).*
Baugham et al. (Am J Respir Crit Care Med vol. 174. pp. 795-802, 2006).*
Bolon, et al., Annals of Rheumatic Diseases, vol. 62, No. Suppl. 1(abstract only), p. 123, Jul. 2003.
Brown, et al., Journal of Immunology, May 1, 1996;156(9):3285-91.
Chung, K. F., New asthma treatments: recent advances and current objectives, revuew Francaise D'Allergologie Et D'Immunologie Clinique, vol. 378, No. 7, pp. S214-S221, 1998.
Colman, P. M., Research in Immunology, 145:33-36, 1994.

(Continued)

*Primary Examiner* — Zachary S Skelding
(74) *Attorney, Agent, or Firm* — Leah M. Octavio; Andrea V. Lockenour

(57) ABSTRACT

The invention relates to anti-TNFR1 polypeptides and antibody single variable domains (dAbs) that are resistant to degradation by a protease, as well as antagonists comprising these. The polypeptides, dAbs and antagonists are useful for as therapeutics and/or prophylactics that are likely to encounter proteases when administered to a patient, for example for pulmonary administration, oral administration, delivery to the lung and delivery to the GI tract of a patient, as well as for treating inflammatory disease, such as arthritis or COPD.

20 Claims, 104 Drawing Sheets

Specification includes a Sequence Listing.

(56) References Cited

OTHER PUBLICATIONS

DeBoer, W.I., Perspectives for cytokine antagonist therapy in COPD, Drug Discovery Today, Elsevier, Rathway. vol. 10, No. 1, pp. 93-106, Jan. 2005.
Domain antibody products treat respirator disease, retrieved from internet: Caliper Life Sciences, www.laboratorytalk.com/news/arg/arg109.html, 2007.
Harmsen, M. M., et al., Applied Microbilogy and Biotechnology, vol. 72, No. 3, Sep. 2006, pp. 544-551.
Holt, L. J., et al., Domain antibodies proteins for therapy, Trends in Biotechnology, Elsevier Publications, vol. 21, No. 11, pp. 484-490, Nov. 2003.
Internation Search report for related PCT Application No. PCT/GB2006/003935.
Kontermann, et al., Journal of Immunotherapy, vol. 31(3), Apr. 2008, pp. 225-234.
Muyldermans, et al., Reviews in Molecular Biotechnology 74 (2001), 277-302.
Neumann, D., et al., Journal of Immunology, vol. 165, No. 6, pp. 3350-3357, Sep. 15, 2000.
Qin, et al., Antisense & Nucleic Acid Drug Development, vol. 10, pp. 11-16, 2000.
Rudikoff, et al., PNAS USA, 79:1979-1983, Mar. 1982.
Saerens, et al., Jornal of Molecular Biology, Sep. 23, 2005, 352(3):597-607.
Stenton, et al., The Journal of Immunology, vol. 169, pp. 1028-1036, 2002.
U.S. Appl. No. 12/084,084 prosecution history. (Parts 1-10).
U.S. Appl. No. 12/663,505 prosecution history. (Parts 1-4).
U.S. Appl. No. 12/663,506 prosecution history. (Parts 1-3).
U.S. Appl. No. 12/663,498 prosecution history.
Vajdos, et al., Journal of Molecular Biology, Jul. 5, 2002, 320(2):415-428.
Woo, et al., American Journal of Physiology Lung Cell Molecular Phsiology, vol. 288, pp. L307-L316, 2005.

\* cited by examiner

```
                                    GAS leader
            M    L    F    K    S    L    S    K    L    A    T    A    A    A     5101
        TA ATG  TTA  TTT  AAA  TCA  TTA  TCA  AAA  TTA  GCA  ACC  GCA  GCA  GCA MULTIPLE CLONING SITE
   F    F    A    G    V    A    T    A                             A    A    A
  TTT  TTT  GCA  GGC  GTG  GCA  ACA  GCG TCG ACA  CA  CTGCAG GAG  GCG  GCC  GCA
                                         SalI        PstI           NotI Gene III seq
   E    T    V    E    S    -
  GAA  ACT  GTT  GAA  CGT  ---
```

FIG. 1

```
                       10        20        30        40        50        60        70        80        90       100
              ....|....|....|....|....|....|....|....|....|....|....|....|....|....|....|....|....|....|....|....|....|
VK Dummy      ...........................S..SSY.M..........S..SSY.M...............AA.S.....................SYST.N.........K.
DOM15-10 4G   DIQMTQSPSSLSASVGDRVTITCRASQWIGPELSWYQQKPGKAPKLLIYEASILQSGVPSRFSGSGSGTDFTLTISSLQPEDFATYYCQQYMPKQPRXEXQGTKVEIKR
DOM15-10-11   .....................R...........R..................................................M...................G
```

FIG. 16

*DOM1h-131-511 derived sequences*

>1-1
GAGGTGCAGCTGTTGGAGTCTGGGGGAGGCATGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCGGTTGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCTGGTCACCGTCTCGAGCG

>1-2
GAGGTGCAGCTGTTGGAGTCTGGGGGAGGCTTGGTACAGCCTGGGGGGTCCCTGCGTCTCTCC
TGTGCAGCCTCCGGATTCGCCTTTGCGCATGAGACGATGGTGTGGGTCCGCCAGGCTCCAGGG
AAGGGTCTAGAGTGGGTCTCACATATTCCCCCGGTTGGTCAGGATCCCTTCTACGCAGACTCCGT
GAAGGGCCGGTTCACCATCTCCCGCGACAATTCCAAGAACACGCTATATCTGCAAATGAACAGC
CTGCGAGCCGAGGACACAGCGGTATATTACTGTGCGCTGCTTCCTAAGAGGGGGCCTTGGTTTG
ACTACTGGGGTCAGGGAACCCTGGTCACCGTCTCGAGCG

>1-3
GAGGTGCAGCTGTTGGAGTCTGGGGGAGGCTTGGTACAGCCTGGGGGGTCCCTGCGTCTCTCC
TGTGCAGCCTCCGGATTCAACTTTGCGCATGAGACGATGGTGTGGGTCCGCCAGGCTCCAGGGA
AGGGTCTAGAGTGGGTCTCACATATTCCCCCGGTTGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCTGGTCACCGTCTCGAGCG

>DOM1h-131-201
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCGGTTGGTCAGGATCCCTTCTACGCAGACTCCGT
GAAGGGCCGGTTCACCATCTCCCGCGACGATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCTGGTCACCGTCTCGAGCG

FIG. 19A

>1-5
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCGGTTGGTCAGGATCCCTTCTATGCAGACTCCGTG
AAGGGCCGGTTCACCATCTCCCGCGACAATTCCAAGAACACGCTATATCTGCAAATGAACAACCT
GCGCGCCGAGGACACAGCGGTATATTACTGTGCGCTGCTTCCTAAGAGGGGGCCTTGGTTTGAC
TACTGGGGTCAGGGAACCCTGGTCACCGTCTCGAGCG
>1-6
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCCCCAGGG
AAGGGTCTAGAGTGGGTCTCACATATTCCCCCGGCTGGTCAGGATCCCTTCTACGCAGACTCCG
TGAAGGGCCGGTTCACCATCTCCCGCGACAATTCCAAGAGCACGCTATATCTGCAAATGAACGG
CCTGCGTGCCGAGGACACAGCGGTATATTACTGTGCGCTGCTTCCTAAGAGGGGGCCTTGGTTT
GACTACTGGGGTCAGGGAACCCTGGTCACCGTCTCGAGCG
>1-7
GAGGTGCAGCTGTTGGAGTCTGGGGGAGGCTTGGTAAAGCCTGGGGGGTCCCTGCGTCTCTCC
TGTGCAGCCTCCGGATTCACCTTTGCGCATGAGACGATGGTGTGGGTCCGCCAGGCTCCTGGGA
AGGGTCTAGAGTGGGTCTCACATATTCCCCCGGCTGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCTGGTCACCGTCTCGAGCG
>DOM1h-131-202
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCCCCAGGG
AAGGGTCTAGAGTGGGTCTCACATATTCCCCCGGACGGTCAAGATCCCTTCTACGCAGACTCCG
TGAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCTGGTCACCGTCTCGAGCG

FIG. 19B

>DOM1h-131-203
GAGGTGCAGCTGTGGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCGGATGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGATTG
ACTACTGGGGTCAGGGAACCCTGGTCACCGTCTCGAGCG

>DOM1h-131-204
GAGGTGCAGCTGTCGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCAGATGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAATAGGGGGCCTTGGTTTG
ACTACTGGGGTCAGGGAACCCTGGTCACCGTCTCGAGCG

>DOM1h-131-205
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCGGATGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCAGGTCACCGTCTCGAGCG

>1-12
GAGGTGCGGCTGTTGGAGTCTGGGGGAGGCTTGGTACAGCCTGGGGGGTCCCTGCGTCTCTCC
TGTACAGCCTCCGGATTCACCTTTGCGCATGAGACGATGGTGTGGGTCCGCCAGGCTCCAGGGA
AGGGTCTAGAGTGGGTCTCACATATTCCCCCGGATGGTCAGGATCCCTTCTACGCAGACTCCGT
GAAGAGCCGGTTCACCATCTCCCGCGACAATTCCAAGAACACGCTATATCTGCAGATGAACAGC
CTGCGTGCCGAGGACACAGCGGTGTATTACTGTGCGCTGCTTCCTAAGAGAGGGCCTTGGTTTG
ACTACTGGGGTCAGGGAACCCAGGTCACCGTCTCGAGCG

FIG. 19C

>1-13
GAGGTGCGGCTGTTGGAGTCTGGGGGAGGCTTGGTACAGCCTGAGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCGGATAGCCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGGGCTGCTTCCTAAGAGGGGGCCTTGGTTTG
ACTACAGGGGTCAGGGAACCCTGGTCACCGTCTCGAGCG
>1-14
GAGGTGCAGCTGTTGGAGTCTGGGGGAGGCTTGGTACAGCCTGGGGGGTCCCTGCGTCTCTCC
TGTGCAGCCTCCGGATTCACCATTGCGCATGAAACGATGGTGTGGGTCCGCCAGGCTCCAGGGA
AGGGTCTAGAGTGGGTCTCACATATTCCCCCGGTTGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACCGGGGTCAGGGAACCCTGGTCACCGTCTCGAGCG
>1-15
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCTCCGGTTGGTCAGGATCCCTTCTACGCAGACTCCGTG
AAGGGCCGGTTCACCATCTCCCGCGACAATTCCAAGAACACGCTATATCTGCAAATGAACAGCCT
GCGTGCCGAGGACACAGCGGTATATTACTGTGCGCGGCTTCCTAAGAGGGGGCCTTGGTTTGAC
TACTGGGGTCAGGGAACCTTGGTCACCGTCTCGAGCG
>DOM1h-131-206
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCACCAGGG
AAGGGTCTAGAGTGGGTCTCACATATTCCCCCGGATGGTCAGGATCCCTTCTACGCAGACTCCG
TGAAGGGCCGGTTCACCATCTCCCGCGACAATTCCAAGAACACGCTATATCTGCAAATGAACAGC
CTGCGTGCCGAGGACACAGCGGTATATCACTGTGCGCTGCTTCCTAAGAGGGGGCCTTGGTTTG
ACTACTGGGGTCAGGGAACCCTGGTCACCGTCTCGAGC

FIG. 19D

>1-18
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCGGGCTCCAGGG
AAGGGTCTAGAGTGGGTCTCACATATTCCCCCGGATGGTCAGGATCCCTTCTACGCAGACTCCG
TGAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCTGGTCACCGTCTCGAGC

>1-19
GAGGTGCAGCTGTTGGAGTCTGGGGGAGGCTTGGTACAGCCTGGGGGGTCCCTGCGTCTCTCC
TGTGCAGCCACCGGATTCACCTTTGCGCATGAGACGATGGTGTGGGTCCGCCAGGCTCCAGGG
AGGGGTCTAGAGTGGGTCTCACATATTCCCCCGGATGGTCAGGATCCCTTCTACGCAGACTCCG
TGAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCTGGTCACCGTCTCGAGC

>1-20
GAGGTGCAGCTGTTGGAGTCTGGGGGAGGCCTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
GGGGTCTAGAGTGGGTCTCACATATTCCCTCGGATGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTCG
ACTACTGGGGTCAGGGAACCCTGGTCACCGTCTCGAGC

>1-21
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCGGATGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAAGGGGCCTTGGTTTG
ACTACTGGGGTCAGGGAACCCTGGTCACCGTCTCGAGC

FIG. 19E

>1-22
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCGTGAGACGATGGTGTGGGTCCGCCAGGCTCCAGGG
AAGGGTCTAGAGTGGGTCTCACATATTCCCCCGGTTGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAGGGGGCCTTGGTTTG
ACTACTGGGGTCAGGGAACCCTGGTCACCGTCTCGAGC

>1-23
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCAAGAGACGATGGTGTGGGTCCGCCAGGCTCCAGGG
AAGGGTCTAGAGTGGGTCTCACATATTCCCCCGGTTGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAAGACACAGCGGTATATTACTGTGCGCGGCTTCCTAAGAGGGGGCCTTGGTTTG
ACTACTGGGGTCAGGGAACCCTGGTCACCGTCTCGAGC

>1-24
GAGGTGCAGCTGTTGGAGTCTGGGGGAGGCTTGGTACAGCCTGGGGGGTCCCTGCGTCTCTCC
TGTGCAGCTTCCGGATTCACCTTTGCGCATGAGACGATGGTGTGGGTCCGCCAGGCTCCAGGGA
AGGGTCTAGAGTGGGTCTCACATATTCCCCCGGTTGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCTGCTTCCTAAGAAGGGGCCTTGGTTTG
ACTACTGGGGTCAGGGAACCCTGGTCACCGTCTCGAGC

>1-25
GAGGTGCAGCTGTTGGAGTCTGGGGGAGGCTTGGTACAGCCTGGGGGGTCCCTGCGTCTCTCC
TGTGCAGCCTCCGGATTCACCTTTGCGCATGAGACGATGGTGTGGGTCCGCCAGGCTCCAGGGA
AGGGTCTAGAGTGGGTCTCACATATTCCCCCGGCTGGTCAGGATCCCTTCTACGCAGACTCCGT
GAAGGGCCGGTTCACCATCTCCCGCGACAATTCCAAGAACACGCTATATCTGCAAATGAACAGC
CTGCGTGCCGAGGACACAGCGGTATATTACTGTGCGCGGCTTCCTAAGAGGGGGCCTTGGTTTG
ACTACTGGGGTCAGGGAACCCTGGTCACCGTCTCGAGC

FIG. 19F

*DOM4-130-54 derived sequences*

>4-1
GACATCCTGATGACCCAGTCTCCATCCTCCCTGTCTGCATCTGTAGGAGACCGTGTCACCATCACTT
GCCGGGCAAGTCAGGATATTTACCTGAATTTAGACTGGTATCAGCAGAAACCAGGGAAGGCCCCT
AAGCTCCTGATCAATCTTGGTTCCGAGTTGCAAAGTGGTGTCCCATCACGTTTCAGTGGCAGTGGA
TATGGGACAGATTTCACTCTCACCATCAGCAGTCTGCAACCTGAAGATGTCGCTACGTACTACTGT
CAACCGTCTTTTTACTTCCCTTATACGTTCGGCCAAGGGACCAAGGTGGAAATCAAACGGG

>4-2
GACATCCTGATGACCCAGTCTCCATCCTCCCTGTCTGCATCTGTAGGAGACCGTGTCACCATCACTT
GCCGGGCAAGTCAGGATATTTACCTGAATTTAGACTGGTATCAGCAGAAACCAGGGAAAGCCCCT
AAGCTCCTGATCAATTTTGGCTCCGAGTTGCAAAGTGGTGTCCCATCACGTTTCAGTGGCAGCGGA
TATGGGACAGATTTCACTCTCACCATCAGCAGTCTGCAACCTGAAGATTTCGCTACGTACTACTGT
CAACCGTCTTTTTACTTCCCTTATACGTTCGGCCAGGGGACCAAGGTGGAAATCAAACGGG

>4-3
GACATCCAGACGACCCAGTCTCCGTCCTCCCTGTCTGCATCTGTAGGAGACCGTGTCACCATCACT
TGCCGGGCAAGTCAGGATATTTACCAGAATTTAGACTGGTATCAGCAGAAACCAGGGAAAGCCCC
TAAGCTCCTGATCAATTTTGGTTCCGAGTTGCAAAGTGGTGTCCCATCTCGTTTCAGTGGCAGTGG
ATATGGGACAGATTTCACTCTCACCATCAGCAGTCTGCAACCTGAAGATTTCGCTACGTACTACTG
TCAACCGTCTTTTTACTTCCCTTATACGTTCGGCCAA
GGGACCAAGGTGGAAATCAAACGGG

>4-4
GACATCCAGGTGACCCAGTCTCCATCCACCCTGTCTGCATCTGTAGGAGACCGTGTCACCATCACT
TGCCGGGCAAGTCAGGATATTTACCTGAATTTAGACTGGTATCAGCAGAAACCAGGGAAAGCCCC
TAAGCTCCTGATCAACTTTGGTTCCGAGTTGCAAAGTGGTGTCCCATCACGTTTCAGTGGCAGTGG
ATATGGGACAGATTTCACTCTCACCATCAGCAGTCTGCAACCTGAAGATTTCGCTACGTACTACTG
TCAACCGTCTTTTTACTTCCCTTATACGTTCGGCCGAGGGACCAAGGTGGAAATCAAACGGG

>4-5
GACATCCAGATGACCCAGTCTCCATCCTTCCTGTCTGCATCTGTAGGAGACCGTGTCACCATCACTT
GCCGGGCAAGTCAGGATATTTACCAGAATTTAGACTGGTATCAGCAGAAACCAGGGAAAGCCCCT
AAGCTCCTGATCAATTTTGGTTCCGAGTTGCAAAGTGGTGTCCCATCACGTTTCAGTGGCAGTGGA
TACGGGACAGATTTCACTCTCACCATCAGCAGTCTGCAACCTGAAGATATCGCTACGTACTACTGT
CAACCGTCTTTTTACTTCCCTTATACGTTGGCCAAGGGACCAAGGTGGAAATCAAAGGGG

GACATCCAGATGACCCAGTCTCCATCCTCCCTGTCGGCATCTGAAGGAGACCGTGTCACCATCACT
TGCCGGGCAAGTCAGGATATTTACCAGAATTTAGACTGGTATCAGCAGAAACCAGGGAAAGCCCC
TAAGCTCCTGATCAATTTTGGTTCCGAGTTGCAAAGTGGTGTCCCATCACGTTTCAGTGGCAGTGG
ATATGGGACAGAATTCACTCTCACCATCAGCAGTCTGCAACCTGAAGACTTCGCTACGTACTACTG
TCAACCGTCTTTTTACTTCCCTTATACGTTCGGCCAAGGGACCAAGGTGGAAATCAAACGGG

>4-7

GACATCCAGATGACCCAGTCTCCATCCTCCCTGTCTGCATCTGTAGGAGACCGTGTCACCGTCACT
TGCCGGGCAAGTCAGGATATTTACCTGAATTTAGACTGGTATCAGCAGAAACCAGGGAAAGCCCC
TAAGCTCCTGATCAATTTTGGTTCCGAGTTGCAAAGTGGTGTCCCATCACGTTTCAGTGGCAGTGG
ATATGGGACAGATTTCACTCTCACCATCAGCAGTCTGCAGCCTGAAGATTTCGCTACGTACTACTG
TCAACCGTCTTTTTACTTCCCTTATACGTTCGGCCAAGGGACCAAGGTGGAAATCAAACGGG

>4-8

GACATCCAGATGACCCAGTCTCCATCCTCCCTGTCTGCATCTGTAGGAGACCGTGTCACCATCACT
TGCCGGGCAAGTCAGGATATTTACCTGGATTTAGACTGGTATCAGCAGAAACCAGGGAAAGCCCC
TAAGCTCCTGATCAATTTTGGTTCCGAGTTGCAAAGTGGTGTCCCATCACGTTTCAGTGGCAGTGG
ATATGGGACAGATTTCACTCTCACCATCAGCGGTCTGCAACCTGAAGATTTCGCTACGTACTACTG
TCAACCGTCTTTTTACTTCCCTTATACGTTCGGCCGAGGGACCAGGGTGGAAATCAAACGGG

>4-9

GACATCCAGATGACCCAGTCTCCATCCTCCCTGTCTGCATCTGTAGGAGACCGTGTCACCATCACT
TGCCGGGCAAGTCAGGATATTTACCTGAATTTAGACTGGTATCAGCAGAAACCAGGGAAAGCCCC
TAAGCTCCTGATCAGTTTTGGTTCCGAGTTGCAAAGTGGTGTCCCATCACGTTTCAGTGGCAGTGG
ATATGGGACAGATTTCACTCTCACCATCAGCAGTCTGCAACCTGAAGATTTCGCTACGTACTACTG
TCAACCGTCTTTTTACTTCCCTTACACGTTCGGCCAAGGGACCAAGGTGGAAATCAAACGGG

>DOM4-130-201

GACATCCAGATGACCCAGTCTCCATCCTCCCTGTCTGCATCTGTAGGAGACCGTGTCACCATCACT
TGCCGGGCAAGTCAGGATATTTACCTGAATTTAGACTGGTATCAGCAGAAACCAGGGAAAGCCCC
TAAGCTCCTGATCAAATTTGGTTCCGAGTTGCAAAGTGGTGTCCCATCACGTTTCAGTGGCAGTGG
ATATGGGACAGATTTCACTCTCACCATCAGCAATCTGCAACCTGAAGATTTCGCTACGTACTACTG
TCAACCGTCTTTTTACTTCCCTTATACGTTCGGCCAAGGGACCAAGGTGGAAATCAAATGGG

FIG. 19H

>4-11
GACATCCAGATGACCCAGTCTCCATCCTCCCTGTCTGCATCTGTAGGAGACCGTGTCACCATCACT
TGCCGGGCAAGTCAGGATATTTACCTGAATTTAGACTGGTATCAGCAGAAACCAGGGAAAGCCCC
TAAGCTCCTGATCATTTATGGTTCCGAGTTGCAAAGTGGTGTCCCACCACGTTTCAGTGGCAGTGG
ATATGGGACAGATTTCACTCTCACCATCAGCAGTCTGCAACCTGAAGATTCCGCTACGTACTACTG
TCAACCGTCTTTTTACTTCCCTTATACGTTCGGCCAAGGGACCAAGGTGGAAATCAAACGGG

>4-12
GACATCCAGATGACCCAGTCTCCATCCTCCCTGTCTGCATCTGTAGGAGACCGTGTCACCATCACT
TGCCGGGCAAGTCAGGATATATACCTGAATTTAGACTGGTATCAGCAGAAACCAGGGAAAGCCCC
TAAGCTCCTGATCAATTTTGGTTCCGAGTTGCAAAGTGGTGTCCCACCACGTTTCAGTGGCAGTGG
ATATGGGACAGATTTCACTCTCACCATCAGCAGTCTGCAACCTGAAGATTTCGCTACGTACTACTG
TCAACCGTCTTTTTACTTCCCTTATACGTTCGGCCAAGGGACCAAGGTGGAAATCAAACAGG

>4-13
GACATCCAGATGACCCAGTCTCCATCCTCCCTGTCTGCATCTGTAGGAGACCGTGTCACCATCACT
TGCCGGGCAAGTCAGGATATTTACCTGAATTTAGACTGGTATCAGCAGAAACCAGGGAAAGCCCC
TAAGCTCCTGATCAATTTTGGTTCCGAGTTGCAAAGTGGTGTCCCATCACGTTTCAGTGGCAGTGG
ATATGGGACAGATTTCGCTCTCACCATCAGCAGTCTGCAACCTGAAGATTCCGCTACGTACTACTG
TCAACCGTCTTTTTACTTCCCATATACGTTCGGCCAAGGGACCAAGGTGGAAATCAAACAGG

>4-14
GACATCCAGATGACCCAGTCTCCATCCTCCCTGTCTGCATCTGTAGGAGACCGTGTCACTATCACTT
GCCGGGCAAGTCAGGATATTTACCTGAATTTAGACTGGTATCAGCAGAAACCAGGGAAAGCCCCT
AAGCTCCTGATCAATTTTGGTTCCGAGTTGCAAAGTGGTGTCCCATCACGTTTCAGTGGCAGTGGA
TATGGGACAGATTTCACTCTCACCATCAGCAGTCTGCAACCTGAAGATGTCGCTACGTACTACTGT
CAACCGTCTTTTTACTTCCCTTATACGTTCGGCCAAGGGACCAAGGTGGAAATCAAACGGG

>4-15
GACATCCAGATGACCCAGTCTCCATCCTCCCTGTCTGCATCTGTAGGAGACCGTGTCACCATCACT
TGCCGGGCAAGTCAGGATATTTACCTGAATTTAGACTGGTATCAGCAGAAACCAGGGAAAGCCCC
TAAGCTCCTGATCAATTTTGGTTCCGAGTTGCAAAGTGGTGTCCCATCACGTTTCAGTGGCAGTGG
ATATGGGACAGATTTCACTCTCACCATCAGCAGTCTGCAACCTGAAGACTTCGCTACGTACTACTG
TCAACCGTCTTTTTACTTCCCATATACGTTTGGCCAAGGGACCAAGGTGGAAATCAAACAGG

FIG. 19I

>4-16
GACATCCAAATGGCCCAGTCTCCATCCTCCCTGTCTGCATCTGTAGGAGACCGTGTCACCATCAC
TTGCCGGGCAAGTCAGGATATTTACCTGAATTTGGACTGGTATCAGCAGAAACCAGGGAAAGCC
CCTAAGCTCCTGATCAGTTTTGGTTCCGAGTTGCAAAGTGGTGTCCCATCACGTTTCAGTGGCAG
TGGATATGGGACAGATTTCACTCTCACCATCAGCAGTCTGCAACCTGAAGATTCCGCTACGTACT
ACTGTCAGCCGTCTTTTTACTTCCCTTATACGTTCGGCCAAGGGACCAAGGTGGAAATCAAACAG
G
>4-17
GACATCCAGATGACCCAGTCACCATCCTCCCTGTCTGCATCTGTAGGAGACCGTGTCACCATCAC
TTGCCGGGCAAGTCAGGACATTTACCTGAATTTAGACTGGTATCAGCAGAAACCAGGGAAAGCC
CCTAAGCTCCTGATCAATTTTGGTTCCGAGTTGCAAAGTGGTGTCCCATCACGTTTCAGTGGCAG
TGGATATGGGACAGATTTCACTCTCACCATCAGCAGTCTGCAACCTGAAGATTTCGCTACGTACT
ACTGTCAACCGTCTTTTTACTTCCCTTATACGTTCGGCCAAGGGACCAAGGTGGAAATCAAACGG
G
>4-18
GACATCCAGATGACCCAGTCTCCATCCTCCCTGTCTGCGTCTGTAGGAGACCGTGTCACCATCAC
TTGCCGGGCAAGTCAGGATATTTACCTGAATTTAGACTGGTATCAGCAGAAACCAGGGAAAGCC
CCTAAGCTCCTGATCAATTTTGGTTCCGAGTTGCAAAGTGGTGTCCCATCACGTTTCAGTGGCAG
TGGATATGGGACAGATTTCACACTCACCATCAGCAGTCTGCAACCTGAAGATTTCGCTACGTACT
ACTGTCAACCGTCTTTTTACTTCCCTTATACGTTCGGCCAAGGGACCAAGGTGGAAATCAAACTG
>4-19
GACATCCAGATAACCCAGTCTCCATCCTCCCTGTCTGCATCTGTAGGAGACCGTGTCACCATCAC
TTGCCGGGCAAGTCAGGATATTTACCTGAATTTAGACTGGTATCAGCAGAAACCAGGGAAAGCC
CCTAAGCTCCTGATCAATTTTGGTTCCGAGTTGCAAAGTGGTGTCCCATCACGTTTCAGTGGCAG
TGGATATGGGACAGATTTCACTCTCACCATCAGCAGTCTGCAACCTGAAGATTTCGCTACGTACT
ACTGTCAACCGTCTTTTTACTTCCCTTATACGTTCGGCCAAGGGACCAAGGTGGAAATCAAACCG
>4-20
GACATCCAGATGACCCAGTCTCCATCCTCCCTGTCTGCATCTGTAGGAGACCGTGTCACCATCAC
TTGCCGGGCAAGTCAGGATATTTACCTGAATTTAGACTGGTATCAGCAGAAACCAGGGAAAGCC
CCTAAGCTCCTGATCAATTTTGGTTCCGAGTTGCAAAGTGGTGTCCCATCACGTTTCAGTGGCAG
TGGATATGGGACAGATTTCACTCTCACCATCAGCAGTCTGCAACCTGAAGATTTCGCTACGTACT
ACTGTCAACCGTCTTTTTACTACCCTTATACGTTCGGCCAAGGGACCAAGGTGGAAATCAAACAG

FIG. 19J

>DOM4-130-202
GACATCCAGATGACACAGTCTCCATCCTCCCTGTCTGCATCTGTAGGAGACCGTGTCACCATCTC
TTGCCGGGCAAGTCAGGATATTTACCTGAATTTAGACTGGTATCAGCAGAAACCAGGGAAAGCC
CCTAAGCTCCTGATCAGTTTTGGTTCCGAGTTGCAAAGTGGTGTTCCTTCACGTTTCAGTGGCAG
TGGATATGGGACAGATTTCACTCTCACCATCAGCAGTCTGCAGCCTGAAGATTCCGCTACGTACT
ACTGTCAACCGTCTTTTTACTACCCTTATACGTTCGGCCAAGGGACCAAGGTGGAAATCAAACGG
>4-22
GACATCCAGATGACCCAGTCTCCATCCTCCCTGTCTGCATCTGTAGGAGACCGTGTCACCATCAC
TTGCCGGGCAAGTCAGGATATTTACCTGAATTTAGACTGGTATCAGCAGAAACCAGGGAAAGCC
CCTAAGCTCCTGATCAATTTTGGTTCCGAGTTGCAAAGTGGTGTCCCATCACGTTTCAGTGGCAG
TGGATATGGGACAGATTTCACTCTCACCATCAGCAGTCTGCAACCTGAAGATTTCGCTACGTACT
ACTGTCAACCGTCTTTTTACTACCCTTATACGTTCGGCCAAGGGACCAAGGTGGAAATCAAACGG
>4-23
GACATCCAGATGACCCAGTCTCCATCCTCCCTGTCTGCATCTGTAGGAGACCGTGTCACCATCAC
TTGCCGGGCAAGTCAGGATATTTACCTGAATTTAGACTGGTATCAGCAGAAACCAGGGAAAGCC
CCTAAGCTCCTGATCAATTTTGGTTCCGAGTTGCAAAGTGGAGTCCCATCACGTTTCAGTGGCAG
TGGATATGGGACAGATTTCACTCTCACCATCAGCAGTCTGCAACCTGAAGATTCCGCTACGTACT
ACTGTCAACCGTCTTTTTACTTCCCTTATACGTTCGGCCAAGGGACCAAGGTGGAAATCAATCGG
>4-24
GACATCCAGATGACCCAGTCTCCATCCTCCCTGTCTGCATATGTAGGAGACCGTGTCACCATCAC
TTGCCGGGCAAGTCAGGATATTTACCTGAATTTAGACTGGTATCAGCAGAAACCAGGGAAAGCC
CCTAAGCTCCTGATCAGTTTTGGTTCCGAGTTGCAAAGTGGTGTCCCATCACGTTTCAGTGGCAG
TGGATATGGGACAGATTTCACTCTCACCATCAGCAGTCTGCAACCTGAAGATTCGGTACGTACT
ACTGTCAACCGTCTTTTTACTTCCCTTATACGTTCGGCCAAGGGACCAAGGTGGAAATCAAACGG
>4-25
GACATCCAGATGACCCAGTCTCCATCCTCCCTGTCTGCATCTGTAGGAGACCGTGTCACCATCAC
TTGTCGGGCAAGTCAGGATATTTACCTGAATTTAGACTGGTATCAGCAGAAACCAGGGAAAGCC
CCTAAGCTCCTGATCAATTTTGGTTCCGAGTTGCAAAGTGGTGTCCCATCACGTTTCAGTGGCAG
TGGATATGGGACAGATTTCACTCTCACCATCAGCAGTCTGCAACCTGAAGATTTCGGTACGTACT
ACTGTCAACCGTCTTTTTACTTCCCTTATACGTTCGGCCAAGGGACCAAGGTGGAAATCAAACGG

FIG. 19K

>4-26
GACATCCAGATGACCCAGTCTCCGTCCTCCCTGTCTGCATCTGTAGGAGACCTTGTCACCATCAC
TTGCCGGGCAAGTCAGGATATTTACCTGAATTTAGACTGGTATCAGCAGAAACCAGGGAAAGCC
CCTAAGCTCCTGATCAATTTAGGTTCCGAGTTGCAAAGTGGTGTCCCATCACGTTTCAGTGGCAG
TGGATATGGGACAGATTTCACTCTCACCATCAGCAGTCTGCAACCTGAAGATTTCGCTACGTACT
ACTGTCAACCGTCTTTTTACTTCCCTTATACGTTCGGCCAAGGGACCAAGGTGGAAATCAAACGT
>4-27
GACATCCTGATGACCCAGTCTCCATCCTCCCTGTCTGCATCTGTAGGAGACCGTGTCACCATCAC
TTGCCGGGCAAGTCAGGATATTTACCTGAATTTAGACTGGTATCAGCAGAAACCAGGGAAGGCC
CCTAAGCTCCTGATCAATCTTGGTTCCGAGTTGCAAAGTGGTGTCCCATCACGTTTCAGTGGCAG
TGGATATGGGACAGATTTCACTCTCACCATCAGCAGTCTGCAACCTGAAGATGTCGCTACGTACT
ACTGTCAACCGTCTTTTTACTTCCCTTATACGTTCGGCCAAGGGACCAAGGTGGAAATCAAACGG

FIG. 19L

>DOM15-26-555
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
CGGAAGTTTGACTACTGGGGTCAGGGAACCCTGGTCACCGTCTCGAGC
>DOM15-26-576
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCCAGAGTGGGTCTCAGAGATTTCGCCTTCGGGTTCTTATACATACTAC
GCAGACTCCGTGAAGGGCCGGTTCACCATCTCCCGTGACAATTCCAAGAACACGCTGTAT
CTGCAAATGAACAGCCTGCGTGCCGAGGACACCGCGGTATATTACTGTGCGAAAGATCCT
CGGAAGTTTGACTACTGGGGTCAGGGAACCCTGGTCACCGTCTCGAGC
>DOM15-26-578
GAGGTGCAGCTGTTGGTGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCCAGAGTGGGTCTCAGAGATTTCGCCTTCGGGTTCTTATACATACTAC
GCAGACTCCGTGAAGGGCCGGTTCACCATCTCCCGCGACAATTCCAAGAACGCGCTGTAT
CTGCAAATGAACAGCCTGCGTGCAGAGGACACCGCGGTATATTACTGTGCGAAAGATCCT
CGGAAGTTTGACTACTGGGGTCAGGGAGCCCTGGTCACCGTCTCGAGC
>DOM15-26-579
GAGGTGCAGCTGTTGGTGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGATCTCAGAGATTTCGCCTTCGGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCAAAAGATCCT
CGGAAGTTTGACTACTGGGGTCAGGGAACCCTGGTCACCGTCTCGAGC
>DOM15-26-580
GAGGTGCAGCTGCTGGTGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCATATACATACTAT
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
CGGAAGTTTGAATACTGGGGTCAGGGAACCCTGGTCACCGTCTCGAGC
>DOM15-26-581
GAGGTGCAGCTGTTGGTGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCGGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAATGATCCT
CGGAAGTTTGACTACTGGGGTCAGGGAACCCTGGTCACCGTCTCGAGC
>DOM15-26-582
GAGGTGCAGCTGTTGGAGTCTGGGGGAGGCTTGGTACAGCCTGGGGGGTCCCTGCGTCTC
TCCTGTGCAGCCTCCGGATTCACATTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAGACTCCGTGAAGGGCCGGTTCACCATCTCCCGCGACAATTCCAAGAACACGCTGTAT
CTGCAAATGAACGGCCTGCGTGCCGAGGACACCGCGGTATATTACTGTGCGAACGATCCT
CGGAAGATTGACTACTGGGGTCAGGGAACCCTGGTCACCGTCTCGAGC

FIG. 20A

>DOM15-26-583
GAGGTGCAGCTGTTGGTGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCATACTCCGTGAAGGGCCGGTTCACCATCTCCCGCGACAATTCCAAGAACACGCTGTAT
CTGCAAATGAACAGCCTGCATGCCGAGGACACCGCGGTATATTACTGTGCGAAAGATCCT
CGGAAGTTAGACTACTGGGGTCAGGGAACCCTGGTCACCGTCTCGAGC
>DOM15-26-584
GAGGTGCAGCTGTTGGAGTCTGGGGGAGGCTTGGTACAGCCAGGGGGGTCCCTGCGTCTC
TCCTGTGCTGCCTCCGGATTCACCTTTAAGGCTTATCCGATGATGTGGGTCCGCCAGGCT
CCAGGGAAGAGTCTAGAGTGGGTCTCAGAGATTTCGCCTTCGGGTTCTTATACATACTAC
GCAGACTCCGTGAAGGGCCGGTTCACAATCTCCCGCGACAATTCCAAGAACACGCTGTAT
CTGCAAATGAACAGCCTGCGTGCCGAGGACACCGCGGTATATTACTGTGCGAAAGATCCT
CGGAAGATTGACTACTGGGGTCAGGGAACCCTGGTCACCGTCTCGAGC
>DOM15-26-585
GAGGTGCAGCTGGTGGAGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAGAGTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTACGAAAGATCCT
CGGAAGTTTGACTACTGGGGTCAGGGAACCCTGGTCACCGTCTCGAGC
>DOM15-26-586
GAGGTGCAGTTGTTGGTGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAGACTCCGTGAAGGGCCGGTTCACCATTTCCCGCGACAATTCCAAGAACACGCTGTAT
CTGCAAATGAACAGCCTGCGTGCCGAGGACACCGCGGTATATTACTGTGCGAAAGATCCT
CGGAAGTTTGACTACTGGGGTCAGGGAACCCTGGTCACCGTCTCGAGC
>DOM15-26-587
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAAACTCCGTGAAGGGTCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
CGGAAGATTGACTACTGGGGTCAGGGAACCCTGGTCACCGTCTCGAGC
>DOM15-26-588
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
CGGAAGTCTGACTACTGGGGTCAGGGAACCCTGGTCACCGTCTCGAGC
>DOM15-26-589
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATCTCGCCTTCGGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
CGGAAGATTGACTACTGGGGTCAGGGAACCCTGGTCACCGTCTCGAGC

FIG. 20B

>DOM15-26-590
GAGGTGCATCTGTTGGAGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAAACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
CGGAAGATTGACTACTGGGGTCAGGGAACCCTGGTCACCGTCTCGAGC
>DOM15-26-591
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
CGGAAGTTAGACTACTGGGGTCAGGGAACCCTGGTCACCGTCTCGAGC
>DOM15-26-592
GAGGTGCAGCTGTTGGTGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTCTCAGAGATTTCGCCTTCGGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTACGAAAGATCCT
CGGAAGTTTGACTACTGGGGTCAGGGAACCCTGGTCACCGTCTCGAGC
>DOM15-26-593
GAGGTGCAGCTGTTGGTGTCTGGGGGAGGCTTGGTACAGCCTGGGGGGTCCCTGCGTCTC
TCCTGTGCAGCCTCCGGATTCACCTTTAAGGCTTATCCGATGATGTGGGTCCGCCAGGCT
CCAGGGAAGGGTCTAGAGTGGGTTTCAGAGATTTCGCCTTCGGGTTCTTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATCCT
CGGAAGTTAGACTACTGGGGTCAGGGAACCCTGGTCACCGTCTCGAGC
>DOM15-10
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCTAAGCTCCTGATCTATCATACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATATGTTTCAGCCTAGGACGTTCGGCCAA
GGGACCAAGGTGGAAATCAGACGG
>DOM15-10-1
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCTAAGCGCCTGATCTATCATTCGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATATGTTTGAGCCTAGGACGTTCGGCCAA
GGGACCAAGGTGGAAATCAGACAG
>DOM15-10-2
GACATCCAGATGACCCAGTCTCCATCCTCCCTGTCTGCATCTGTAGGAGACCGTGTCACC
ATCACTTGTCGGGCAAGTCAGTGGATTGGTCCGGAGTTAAGATGGTACCAGAAGAAACCA
GGGAAAGCCCCTAAGCTCCTGATCTATCATACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATATGTTTCAGCCTAGGACGTTCGGCCAA
GGGACCAAGGTGGAAATCAGACGG

FIG. 20C

\>DOM15-10-3
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCTAAGCACCTGATCTATCATACGTCCATTTTGCAAAGTGGGGTCCCATCA
CGTTTCAGTGGCAGTAGATCTGGGACAGATTTCACTCTCACCATCAGCAGTCTGCAACCT
GAAGATTTTGCTACGTACTACTGTCAACAGTATATGTTTCAGCCTAAGACGTTCGGCCAA
GGGACCAAGGTGGAAATCAGATGG
\>DOM15-10-4
GACATCCAGATGACCCAGTCTCCATCCTCCCTGTCTGCATCTGTAGGAGACCGTGTCACC
ATCACTTGCCGGGCAAGTCAGTGGATTGGTCCTGAGTTAAGATGGTACCAGAAGAAACCA
GGGAAAGCCCCTAAGCTCCTGATCTATCATACGTCCATTTTGCAAAGTGGGGTCCCATCA
CGTTTCAGTGGCAGTGGATATGGGACAGATTTCACTTTCACCATCAGCAGTCTGCAACCT
GAAGATTTTGCTACGTACTACTGTCAACAGTATATGTTTCAGCCTAGGACGTTCGGCCCA
GGGACCAAGGTGGAAATTAGACGG
\>DOM15-10-5
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCTAAGCTCCTGATCTATCATACGTCCATTTTGCGAAGTGGGGTCCCATCT
CGTTTCAGTGGCAGTGGATCTGGGACAGATTTCACTCTCACCATCAGCAGTCTGCAACCT
GAAGATTTTGCTACGTACTACTGTCAACAGTATATGTTTCAGCCTAGGACGTTCGGCCAA
GGGACCAAGGTGGAAATCAGATGG
\>DOM15-10-6
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCTAAGCGCCTGATCTATCATACGTCCATTTTACAGAGTGGGGTCCCATCA
CGTTTCAGTGGCAGTGGATATGGGACAGATTTCACTCTCACCATCAGCAGTCTGCAACCT
GCAGATTTTGCAACGTACTACTGTCAACAGTATATGTTTCAGCCTAGGACGTTCGGCCAA
GGGACCAAGGTGGAAATCAGACAG
\>DOM15-10-7
GACATCCAGATGACCCAGTCCCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCTAAGCTCCTGATCTATCATACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATATGTTTTGGCCTAGGACGTTCGGCCAA
GGGACCAAGGTGGAAATCAGACAA
\>DOM15-10-8
GACATCCAGATGACCCAGTCTCCATCCTCCCTGTCCGCATCTGTAGGAGACCGTGTCACC
ATCACTTGCCGGGCAAGTCAGTGGATTGGTCCGGAGTTAAGTTGGTACCAGCAGAAACCA
GGGAAAGCTCCTAAGCTCCTGATCTATCATACGTCCATTTTGCAAAGTGGGGTCCCATCA
CGTTTCAGTGGCAGTGGATATGGGACAGATTTCACTCTCACCATCAGCAGTCTGCAACTT
GAAGATTTTGCTACGTACTACTGTCAACAGTATATGTTTCTGCCTAGGACGTTCGGCCAA
GGGACCAAGGTGGAAATCAGAGGG
\>DOM15-10-9
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCTAAGTTCCTGATCTATCATACGTCCATTTTGCAAAGTGGGGTCCCATCA
CGTTTCAGTGGCAGTGGATATGGGACAGATTTCACTCTCACCATCAACAGTCTGCAACCT
GGAGATTTTGCTACGTACTACTGTCAACAGTATATGTTTCAGCCTAGGACGTTCGGCCAA
GGGACCAAGGTGGAAATCAGACGG

FIG. 20D

```
>DOM15-10-10
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCTAAGCTCCTGATCTATCATACGTCCATTTTGCAAAGTGGGGTCCCATCA
CGTTTCAGTGGCAGTGGATATGGGACAGATTTCACTCTCACCATCAGCAGTCTGCAACCT
GAAGATTTTGCTACGTACTACTGTCAACAGTATATGTATCAGCCTAGGACGTTCGGCCAA
GGGACCAAGGTGGAAATCAGACAG
>DOM15-10-11
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGATGGTACCAGCAGAAACCA
GGGAAAGCCCCTAAGCTCCTGATCTATCATACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATATGTTTCAGCCTATGACGTTCGGCCAA
GGGACCAAGGTGGAAATCAGAGGG
>DOM15-10-12
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGATGGTACCAGAAGAAACCA
GGGAAAGCCCCTAAGCTCCTGATCTATCATACGTCCATTTTGCAAAGTGGGGTCCCATCA
CGTTTCAGTGGCAGTGGATCTGGGACAGATTTCACTCTCACCATCAGCAGTCTGCAAGCT
GAAGATTCTGCTACGTACTACTGTCAACAGTATATGTTTCAGCCTAGGACGTTCGGCCAA
GGGACCAAGGTGGAAACCAGACGG
>DOM15-10-13
GACATCCAGATGACCCAGTCTCCATCCTCCCTGTCTGCATCTGAAGGAGACCGTGTCACC
ATCACTTGCCGGGCAAGTCAGTGGATTGGTCCGGAGTTAAGTTGGTACCAGCAGAAACCA
CGGAAAGCCCCTAAGCTCCTGATCTATCATACGTCCATTTTGCAAAGTGGGGTCCCATCA
CGTTTCACTGGCAGTGGATCTGGGACAGATTTCACTCTCACCATCAGCAGTCTGCAACCT
GAAGATTTTGCTACGTACTACTGTCAACAGTATATGTTTCAGCCTATGACGTTCGGCCAA
GGGACCAAGGTGGAAATCAGACGG
>DOM15-10-14
GACATCCTGATGACCCAGTCTCCATCCTCCCTGTCTGCATCTGTAGGAGACCGTGTCACC
ATCACTTGCCGGGCAAGTCAGTGGATTGGTCCGGAGTTACGTTGGTACCAGCATAAACCA
GGGAAAGCCCCTAAGCTCCTGATCTATCATACGTCCATTTTGCAAAGTGGGGTCCCATCA
CGTTTCAGTGGCAGTGGATATGGGACAGATTTCACTCTCTCCATCAGCAGTCTGCAACCT
GAAGATTTCGCTACGTACTACTGTCAACAGTATATGTTTCAGCCTAGGACGTTCGGCCAA
GGGACCAAGGTGGAAATCAGATGG
>DOM15-10-15
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTAAGTTGGTACCAGCAGAAACCA
GGGAAAGCCCCAAAGCTCCTGATCTATCATACGTCCATTTTGCAAGGTGGGGTCCCATCA
CGTTTCAGTGGCAGTGGATCTGGGACAGATTTCACTCTCACCATCAGCAGTCTGCAACCT
GAGGATTTTGCTACGTACTACTGTCAACAGTATATGTTTTGGCCTAGGACGTTCGGCCAA
GGGACCAAGGTGGAAATCAGACAG
>DOM15-10-16
GACATCCAGATGACCCAGTCTCCATCCTCCCTGTCTGCATCTGTAGGAGACCGTGTCACC
ATCACTTGCCGGGCAAGTCAGTGGATTGGTCCGGAGTTACGTTGGTACCAGCAGAAACCA
GGGAAAGCCCCTAAGCTCCTGATCTATCATACGTCCATTTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATATGTTTCAGCCTATGACGTTCGGCCAA
```

| Kabat Numbering | 74 | | | | | | | | | | | | | | | | | | | | 79 | | | | | | | | | | | | | | | | 82a | | | | | | | | | | | | | | | | | | | 83 | | | | | | | | | | | | | | | | 91 | | | | | | | | | | | | 96 | | | | | | | | | | | 103 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| DOM7h-23 | S | N | D | R | S | S | K | N | T | L | Y | L | Q | M | N | S | L | R | A | E | D | T | A | V | Y | Y | C | A | K | G | Q | G | Y | G | T | P | D | F | W | G | Q | G | T | L | V | T | V | S | S | — | — | — | — | — | — | — | — |
| DOM7h-21 | S | N | D | R | S | S | K | N | T | L | Y | L | Q | M | N | S | L | R | A | E | D | T | A | V | Y | Y | C | A | K | G | H | G | Y | R | T | P | D | F | W | G | Q | G | T | L | V | T | V | S | S | P | — | — | — | — | — | — | — |
| DOM7h-22 | S | R | D | R | S | S | K | N | T | L | Y | L | Q | M | N | S | L | R | A | E | D | T | A | V | Y | Y | C | A | K | G | T | G | Y | R | I | P | D | F | W | G | Q | G | T | L | V | T | V | S | S | — | — | — | — | — | — | — | — |
| DOM7h-24 | S | N | D | R | S | S | K | N | T | L | Y | L | Q | M | N | S | L | R | A | E | D | T | A | V | Y | Y | C | A | K | G | H | G | Y | R | T | P | D | F | W | G | Q | G | T | L | V | T | V | S | S | — | — | — | — | — | — | — |
| DOM7h-25 | S | N | D | R | S | S | K | N | T | L | Y | L | Q | M | N | S | L | R | A | E | D | T | A | V | Y | Y | C | A | K | G | Q | G | Y | G | T | P | D | F | W | G | Q | G | T | L | V | T | V | S | S | — | — | — | — | — | — | — |
| DOM7h-26 | S | N | D | R | S | S | K | N | T | L | Y | L | Q | M | N | S | L | R | A | E | D | T | A | V | Y | Y | C | A | K | G | Q | G | Y | G | T | P | D | F | W | G | Q | G | T | L | V | T | V | S | S | — | — | — | — | — | — | — |
| DOM7h-27 | S | N | D | R | S | S | K | N | T | L | Y | L | Q | M | N | S | L | R | A | E | D | T | A | V | Y | Y | C | A | K | G | Q | G | Y | G | T | P | D | F | W | G | Q | G | T | L | V | T | V | S | S | — | — | — | — | — | — | — |
| DOM7h-30 | S | N | D | R | S | S | K | N | T | L | Y | L | Q | M | N | S | L | R | A | E | D | T | A | V | Y | Y | C | A | K | G | Q | G | Y | G | T | P | D | F | W | G | Q | G | T | L | V | T | V | S | S | — | — | — | — | — | — | — |
| DOM7h-31 | R | N | D | R | S | S | K | N | T | L | Y | L | Q | M | N | S | L | R | A | E | D | T | A | V | Y | Y | C | A | R | T | G | T | G | T | I | S | T | A | F | W | G | T | G | T | T | V | S | S | D | — | — | — | — | — | — | — |

FIG. 51A CONTINUE-7

FIG. 51A
CONTINUE-8 dAb 2, 4, 7, 41
DIQMTQSPSSLSASVGDRVTITCRASQSISSYLNWYQQKPGKAPKLLIYAASPLQSGVP
SRFSGSGSGTDFTLTISSLQPEDFATYYCQQTYSVPPTFGQGTKVEIKR dAb 38, 54
DIQMTQSPSSLSASVGDRVTITCRASQSISSYLNWYQQKPGKAPKLLIYRASPLQSGVP
SRFSGSGSGTDFTLTISSLQPEDFATYYCQQTYRIPPTFGQGTKVEIKR dAb 46, 47, 52, 56
DIQMTQSPSSLSASVGDRVTITCRASQSIFKSLKWYQQKPGKAPKLLIYNASYLQSGVP
SRFSGSGSGTDFTLTISSLQPEDFATYYCQQVVYWPVTFGQGTKVEIKR dAb 13, 15
DIQMTQSPSSLSASVGDRVTITCRASQSIYYHLKWYQQKPGKAPKLLIYKSTLQSGVP
SRFSGSGSGTDFTLTISSLQPEDFATYYCQQVRKVPRTFGQGTKVEIKR dAb 30, 35
DIQMTQSPSSLSASVGDRVTITCRASQSIRRYLKWYQQKPGKAPKLLIYQASVLQSGVP
SRFSGSGSGTDFTLTISSLQPEDFATYYCQQGLYPPITFGQGTKVEIKR dAb 19,
DIQMTQSPSSLSASVGDRVTITCRASQSIYNWLKWYQQKPGKAPKLLIYRASSLQSGVP
SRFSGSGSGTDFTLTISSLQPEDFATYYCQQNVVIPRTFGQGTKVEIKR dAb22
DIQMTQSPSSLSASVGDRVTITCRASQSILWHLRWYQQKPGKAPKLLIYHASLLQSGVP
SRFSGSGSGTDFTLTISSLQPEDFATYYCQQSAVYPKTFGQGTKVEIKR dAb23
DIQMTQSPSSLSASVGDRVTITCRASQSIFRYLAWYQQKPGKAPKLLIYHASHLQSGVP
SRFSGSGSGTDFTLTISSLQPEDFATYYCQQRLLYPKTFGQGTKVEIKR dAb24
DIQMTQSPSSLSASVGDRVTITCRASQSIFYHLAWYQQKPGKAPKLLIYPASKLQSGVP
SRFSGSGSGTDFTLTISSLQPEDFATYYCQQRARWPRTFGQGTKVEIKR dAb31
DIQMTQSPSSLSASVGDRVTITCRASQSIIWHLNWYQQKPGKAPKLLIYRASRLQSGVP
SRFSGSGSGTDFTLTISSLQPEDFATYYCQQVARVPRTFGQGTKVEIKR

FIG. 51A
*CONTINUE-9*

```
dAb33
DIQMTQSPSSLSASVGDRVTITCRASQSIYRYLRWYQQKPGKAPKLLIYKASSLQSGVP
SRFSGSGSGTDFTLTISSLQPEDFATYYCQQYVGYPRTFGQGTKVEIKR dAb34
DIQMTQSPSSLSASVGDRVTITCRASQSILKYLKWYQQKPGKAPKLLIYNASHLQSGVP
SRFSGSGSGTDFTLTISSLQPEDFATYYCQQTTYYPITFGQGTKVEIKR dAb53
DIQMTQSPSSLSASVGDRVTITCRASQSILRYLRWYQQKPGKAPKLLIYKASWLQSGVP
SRFSGSGSGTDFTLTISSLQPEDFATYYCQQVLYYPQTFGQGTKVEIKR dAb11
DIQMTQSPSSLSASVGDRVTITCRASQSILRSLKWYQQKPGKAPKLLIYAASRLQSGVP
SRFSGSGSGTDFTLTISSLQPEDFATYYCQQVVYWPATFGQGTKVEIKR dAb12
DIQMTQSPSSLSASVGDRVTITCRASQSIFRHLKWYQQKPGKAPKLLIYAASRLQSGVP
SRFSGSGSGTDFTLTISSLQPEDFATYYCQQVALYPKTFGQGTKVEIKR dAb17
DIQMTQSPSSLSASVGDRVTITCRASQSIRKYLRWYQQKPGKAPKLLIYTASSLQSGVP
SRFSGSGSGTDFTLTISSLQPEDFATYYCQQNLFWPRTFGQGTKVEIKR dAb18
DIQMTQSPSSLSASVGDRVTITCRASQSIRRYLNWYQQKPGKAPKLLIYAASSLQSGVP
SRFSGSGSGTDFTLTISSLQPEDFATYYCQQMLFYPKTFGQGTKVEIKR dAb16, 21
DIQMTQSPSSLSASVGDRVTITCRASQSIIKHLKWYQQKPGKAPKLLIYGASRLQSGVP
SRFSGSGSGTDFTLTISSLQPEDFATYYCQQGARWPQTFGQGTKVEIKR dAb25, 26
DIQMTQSPSSLSASVGDRVTITCRASQSIYYHLKWYQQKPGKAPKLLIYKASTLQSGVP
SRFSGSGSGTDFTLTISSLQPEDFATYYCQQVRKVPRTFGQGTKVEIKR
```

FIG. 51A
*CONTINUE-10*

```
dAb27
DIQMTQSPSSLSASVGDRVTITCRASQSIYKHLKWYQQKPGKAPKLLIYNASHLQSGVP
SRFSGSGSGTDFTLTISSLQPEDFATYYCQQVGRYPKTFGQGTKVEIKR dAb55
DIQMTQSPSSLSASVGDRVTITCRASQSIFKSLKWYQQKPGKAPKLLIYNASYLQSGVP
SRFSGSGSGTDFTLTISSLQPEDFATYYCQQVVYWPVTFGQGTKVEIKR dAb 8, 10
EVQLLESGGGLVQPGGSLRLSCAASGFTFWVYQMDWVRQAPGKGLEWVSSISAFGAKTL
YADSVKGRFTISRDNSKNTLYLQMNSLRAEDTAVYYCAKLSGKFDYWGQGTLVTVSS dAb 36
EVQLLESGGGLVQPGGSLRLSCAASGFTFWSYQMTWVRQAPGKGLEWVSSISSFGSSTL
YADSVKGRFTISRDNSKNTLYLQMNSLRAEDTAVYYCAKGRDHNYSLFDYWGQGTLVTVSS
```

*FIG. 51A*
*CONTINUE-11*

\>DOM7h-1
GACATCCAGA TGACCCAGTC TCCATCCTCC CTGTCTGCAT CTGTAGGAGA CCGTGTCACC
ATCACTTGCC GGGCAAGTCA GAGCATTAGC AGCTATTTAA ATTGGTACCA GCAGAAACCA
GGGAAAGCCC CTAAGCTCCT GATCTATCGG AATTCCTTTT TGCAAAGTGG GGTCCCATCA
CGTTTCAGTG GCAGTGGATC TGGGACAGAT TCACTCTCA CCATCAGCAG TCTGCAACCC
GAAGATTTTG CTACGTACTA CTGTCAACAG ACGTATACTG TTCCTCCTAC GTTTGGCCAA
GGGACCAAGG TGGAAATCAA ACAG

\>DOM7h-10
GACATCCAGA TGACCCAGTC TCCACCCTCC CTGTCCGCAT CTGTAGGAGA CCGTGTCACC
ATCACTTGCC GGGCAAGTCA GAGCATTAGC AGCTATTTAA ATTGGTATCA GCAGAAACCA
GGGAAAGCCC CTAAGCTCCT GATCTATCGG AATTCCCCTT TGCAAAGTGG GGTCCCATCA
CGGTTCAGTG GCAGTGGATC TGGGACAGAT TCACTCTCA CCATCAGCAG TCTGCAACCT
GAAGATTTTG CTACGTACTA CTGTCAACAG ACTTATTCGA TTCCTCCTAC GTTCGGCCAA
GGGACCAAGG TGGAAATCAA ACGG

\>DOM7h-11
GACATCCAGA TGACCCAGTC TCCATCCTCC CTGTCTGCAT CTGTAGGAGA CCGTGTCACC
ATCACTTGCC GGGCAAGTCG TCCGATTGGG ACGACGTTAA GTTGGTACCA GCAGAAACCA
GGGAAAGCCC CTAAGCTCCT GATCTGGTTT GGTTCCCGGT TGCAAAGTGG GGTCCCATCA
CGTTTCAGTG GCAGTGGATC TGGGACAGAT TCACTCTCA CCATCAGCAG TCTGCAACCT
GAAGATTTTG CTACGTACTA CTGTGCGCAG GCTGGACGC ATCCTACGAC GTTCGGCCAA
GGGACCAAGG TGGAAATCAA ACGG

*FIG. 51B*

>DOM7h-12
GACATCCAGA TGACCCAGTC TCCATCCTCC CTGTCTGCAT CTGTAGGAGA CCGTGTCACC
ATCACTTGCC GGGCAAGTAA GTATATTGGT TCGCAGTTAA ATTGGTACCA GCAGAAACCA
GGGAAAGCCC CTAAGCTCCT GATCGCTTGG GCGTCCGTTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCGTCAG GGTGCTGCGT CGCCTCGGAC GTTCGGCCAA
GGGACCAAGG TGGAAATCAA ACGG

>DOM7h-13
GACATTCAGA TGACCCAGTC TCCATCCTCC CTGTCTGCAT CTGTAGGAGA CCGTGTCACC
ATCACTTGCC GGGCAAGTCA GTTTATTTAT CGGTATTTAT CGTGGTATCA GCAGAAACCA
GGGAAAGTCC CTAAGCTCCT GATCTATAAT GCGTCCTATT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CATGCTCATT TGCCTCGTAC GTTCGGCCAA
GGGACCAAGG TGGAAATCAA ACGG

>DOM7h-14
GACATCCAGA TGACCCAGTC TCCATCCTCC CTGTCTGCAT CTGTAGGAGA CCGTGTCACC
ATCACTTGCC GGGCAAGTCA GTGGATTGGG TCTCAGTTAT CTTGGTACCA GCAGAAACCA
GGGAAAGCCC CTAAGCTCCT GATCATGTGG CGTTCCTCGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTGCTCAG GGTGCGGCGT TGCCTAGGAC GTTCGGCCAA
GGGACCAAGG TGGAAATCAA ACGG

>DOM7h-2
GACATCCAGA TGACCCAGTC TCCATCCTCC CTGTCTGCAT CTGTAGGAGA CCGTGTCACC
ATCACTTGCC GGGCAAGTCA GAAGATTGCT ACTTATTTAA ATTGGTATCA GCAGAAACCA
GGGAAAGCCC CTAAGCTCCT GATCTATAGG TCTTCCTCTT TGCAAAGCGC GGTCCCATCA
CGTTTCAGTG GCAGTGGATC TGGGACAGTT TTCACACTCA CCATCAGCAG TCTGCAACCT
GAAGATTTTG CTACGTACTA CTGTCAACAG ACGTATGCTG TTCCTCCTAC GTTCGGCCAA
GGGACCAAGG TGGAAATCAA ACGG

*FIG. 51B*
*CONTINUE-1*

```
>DOM7h-3
GACATCCAGA TGACCCAGTC TCCATCCTCC CTGTCTGCAT CTGTAGGAGA CCGTGTCACC
ATCACTTGCC GGGCAAGTCA GTGGATTGAT ACTGGGTTAG CGTGGTACCA GCAGAAACCA
GGGAAAGCCC CTAGGCTCCT GATCTATAAT GTGTCCAGGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG TATTGGGTA GTCCTACGAC GTTCGGCCAA
GGGACCAAGG TGGAAATCAA ACGG

>DOM7h-4
GACATCCAGA TGACCCAGTC TCCATCCTCC CTGTCTGCAT CTGTAGGAGA CCGTGTCACC
ATCACTTGCC GGGCAAGTCA GGAGATTTAT TCGTGGTTAG CGTGGTACCA GCAGAGACCA
GGGAAAGCCC CTAAGCTCCT GATCTATAAT GCTTCCCATT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GTGATTGGTG ATCCTGTTAC GTTCGGCCAA
GGGACCAAGG TGGAAATCAA ACGG

>DOM7h-6
GACATCCAGA TGACCCAGTC TCCATCCTCC CTGTCTGCAT CTGTAGGAGA CCGTGTCACC
ATCACTTGCC GGGCAAGTCA GAGCATTAGC AGCTATTTAA ATTGGTACCA GCAGAAACCA
GGGAAAGCCC CTACGCTCCT GATCTATCGG TTGTCCGTGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG ACTTATAATG TTCCTCCTAC GTTCGGCCAA
GGGACCAAGG TGCAAATCAA ACGG

>DOM7h-7
GACATCCAGA TGACCCAGTC TCCATCCTCC CTGTCTGCAT CTGTAGGAGA CCGTGTCACC
ATCACTTGCC GGGCAAGTCA GAGCATTAGC AGCTATCTAA ATTGGTACCA GCAGAAACCA
GGGAAAGCCC CTAAGCTCCT GATCTATAGG AATTCCCAGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG ACTTTTGCGG TTCCTCCTAC GTTCGGCCAA
GGGACCAAGG TGGAGATCAA ACGG

>DOM7h-8
GACATCCAGA TGACCCAGTC TCCATCCTCC CTGTCTGCAT CTGTAGGAGA CCGTGTCACC
ATCACTTGCC GGGCAAGTCA GAGCATTAGC AGCTATTTAA ATTGGTATCA GCAGAAACCA
GGGAAAGCCC CTAAGCTCCT GATCTATCGG AATTCCCCTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG ACGTATAGGG TGCCTCCTAC GTTCGGCCAA
GGGACCAAGG TGGAAATCAA ACGG
```

*FIG. 51B*
*CONTINUE-2*

>DOM7h-9
GACATCCAGA TGACCCAGTC TCCATCCTCC CTGTCTGCAT CTGTAGGAGA CCGTGTCACC
ATCACTTGCC GGGCAAGTCA GCATATTGGG TTGTGGTTAC ATTGGTATCA GCAGAAACCA
GGGAAAGCCC CTAAGCTCCT GATCTATAGG TCTTCCTTGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG AAGTATAATT TGCCTTATAC GTCCGGCCAA
GGGACCAAGG TGGAAATCAA ACGG

>DOM7m-12
GACATCCAGA TGACCCAGTC TCCATCCTCC CTGTCTGCAT CTGTAGGAGA CCGTGTCACC
ATCACTTGCC GGGCAAGTCA GAGCATTTTT CGGCATTTAA AGTGGTACCA GCAGAAACCA
GGGAAAGCCC CTAAGCTCCT GATCTATGCG GCATCCCGTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GTTGCGCTGT ATCCTAAGAC GTTCGGCCAA
GGGACCAAGG TGGAAATCAA ACGG

>DOM7m-16
GACATCCAGA TGACCCAGTC TCCATCCTCC CTGTCTGCAT CTGTAGGAGA CCGTGTCACC
ATCACTTGCC GGGCAAGTCA GAGCATTATT AAGCATTTAA AGTGGTACCA GCAGAAACCA
GGGAAAGCCC CTAAGCTCCT GATCTATGGT GCATCCCGGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GGGGCTCGGT GCCCTCAGAC GTTCGGCCAA
GGGACCAAGG TGGAAATCAA ACGG

>DOM7m-26
GACATCCAGA TGACCCAGTC TCCATCCTCC CTGTCTGCAT CTGTAGGAGA CCGTGTCACC
ATCACTTGCC GGGCAAGTCA GAGCATTTAT TATCATTTAA AGTGGTACCA GCAGAAACCA
GGGAAAGCCC CTAAGCTCCT GATCTATAAG GCATCCACGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG GTTCGGAAGG TGCCTCGGAC GTTCGGCCAA
GGGACCAAGG TGGAAATCAA ACGG

>DOM7r-1
GACATCCAGA CGACCCAGTC TCCATCCTCC CTGTCTGCAT CTGTAGGAGA CCGTGTCACC
ATCACTTGCC GGGCAAGTCA GTATATTGGT AGGTATTTAC GTTGGTATCA GCAGAAACCA
GGGAAAGCCC CTAAGCTCCT GATCTATGAT TCTTCCGTGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CGTTATCGTA TGCCTTATAC GTTCGGCCAA
GGGACCAGGG TAGAAATCAA ACGG

*FIG. 51B*
*CONTINUE-3*

```
>DOM7r-13
GACATCCAGA TGACCCAGTC TCCATCCTCC CTGTCTGCAT CTGTAGGAGA CCGTGTCACC
ATCACTTGCC GGGCAAGTCA GCATATTCAT AGGGAGTTAA GGTGGTATCA GCAGAAACCA
GGGAAAGCCC CTAAGCTCCT GATCTATCAG GCGTCCCGTT TGCAAAGTGG GGTCCCATCA
CGTTTCAGTG GCAGTGGATC TGGACAGAT TTCACTCTCA CCATCAGCAG TCTGCAACCT
GAAGATTTTG CTACGTACTA CTGTCAACAG AAGTATCTGC CTCCTTATAC GTTCGGCCAA
GGGACCAAGG TGGAAATCAA ACGG

>DOM7r-14
GACATCCAGA TGACCCAGTC TCCATCCTCC CTGTCTGCAT CTGTAGGAGA CCGTGTCACC
ATCACTTGCC GGGCAAGTCA GCATATTCAT AGGGAGTTAA GGTGGTATCA GCAGAAACCA
GGGAAAGCCC CTAAGCTCCT GATCTATCAG GCGTCCCGTT TGCAAAGTGG GGTCCCATCA
CGTTTCAGTG GCAGTGGATC TGGACAGAT TTCACTCTCA CCATCAGCAG TCTGCAACCT
GAAGATTTTG CTACGTACTA CTGTCAACAG CGTTATAGGG TGCCTTATAC GTTCGGCCAA
GGGACCAAGG TGGAAATCAA ACGG

>DOM7r-15
GACATCCAGA TGACCCAGTC TCCATCCTCC CTGTCTGCAT CTGTAGGAGA CCGTGTCACC
ATCACTTGCC GGGCAAGTCA GAGTATTGGG CGGAGGTTAA AGTGGTACCA GCAGAAACCA
GGGGCAGCCC CTAGGCTCCT GATCTATCGT ACGTCCTGGT TGCAAAGTGG GGTCCCATCA
CGTTTCAGTG GCAGTGGATC TGGACAGAT TTCACTCTCA CCATCAGCAG TCTGCAACCT
GAAGATTTTG CTACGTACTA CTGTCAACAG ACGTCGCAGT GGCCTCATAC GTTCGGCCAA
GGGACCAAGG TGGAAATCAA ACGG

>DOM7r-16
GACATCCAGA TGACCCAGTC TCCATCCTCC CTGTCTGCAT CTGTAGGAGA CCGTGTCACC
ATCACTTGCC GGGCAAGTCA GAAGATTTAT AAGAATTTAC GTTGGTATCA GCAGAAACCA
GGGAAAGCCC CTAAGCTCCT GATCTATAAT TCTTCCATTT TGCAAAGTGG GGTCCCATCA
CGTTTCAGTG GCAGTGGATC TGGACAGAT TTCACTCTCA CCATCAGCAG TCTGCAACCT
GAAGATTTTG CTACGTACTA CTGTCAACAG AGGTATCTGT CGCCTTATAC GTTCGGCCAA
GGGACCAAGG TGGAAATCAA ACGG
```

*FIG. 51B*
*CONTINUE-4*

```
>DOM7r-17
GACATCCAGA TGACCCAGTC TCCATCCTCC CTGTCTGCAT CTGTAGGAGA CCGTGTCACC
ATCACTTGCC GGGCAAGTCA GAAGATTTAT AATAATTTAA GGTGGTACCA GCAGAAACCA
GGGAAAGCCC CTAAGCTCCT GATCTATAAT ACTTCCATTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CGATGGCGTG CGCCTTATAC GTTCGGCCAA
GGGACCAAGG TGGAAATCAA ACGG

>DOM7r-18
GACATTCAGA TGACCCAGTC TCCATCCTCC CTGTCTGCAT CTGTAGGAGA CCGTGTCACC
ATCACTTGCC GGGCAAGTCA GTGGATTTAT AAGTCGTTAG GGTGGTACCA GCAGAAACCA
GGGAAAGCCC CTAAGCTCCT GATCTATCAG TCTTCTTTGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG TATCATCAGA TGCCTCGGAC GTTCGGCCAA
GGGACCAAGG TGGAAATCAA ACGG

>DOM7r-19
GACATCCAGA TGACCCAGTC TCCATCCTCC CTATCTGCAT CTGTAGGAGA CCGTGTCACC
ATCACTTGCC GGGCAAGTCA GTGGATTTAT AGGCATTTAA GGTGGTACCA GCAGAAACCA
GGGAAAGCCC CTAAGCTCCT GATCTATGAT GCGTCCAGGT TGCAAAGTGG GGTCCCAACA
CGTTTCAGTG GCAGTGGATC TGGGACAGAT TTCACTCTCA CCATCAGCAG TCTGCAACCT
GAAGATTTTG CTACGTACTA CTGTCAACAG ACTCATAATC CTCCTAAGAC GTTCGGCCAA
GGGACCAAGG TGGAAATCAA ACGG
```

*FIG. 51B*
*CONTINUE-5*

```
>DOM7r-3
GACATCCAGA TGACCCAGTC TCCATCCTCC CTGTCTGCAT CTGTAGGAGA CCGTGTCACC
ATCACTTGCC GGGCAAGTCA GTATATTGGT AGGTATTTAC GTTGGTATCA GCAGAAACCA
GGGAAAGCCC CTAAGCTCCT GATCTATGAT TCTTCCGTGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG AGGTATATGC AGCCTTTTAC GTTCGGCCAA
GGGACCAAGG TGGAAATCAA ACGG

>DOM7r-4
GACATCCAGA TGACCCAGTC TCCATCCTCC CTGTCCGCAT CTGTAGGAGA CCGTGTCACC
ATCACTTGCC GGGCAAGTCA GTGGATTGGT CGGTATTTAC GGTGGTACCA GCAGAAACCA
GGGAAAGCCC CTAAGCTCCT GATCTATAAT GGGTCCCAGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CGGTATCTTC AGCCTTATAC GTTCGGCCAA
GGGACCAAGG TGGAAATCAA ACGG

>DOM7r-7
GACATCCAGA TGACCCAGTC TCCATCCTCC CTGTCTGCAT CTGTAGGAGA CCGTGTCACC
ATCACTTGCC GGGCAAGTCA GTATATTGGT AGGTATTTAC GTTGGTATCA GCAGAAACCA
GGGAAAGCCC CTAAGCTCCT GATCTATGAT TCTTCCGTGT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG CGTTATTCTT CGCCTTATAC GTTCGGCCAA
GGGACCAAGG TGGAAATCAA GCGG

>DOM7r-5
GACATCCAGA TGACCCAGTC TCCATCCTCC CTGTCTGCAT CTGTAGGAGA CCGTGTCACC
ATCACTTGCC GGGCAAGTCA GTATATTTCG CGTCAGTTAA GGTGGTACCA GCAGAAACCA
GGGAAAGCCC CTAGGCTCCT GATCTATGGG GCGTCCGTTT TGCAAAGCGG GATCCCATCA
CGTTTCAGTG GCAGTGGATC TGGGACAGAT TTCACTCTCA CCATCAGCAG TCTGCAACCT
GAAGATTTTG CTACGTACTA CTGTCAACAG AGGTATATTA CTCCTTATAC GTTCGGCCAA
GGGACCAAGG TGGAAGTCAA ACGG

>DOM7r-8
GACATCCAGA TGACCCAGTC TCCATCCTCC CTGTCTGCAT CTGTAGGAGA CCGTGTCACC
ATCACTTGCC GGGCAAGTCA GTGGATTCAT AGGCAGTTAA AGTGGTACCA GCAGAAACCA
GGGAAAGCCC CTAAGCTCCT GATCTATTAT GCTTCCATTT TGCAAAGTGG GGTCCCATCA
CGTTTCAGTG GCAGTGGATC TGGGACAGAT TTCACTCTCA CCATCAGCAG TCTGCAACCT
GAAGATTTTG CTACGTACTA CTGTCAACAG ACGTTTCTA AGCCTTCTAC GTTCGGCCAA
GGGACCAAGG TGGAAATCAA ACGG
```

FIG. 51B
CONTINUE-6

```
>DOM7h-23
GAGGTGCAGC TGTTGGAGTC TGGGGGAGGC TTGGTACAGC CTGGGGGGTC CCTGCGTCTC
TCCTGTGCAG CCTCCGGATT CACCTTTTAT GATTATAATA TGTCTTGGGT CCGCCAGGCT
CCAGGGAAGG GTCTAGAGTG GGTCTCAACT ATTACGCATA CGGGTGGGGT TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAACAGAAT
CCTTCTTATC AGTTTGACTA CTGGGGTCAG GGAACCCTGG TCACCGTCTC GAGC

>DOM7h-21
GAGGTGCAGC TGTTGGAGTC TGGGGGAGGC TTGGTACAGC CTGGGGGGTC CCTGCGTCTC
TCCTGTGCAG CCTCCGGATT CACCTTTGAT CTTTATGATA TGTCGTGGGT CCGCCAGGCT
CCAGGGAAGG GTCTAGAGTG GGTCTCATCG ATTGTTAATT CGGGTGTTAG GACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAACTTAAT
CAGAGTTATC ATTGGGATTT TGACTACTGG GGTCAGGGAA CCCTGGTCAC CGTCTCGAGC

>DOM7h-22
GAGGTGCAGC TGTTGGAGTC TGGGGGAGGC TTGGTACAGC CTGGGGGGTC CCTGCGTCTC
TCCTGTGCAG CCTCCGGATT CACCTTTTCG AAGTATTGGA TGTCGTGGGT CCGCCAGGCT
CCAGGGAAGG GTCTAGAGTG GGTCTCATCT ATTGATTTTA TGGGTCCGCA TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAAGGGAGG
ACGTCGATGT TGCCGATGAA GGGGAAGTTT GACTACTGGG GTCAGGGAAC CCTGGTCACC
GTCTCGAGC

>DOM7h-24
GAGGTGCAGC TGTTGGAGTC TGGGGGAGGC TTGGTACAGC CTGGGGGGTC CCTGCGTCTC
TCCTGTGCAG CCTCCGGATT CACCTTTCAT CGTTATTCGA TGTCTTGGGT CCGCCAGGCT
CCAGGGAAGG GTCTAGAGTG GGTCTCAACG ATTTTGCCTG GTGGTGATGT TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAACAGACG
CCTGATTATA TGTTTGACTA CTGGGGTCAG GGAACCCTGG TCACCGTCTC GAGC
```

*FIG. 51B*
*CONTINUE-7*

```
>DOM7h-25
GAGGTGCAGC TGTTGGAGTC TGGGGGAGGC TTGGTACAGC CTGGGGGGTC CCTGCGTCTC
TCCTGTGCAG CCTCCGGATT CACCTTTTGG AAGTATAATA TGGCGTGGGT CCGCCAGGCT
CCAGGGAAGG GTCTAGAGTG GGTCTCAACT ATTCTTGGTG AGGGTAATAA TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAAACGATG
GATTATAAGT TTGACTACTG GGGTCAGGGA ACCCTGGTCA CCGTCTCGAG C

>DOM7h-26
GAGGTGCAGC TGTTGGAGTC TGGGGGAGGC TTGGTACAGC CTGGGGGGTC CCTGCGTCTC
TCCTGTACAG CCTCCGGATT CACCTTTGAT GAGTATAATA TGTCTTGGGT CCGCCAGGCT
CCAGGGAAGG GTCTAGAGTG GGTCTCAACG ATTCTGCCGC ATGGTGATCG GACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAACAGGAT
CCTTTGTATA GGTTTGACTA CTGGGGTCAG GGAACCCTGG TCACCGTCTC GAGC

>DOM7h-27
GAGGTGCAGC TGTTGGAGTC TGGGGGAGGC TTGGTACAGC CTGGGGGGTC CCTGCGTCTC
TCCTGTGCAG CCTCCGGATT CACCTTTTCG GATTATCGGA TGAGTTGGGT CCGCCAGGCT
CCAGGGAAGG GTCTAGAGTG GGTCTCAACG ATTATTTCGA ATGGTAAGTT TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAACAGGAT
TGGATGTATA TGTTTGACTA CTGGGGTCAG GGAACCCTGG TCACCGTCTC GAGC

>DOM7h-30
GAGGTGCAGC TGTTGGAGTC TGGGGGAGGC TTGGTACAGC CTGGGGGGTC CCTGCGTCTC
TCCTGTGCAG CCTCCGGATT CACCTTTCGG ACGTATACTA TGGCTTGGGT CCGCCAGGCC
CCAGGGAAGG GTCTAGAGTG GGTCTCATCG ATTACTAGTA GTGGTTCTTC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAAGTGAAT
TCTTTGTATA AGTTTGACTA CTGGGGTCAG GGAACCCTGG TCACCGTCTC GAGC

>DOM7h-31
GAGGTGCAGC TGTTGGAGTC TGGGGGAGGC TTGGTACAGC CTGGGGGGTC CCTGCGTCTC
TCCTGTGCAG CCTCCGGATT CACCTTTCGG CCGACTAATA TGTCGTGGGT CCGCCAGGCT
CCAGGGAAGG GTCTAGAGTG GGTCTCAACT ATTACTGGTA CTGGTGCTGC GACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAACAGAAT
TCTCGTTATA GGTTTGACTA CTGGGGTCAG GGAACCCTGG TCACCGTCTC GAGCG
```

*FIG. 51B*
*CONTINUE-8*

```
>DOM7r-20
GAGGTGCAGC TGTTGGAGTC TGGGGGAGGC TTGGTACAGC CTGGGGGGTC CCTGCGTCTC
TCCTGTGCAG CCTCCGGATT CACCTTTTGG CCGTATACGA TGAGTTGGGT CCGCCAGGCT
CCAGGGAAGG GTCTAGAGTG GGTCTCAACG ATTTCGCCGT TTGGTTCGAC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAGGGGGG
AAGGATTTTG ACTACTGGGG TCAGGGAACC CTGGTCACCG TCTCGAGCG

>DOM7r-27
GAGGTGCAGC TGTTGGAGTC TGGGGGAGGC TTGGTACAGC CTGGGGGGTC CCTGCGTCTC
TCCTGTGCAG CCTCCGGATT CACCTTTTGG CCGTATACGA TGAGTTGGGT CCGCCAGGCT
CCAGGGAAGG GTCTAGAGTG GGTCTCAACG ATTTCGCCGT TTGGTTCGAC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAAGTGAT
GTTCTTAAGA CGGGTCTGGA TGGTTTTGAC TACTGGGGTC AGGGAACCCT GGTCACCGTC
TCGAGCG

>DOM7r-28
GAGGTGCAGC TGTTGGAGTC TGGGGGAGGC TTGGTACAGC CTGGGGGGTC CCTGCGTCTC
TCCTGTGCAG CCTCCGGATT CACCTTTATG GCGTATCAGA TGGCTTGGGT CCGCCAGGCT
CCAGGGAAGG GTCTAGAGTG GGTCTCAACT ATTCATCAGA CGGGTTTTTC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAAGTGCGT
TCTATGCGTC CTTATAAGTT TGACTACTGG GGTCAGGGAA CCCTGGTCAC CGTCTCGAGC
G

>DOM7r-21
GAGGTGCAGC TGTTGGAGTC TGGGGGAGGC TTGGTACAGC CTGGGGGGTC CCTGCGTCTC
TCCTGTGCAG CCTCCGGATT CACCTTTTGG CCGTATACGA TGAGTTGGGT CCGCCAGGCT
CCAGGGAAGG GTCTAGAGTG GGTCTCAACG ATTTCGCCGT TTGGTTCGAC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAGGTAAT
CTTGAGCCGT TTGACTACTG GGGTCAGGGA ACCTGGTCA CCGTCTCGAG CG

>DOM7r-25
GAGGTGCAGC TGTTGGAGTC TGGGGGAGGC TTGGTACAGC CTGGGGGGTC CCTGCGTCTC
TCCTGTGCAG CCTCCGGATT CACCTTTTGG CCGTATACGA TGAGTTGGGT CCGCCAGGCT
CCAGGGAAGG GTCTAGAGTG GGTCTCAACG ATTTCGCCGT TTGGTTCGAC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAAGACG
GGTCCGTCGT CGTTTGACTA CTGGGGTCAG GGAACCCTGG TCACCGTCTC GAGCG
```

*FIG. 51B*
*CONTINUE-9*

```
>DOM7r-22
GAGGTGCAGC TGTTGGAGTC TGGGGGAGGT TTGGTACAGC CTGGGGGGTC CCTGCGTCTC
TCCTGTGCAG CCTCCGGATT CACCTTTTGG CCGTATACGA TGAGTTGGGT CCGCCAGGCT
CCAGGGAAGG GTCTAGAGTG GGTCTCAACG ATTTCGCCGT TGGTTCGAC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAT ACCGCGGTAT ATTACTGTGC GAAAAAGCTT
AGTAATGGTT TTGACTACTG GGGTCAGGGA ACCCTGGTCA CCGTCTCGAG CG

>DOM7r-23
GAGGTGCAGC TGTTGGAGTC TGGGGGAGGC TTGGTACAGC CTGGGGGGTC CCTGCGTCTC
TCCTGTGCAG CCTCCGGATT CACCTTTTGG CCGTATACGA TGAGTTGGGT CCGCCAGGCT
CCAGGGAAGG GTCTAGAGTG GGTCTCAACG ATTTCGCCGT TGGTTCGAC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAGTGGTT
AAGGATAATA CGTTTGACTA CTGGGGTCAG GGAACCCTGG TCACCGTCTC GAGCG

>DOM7r-24
GAGGTGCAGC TGTTGGAGTC TGGGGGAGGC TTGGTACAGC CTGGGGGGTC CCTGCGTCTC
TCCTGTGCAG CCTCCGGATT CACCTTTTGG CCGTATACGA TGAGTTGGGT CCGCCAGGCT
CCAGGGAAGG GTCTAGAGTG GGTCTCAACG ATTTCGCCGT TGGTTCGAC TACATACTAC
GCAGACTCCG TGAAGGGCCG GTTCACCATT TCCCGCGACA ATTCCAAGAA CACGCTGTAT
CTGCAAATGA ACAGCCTGCG TGCCGAGGAC ACCGCGGTAT ATTACTGTGC GAAAAATACT
GGGGGTAAGC AGTTTGACTA CTGGGGTCAG GGAACCCTGG TCACCGTCTC GAGCG

>DOM7r-26
GAGGTGCAGC TGTTGGAGTC TGGGGGAGGC TTGGTACAGC CTGGGGGGTC CCTGCGTCTC
TCCTGTGCAG CCTCCGGATT CACCTTTTGG CCGTATACGA TGAGTTGGGT CCGCCAGGCT
CCAGGGAAGG GTCTAGAGTG GGTCTCAACG ATTTCGCCGT TGGTTCGAC TACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAAGGACT
GAGAATAGGG GGGTTTCTTT TGACTACTGG GGTCAGGGAA CCCTGGTCAC CGTCTCGAGC
G

>DOM7r-29
GAGGTGCAGC TGTTGGAGTC TGGGGGAGGC TTGGTACAGC CTGGGGGGTC CCTGCGTCTC
TCCTGTGCAG CCTCCGGATT CACCTTTAAG GATTATGATA TGACTTGGGT CCGCCAGGCT

CCAGGGAAGG GTCTAGAGTG GGTCTCAATG ATTTCTTCGT CGGGTCTTTG GACATACTAC
GCAGACTCCG TGAAGGGCCG GTTCACCATC TCCCGCGACA ATTCCAAGAA CACGCTGTAT
CTGCAAATGA ACAGCCTGCG TGCCGAGGAC ACCGCGGTAT ATTACTGTGC GAAAGGTTTT
AGGCTGTTTC CTCGGACTTT TGACTACTGG GGTCAGGGAA CCCTGGTCAC CGTCTCGAGC
G
```

*FIG. 51B*
*CONTINUE-10*

Dom 15-26-593-FC fusion
EVQLLVSGGGLVQPGGSLRLSCAASGFTFKAYPMWVRQAPGKGLEWVSEISPSGSY
TYYADSVKGRFTISRDNSKNTLYLQMNSLRAEDTAVYYCAKDPSKLDTNSQSILVTV
SSASTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPG
K

FIG. 52A

Human IgG1 Fc
THTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK

FIG. 52B

Dom 15-26-593-FC fusion
GAGGTGCAGCTGTTGGTGTCTGGGGGAGGCTTGGTACAGCCTGGGGGTCCCTGCGT
CTCTCCTGTGCAGCCTCCGGATTCACCTTTAAGGCTTATCCGATGATGTGGGTCCGC
CAGGCTCCAGGGAAGGGTCTAGAGTGGGTTCAGAGATTTCGCCTTCGGGCTCCATAT
ACATATTACGCAGACTCCGTGAAGGGCCGGTTCACCATCTCCCGCGACAATTCCAAG
AACACGCTGTATCTGCAAATGAACAGCCTGCGTGCCGAGGACACCGCGGTATATTAC
TGTGCGAAAGATCCTAGCAAGTTAGACACTAACAGCCAGAGCATCCTCGTCACCGTC
TCGAGTGCTAGCACCCACACCTGCCCCCCTGCCCTGCCCCCGGAGCTGCTGGGCGGA
CCTAGCGTGTTCCTGTTCCCCCCAAGCCTAAGGACACCCTGATGATCAGCAGGACC
CCCGAAGTGACCTGCGTGGTGGTGGATGTGAGCCACGAGGACCCTGAAGTGAAGTTC
AACTGGTACGTGGACGGCGTGGAAGTGCACAACGCCAAGACCAAGCCCAGAGAGGAG
CAGTACAACAGTACCTACCGCGTGGTCTCTGTCCTGACCGTGCTGCACCAGGATTGG
CTGAACGGCAAGGAGTACAAGTGCAAAGTGAGCAACAAGGCCCTGCCTGCCCCTATC
GAGAAAACCATCAGCAAGGCCAAGGGCCAGCCTAGAGAGCCCCAGGTCTACACCCTG
CCTCCCTCCAGAGATGAGCTGACCAAGAACCAGGTGTCCCTGACCTGTCTGGTGAAG
GGCTTCTACCCAAGCGACATCGCCGTGGAGTGGGAGAGCAACGGCCAGCCCGAGAAC
AACTACAAGACCACCCCCCCTGTGCTGGACAGCGATGGCAGCTTCTTCCTGTACTCC
AAGCTGACCGTGGACAAGAGCAGATGGCAGCAGGGCAACGTGTTCAGCTGCAGCGTG
ATGCACGAGGCCCTGCACAATCACTACACCCAGAAGAGTCTGAGCCTCTCCCCTGGC
AAG

Codon Optimised Sequence 1

DNA Sequence

Gaggttcaattgttggaatccggtggtggattggttcaacctggtggttcttttgagattgtcctgtgctgcttccgg
ttttactttcgctcacgagactatggtttgggttagacaggctccaggtaaaggattggaatgggtttcccacattc
caccagatggtcaagatccattctacgctgactccgttaagggaagattcactatctccagagacaactccaagaac
actttgtacttgcagatgaactccttgagagctgaggatactgctgtttaccactgtgctttgttgccaaagagagg
accttggtttgattactggggacagggaactttggttactgtttcttcc (SEQ ID NO: 223)

Corresponding AA Sequence

Evqllesggglvqpggslrlscaasgftfahetmvwvrqapgkglewvshippdgqdpfyadsvkgrftisrdnskn
tlylqmnslraedtavyhcallpkrgpwfdywgqgtlvtvss (SEQ ID NO: 224)

- 74.1% nucleotide sequence identity to WT sequence (nucleic acid sequences shown below correspond to SEQ ID NO:s 225-228)

```
                                          1                                                50
Dom1h-131-206 Codon Optimised       (1)   GAGGTTCAATTGTTGGAATCCGGTGGTGGATTGGTTCAACCTGGTGGTTC
         Dom1h-131-206 WT           (1)   GAGGTGCAGCTGTTGGAGTCTGGGGGAGGCTTGGTACAGCCTGGGGGGTC
                      Consensus     (1)   GAGGT CA  TGTTGGA TC GG GG GG TTGGT CA CCTGG GG TC
                                          51                                               100
Dom1h-131-206 Codon Optimised      (51)   TTTGAGATTGTCCTGTGCTGCTTCCGGTTTTACTTTCGCTCACGAGACTA
         Dom1h-131-206 WT          (51)   CCTGCGTCTCTCCTGTGCAGCCTCCGGATTCACCTTTGCGCATGAGACGA
                      Consensus    (51)      TG G  T TCCTGTGC GC TCCGG TT AC TT GC CA GAGAC A
                                          101                                              150
Dom1h-131-206 Codon Optimised     (101)   TGGTTTGGGTTAGACAGGCTCCAGGTAAAGGATTGGAATGGGTTTCCCAC
         Dom1h-131-206 WT         (101)   TGGTGTGGGTCCGCCAGGCACCAGGGAAGGGTCTAGAGTGGGTCTCACAT
                      Consensus   (101)   TGGT TGGGT  G CAGGC CCAGG AA GG   T GA TGGGT TC CA
                                          151                                              200
Dom1h-131-206 Codon Optimised     (151)   ATTCCACCAGATGGTCAAGATCCATTCTACGCTGACTCCGTTAAGGGAAG
         Dom1h-131-206 WT         (151)   ATTCCCCCGGATGGTCAGGATCCCTTCTACGCAGACTCCGTGAAGGGCCG
                      Consensus   (151)   ATTCC CC GATGGTCA GATCC TTCTACG GACTCCGT AAGGG  G
                                          201                                              250
Dom1h-131-206 Codon Optimised     (201)   ATTCACTATCTCCAGAGACAACTCCAAGAACACTTTGTACTTGCAGATGA
         Dom1h-131-206 WT         (201)   GTTCACCATCTCCCGCGACAATTCCAAGAACACGCTATATCTGCAAATGA
                      Consensus   (201)    TTCAC ATCTCC G GACAA TCCAAGAACAC   T TA  TGCA ATGA
                                          251                                              300
Dom1h-131-206 Codon Optimised     (251)   ACTCCTTGAGAGCTGAGGATACTGCTGTTTACCACTGTGCTTTGTTGCCA
         Dom1h-131-206 WT         (251)   ACAGCCTGCGTGCCGAGGACACAGCGGTATATCACTGTGCGCTGCTTCCT
                      Consensus   (251)   AC  C TG G GC GAGGA AC GC GT TA CACTGTGC  TG T CC
                                          301                                              350
Dom1h-131-206 Codon Optimised     (301)   AAGAGAGGACCTTGGTTTGATTACTGGGGACAGGGAACTTTGGTTACTGT
         Dom1h-131-206 WT         (301)   AAGAGGGGCCCTTGGTTTGACTACTGGGGTCAGGGAACCCTGGTCACCGT
                      Consensus   (301)   AAGAG GG CCTTGGTTTGA TACTGGGG CAGGGAAC  TGGT AC GT
                                          351          363
Dom1h-131-206 Codon Optimised     (351)   TTCTTCCTAATGA
         Dom1h-131-206 WT         (351)   CTCGAGC------
                      Consensus   (351)    TC  C
```

FIG. 54

Codon Optimised Sequence 2

DNA Sequence

Gagaaaagagaggttcaattgcttgaatctggaggaggtttggtccagccaggagggtcccttcgactaagttgtgc
tgccagtgggtttacgtttgctcatgaaactatggtatgggtccgacaggcacctggtaaaggtcttgaatgggttt
cacatatccctccagacggtcaagacccattttacgctgattccgtgaaaggcagatttacaatttcacgagataat
tctaaaaacaccttgtacttacaaatgaactcattgagagctgaggacactgcagtttatcactgcgctttactacc
aaaacgtggaccttggtttgattattggggccaaggtacgttagtgactgttagttct (SEQ ID NO: 229)

Corresponding AA Sequence

Ekrevqllesggglvqpggslrlscaasgftfahetmvwvrqapgkglewvshippdgqdpfyadsvkgrftisrdn
skntlylqmnslraedtavyhcallpkrgpwfdywgqgtlvtvss (SEQ ID NO: 230)

- 71.1% nucleotide sequence identity to WT sequence (nucleic acid sequences shown below correspond to SEQ ID NO:s 231-233)

```
                              1                                                50
     Dom1h-131-206 WT      (1) ---------GAGGTGCAGCTGTTGGAGTCTGGGGGAGGCTTGGTACAGCC
Pichia MFa 206 DABTM only  (1) GAGAAAAGAGAGGTTCAATTGCTTGAATCTGGAGGAGGTTTGGTCCAGCC
             Consensus    (1)          GAGGT CA  TG T GA TCTGG GGAGG TTGGT CAGCC
                             51                                               100
     Dom1h-131-206 WT     (42) TGGGGGGTCCCTGCGTCTCTCCTGTGCAGCCTCCGGATTCACCTTTGCGC
Pichia MFa 206 DABTM only (51) AGGAGGGTCCCTTCGACTAAGTTGTGCTGCCAGTGGGTTTACGTTTGCTC
             Consensus   (51) GG GGGTCCCT CG CT    TGTGC GCC   GG TT AC TTTGC C
                            101                                               150
     Dom1h-131-206 WT     (92) ATGAGACGATGGTGTGGGTCCGCCAGGCACCAGGGAAGGGTCTAGAGTGG
Pichia MFa 206 DABTM only(101) ATGAAACTATGGTATGGGTCCGACAGGCACCTGGTAAAGGTCTTGAATGG
             Consensus  (101) ATGA AC ATGGT TGGGTCCG CAGGCACC GG AA GGTCT GA TGG
                            151                                               200
     Dom1h-131-206 WT    (142) GTCTCACATATTCCCCCGGATGGTCAGGATCCCTTCTACGCAGACTCCGT
Pichia MFa 206 DABTM only(151) GTTTCACATATCCCTCCAGACGGTCAAGACCCATTTTACGCTGATTCCGT
             Consensus  (151) GT TCACATAT CC CC GA GGTCA GA CC TT TACGC GA TCCGT
                            201                                               250
     Dom1h-131-206 WT    (192) GAAGGGCCGGTTCACCATCTCCCGCGACAATTCCAAGAACACGCTATATC
Pichia MFa 206 DABTM only(201) GAAAGGCAGATTTACAATTTCACGAGATAATTCTAAAAACACCTTGTACT
             Consensus  (201) GAA GGC G TT AC AT TC CG GA AATTC AA AACAC  T TA
                            251                                               300
     Dom1h-131-206 WT    (242) TGCAAATGAACAGCCTGCGTGCCGAGGACACAGCGGTATATCACTGTGCG
Pichia MFa 206 DABTM only(251) TACAAATGAACTCATTGAGAGCTGAGGACACTGCAGTTTATCACTGCGCT
             Consensus  (251) T CAAATGAAC    TG G GC GAGGACAC GC GT TATCACTG GC
                            301                                               350
     Dom1h-131-206 WT    (292) CTGCTTCCTAAGAGGGGGCCTTGGTTTGACTACTGGGGTCAGGGAACCCT
Pichia MFa 206 DABTM only(301) TTACTACCAAAACGTGGACCTTGGTTTGATTATTGGGGCCAAGGTACGTT
             Consensus  (301)  T CT CC AA  G GG CCTTGGTTTGA TA TGGGG CA GG AC  T
                            351       367
     Dom1h-131-206 WT    (342) GGTCACCGTCTCGAGC-
Pichia MFa 206 DABTM only(351) AGTGACTGT-TAGTTCT
             Consensus  (351)  GT AC GT T G  C
```

FIG. 55

Codon Optimised Sequence 3

DNA Sequence

Gaagtgcagcttcttgaaagtggtggagggctagtgcagccaggggatctttaagattatcatgcgctgccagtgg
atttacttttgctcacgagacgatggtctgggtgagacaagctcctggaaaaggtttagagtgggtttctcacattc
cacctgatggtcaagatcctttctacgcagattccgtcaaaggaagatttactatctccagagataatagtaaaaac
actttgtacctacagatgaactcacttagagccgaagataccgctgtgtaccactgcgccttgttgccaaagagagg
tccttggttcgattactggggtcagggtactctggttacagtctcatct (SEQ ID NO: 234)

Corresponding AA Sequence

Evqllesggglvqpggslrlscaasgftfahetmvwvrqapgkglewvshippdgqdpfyadsvkgrftisrdnskn
tlylqmnslraedtavyhcallpkrgpwfdywgqgtlvtvss (SEQ ID NO: 235)

- 72.6% nucleotide sequence identity to WT sequence (nucleic acid sequences shown below correspond to SEQ ID NO:s 236-240)

```
                                 1                                                  50
         Dom1h-131-206 WT    (1) GAGGTGCAGCTGTTGGAGTCTGGGGGAGGCTTGGTACAGCCTGGGGGGTC
Pichia Pre 206 DABTM only    (1) GAAGTGCAGCTTCTTGAAAGTGGTGGAGGGCTAGTGCAGCCAGGGGGATC
               Consensus    (1) GA GTGCAGCT  T GA   TGG GGAGG  T GT CAGCC GGGGG TC
                                 51                                                 100
         Dom1h-131-206 WT   (51) CCTGCGTCTCTCCTGTGCAGCCTCCGGATTCACCTTTGCGCATGAGACGA
Pichia Pre 206 DABTM only   (51) TTTAAGATTATCATGCGCTGCCAGTGGATTTACTTTTGCTCACGAGACGA
               Consensus   (51)     T  G  T TC TG GC GCC   GGATT AC TTTGC CA GAGACGA
                                 101                                                150
         Dom1h-131-206 WT  (101) TGGTGTGGGTCCGCCAGGCACCAGGGAAGGGTCTAGAGTGGGTCTCACAT
Pichia Pre 206 DABTM only  (101) TGGTCTGGGTGAGACAAGCTCCTGGAAAAGGTTTAGAGTGGGTTTCTCAC
               Consensus  (101) TGGT TGGGT  G CA GC CC GG AA GGT TAGAGTGGGT TC CA
                                 151                                                200
         Dom1h-131-206 WT  (151) ATTCCCCCGGATGGTCAGGATCCCTTCTACGCAGACTCCGTGAAGGGCCG
Pichia Pre 206 DABTM only  (151) ATTCCACCTGATGGTCAAGATCCTTTCTACGCAGATTCCGTCAAAGGAAG
               Consensus  (151) ATTCC CC GATGGTCA GATCC TTCTACGCAGA TCCGT AA GG  G
                                 201                                                250
         Dom1h-131-206 WT  (201) GTTCACCATCTCCCGCGACAATTCCAAGAACACGCTATATCTGCAAATGA
Pichia Pre 206 DABTM only  (201) ATTTACTATCTCCAGAGATAATAGTAAAAACACTTTGTACCTACAGATGA
               Consensus  (201)  TT AC ATCTCC G GA AAT   AA AACAC  T TA CT CA ATGA
                                 251                                                300
         Dom1h-131-206 WT  (251) ACAGCCTGCGTGCCGAGGACACAGCGGTATATCACTGTGCGCTGCTTCCT
Pichia Pre 206 DABTM only  (251) ACTCACTTAGAGCCGAAGATACCGCTGTGTACCACTGCGCCTTGTTGCCA
               Consensus  (251) AC   CT  G GCCGA GA AC GC GT TA CACTG GC  TG T CC
                                 301                                                350
         Dom1h-131-206 WT  (301) AAGAGGGGGCCTTGGTTTGACTACTGGGGTCAGGGAACCCTGGTCACCGT
Pichia Pre 206 DABTM only  (301) AAGAGAGGTCCTTGGTTCGATTACTGGGGTCAGGGTACTCTGGTTACAGT
               Consensus  (301) AAGAG GG CCTTGGTT GA TACTGGGGTCAGGG AC CTGGT AC GT
                                 351
         Dom1h-131-206 WT  (351) CTCGAGC-
Pichia Pre 206 DABTM only  (351) CTC-ATCT
               Consensus  (351) CTC A C
```

FIG. 56

Codon Optimised Sequence 4

DNA Sequence

Gaagtacaactgctggagagcggtggcggcctggttcaaccgggtggttccctgcgcctgtcctgtgcggcatctgg
tttcaccttcgcacacgaaaccatggtgtgggttcgccaagctccgggcaaaggcctggaatgggtaagccacattc
ctccagatggccaggacccattctatgcggattccgttaagggtcgctttaccatttctcgtgataactccaaaaac
accctgtacctgcagatgaactccctgcgcgccgaggatactgcggtgtaccattgtgcgctgctgcctaaacgtgg
cccgtggttcgattactggggtcagggtactctggtcaccgtaagcagc (SEQ ID NO: 241)

Corresponding AA Sequence

Evqllesggglvqpggslrlscaasgftfahetmvwvrqapgkglewvshippdgqdpfyadsvkgrftisrdnskn
tlylqmnslraedtavyhcallpkrgpwfdywgqgtlvtvss (SEQ ID NO: 242)

- 76.5% nucleotide sequence identity to WT sequence (nucleic acid sequences shown below correspond to SEQ ID NO:s 243-248)

```
                                    1                                                50
         Dom1h-131-206 WT       (1) GAGGTGCAGCTGTTGGAGTCTGGGGGAGGCTTGGTACAGCCTGGGGGGTC
Ecoli Sec 206 DABTM only       (1) GAAGTACAACTGCTGGAGAGCGGTGGCGGCCTGGTTCAACCGGGTGGTTC
              Consensus        (1) GA GT CA CTG TGGAG    GG GG GGC TGGT CA CC GG GG TC
                                   51                                               100
         Dom1h-131-206 WT      (51) CCTGCGTCTCTCCTGTGCAGCCTCCGGATTCACCTTTGCGCATGAGACGA
Ecoli Sec 206 DABTM only      (51) CCTGCGCCTGTCCTGTGCGGCATCTGGTTTCACCTTCGCACACGAAACCA
              Consensus       (51) CCTGCG CT TCCTGTGC GC TC GG TTCACCTT GC CA GA AC A
                                   101                                              150
         Dom1h-131-206 WT     (101) TGGTGTGGGTCCGCCAGGCACCAGGGAAGGGTCTAGAGTGGGTCTCACAT
Ecoli Sec 206 DABTM only     (101) TGGTGTGGGTTCGCCAAGCTCCGGGCAAAGGCCTGGAATGGGTAAGCCAC
              Consensus      (101) TGGTGTGGGT CGCCA GC CC GG AA GG CT GA TGGGT    CA
                                   151                                              200
         Dom1h-131-206 WT     (151) ATTCCCCCGGATGGTCAGGATCCCTTCTACGCAGACTCCGTGAAGGGCCG
Ecoli Sec 206 DABTM only     (151) ATTCCTCCAGATGGCCAGGACCCATTCTATGCGGATTCCGTTAAGGGTCG
              Consensus      (151) ATTCC CC GATGG CAGGA CC TTCTA GC GA TCCGT AAGGG CG
                                   201                                              250
         Dom1h-131-206 WT     (201) GTTCACCATCTCCCGCGACAATTCCAAGAACACGCTATATCTGCAAATGA
Ecoli Sec 206 DABTM only     (201) CTTTACCATTTCTCGTGATAACTCCAAAAACACCCTGTACCTGCAGATGA
              Consensus      (201)    TT ACCAT TC CG GA AA TCCAA AACAC CT TA CTGCA ATGA
                                   251                                              300
         Dom1h-131-206 WT     (251) ACAGCCTGCGTGCCGAGGACACAGCGGTATATCACTGTGCGCTGCTTCCT
Ecoli Sec 206 DABTM only     (251) ACTCCCTGCGCGCCGAGGATACTGCGGTGTACCATTGTGCGCTGCTGCCT
              Consensus      (251) AC   CCTGCG GCCAGGA AC GCGGT TA CA TGTGCGCTGCT  CCT
                                   301                                              350
         Dom1h-131-206 WT     (301) AAGAGGGGGCCTTGGTTTGACTACTGGGGTCAGGGAACCCTGGTCACCGT
Ecoli Sec 206 DABTM only     (301) AAACGTGGCCCGTGGTTCGATTACTGGGGTCAGGGTACTCTGGTCACCGT
              Consensus      (301) AA  G GG CC TGGTT GA TACTGGGGTCAGGG AC CTGGTCACCGT
                                   351
         Dom1h-131-206 WT     (351) CTCGAGC
Ecoli Sec 206 DABTM only     (351) AAGCAGC
              Consensus      (351)    AGC
```

FIG. 57

Codon Optimised Sequence 5

DNA Sequence

Gaggttcaactgctggaatctggtggtggtctggtacaaccgggtggttccctgcgtctgagctgtgcagcctctgg
tttcaccttcgctcatgagaccatggtttgggtacgccaggctccgggtaaaggcctggagtgggtaagccatatcc
ctcctgatggtcaggacccgttctatgctgattccgtcaaaggccgttttaccatttctcgtgacaacagcaaaaac
actctgtacctgcaaatgaactccctgcgtgcagaagacacggcggtttatcactgtgcactgctgccaaaacgcgg
cccttggttcgactactggggccagggtactctggtcactgtatcttct (SEQ ID NO: 249)

Corresponding AA Sequence

Evqllesggglvqpggslrlscaasgftfahetmvwvrqapgkglewvshippdgqdpfyadsvkgrftisrdnskn
tlylqmnslraedtavyhcallpkrgpwfdywgqgtlvtvss (SEQ ID NO: 250)

- 78.4% nucleotide sequence identity to WT sequence (nucleic acid sequences shown below correspond to SEQ ID NO:s 251-257)

```
                              1                                                  50
    Dom1h-131-206 WT      (1) GAGGTGCAGCTGTTGGAGTCTGGGGGAGGCTTGGTACAGCCTGGGGGGTC
Ecoli IC 206 DABTM only   (1) GAGGTTCAACTGCTGGAATCTGGTGGTGGTCTGGTACAACCGGGTGGTTC
              Consensus   (1) GAGGT CA CTG TGGA TCTGG GG GG  TGGTACA CC GG GG TC
                              51                                                 100
    Dom1h-131-206 WT     (51) CCTGCGTCTCTCCTGTGCAGCCTCCGGATTCACCTTTGCGCATGAGACGA
Ecoli IC 206 DABTM only  (51) CCTGCGTCTGAGCTGTGCAGCCTCTGGTTTCACCTTCGCTCATGAGACCA
              Consensus  (51) CCTGCGTCT    CTGTGCAGCCTC GG TTCACCTT GC CATGAGAC A
                              101                                                150
    Dom1h-131-206 WT    (101) TGGTGTGGGTCCGCCAGGCACCAGGGAAGGGTCTAGAGTGGGTCTCACAT
Ecoli IC 206 DABTM only (101) TGGTTTGGGTACGCCAGGCTCCGGGTAAAGGCCTGGAGTGGGTAAGCCAT
              Consensus (101) TGGT TGGGT CGCCAGGC CC GG AA GG CT GAGTGGGT    CAT
                              151                                                200
    Dom1h-131-206 WT    (151) ATTCCCCCGGATGGTCAGGATCCCTTCTACGCAGACTCCGTGAAGGGCCG
Ecoli IC 206 DABTM only (151) ATCCCTCCTGATGGTCAGGACCCGTTCTATGCTGATTCCGTCAAAGGCCG
              Consensus (151) AT CC CC GATGGTCAGGA CC TTCTA GC GA TCCGT AA GGCCG
                              201                                                250
    Dom1h-131-206 WT    (201) GTTCACCATCTCCCGCGACAATTCCAAGAACACGCTATATCTGCAAATGA
Ecoli IC 206 DABTM only (201) TTTTACCATTTCTCGTGACAACAGCAAAAACACTCTGTACCTGCAAATGA
              Consensus (201)  TT ACCAT TC CG GACAA  CAA AACAC CT TA CTGCAAATGA
                              251                                                300
    Dom1h-131-206 WT    (251) ACAGCCTGCGTGCCGAGGACACAGCGGTATATCACTGTGCGCTGCTTCCT
Ecoli IC 206 DABTM only (251) ACTCCCTGCGTGCAGAAGACACGGCGGTTTATCACTGTGCACTGCTGCCA
              Consensus (251) AC  CCTGCGTGC GA GACAC GCGGT TATCACTGTGC CTGCT CC
                              301                                                350
    Dom1h-131-206 WT    (301) AAGAGGGGGCCTTGGTTTGACTACTGGGGTCAGGGAACCCTGGTCACCGT
Ecoli IC 206 DABTM only (301) AAACGCGGCCCTTGGTTCGACTACTGGGGCCAGGGTACTCTGGTCACTGT
              Consensus (301) AA  G GG CCTTGGTT GACTACTGGGG CAGGG AC CTGGTCAC GT
                              351
    Dom1h-131-206 WT    (351) CTCGAGC
Ecoli IC 206 DABTM only (351) ATCTTCT
              Consensus (351) TC
```

POLYPEPTIDES, ANTIBODY VARIABLE DOMAINS AND ANTAGONISTS

RELATED APPLICATIONS

This application is a divisional of U.S. application Ser. No. 13/763,768 filed on Feb. 11, 2013, which is a continuation of the US National Stage application Ser. No. 12/663, 502 filed Jun. 8, 2010, made under 35 USC § 371, of International Application No. PCT/GB2008/050405, filed Jun. 4, 2008 and published in English which claims priority under 35 USC § 119, or 35 USC § 365, to U.S. Provisional Application No. 60/933,632 filed Jun. 6, 2007 and United Kingdom, Application No. 0724331.4, filed Dec. 13, 2007. The entire teachings of the above applications are incorporated herein by reference.

The present invention relates to protease resistant polypeptides, immunoglobulin (antibody) single variable domains and anti-Tumor Necrosis Factor 1 (TNFR1, p55, CD120a, P60, TNF receptor superfamily member 1A, TNFRSF1A) antagonists comprising these. The invention further relates to uses, formulations, compositions and devices comprising such anti-TNFR1 ligands.

BACKGROUND OF THE INVENTION

Polypeptides and peptides have become increasingly important agents in a variety of applications, including industrial applications and use as medical, therapeutic and diagnostic agents. However, in certain physiological states, such as inflammatory states (e.g., COPD) and cancer, the amount of proteases present in a tissue, organ or animal (e.g., in the lung, in or adjacent to a tumor) can increase. This increase in proteases can result in accelerated degradation and inactivation of endogenous proteins and of therapeutic peptides, polypeptides and proteins that are administered to treat disease. Accordingly, some agents that have potential for in vivo use (e.g., use in treating, diagnosing or preventing disease) have only limited efficacy because they are rapidly degraded and inactivated by proteases.

Protease resistant polypeptides provide several advantages. For example, protease resistant polypeptides remaining active in vivo longer than protease sensitive agents and, accordingly, remaining functional for a period of time that is sufficient to produce biological effects. A need exists for improved methods to select polypeptides that are resistant to protease degradation and also have desirable biological activity.

TNFR1

TNFR1 is a transmembrane receptor containing an extracellular region that binds ligand and an intracellular domain that lacks intrinsic signal transduction activity but can associate with signal transduction molecules. The complex of TNFR1 with bound TNF contains three TNFR1 chains and three TNF chains. (Banner et al., *Cell*, 73(3) 431-445 (1993).) The TNF ligand is present as a trimer, which is bound by three TNFR1 chains. (Id.) The three TNFR1 chains are clustered closely together in the receptor-ligand complex, and this clustering is a prerequisite to TNFR1-mediated signal transduction. In fact, multivalent agents that bind TNFR1, such as anti-TNFR1 antibodies, can induce TNFR1 clustering and signal transduction in the absence of TNF and are commonly used as TNFR1 agonists. (See, e.g., Belka et al., *EMBO*, 14(6):1156-1165 (1995); Mandik-Nayak et al., *J. Immunol*, 167:1920-1928 (2001).) Accordingly, multivalent agents that bind TNFR1, are generally not effective antagonists of TNFR1 even if they block the binding of TNFα to TNFR1.

The extracellular region of TNFR1 comprises a thirteen amino acid amino-terminal segment (amino acids 1-13 of human TNFR1; amino acids 1-13 of mouse TNFR1), Domain 1 (amino acids 14-53 of human TNFR1; amino acids 14-53 of mouse TNFR1), Domain 2 (amino acids 54-97 of human TNFR1; amino acids 54-97 of mouse TNFR1), Domain 3 (amino acids 98-138 of human TNFR1; amino acid 98-138 of mouse TNFR1), and Domain 4 (amino acids 139-167 human TNFR1; amino acids 139-167 of mouse TNFR1) which is followed by a membrane-proximal region (amino acids 168-182 of human TNFR1; amino acids 168-183 mouse TNFR1). (See, Banner et al., *Cell* 73(3) 431-445 (1993) and Loetscher et al., *Cell* 61(2) 351-359 (1990).) Domains 2 and 3 make contact with bound ligand (TNFβ, TNFα). (Banner et al., *Cell*, 73(3) 431-445 (1993).) The extracellular region of TNFR1 also contains a region referred to as the pre-ligand binding assembly domain or PLAD domain (amino acids 1-53 of human TNFR1; amino acids 1-53 of mouse TNFR1) (The Government of the USA, WO 01/58953; Deng et al., *Nature Medicine*, doi: 10.1038/nm 1304 (2005)).

TNFR1 is shed from the surface of cells in vivo through a process that includes proteolysis of TNFR1 in Domain 4 or in the membrane-proximal region (amino acids 168-182 of human TNFR1; amino acids 168-183 of mouse TNFR1), to produce a soluble form of TNFR1. Soluble TNFR1 retains the capacity to bind TNFα, and thereby functions as an endogenous inhibitor of the activity of TNFα.

SUMMARY OF THE INVENTION

In one aspect, the invention provides a polypeptide comprising an amino acid sequence that is at least 93% identical to the amino acid sequence of DOM1h-131-206 (shown in FIG. 3 and SEQ ID NO: 4). In one embodiment, the percent identity is at least 94, 95, 96, 97, 98 or 99%. In one embodiment, the polypeptide is DOM1h-131-206. The invention further provides (substantially) pure DOM1h-131-206 monomer. In one embodiment, the DOM1h-131-206 is at least 98, 99, 99.5% pure or 100% pure monomer.

In one aspect, the invention provides a polypeptide encoded by an amino acid sequence that is at least 80% identical to the nucleotide sequence of the nucleotide sequence of DOM1h-131-206 (shown in FIG. 19). In one embodiment, the percent identity is at least 70, 80, 85, 90, 91, 92, 93, 94, 95, 96, 97, 98 or 99%.

In one aspect, the invention provides a polypeptide encoded by a nucleotide sequence that is at least 57% identical to the nucleotide sequence of DOM1h-131-206 (shown in FIG. 19) and wherein the polypeptide comprises an amino acid sequence that is at least 93% identical to the amino acid sequence of DOM1h-131-206 (shown in FIG. 3). In one embodiment, the percent identity of the nucleotide sequence is at least 60, 65, 70, 75, 80, 85, 90, 91, 92, 93, 94, 95, 96, 97, 98 or 99%. In one embodiment, the percent identity of the amino acid sequence is at least 94, 95, 96, 97, 98 or 99% or 100%. For example, the nucleotide sequence may be a codon-optimised version of the nucleotide sequence of DOM1h-131-206 (shown in FIG. 19). Codon optimization of sequences is known in the art. In one embodiment, the nucleotide sequence is optimized for expression in a bacterial (eg, *E. coli* or *Pseudomonas*, eg *P fluorescens*), mammalian (eg, CHO) or yeast host cell (eg. *Picchia* or *Saccharomyces*, eg *P. pastoris* or *S. cerevisiae*).

In one aspect, the invention provides a fusion protein comprising the polypeptide of the invention.

In one aspect, the invention provides an anti-TNFα receptor type 1 (TNFR1; p55) immunoglobulin single variable domain comprising an amino acid sequence that is at least 93% identical to the amino acid sequence of DOM1h-131-206 (shown in FIG. 3). In one embodiment, the percent identity is at least 94, 95, 96, 97, 98 or 99%.

In one aspect, the invention provides a protease resistant anti-TNFα receptor type 1 (TNFR1; p55) immunoglobulin single variable domain comprising an amino acid sequence that is at least 90% identical to the amino acid sequence of DOM1h-131-206. In one embodiment of these aspects, the percent identity is at least 80, 85, 90, 91, 92, 93, 94, 95, 96, 97, 98 or 99%.

In one embodiment, the immunoglobulin single variable domain comprises aspartic acid at position 53, wherein numbering is according to Kabat ("Sequences of Proteins of Immunological Interest", US Department of Health and Human Services 1991).

In one embodiment, the immunoglobulin single variable domain comprises histidine at position 91, wherein numbering is according to Kabat.

In one aspect, the invention provides an anti-TNFα receptor type 1 (TNFR1; p55) immunoglobulin single variable domain comprising an amino acid sequence that is identical to the amino acid sequence of DOM1h-131-206.

In one aspect, the invention provides an anti-TNFα receptor type 1 (TNFR1; p55) immunoglobulin single variable domain encoded by a nucleotide sequence that is at least 80% identical to the nucleotide sequence of DOM1h-131-206 (shown in FIG. 19). In one embodiment, the percent identity is at least 70, 80, 85, 90, 91, 92, 93, 94, 95, 96, 97, 98 or 99%.

In one aspect, the invention provides an anti-TNFα receptor type 1 (TNFR1; p55) immunoglobulin single variable domain encoded by a nucleotide sequence that is at least 57% identical to the nucleotide sequence of DOM1h-131-206 (shown in FIG. 19) and wherein the variable domain comprises an amino acid sequence that is at least 93% identical to the amino acid sequence of DOM1h-131-206 (shown in FIG. 3). In one embodiment, the percent identity of the nucleotide sequence is at least 60, 65, 70, 75, 80, 85, 90, 91, 92, 93, 94, 95, 96, 97, 98 or 99%. In one embodiment, the percent identity of the amino acid sequence is at least 94, 95, 96, 97, 98 or 99% or 100%. For example, the nucleotide sequence may be a codon-optimised version of the nucleotide sequence of DOM1h-131-206 (shown in FIG. 19). Codon optimization of sequences is known in the art. In one embodiment, the nucleotide sequence is optimized for expression in a bacterial (eg, *E. coli* or *Pseudomonas*, eg *P fluorescens*), mammalian (eg, CHO) or yeast host cell (eg. *Picchia* or *Saccharomyces*, eg *P. pastoris* or *S. cerevisiae*).

In one aspect, the invention provides an anti-TNFα receptor type 1 (TNFR1; p55) immunoglobulin single variable domain encoded by a sequence that is identical to the nucleotide sequence of DOM1h-131-206 (shown in FIG. 19).

In one aspect, the invention provides a TNFα receptor type 1 (TNFR1; p55) antagonist comprising an anti-TNFR1 immunoglobulin single variable domain according to the invention. In one embodiment, the antagonist comprises first and second immunoglobulin single variable domains, wherein each variable domain is according to invention. For example, wherein the antagonist comprises a monomer of said single variable domain or a homodimer of said single variable domain. In one embodiment, the amino acid sequence of the or each single variable domain is identical to the amino acid sequence of DOM1h-131-206 (shown in FIG. 3).

In one aspect, the invention provides an anti-TNFα receptor type 1 (TNFR1; p55) immunoglobulin single variable domain comprising an amino acid sequence that is identical to the amino acid sequence of DOM1h-131-206 (shown in FIG. 3) or differs from the amino acid sequence of DOM1h-131-206 at no more than 25 amino acid positions and has a CDR1 sequence that is at least 50% identical to the CDR1 sequence of DOM1h-131-206. In one embodiment, the difference is no more than 24, 23, 22, 21, 20, 19, 18, 17, 16, 15, 14, 13, 12, 11, 10, 9, 8, 7, 6, 5, 4, 3, 2 or 1 amino acid position. In one embodiment, the CDR sequence identity is at least 55, 60, 65, 70, 75, 80, 85, 90, 95, 96, 97, 98 or 99%.

In one aspect, the invention provides an anti-TNFα receptor type 1 (TNFR1; p55) immunoglobulin single variable domain comprising an amino acid sequence that is identical to the amino acid sequence of DOM1h-131-206 (shown in FIG. 3) or differs from the amino acid sequence of DOM1h-131-206 at no more 25 than amino acid positions and has a CDR2 sequence that is at least 50% identical to the CDR2 sequence of DOM1h-131-206. In one embodiment, the difference is no more than 24, 23, 22, 21, 20, 19, 18, 17, 16, 15, 14, 13, 12, 11, 10, 9, 8, 7, 6, 5, 4, 3, 2 or 1 amino acid position. In one embodiment, the CDR sequence identity is at least 55, 60, 65, 70, 75, 80, 85, 90, 95, 96, 97, 98 or 99%.

In one aspect, the invention provides an anti-TNFα receptor type 1 (TNFR1; p55) immunoglobulin single variable domain comprising an amino acid sequence that is identical to the amino acid sequence of DOM1h-131-206 (shown in FIG. 3) or differs from the amino acid sequence of DOM1h-131-206 at no more than 25 amino acid positions and has a CDR3 sequence that is at least 50% identical to the CDR3 sequence of DOM1h-131-206. In one embodiment, the difference is no more than 24, 23, 22, 21, 20, 19, 18, 17, 16, 15, 14, 13, 12, 11, 10, 9, 8, 7, 6, 5, 4, 3, 2 or 1 amino acid position. In one embodiment, the CDR sequence identity is at least 55, 60, 65, 70, 75, 80, 85, 90, 95, 96, 97, 98 or 99%.

In one aspect, the invention provides an anti-TNFα receptor type 1 (TNFR1; p55) immunoglobulin single variable domain comprising an amino acid sequence that is identical to the amino acid sequence of DOM1h-131-206 (shown in FIG. 3) or differs from the amino acid sequence of DOM1h-131-206 at no more than 25 amino acid positions and has a CDR1 sequence that is at least 50% identical to the CDR1 sequence of DOM1h-131-206 and has a CDR2 sequence that is at least 50% identical to the CDR2 sequence of DOM1h-131-206. In one embodiment, the difference is no more than 24, 23, 22, 21, 20, 19, 18, 17, 16, 15, 14, 13, 12, 11, 10, 9, 8, 7, 6, 5, 4, 3, 2 or 1 amino acid position. In one embodiment, one or both CDR sequence identities is respectively at least 55, 60, 65, 70, 75, 80, 85, 90, 95, 96, 97, 98 or 99%.

In one aspect, the invention provides an anti-TNFα receptor type 1 (TNFR1; p55) immunoglobulin single variable domain comprising an amino acid sequence that is identical to the amino acid sequence of DOM1h-131-206 (shown in FIG. 3) or differs from the amino acid sequence of DOM1h-131-206 at no more than 25 amino acid positions and has a CDR1 sequence that is at least 50% identical to the CDR1 sequence of DOM1h-131-206 and has a CDR3 sequence that is at least 50% identical to the CDR3 sequence of DOM1h-131-206. In one embodiment, the difference is no more than 24, 23, 22, 21, 20, 19, 18, 17, 16, 15, 14, 13, 12, 11, 10, 9, 8, 7, 6, 5, 4, 3, 2 or 1 amino acid position. In one embodiment, one or both CDR sequence identities is respectively at least 55, 60, 65, 70, 75, 80, 85, 90, 95, 96, 97, 98 or 99%.

In one aspect, the invention provides an anti-TNFα receptor type 1 (TNFR1; p55) immunoglobulin single variable domain comprising an amino acid sequence that is identical to the amino acid sequence of DOM1h-131-206 (shown in FIG. 3) or differs from the amino acid sequence of DOM1h-131-206 at no more than 25 amino acid positions and has a CDR2 sequence that is at least 50% identical to the CDR2 sequence of DOM1h-131-206 and has a CDR3 sequence that is at least 50% identical to the CDR3 sequence of DOM1h-131-206. In one embodiment, the difference is no more than 24, 23, 22, 21, 20, 19, 18, 17, 16, 15, 14, 13, 12, 11, 10, 9, 8, 7, 6, 5, 4, 3, 2 or 1 amino acid position. In one embodiment, one or both CDR sequence identities is respectively at least 55, 60, 65, 70, 75, 80, 85, 90, 95, 96, 97, 98 or 99%.

In one aspect, the invention provides an anti-TNFα receptor type 1 (TNFR1; p55) immunoglobulin single variable domain comprising an amino acid sequence that is identical to the amino acid sequence of DOM1h-131-206 (shown in FIG. 3) or differs from the amino acid sequence of DOM1h-131-206 at no more than 25 amino acid positions and has a CDR1 sequence that is at least 50% identical to the CDR1 sequence of DOM1h-131-206 and has a CDR2 sequence that is at least 50% identical to the CDR2 sequence of DOM1h-131-206 and has a CDR3 sequence that is at least 50% identical to the CDR3 sequence of DOM1h-131-206. In one embodiment, In one embodiment, the difference is no more than 24, 23, 22, 21, 20, 19, 18, 17, 16, 15, 14, 13, 12, 11, 10, 9, 8, 7, 6, 5, 4, 3, 2 or 1 amino acid position. In one embodiment, one or two or each CDR sequence identity is at least 55, 60, 65, 70, 75, 80, 85, 90, 95, 96, 97, 98 or 99% respectively.

In one aspect, the invention provides a TNFα receptor type 1 (TNFR1; p55) antagonist having a CDR1 sequence that is at least 50% identical to the CDR1 sequence of DOM1h-131-206 (shown in FIG. 3). In one embodiment, the CDR sequence identity is at least 55, 60, 65, 70, 75, 80, 85, 90, 95, 96, 97, 98 or 99%. The antagonist may be resistant to protease, for example one or more of the proteases as herein described, for example under a set of conditions as herein described.

In one aspect, the invention provides a TNFα receptor type 1 (TNFR1; p55) antagonist having a CDR2 sequence that is at least 50% identical to the CDR1 sequence of DOM1h-131-206 (shown in FIG. 3). In one embodiment, the CDR sequence identity is at least 55, 60, 65, 70, 75, 80, 85, 90, 95, 96, 97, 98 or 99%. The antagonist may be resistant to protease, for example one or more of the proteases as herein described, for example under a set of conditions as herein described.

In one aspect, the invention provides a TNFα receptor type 1 (TNFR1; p55) antagonist having a CDR3 sequence that is at least 50% identical to the CDR1 sequence of DOM1h-131-206 (shown in FIG. 3). In one embodiment, the CDR sequence identity is at least 55, 60, 65, 70, 75, 80, 85, 90, 95, 96, 97, 98 or 99%. The antagonist may be resistant to protease, for example one or more of the proteases as herein described, for example under a set of conditions as herein described.

In one aspect, the invention provides a TNFα receptor type 1 (TNFR1; p55) antagonist having a CDR1 sequence that is at least 50% identical to the CDR1 sequence of DOM1h-131-206 (shown in FIG. 3) and a CDR2 sequence that is at least 50% identical to the CDR2 sequence of DOM1h-131-206. In one embodiment, the CDR sequence identity of one or both CDRs is at least 55, 60, 65, 70, 75, 80, 85, 90, 95, 96, 97, 98 or 99% respectively. The antagonist may be resistant to protease, for example one or more of the proteases as herein described, for example under a set of conditions as herein described.

In one aspect, the invention provides a TNFα receptor type 1 (TNFR1; p55) antagonist having a CDR1 sequence that is at least 50% identical to the CDR1 sequence of DOM1h-131-206 (shown in FIG. 3) and a CDR3 sequence that is at least 50% identical to the CDR3 sequence of DOM1h-131-206. In one embodiment, the CDR sequence identity of one or both CDRs is at least 55, 60, 65, 70, 75, 80, 85, 90, 95, 96, 97, 98 or 99% respectively. The antagonist may be resistant to protease, for example one or more of the proteases as herein described, for example under a set of conditions as herein described.

In one aspect, the invention provides a TNFα receptor type 1 (TNFR1; p55) antagonist having a CDR2 sequence that is at least 50% identical to the CDR2 sequence of DOM1h-131-206 (shown in FIG. 3) and a CDR3 sequence that is at least 50% identical to the CDR3 sequence of DOM1h-131-206. In one embodiment, the CDR sequence identity of one or both CDRs is at least 55, 60, 65, 70, 75, 80, 85, 90, 95, 96, 97, 98 or 99% respectively. The antagonist may be resistant to protease, for example one or more of the proteases as herein described, for example under a set of conditions as herein described.

In one aspect, the invention provides a TNFα receptor type 1 (TNFR1; p55) antagonist having a CDR1 sequence that is at least 50% identical to the CDR1 sequence of DOM1h-131-206 (shown in FIG. 3) and a CDR2 sequence that is at least 50% identical to the CDR2 sequence of DOM1h-131-206 and a CDR3 sequence that is at least 50% identical to the CDR3 sequence of DOM1h-131-206. In one embodiment, the CDR sequence identity of one or two or each of the CDRs is at least 55, 60, 65, 70, 75, 80, 85, 90, 95, 96, 97, 98 or 99% respectively. The antagonist may be resistant to protease, for example one or more of the proteases as herein described, for example under a set of conditions as herein described.

In one aspect, the invention provides a TNFα receptor type 1 (TNFR1; p55) antagonist comprising an immunoglobulin single variable domain comprising the sequence of CDR1, CDR2, and/or CDR3 (eg, CDR1, CDR2, CDR3, CDR1 and 2, CDR1 and 3, CDR2 and 3 or CDR1, 2 and 3) of DOM1h-131-206 (shown in FIG. 3). The antagonist may be resistant to protease, for example one or more of the proteases as herein described, for example under a set of conditions as herein described.

In one aspect, the invention provides a TNFα receptor type 1 (TNFR1; p55) antagonist that competes with DOM1h-131-511-206 for binding to TNFR1. Thus, the antagonist may bind the same epitope as DOM1h-131-206 or an overlapping epitope. In one embodiment, the antagonist comprises an immunoglobulin single variable domain having an amino acid sequence that is at least 93% identical to the amino acid sequence of DOM1h-131-206 (shown in FIG. 3). In one embodiment, the percent identity is at least 94, 95, 96, 97, 98 or 99%. The antagonist may be resistant to protease, for example one or more of the proteases as herein described, for example under a set of conditions as herein described. In one embodiment, the antagonist is an antibody or antigen-binding fragment thereof, such as a monovalent antigen-binding fragment (e.g., scFv, Fab, Fab', DAB™) that has binding specificity for TNFR1. Other examples of antagonists are ligands described herein that bind TNFR1. The ligands may comprise an immunoglobulin single variable domain or domain antibody (DAB™) that has binding specificity for TNFR1, or the complementarity determining regions of such a DAB™ in a suitable format. In some embodiments, the ligand is a DAB™ monomer that consists essentially of, or consists of, an immunoglobulin single variable domain or DAB™ that has binding specificity for TNFR1. In other embodiments, the ligand is a polypeptide that comprises a DAB™ (or the CDRs of a DAB™) in a suitable format, such as an antibody format.

Some antagonist of TNFR1 of the invention do not inhibit binding of TNFα to TNFR1, but do inhibit signal transduction mediated through TNFR1. For example, an antagonist of TNFR1 can inhibit TNFα-induced clustering of TNFR1, which precedes signal transduction through TNFR1. Such antagonists provide several advantages. For example, in the presence of such an antagonist, TNFα can bind TNFR1 expressed on the surface of cells and be removed from the cellular environment, but TNFR1 mediated signal transduction will not be activated. Thus, TNFR1 signal-induced production of additional TNFα and other mediators of inflammation will be inhibited. Similarly, antagonists of TNFR1 that bind TNFR1 and inhibit signal transduction mediated through TNFR1, but do no inhibit binding of TNFα to TNFR1, will not inhibit the TNFα-binding and inhibiting activity of endogenously produced soluble TNFR1. Accordingly, administering such an antagonist to a mammal in need thereof can complement the endogenous regulatory pathways that inhibit the activity TNFα and the activity of TNFR1 in vivo. The invention also relates to ligands that (i) bind TNFR1 (eg, in Domain1), (ii) antagonize the activation of TNFR1 mediated signal transduction, and (iii) do not inhibit the binding of TNFα to TNFR1. Such a ligand binds soluble TNFR1 and does not prevent the soluble receptor from binding TNFα, and thus administering such an antagonist to a mammal in need thereof can complement the endogenous regulatory pathways that inhibit the activity TNF in vivo by increasing the half-life of the soluble receptor in the serum. These advantages are particularly relevant to ligands that have been formatted to have a larger hydrodynamic size, for example, by attachment of a PEG group, serum albumin, transferrin, transferrin receptor or at least the transferrin-binding portion thereof, an antibody Fc region, or by conjugation to an antibody domain. For example, an agent (e.g., polypeptide, variable domain or antagonist) that i) binds TNFR1 (eg., in Domain1), (ii) antagonizes the activation of TNFR1 mediated signal transduction, and (iii) does not inhibit the binding of TNFα to TNFR1, such as a DAB™ monomer, can be formatted as a larger antigen-binding fragment of an antibody or as and antibody (e.g., formatted as a Fab, Fab', F(ab)$_2$, F(ab')2, IgG, scFv). The hydrodynaminc size of a ligand and its serum half-life can also be increased by conjugating or linking a TNFR1 binding agent (antagonist; variable domain) to a binding domain (e.g., antibody or antibody fragment) that binds an antigen or epitope that increases half-live in vivo, as described herein (see, Annex 1 of WO2006038027 incorporated herein by reference in its entirety). For example, the TNFR1 binding agent (e.g., polypeptide) can be conjugated or linked to an anti-serum albumin or anti-neonatal Fc receptor antibody or antibody fragment, eg an anti-SA or anti-neonatal Fc receptor DAB™, Fab, Fab' or scFv, or to an anti-SA affibody or anti-neonatal Fc receptor affibody.

Examples of suitable albumin, albumin fragments or albumin variants for use in a TNFR1-binding ligand according to the invention are described in WO 2005/077042A2 and WO2006038027, which are incorporated herein by reference in their entirety.

In other embodiments of the invention described throughout this disclosure, instead of the use of a "DAB™" in an antagonist or ligand of the invention, it is contemplated that the skilled addressee can use a domain that comprises the CDRs of a DAB™ that binds TNFR1 (e.g., CDRs grafted onto a suitable protein scaffold or skeleton, eg an affibody, an SpA scaffold, an LDL receptor class A domain or an EGF domain) or can be a protein domain comprising a binding site for TNFR1, e.g., wherein the domain is selected from an affibody, an SpA domain, an LDL receptor class A domain or an EGF domain. The disclosure as a whole is to be construed accordingly to provide disclosure of antagonists, ligands and methods using such domains in place of a DAB™.

Polypeptides, immunoglobulin single variable domains and antagonists of the invention may be resistant to one or more of the following: serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leukozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actinidain, bromelain, and separase. In particular embodiments, the protease is trypsin, elastase or leucozyme. The protease can also be provided by a biological extract, biological homogenate or biological preparation. In one embodiment, the protease is a protease found in sputum, mucus (e.g., gastric mucus, nasal mucus, bronchial mucus), bronchoalveolar lavage, lung homogenate, lung extract, pancreatic extract, gastric fluid, saliva or tears. In one embodiment, the protease is one found in the eye and/or tears. In one embodiment, the protease is a non-bacterial protease. In an embodiment, the protease is an animal, eg, mammalian, eg, human, protease. In an embodiment, the protease is a GI tract protease or a pulmonary tissue protease, eg, a GI tract protease or a pulmonary tissue protease found in humans. Such protease listed here can also be used in the methods described herein involving exposure of a repertoire of library to a protease.

In one aspect, the invention provides a protease resistant immunoglobulin single variable domain comprising a TNFα receptor type 1 (TNFR1; p55) binding site, wherein the variable domain is resistant to protease, eg trypsin, when incubated with (i) a concentration (c) of at least 10 micrograms/ml protease at 37° C. for time (t) of at least one hour; or (ii) a concentration (c') of at least 40 micrograms/ml protease at 30° C. for time (t) of at least one hour, wherein the variable domain comprises and amino acid sequence that is at least 90% identical to the amino acid sequence of DOM1h-131-206 (shown in FIG. 3). In one embodiment, the ratio (on a mole/mole basis) of protease, eg trypsin, to variable domain is 8,000 to 80,000 protease:variable domain, eg when C is 10 micrograms/ml, the ratio is 800 to 80,000 protease:variable domain; or when C or C' is 100 micrograms/ml, the ratio is 8,000 to 80,000 protease:variable domain. In one embodiment the ratio (on a weight/weight, eg microgram/microgram basis) of protease (eg, trypsin) to variable domain is 16,000 to 160,000 protease:variable domain eg when C is 10 micrograms/ml, the ratio is 1,600 to 160,000 protease:variable domain; or when C or C' is 100 micrograms/ml, the ratio is 1,6000 to 160,000 protease:variable domain. In one embodiment, the concentration (c or c') is at least 100 or 1000 micrograms/ml protease. In one embodiment, the concentration (c or c') is at least 100 or 1000 micrograms/ml protease. Reference is made to the description herein of the conditions suitable for proteolytic activity of the protease for use when working with repertoires or libraries of peptides or polypeptides (eg, w/w parameters). These conditions can be used for conditions to determine the protease resistance of a particular immunoglobulin single variable domain. In one embodiment, time (t) is or is about one, three or 24 hours or overnight (e.g., about 12-16 hours). In one embodiment, the variable domain is resistant under conditions (i) and the concentration (c) is or is about 10 or 100 micrograms/ml protease and time (t) is 1 hour. In one embodiment, the variable domain is resistant under conditions (ii) and the concentration (c') is or is about 40 micrograms/ml protease and time (t) is or is about 3 hours. In one embodiment, the protease is selected from trypsin, elastase, leucozyme and pancreatin. In one embodiment, the protease is trypsin. In one embodiment, the protease is a protease found in sputum, mucus (e.g., gastric mucus, nasal mucus, bronchial mucus), bronchoalveolar lavage, lung homogenate, lung extract, pancreatic extract, gastric fluid, saliva or tears. In one embodiment, the protease is one found in the eye and/or tears. In one embodiment, the protease is a non-bacterial protease. In an embodiment, the protease is an animal, eg, mammalian, eg, human, protease. In an embodiment, the protease is a GI tract protease or a pulmonary tissue protease, eg, a GI tract protease or a pulmonary tissue protease found in humans. Such protease listed here can also be used in the methods described herein involving exposure of a repertoire of library to a protease.

In one embodiment, the variable domain is resistant to trypsin and/or at least one other protease selected from elastase, leucozyme and pancreatin. For example, resistance is to trypsin and elastase; trypsin and leucozyme; trypsin and pacreatin; trypsin, elastase and leucozyme; trypsin, elastase and pancreatin; trypsin, elastase, pancreatin and leucozyme; or trypsin, pancreatin and leucozyme.

In one embodiment, the variable domain is displayed on bacteriophage when incubated under condition (i) or (ii), for example at a phage library size of $10^6$ to $10^{13}$, eg $10^8$ to $10^{12}$ replicative units (infective virions).

In one embodiment, the variable domain specifically binds TNFR1 following incubation under condition (i) or (ii), eg assessed using BIACORE™ or ELISA, eg phage ELISA or monoclonal phage ELISA.

In one embodiment, the variable domains of the invention specifically bind protein A or protein L. In one embodiment, specific binding to protein A or L is present following incubation under condition (i) or (ii).

In one embodiment, the variable domains of the invention may have an $OD_{450}$ reading in ELISA, eg phage ELISA or monoclonal phage ELISA) of at least 0.404, eg, following incubation under condition (i) or (ii).

In one embodiment, the variable domains of the invention display (substantially) a single band in gel electrophoresis, eg following incubation under condition (i) or (ii).

In certain embodiments, the invention provides a TNFR1 antagonist that is a dual-specific ligand that comprises a first DAB™ according to the invention that binds TNFR1 and a second DAB™ that has the same or a different binding specificity from the first DAB™. The second DAB™ may bind a target selected from ApoE, Apo-SAA, BDNF, Cardiotrophin-1, CEA, CD40, CD40 Ligand, CD56, CD38, CD138, EGF, EGF receptor, ENA-78, Eotaxin, Eotaxin-2, Exodus-2, FAPα, FGF-acidic, FGF-basic, fibroblast growth factor-10, FLT3 ligand, Fractalkine (CX3C), GDNF, G-CSF, GM-CSF, GF-β1, human serum albumin, insulin, IFN-γ, IGF-I, IGF-II, IL-1α, IL-1β, IL-1 receptor, IL-1 receptor type 1, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF A, VEGF B, VEGF C, VEGF D, VEGF receptor 1, VEGF receptor 2, VEGF receptor 3, GCP-2, GRO/MGSA, GRO-β, GRO-γ, HCC1, 1-309, HER 1, HER 2, HER 3, HER 4, serum albumin, vWF, amyloid proteins (e.g., amyloid alpha), MMP12, PDK1, IgE, IL-13Rα1, IL-13Ra2, IL-15, IL-15R, IL-16, IL-17R, IL-17, IL-18, IL-18R, IL-23 IL-23R, IL-25, CD2, CD4, CD11a, CD23, CD25, CD27, CD28, CD30, CD40, CD40L, CD56, CD138, ALK5, EGFR, FcER1, TGFb, CCL2, CCL18, CEA, CR8, CTGF, CXCL12 (SDF-1), chymase, FGF, Furin, Endothelin-1, Eotaxins (e.g., Eotaxin, Eotaxin-2, Eotaxin-3), GM-CSF, ICAM-1, ICOS, IgE, IFNa, 1-309, integrins, L-selectin, MIF, MIP4, MDC, MCP-1, MMPs, neutrophil elastase, osteopontin, OX-40, PARC, PD-1, RANTES, SCF, SDF-1, siglec8, TARC, TGFb, Thrombin, Tim-1, TNF, TRANCE, Tryptase, VEGF, VLA-4, VCAM, α4β7, CCR2, CCR3, CCR4, CCR5, CCR7, CCR8, alphavbeta6, alphavbeta8, cMET, CD8, vWF, amyloid proteins (e.g., amyloid alpha), MMP12, PDK1, and IgE.

In one example, the dual-specific ligand comprises a first DAB™ that binds a first epitope on TNFR1 and a second DAB™ that binds an epitope on a different target. In another example, the second DAB™ binds an epitope on serum albumin.

In other embodiments, the ligand is a multispecific ligand that comprises a first epitope binding domain that has binding specificity for TNFR1 and at least one other epitope binding domain that has binding specificity different from the first epitope binding domain. For example, the first epitope binding domain can be a DAB™ that binds TNFR1 or can be a domain that comprises the CDRs of a DAB™ that binds TNFR1 (e.g., CDRs grafted onto a suitable protein scaffold or skeleton, e.g., an affibody, an SpA scaffold, an LDL receptor class A domain or an EGF domain) or can be a domain that binds TNFR1, wherein the domain is selected from an affibody, an SpA domain, an LDL receptor class A domain or an EGF domain).

In certain embodiments, the polypeptide, antagonist, ligand or anti-TNFR1 DAB™ monomer is characterized by one or more of the following: 1) dissociates from human TNFR1 with a dissociation constant ($K_d$) of 50 nM to 20 pM, and a $K_{off}$ rate constant of $5 \times 10^{-1}$ to $1 \times 10^{-7}$ s$^{-1}$ as determined by surface plasmon resonance; 2) inhibits binding of Tumor Necrosis Factor Alpha (TNFα) to TNFR1 with an IC50 of 500 nM to 50 pM; 3) neutralizes human TNFR1 in a standard L929 cell assay with an ND50 of 500 nM to 50 pM; 4) antagonizes the activity of the TNFR1 in a standard cell assay with an $ND_{50}$ of ≤100 nM, and at a concentration of ≤10 µM the DAB™ agonizes the activity of the TNFR1 by ≤5% in the assay; 5) inhibits lethality in the mouse LPS/D-galactosamine-induced septic shock model; 6) resists aggregation; 7) is secreted in a quantity of at least about 0.5 mg/L when expressed in *E. coli* or *Pichia* species (e.g., *P. pastoris*); 8) unfolds reversibly; 9) has efficacy in a model of chronic inflammatory disease selected from the group consisting of mouse collagen-induced arthritis model, mouse ΔARE model of arthritis, mouse ΔARE model of inflammatory bowel disease, mouse dextran sulfate sodium-induced model of inflammatory bowel disease, mouse tobacco smoke model of chronic obstructive pulmonary disease, and suitable primate models (e.g., primate collagen-induced arthritis model); and/or 10) has efficacy in treating, suppressing or preventing a chronic inflammatory disease. Reference is made to WO2006038027 for details of assays and tests and parameters applicable to conditions (1) to (10), and this incorporated herein by reference.

In particular embodiments, the polypeptide, antagonist, ligand or DAB™ monomer dissociates from human TNFR1 with a dissociation constant ($K_d$) of 50 nM to 20 pM, and a $K_{off}$ rate constant of $5 \times 10^{-1}$ to $1 \times 10^{-7}$ s$^{-1}$ as determined by surface plasmon resonance; inhibits binding of Tumor Necrosis Factor Alpha (TNFα t) to TNFR1 with an IC50 of 500 nM to 50 pM; and neutralizes human TNFR1 in a standard L929 cell assay with an ND50 of 500 nM to 50 pM. In other particular embodiments, the polypeptide, antagonist, ligand or DAB™ monomer dissociates from human TNFR1 with a dissociation constant ($K_d$) of 50 nM to 20 pM, and a $K_{off}$ rate constant of $5 \times 10^{-1}$ to $1 \times 10^{-7}$ s$^{-1}$; inhibits binding of Tumor Necrosis Factor Alpha (TNFα) to TNFR1 with an IC50 of 500 nM to 50 pM; and has efficacy in a model of chronic inflammatory disease selected from the group consisting of mouse collagen-induced arthritis model, mouse ΔARE model of arthritis, mouse ΔARE model of inflammatory bowel disease, mouse dextran sulfate sodium-induced model of inflammatory bowel disease, mouse tobacco smoke model of chronic obstructive pulmonary disease, and suitable primate models (e.g., primate collagen-induced arthritis model). In other particular embodiments, the polypeptide, antagonist, ligand or DAB™ monomer dissociates from human TNFR1 with a dissociation constant ($K_d$) of 50 nM to 20 pM, and a $K_{off}$ rate constant of $5 \times 10^{-1}$ to $1 \times 10^{-7}$ s$^{-1}$ as determined by surface plasmon resonance; neutralizes human TNFR1 in a standard L929 cell assay with an ND50 of 500 nM to 50 pM; and antagonizes the activity of the TNFR1 in a standard cell assay with an $ND_{50}$ of ≤100 nM, and at a concentration of ≤10 µM the DAB™ agonizes the activity of the TNFR1 by ≤5% in the assay.

The protease resistant polypeptides, immunoglobulin single variable domains and antagonists of the invention have utility in therapy, prophylaxis and diagnosis of disease or conditions in mammals, eg, humans. In particular, they have utility as the basis of drugs that are likely to encounter proteases when administered to a patient, such as a human. For example, when administered to the GI tract (eg, orally, sublingually, rectally administered), in which case the polypeptides, immunoglobulin single variable domains and antagonists may be subjected to protease in one or more of the upper GI tract, lower GI tract, mouth, stomach, small intestine and large intestine. One embodiment, therefore, provides for a protease resistant polypeptide, immunoglobulin single variable domain or antagonist to be administered orally, sublingually or rectally to the GI tract of a patient to treat and/or prevent a disease or condition in the patient. For example, oral administration to a patient (eg, a human patient) for the treatment and/or prevention of a TNF alpha-mediated condition or disease such as arthritis (eg, rheumatoid arthritis), IBD, psoriasis or Crohn's disease. In another example, the polypeptide, variable domain or antagonist is likely to encounter protease when administered (eg, by inhalation or intranasally) to pulmonary tissue (eg, the lung or airways). One embodiment, therefore, provides for administration of the protease resistant polypeptide, immunoglobulin single variable domain or antagonist to a patient (eg, to a human) by inhalation or intranasally to pulmonary tissue of the patient to treat and/or prevent a disease or condition in the patient. Such condition may be asthma (eg, allergic asthma), COPD, influenza or any other pulmonary disease or condition disclosed in WO2006038027, incorporated herein by reference. In another example, the polypeptide, variable domain or antagonist is likely to encounter protease when administered (eg, by intraocular injection or as eye drops) to an eye of a patient. One embodiment, therefore, provides for ocular administration of the protease resistant polypeptide, immunoglobulin single variable domain or antagonist to a patient (eg, to a human) by to treat and/or prevent a disease or condition (eg, a disease or condition of the eye) in the patient. Administration could be topical administration to the eye, in the form of eye drops or by injection into the eye, eg into the vitreous humour.

The antagonists, polypeptides and immunoglobulin single variable domains according to the invention may display improved or relatively high melting temperatures (Tm), providing enhanced stability. High affinity target binding may also or alternatively be a feature of the antagonists, polypeptides and variable domains. One or more of these features, combined with protease resistance, makes the antagonists, variable domains and polypeptides amenable to use as drugs in mammals, such as humans, where proteases are likely to be encountered, eg for GI tract or pulmonary tissue administration.

Thus, in one aspect, the invention provides the TNFR1 antagonist for oral delivery. In one aspect, the invention provides the TNFR1 antagonist for delivery to the GI tract of a patient. In one aspect, the invention provides the use of the TNFR1 antagonist in the manufacture of a medicament for oral delivery. In one aspect, the invention provides the use of the TNFR1 antagonist in the manufacture of a medicament for delivery to the GI tract of a patient. In one embodiment, the variable domain is resistant to trypsin and/or at least one other protease selected from elastase, leucozyme and pancreatin. For example, resistance is to trypsin and elastase; trypsin and leucozyme; trypsin and pacreatin; trypsin, elastase and leucozyme; trypsin, elastase and pancreatin; trypsin, elastase, pancreatin and leucozyme; or trypsin, pancreatin and leucozyme.

In one aspect, the invention provides the TNFR1 antagonist for pulmonary delivery. In one aspect, the invention provides the TNFR1 antagonist for delivery to the lung of a patient. In one aspect, the invention provides the use of the TNFR1 antagonist in the manufacture of a medicament for pulmonary delivery. In one aspect, the invention provides the use of the TNFR1 antagonist in the manufacture of a medicament for delivery to the lung of a patient. In one embodiment, the variable domain is resistant to leucozyme.

In one aspect, the invention provides a method of oral delivery or delivery of a medicament to the GI tract of a patient or to the lung or pulmonary tissue of a patient, wherein the method comprises administering to the patient a pharmaceutically effective amount of a TNFR1 antagonist of the invention.

In one aspect, the invention provides the TNFR1 antagonist of the invention for treating and/or prophylaxis of an inflammatory condition. In one aspect, the invention provides the use of the TNFR1 antagonist in the manufacture of a medicament for treating and/or prophylaxis of an inflammatory condition. In one embodiment, the condition is selected from the group consisting of arthritis, multiple sclerosis, inflammatory bowel disease and chronic obstructive pulmonary disease. For example, said arthritis is rheumatoid arthritis or juvenile rheumatoid arthritis. For example, said inflammatory bowel disease is selected from the group consisting of Crohn's disease and ulcerative colitis. For example, said chronic obstructive pulmonary disease is selected from the group consisting of chronic bronchitis, chronic obstructive bronchitis and emphysema. For example, said pneumonia is bacterial pneumonia. For example, said bacterial pneumonia is Staphylococcal pneumonia.

In one aspect, the invention provides the TNFR1 antagonist for treating and/or prophylaxis of a respiratory disease. In one aspect, the invention provides the use of the TNFR1 antagonist in the manufacture of a medicament for treating and/or prophylaxis of a respiratory disease. For example, said respiratory disease is selected from the group consisting of lung inflammation, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis. For example, the disease is chronic obstructive pulmonary disease (COPD). For example, the disease is asthma.

An antagonist of the invention comprising an agent that inhibts TNFR1 (e.g., wherein the agent is selected from the group consisting of antibody fragments (e.g, Fab fragment, Fab' fragment, Fv fragment (e.g., scFv, disulfide bonded Fv), F(ab')2 fragment, DAB™), ligands and DAB™ monomers and multimers (eg, homo- or heterodimers) can be locally administered to pulmonary tissue (e.g., lung) of a subject using any suitable method. For example, an agent can be locally administered to pulmonary tissue via inhalation or intranasal administration. For inhalation or intranasal administration, the antagonist of TNFR1 can be administered using a nebulizer, inhaler, atomizer, aerosolizer, mister, dry powder inhaler, metered dose inhaler, metered dose sprayer, metered dose mister, metered dose atomizer, or other suitable inhaler or intranasal delivery device. Thus, in one embodiment, the invention provides a pulmonary delivery device containing the TNFR1 antagonist. In one embodiment, the device is an inhaler or an intranasal delivery device.

In one aspect, the invention provides an oral formulation comprising the TNFR1 antagonist. The formulation can be a tablet, pill, capsule, liquid or syrup.

In one embodiment, the invention provides a pulmonary formulation for delivery to the lung, wherein the formulation comprise an antagonist, polypeptide or variable domain of the invention with a particle size range of less than 5 microns, for example less than 4.5, 4, 3.5 or 3 microns (eg, when in Britton-Robinson buffer, eg at a pH of 6.5 to 8.0, eg at a pH of 7 to 7.5, eg at pH7 or at pH7.5).

In one embodiment, the formulations and compositions of the invention are provided at a pH from 6.5 to 8.0, for example 7 to 7.5, for example 7, for example 7.5.

Variable domains according to any aspect of the invention may have a Tm of at least 50° C., or at least 55° C., or at least 60° C., or at least 65° C., or at least 70° C. An antagonist, use, method, device or formulation of the invention may comprise such a variable domain.

In one aspect of the invention, the polypeptides, variable domains, antagonists, compositions or formulations of the invention are substantially stable after incubation (at a concentration of polypeptide or variable domain of 1 mg/ml) at 37 to 50° C. for 14 days in Britton-Robinson buffer. In one embodiment, at least 65, 70, 75, 80, 85, 86, 87, 88, 90, 91, 92, 93, 94, 95, 96, 97, 98, 99% of the polypeptide, antagonist or variable domain remains unaggregated after such incubation at 37 degrees C. In one embodiment, at least 65, 70, 75, 80, 85, 86, 87, 88, 90, 91, 92, 93, 94, 95, 96, 97, 98, 99% of the polypeptide or variable domain remains monomeric after such incubation at 37 degrees C. In one embodiment, at least 5, 10, 15, 20, 25, 30, 35, 40, 45, 50, 55, 60, 65, 70, 75, 80, 85, 86, 87, 88, 90, 91, 92, 93, 94, 95, 96, 97, 98, 99% of the polypeptide, antagonist or variable domain remains unaggregated after such incubation at 50 degrees C. In one embodiment, at least 5, 10, 15, 20, 25, 30, 35, 40, 45, 50, 55, 60, 65, 70, 75, 80, 85, 86, 87, 88, 90, 91, 92, 93, 94, 95, 96, 97, 98, 99% of the polypeptide or variable domain remains monomeric after such incubation at 50 degrees C. In one embodiment, no aggregation of the polypeptides, variable domains, antagonists is seen after any one of such incubations. In one embodiment, the pI of the polypeptide or variable domain remains unchanged or substantially unchanged after incubation at 37 degrees C. at a concentration of polypeptide or variable domain of 1 mg/ml in Britton-Robinson buffer.

In one aspect of the invention, the polypeptides, variable domains, antagonists, compositions or formulations of the invention are substantially stable after incubation (at a concentration of polypeptide or variable domain of 100 mg/ml) at 4° C. for 7 days in Britton-Robinson buffer at a pH of 7 to 7.5 (eg, at pH7 or pH7.5). In one embodiment, at least 95, 95.5, 96, 96.5, 97, 97.5, 98, 98.5, 99 or 99.5% of the polypeptide, antagonist or variable domain remains unaggregated after such incubation. In one embodiment, at least 95, 95.5, 96, 96.5, 97, 97.5, 98, 98.5, 99 or 99.5% of the polypeptide or variable domain remains monomeric after such incubation. In one embodiment, no aggregation of the polypeptides, variable domains, antagonists is seen after any one of such incubations.

In one aspect of the invention, the polypeptides, variable domains, antagonists, compositions or formulations of the invention are substantially stable after nebulisation (at a concentration of polypeptide or variable domain of 40 mg/ml) eg, at room temperature, 20 degrees C. or 37° C., for 1 hour, eg in a jet nebuliser, eg a PARI LC+™ cup. In one embodiment, at least 65, 70, 75, 80, 85, 86, 87, 88, 90, 91, 92, 93, 94, 95, 95.5, 96, 96.5, 97, 97.5, 98, 98.5, 99 or 99.5% of the polypeptide, antagonist or variable domain remains unaggregated after such nebulisation. In one embodiment, at least 65, 70, 75, 80, 85, 86, 87, 88, 90, 91, 92, 93, 94, 95, 95.5, 96, 96.5, 97, 97.5, 98, 98.5, 99 or 99.5% of the polypeptide or variable domain remains monomeric after such nebulisation. In one embodiment, no aggregation of the polypeptides, variable domains, antagonists is seen after any one of such nebulisation.

Variable domains according to any aspect of the invention may neutralize TNFα stimulated IL-8 release in an MRC-5 cell assay with an ND50 of 2 nM to 50 pM. An antagonist, use, method, device or formulation of the invention may comprise such a variable domain.

In one aspect, the invention provides an isolated or recombinant nucleic acid encoding a polypeptide comprising an immunoglobulin single variable domain according to any aspect of the invention or encoding a polypeptide, antagonist or variable domain according to any aspect of the invention. In one aspect, the invention provides a vector comprising the nucleic acid. In one aspect, the invention provides a host cell comprising the nucleic acid or the vector. In one aspect, the invention provides a method of producing polypeptide comprising an immunoglobulin single variable domain, the method comprising maintaining the host cell under conditions suitable for expression of said nucleic acid or vector, whereby a polypeptide comprising an immunoglobulin single variable domain is produced. The method may further comprise isolating the polypeptide, variable domain or antagonist and optionally producing a variant, eg a mutated variant, having an improved affinity and/or ND50 than the isolated polypeptide, variable domain or antagonist. Techniques for improving binding affinity of immunoglobulin single variable domain are known in the art, eg techniques for affinity maturation.

In one aspect, the invention provides a pharmaceutical composition comprising an immunoglobulin single variable domain, polypeptide or an antagonist of any aspect of the invention, and a pharmaceutically acceptable carrier, excipient or diluent.

In one embodiment, the immunoglobulin single variable domain or the antagonist of any aspect of the invention comprises an antibody constant domain, for example, an antibody Fc, optionally wherein the N-terminus of the Fc is linked (optionally directly linked) to the C-terminus of the variable domain.

The polypeptide or variable domain of the invention can be isolated and/or recombinant.

There is herein described a method for selecting a protease resistant peptide or polypeptide. The method comprises providing a repertoire of peptides or polypeptides, combining the repertoire and a protease under conditions suitable for protease activity, and recovering a peptide or polypeptide that has a desired biological activity (eg, specific binding to TNFR1), whereby a protease resistant peptide or polypeptide is selected.

The repertoire and the protease are generally incubated for a period of at least about 30 minutes. Any desired protease can be used in the method, such as one or more of the following, serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leukozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actinidain, bromelain, and separase. In particular embodiments, the protease is trypsin, elastase or leucozyme. The protease can also be provided by a biological extract, biological homogenate or biological preparation. If desired, the method further comprises adding a protease inhibitor to the combination of the repertoire and the protease after incubation is complete.

In some embodiments, a peptide or polypeptide that has a desired biological activity is recovered base on a binding activity. For example, the peptide or polypeptide can be recovered based on binding a generic ligand, such as protein A, protein G or protein L. The binding activity can also be specific binding to a target ligand. Exemplary target ligands include ApoE, Apo-SAA, BDNF, Cardiotrophin-1, CEA, CD40, CD40 Ligand, CD56, CD38, CD138, EGF, EGF receptor, ENA-78, Eotaxin, Eotaxin-2, Exodus-2, FAPα, FGF-acidic, FGF-basic, fibroblast growth factor-10, FLT3 ligand, Fractalkine (CX3C), GDNF, G-CSF, GM-CSF, GF-31, human serum albumin, insulin, IFN-γ, IGF-I, IGF-II, IL-1α, IL-1β, IL-1 receptor, IL-1 receptor type 1, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF A, VEGF B, VEGF C, VEGF D, VEGF receptor 1, VEGF receptor 2, VEGF receptor 3, GCP-2, GRO/MGSA, GRO-β, GRO-γ, HCC1, 1-309, HER 1, HER 2, HER 3, HER 4, serum albumin, vWF, amyloid proteins (e.g., amyloid alpha), MMP12, PDK1, IgE, IL-13Rα1, IL-13Ra2, IL-15, IL-15R, IL-16, IL-17R, IL-17, IL-18, IL-18R, IL-23 IL-23R, IL-25, CD2, CD4, CD11a, CD23, CD25, CD27, CD28, CD30, CD40, CD40L, CD56, CD138, ALK5, EGFR, FcER1, TGFb, CCL2, CCL18, CEA, CR8, CTGF, CXCL12 (SDF-1), chymase, FGF, Furin, Endothelin-1, Eotaxins (e.g., Eotaxin, Eotaxin-2, Eotaxin-3), GM-CSF, ICAM-1, ICOS, IgE, IFNa, 1-309, integrins, L-selectin, MIF, MIP4, MDC, MCP-1, MMPs, neutrophil elastase, osteopontin, OX-40, PARC, PD-1, RANTES, SCF, SDF-1, siglec8, TARC, TGFb, Thrombin, Tim-1, TNF, TRANCE, Tryptase, VEGF, VLA-4, VCAM, α4β7, CCR2, CCR3, CCR4, CCR5, CCR7, CCR8, alphavbeta6, alphavbeta8, cMET, CD8, vWF, amyloid proteins (e.g., amyloid alpha), MMP12, PDK1, and IgE.

In particular embodiments, the peptide or polypeptide is recovered by panning.

In some embodiments, the repertoire comprises a display system. For example, the display system can be bacteriophage display, ribosome display, emulsion compartmentalization and display, yeast display, puromycin display, bacterial display, display on plasmid, or covalent display. Exemplary display systems link coding function of a nucleic acid and functional characteristics of the peptide or polypeptide encoded by the nucleic acid. In particular embodiments, the display system comprises replicable genetic packages.

In some embodiments, the display system comprises bacteriophage display. For example, the bacteriophage can be fd, M13, lambda, MS2 or T7. In particular embodiments, the bacteriophage display system is multivalent. In some embodiments, the peptide or polypeptide is displayed as a pIII fusion protein.

In other embodiments, the method further comprises amplifying the nucleic acid encoding a peptide or polypeptide that has a desired biological activity. In particular embodiments, the nucleic acid is amplified by phage amplification, cell growth or polymerase chain reaction.

In some embodiments, the repertoire is a repertoire of immunoglobulin single variable domains. In particular embodiments, the immunoglobulin single variable domain is a heavy chain variable domain. In more particular embodiments, the heavy chain variable domain is a human heavy chain variable domain. In other embodiments, the immunoglobulin single variable domain is a light chain variable domain. In particular embodiments, the light chain variable domain is a human light chain variable domain.

In another aspect, there is provided a method for selecting a peptide or polypeptide that binds a target ligand (eg, TNFR1) with high affinity from a repertoire of peptides or polypeptides. The method comprises providing a repertoire of peptides or polypeptides, combining the repertoire and a protease under conditions suitable for protease activity, and recovering a peptide or polypeptide that binds the target ligand.

The repertoire and the protease are generally incubated for a period of at least about 30 minutes. Any desired protease can be used in the method, such as one or more of the following, serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leukozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actinidain, bromelain, and separase. In particular embodiments, the protease is trypsin, elastase or leucozyme. The protease can also be provided by a biological extract, biological homogenate or biological preparation. If desired, the method further comprises adding a protease inhibitor to the combination of the repertoire and the protease after incubation is complete.

The peptide or polypeptide can be recovered based on binding any desired target ligand, such as the target ligands disclosed herein (eg, TNFR1). In particular embodiments, the peptide or polypeptide is recovered by panning.

In some embodiments, the repertoire comprises a display system. For example, the display system can be bacteriophage display, ribosome display, emulsion compartmentalization and display, yeast display, puromycin display, bacterial display, display on plasmid, or covalent display. Exemplary display systems link coding function of a nucleic acid and functional characteristics of the peptide or polypeptide encoded by the nucleic acid. In particular embodiments, the display system comprises replicable genetic packages.

In some embodiments, the display system comprises bacteriophage display. For example, the bacteriophage can be fd, M13, lambda, MS2 or T7. In particular embodiments, the bacteriophage display system is multivalent. In some embodiments, the peptide or polypeptide is displayed as a pIII fusion protein.

In other embodiments, the method further comprises amplifying the nucleic acid encoding a peptide or polypeptide that has a desired biological activity. In particular embodiments, the nucleic acid is amplified by phage amplification, cell growth or polymerase chain reaction.

In some embodiments, the repertoire is a repertoire of immunoglobulin single variable domains. In particular embodiments, the immunoglobulin single variable domain is a heavy chain variable domain. In more particular embodiments, the heavy chain variable domain is a human heavy chain variable domain. In other embodiments, the immunoglobulin single variable domain is a light chain variable domain. In particular embodiments, the light chain variable domain is a human light chain variable domain.

In another aspect, there is herein described a method of producing a repertoire of protease resistant peptides or polypeptides. The method comprises providing a repertoire of peptides or polypeptides, combining the repertoire of peptides or polypeptides and a protease under suitable conditions for protease activity, and recovering a plurality of peptides or polypeptides that have a desired biological activity, whereby a repertoire of protease resistant peptides or polypeptides is produced.

In some embodiments, the repertoire and the protease are incubated for a period of at least about 30 minutes. For example, the protease used in the method can be one or more of the following, serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leukozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actinidain, bromelain, and separase. In particular embodiments, the protease is trypsin, elastase or leucozyme. The protease can also be provided by a biological extract, biological homogenate or biological preparation. If desired, the method further comprises adding a protease inhibitor to the combination of the repertoire and the protease after incubation is complete.

In some embodiments, a plurality of peptides or polypeptides that have a desired biological activity is recovered based on a binding activity. For example, a plurality of peptides or polypeptides can be recovered based on binding a generic ligand, such as protein A, protein G or protein L. The binding activity can also be specific binding to a target ligand, such as a target ligand described herein. In particular embodiments, a plurality of peptides or polypeptides that has the desired biological activity is recovered by panning.

In some embodiments, the repertoire comprises a display system. For example, the display system can be bacteriophage display, ribosome display, emulsion compartmentalization and display, yeast display, puromycin display, bacterial display, display on plasmid, or covalent display. In particular embodiments, the display system links coding function of a nucleic acid and functional characteristics of the peptide or polypeptide encoded by the nucleic acid. In particular embodiments, the display system comprises replicable genetic packages.

In some embodiments, the display system comprises bacteriophage display. For example, the bacteriophage can be fd, M13, lambda, MS2 or T7. In particular embodiments, the bacteriophage display system is multivalent. In some embodiments, the peptide or polypeptide is displayed as a pIII fusion protein.

In other embodiments, the method further comprises amplifying the nucleic acids encoding a plurality of peptides or polypeptides that have a desired biological activity. In particular embodiments, the nucleic acids are amplified by phage amplification, cell growth or polymerase chain reaction.

In some embodiments, the repertoire is a repertoire of immunoglobulin single variable domains. In particular embodiments, the immunoglobulin single variable domain is a heavy chain variable domain. In more particular embodiments, the heavy chain variable domain is a human heavy chain variable domain. In other embodiments, the immunoglobulin single variable domain is a light chain variable domain. In particular embodiments, the light chain variable domain is a human light chain variable domain.

In another aspect, there is herein described a method for selecting a protease resistant polypeptide comprising an immunoglobulin single variable domain (DAB™) that binds a target ligand (eg, TNFR1) from a repertoire. In one embodiment, the method comprises providing a phage display system comprising a repertoire of polypeptides that comprise an immunoglobulin single variable domain, combining the phage display system and a protease selected from the group consisting of elastase, leucozyme and trypsin, under conditions suitable for protease activity, and recovering a phage that displays a polypeptide comprising an immunoglobulin single variable domain that binds the target ligand.

In some embodiments, the protease is used at 100 μg/ml, and the combined phage display system and protease are incubated at about 37° C. overnight.

In some embodiments, the phage that displays a polypeptide comprising an immunoglobulin single variable domain that binds the target ligand is recovered by binding to said target. In other embodiments, the phage that displays a polypeptide comprising an immunoglobulin single variable domain that binds the target ligand is recovered by panning.

There is also described an isolated protease resistant peptide or polypeptide selectable or selected by the methods described herein. In a particular embodiment, there is provided an isolated protease (e.g., trypsin, elastase, leucozyme) resistant immunoglobulin single variable domain (e.g., human antibody heavy chain variable domain, human antibody light chain variable domain) selectable or selected by the methods described herein.

There is further described herein an isolated or recombinant nucleic acid that encodes a protease resistant peptide or polypeptide (e.g., trypsin-, elastase-, or leucozyme-resistant immunoglobulin single variable domain) selectable or selected by the methods described herein, and to vectors (e.g., expression vectors) and host cells that comprise the nucleic acids.

There is further described herein a method for making a protease resistant peptide or polypeptide (e.g., trypsin-, elastase-, or leucozyme-resistant immunoglobulin single variable domain) selectable or selected by the methods described herein, comprising maintaining a host cell that contains a recombinant nucleic acid encoding the protease resistant peptide or polypeptide under conditions suitable for expression, whereby a protease resistant peptide or polypeptide is produced.

There is further described herein a protease resistant peptide or polypeptide (e.g., trypsin-, elastase-, or leucozyme-resistant immunoglobulin single variable domain) selectable or selected by the methods described herein for use in medicine (e.g., for therapy or diagnosis). There is further described herein the use of a protease resistant peptide or polypeptide (e.g., trypsin-, elastase-, or leucozyme-resistant immunoglobulin single variable domain) selectable or selected by the methods described herein for the manufacture of a medicament for treating disease. There is further described herein a method of treating a disease, comprising administering to a subject in need thereof, an effective amount of a protease resistant peptide or polypeptide (e.g., trypsin-, elastase-, or leucozyme-resistant immunoglobulin single variable domain) selectable or selected by the methods described herein. There is further described herein a diagnostic kit for determine whether TNFR1 is present in a sample or how much TNFR1 is present in a sample, comprising a polypeptide, immunoglobulin variable domain (DAB™) or antagonist of the invention and instructions for use (e.g., to determine the presence and/or quantity of TNFR1 in the sample). In some embodiments, the kit further comprises one or more ancillary reagents, such as a suitable buffer or suitable detecting reagent (e.g., a detectably labeled antibody or antigen-binding fragment thereof that binds the polypeptide or DAB™ of the invention or a moiety associated or conjugated thereto.

The invention also relates to a device comprising a solid surface on which a polypeptide, antagonist or DAB™ of the invention is immobilized such that the immobilized polypeptide or DAB™ binds TNFR1. Any suitable solid surfaces on which an antibody or antigen-binding fragment thereof can be immobilized can be used, for example, glass, plastics, carbohydrates (e.g., agarose beads). If desired the support can contain or be modified to contain desired functional groups to facilitate immobilization. The device, and or support, can have any suitable shape, for example, a sheet, rod, strip, plate, slide, bead, pellet, disk, gel, tube, sphere, chip, plate or dish, and the like. In some embodiments, the device is a dipstick.

BRIEF DESCRIPTION OF THE DRAWINGS

FIG. 1 is an illustration of the multiple cloning site of pDOM13 (aka pDOM33), as shown in SEQ ID NO: 2 (GAS leader is shown in SEQ ID NO: 1) which was used to prepare a phage display repertoire.

FIG. 16 is an illustration of the amino acid sequence of DOM15-10 (SEQ ID NO: 14) and a variant, DOM15-10-11. The amino acids that differ from the parent sequence in the variant are highlighted (those that are identical are marked by dots). SYST (SEQ ID NO: 13) is also shown.

FIGS. 19A-19L illustrate the nucleotide sequences of several nucleic acids (as shown in SEQ ID NO:s 15-67) encoding DAB™s that are variants of DOM1h-131-511 or DOM4-130-54. The nucleotide sequences encode the amino acid sequences presented in FIG. 3 and FIG. 4, respectively.

FIGS. 20A-20E illustrate the nucleotide sequences of several nucleic acids (as shown in SEQ ID NO:s 68-102) encoding DAB™s that are variants of DOM15-26-555 or DOM15-10. The nucleotide sequences encode the amino acid sequences presented in FIG. 5 and FIG. 6, respectively.

26I). Also shown is the percentage of monomer left in solution relative to the T=0 at the given time point.

Figure 27:
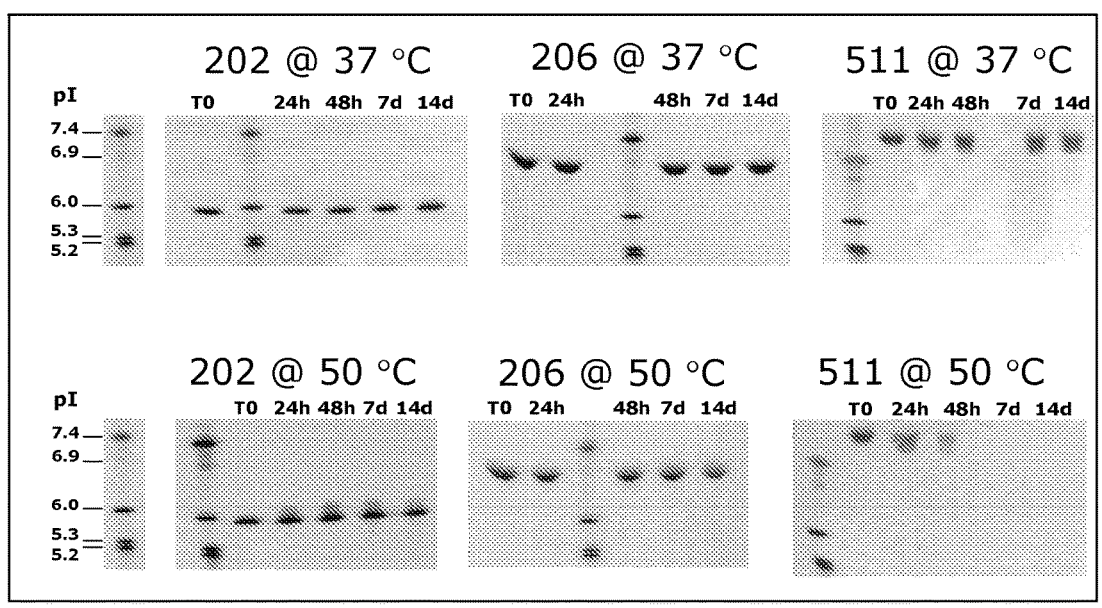

FIG. 27: Shows IEF analysis of DOM1h-131-202, DOM1h-131-206 and DOM1h-131-511 at 24 hr, 48 hr and 7 and 14 days thermal stress. The samples had been incubated at either 37 or 50° C. in Britton-Robinson buffer.

Figure 28:
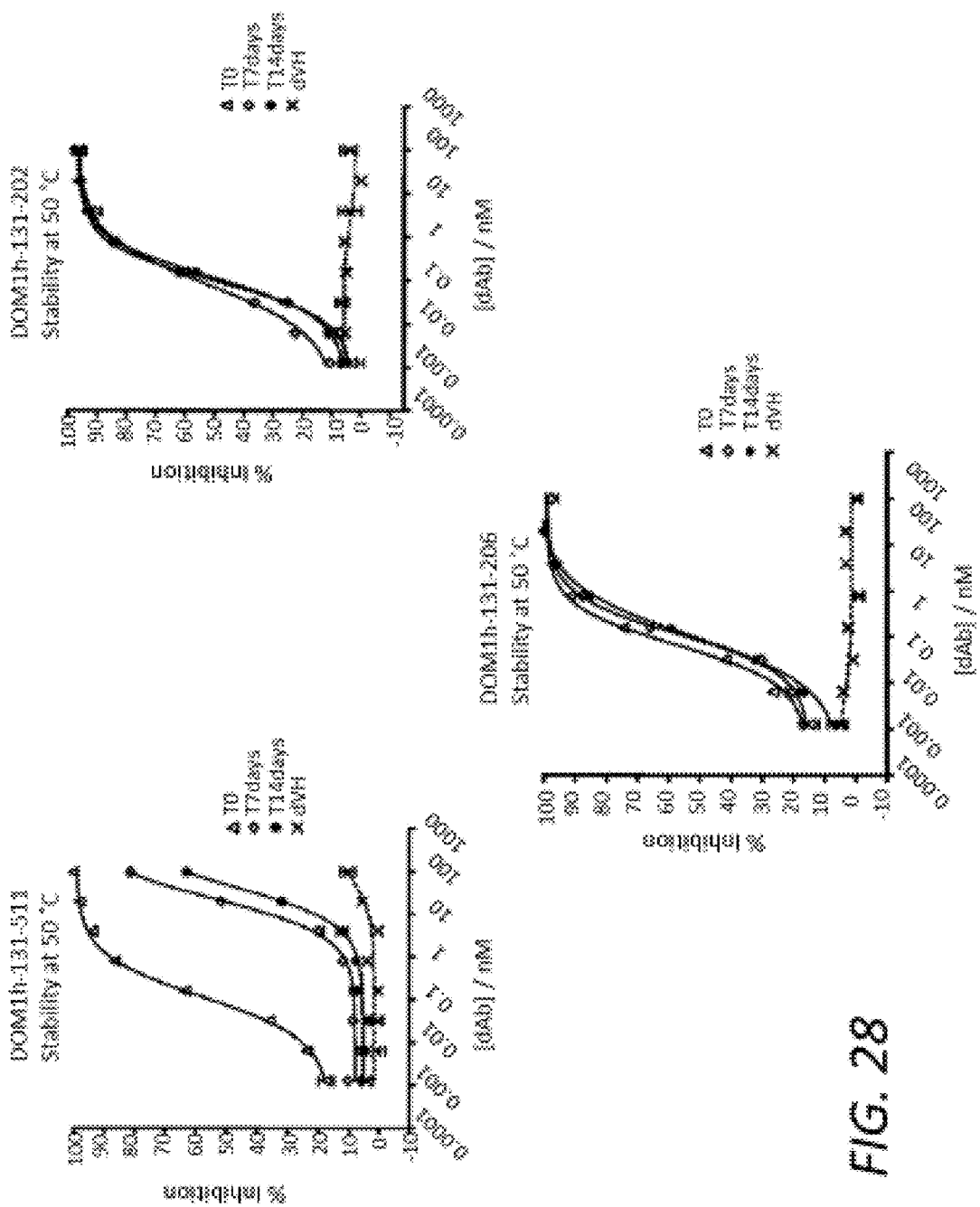

FIG. 28: TNFR-1 RBA showing the effect of 14 days incubation of DOM1h-131-202, DOM1h-131-206 and DOM1h-131-511 at 50° C. The protein concentration was assumed to be 1 mg/ml. A negative control DAB™ (VH dummy) which does not bind antigen is also shown.

Figure 29:
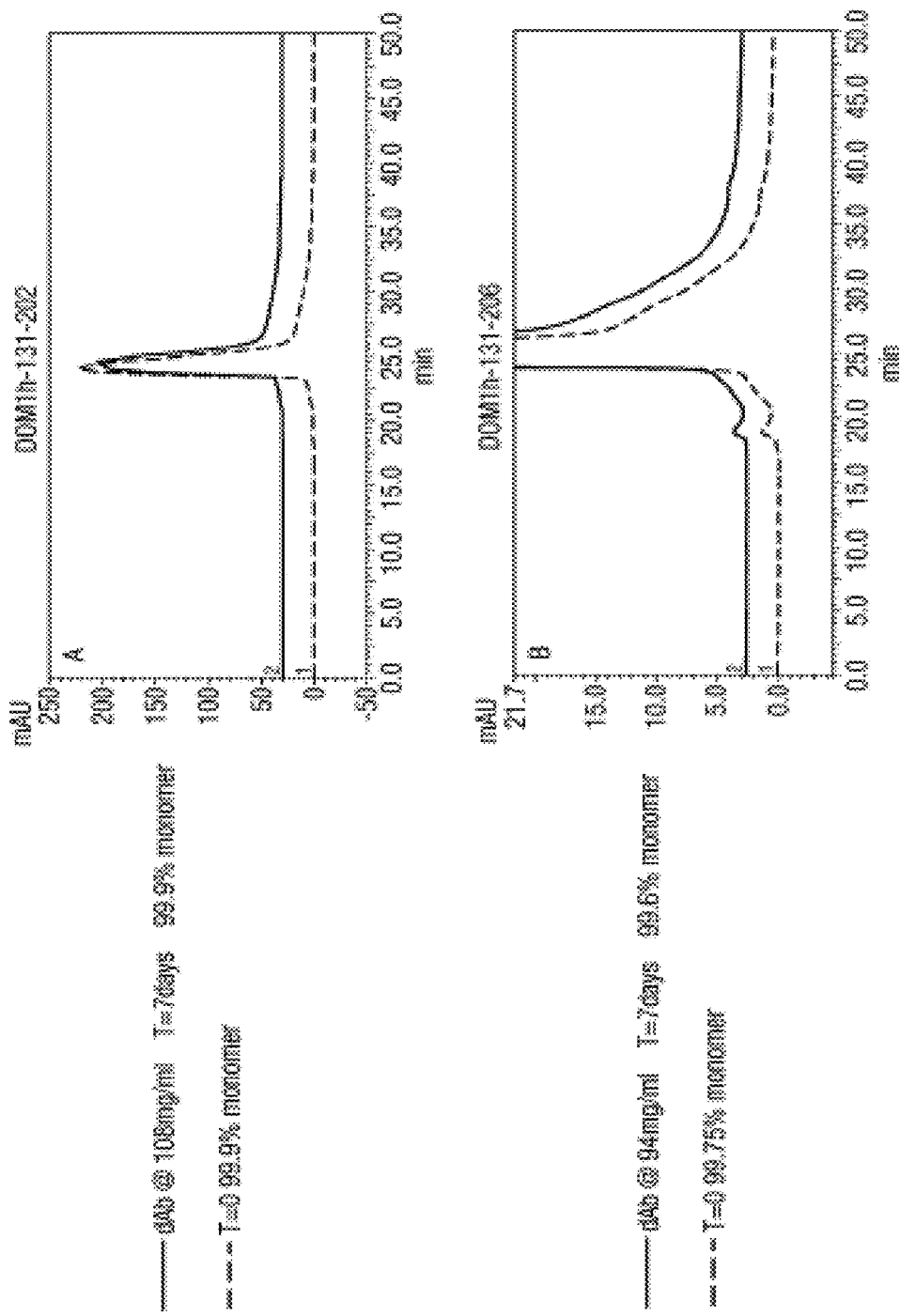
Figure 29:
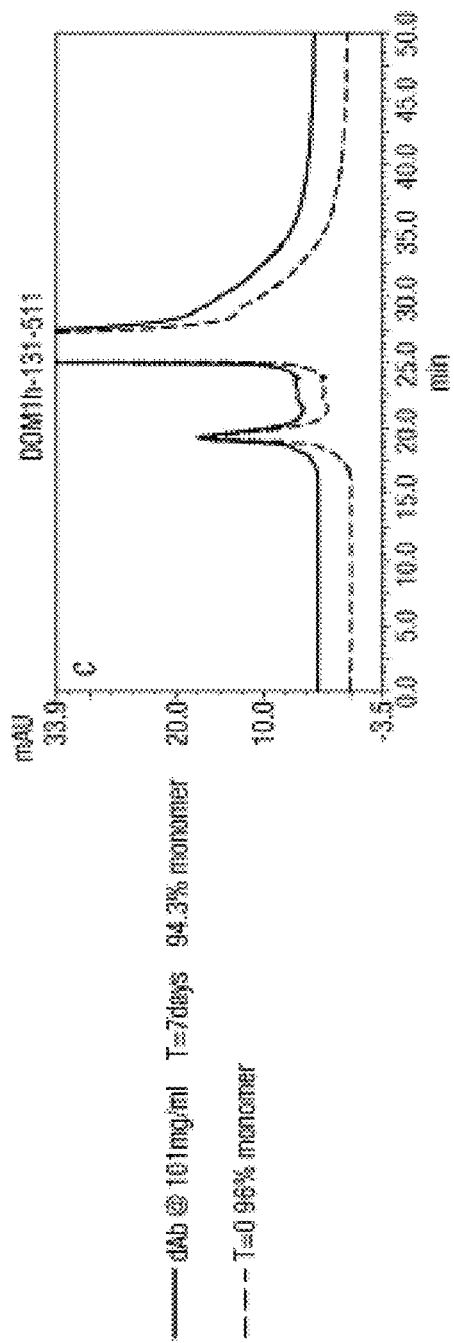

FIG. 29: Illustrates Effects of storing A: DOM1h-131-202, B: DOM1h-131-206 and C: DOM1h-131-511 at ~100 mg/ml for 7 days in Britton-Robinson buffer at +4° C. The UV was monitored at 280 nm.

Figure 30:
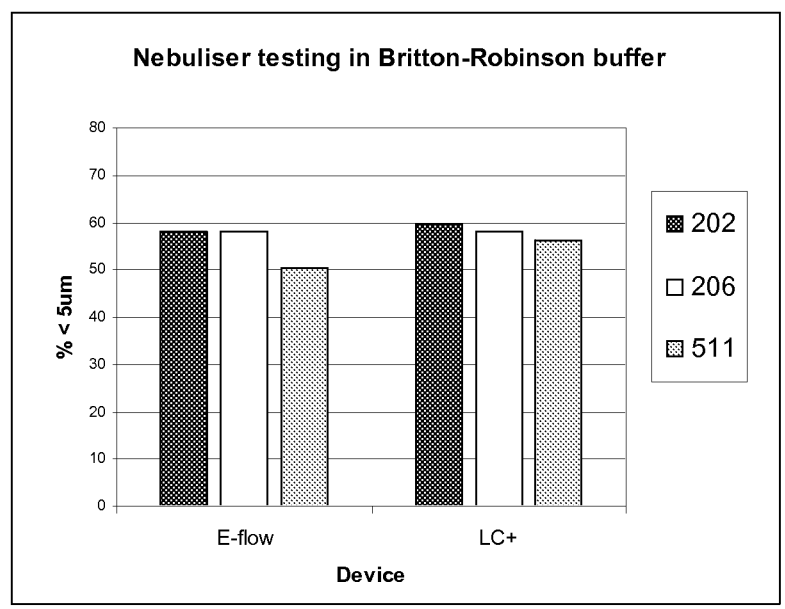

FIG. 30: Shows data from Nebuliser testing of DOM1h-131-202, DOM1h-131-206 and DOM1h-131-511 in the PARI EFLOW™ and PARI LC+™. The protein concentration was 5 mg/ml in either Britton-Robinson buffer.

Figure 31:
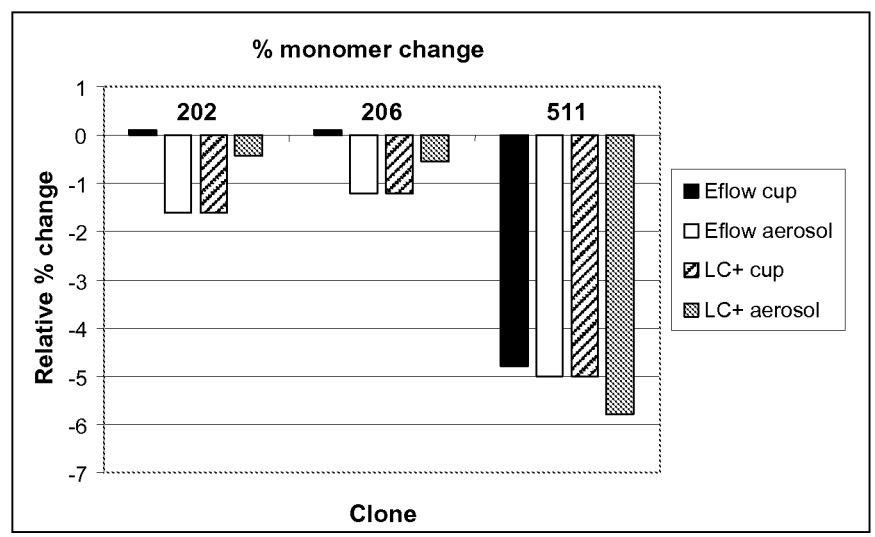

FIG. 31: Illustrates the Relative percentage changes in monomer concentrations during nebulisation of DOM1h-131-202, DOM1h-131-206 and DOM1h-131-511 in Britton-Robinson buffer at 5 mg/ml.

Figure 32:
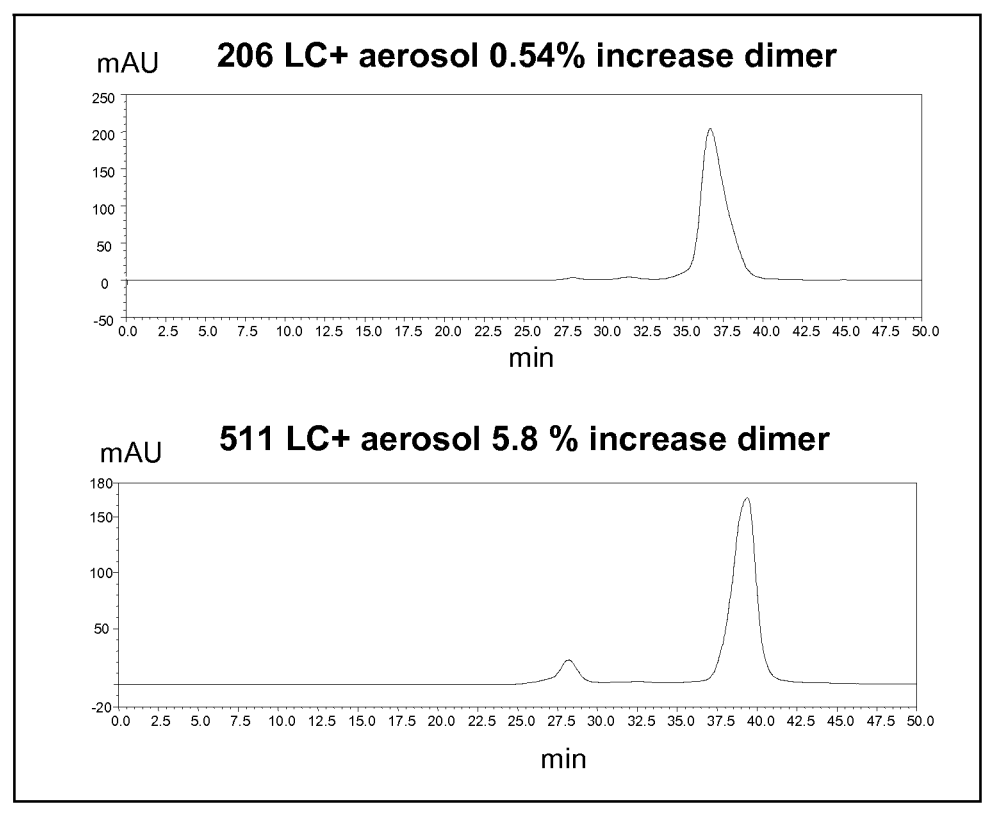

FIG. 32: Shows SEC traces of DOM1h-131-206 and DOM1h-131-511 in Britton-Robinson buffer post nebulisation from the PARI LC+™.

Figure 33:
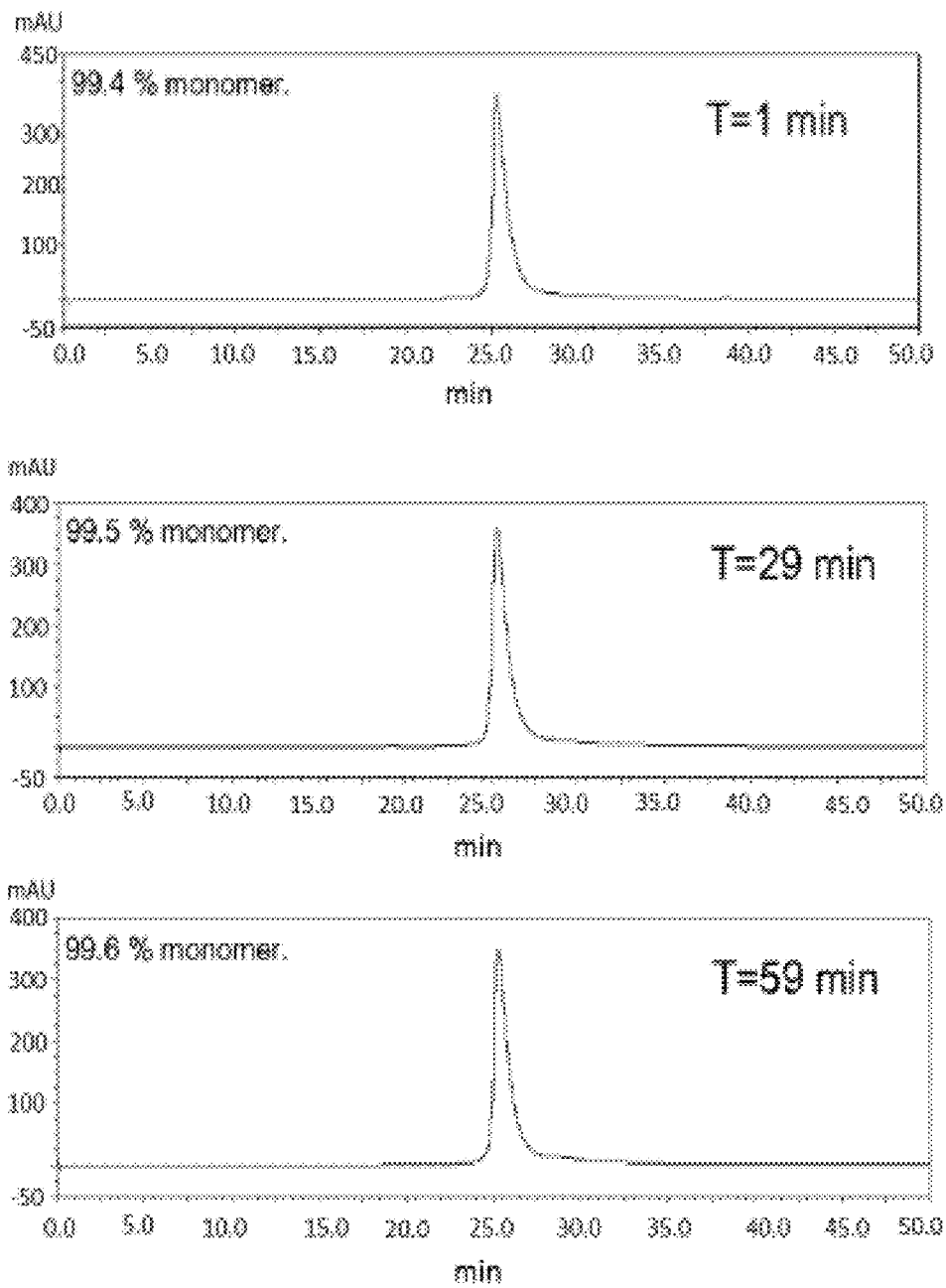

FIG. 33: Shows SEC traces of DOM1h-131-206 during the nebulisation process over 1 hour at 40 mg/ml in PBS. The protein in both the nebuliser cup and aerosol are highly resistance to the effects of shear and thermal stress that may be experienced by the DAB™ during nebulisation.

FIG. 34: Shows the sedimentation velocity curves for each of the three lead proteins (DOM1h-131-206 and DOM1h-131-511 and DOM1h-131-202) The bimodal peak observed for the lower concentration sample of DOM1h-131-206 is an artefact owing to a sample leak from the cell in this instance.

FIG. 35: Shows the effect of buffer and device on nebulised droplet size of GSK 1995056A (DOM1h-131-511).

FIG. 36: Stability of GSK1995056A (DOM1h-131-511) after nebulisation in various devices assessed by dimer formation as measured by SEC.

FIG. 37: Shows nebuliser testing of GSK1922567A (202), GSK1995057A (206) and GSK1995056A (511) in the PARI EFLOW™ and LC+. A) testing in Britton-Robinson buffer, B) testing in PEG 1000/sucrose buffer.

FIG. 38: Depicts a TNF-α dose curve in the human TNFR1 receptor binding assay. Each sample was tested as four replicates.

FIG. 39: Shows Inhibition by GSK1922567A (DOM1h-131-202), GSK1995057A (DOM1h-131-206) and GSK1995056A (DOM1h-131-511) in the human TNFR1 receptor binding assay. Each sample was tested as four replicates.

FIG. 40: Illustrates potency of the DOM15-26 and DOM15-26-593 DAB™s in the VEGF RBA.

FIG. 41: Shows pharmacokinetics of DMS 1529 (DOM15-26-593) and DMS1545 (DOM15-26-501) after single bolus dose i.v. administration to rats at 5 mg/mg FIG. 42A: Shows SEC-MALLs (Size exclusion chromatograph-multi-angle laser light scattering) analysis of DMS1529 Fc fusion (DOM15-26-593 Fc fusion) confirming monomeric properties. Two different batches are shown that demonstrate similar properties with regard to refractive index (i.e. concentration; broken lines) and light scattering (solid lines). The line marked with the arrow signifies the molecular mass calculation.

FIG. 42B: Shows AUC (analytical ultracentrifugation) analysis of DMS 1529 Fc fusion (DOM15-26-593 Fc fusion) confirming monomeric properties. One batch of material was tested at three different concentrations, approximating to 0.2, 0.5 & 1.0 mg/ml in PBS buffer. The analysis of the sedimentation rate confirmed a molecular mass of approx. 80 kDa.

FIG. 43: Shows DSC traces of DMS1529 (DOM15-26-593) and DOM15-26-501.

FIG. 44: Is a VEGF Binding ELISA for DMS 1529 (DOM15-26-593) before and after, 10 freeze-thaw cycles on two different batches of material.

FIG. 45: Shows the consistency of DOM15-26-593 SEC profile before and after 10 freeze thaw cycles.

FIG. 46: Illustrates results from an accelerated stability study of the DMS 1529 fusion (DOM15-26-593 Fc fusion); binding ELISA demonstrating activity after 7 days incubation at the temperature shown.

FIG. 47A: Shows stability of DMS1529 (DOM15-26-593) in cynomolgus serum after 14 & 15 days incubation at 37° C.

FIG. 47B: Shows stability of DMS1529 (DOM15-26-593) in human serum after 14 & 15 days incubation at 37° C.

FIG. 48: Shows potency of DOM15-26 & DOM15-26-593 DAB™s as Fc fusions (DMS1564 & 1529 respectively) in the VEGF RBA.

FIG. 49: Illustrates inhibition of HUVEC cell proliferation by the DMS 1529 fusion (DOM15-26-593 FC fusion).

FIG. 50: pDom33 vector map.

Figure 51A:
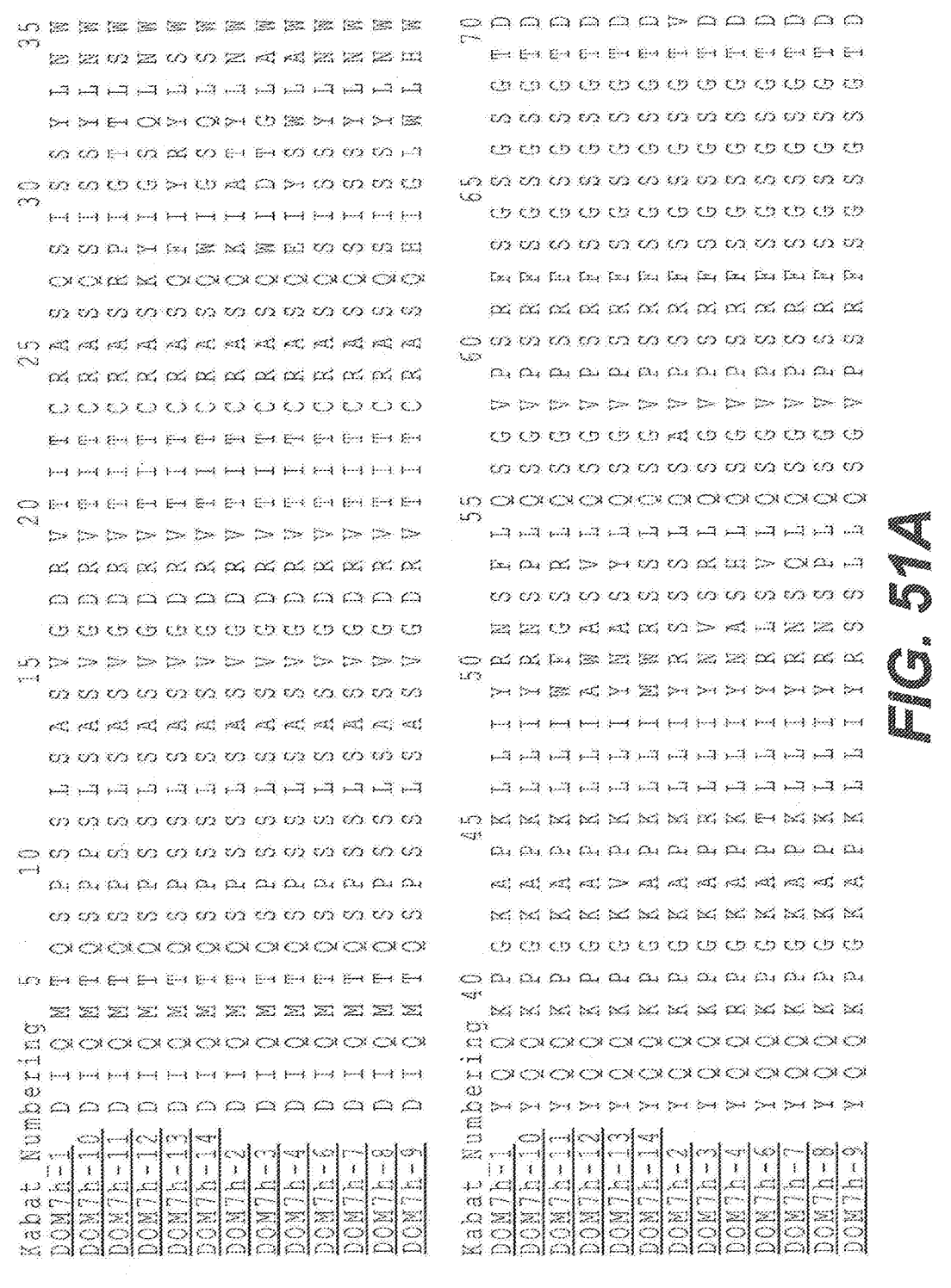
Figure 51A:
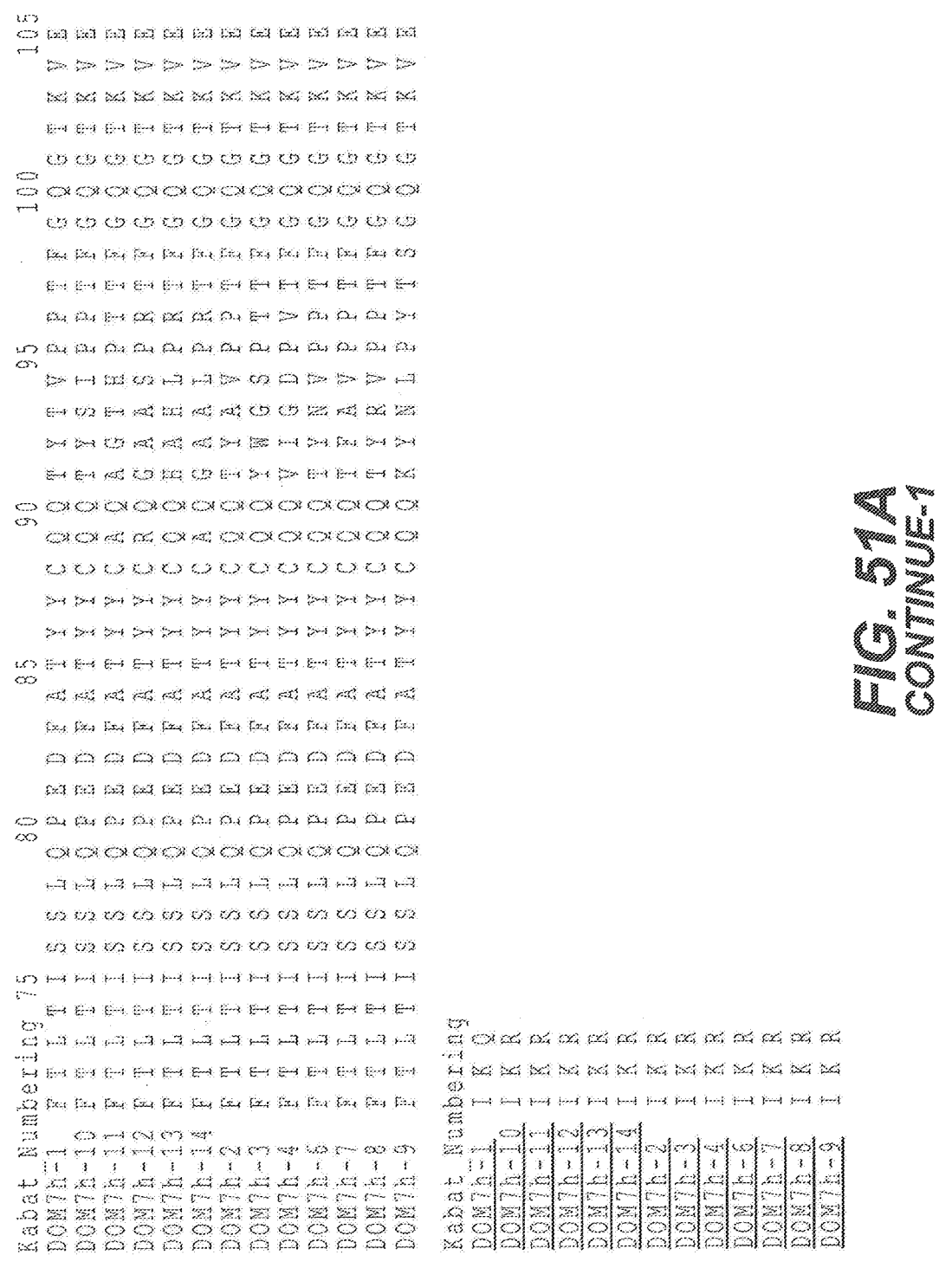
Figure 51A:
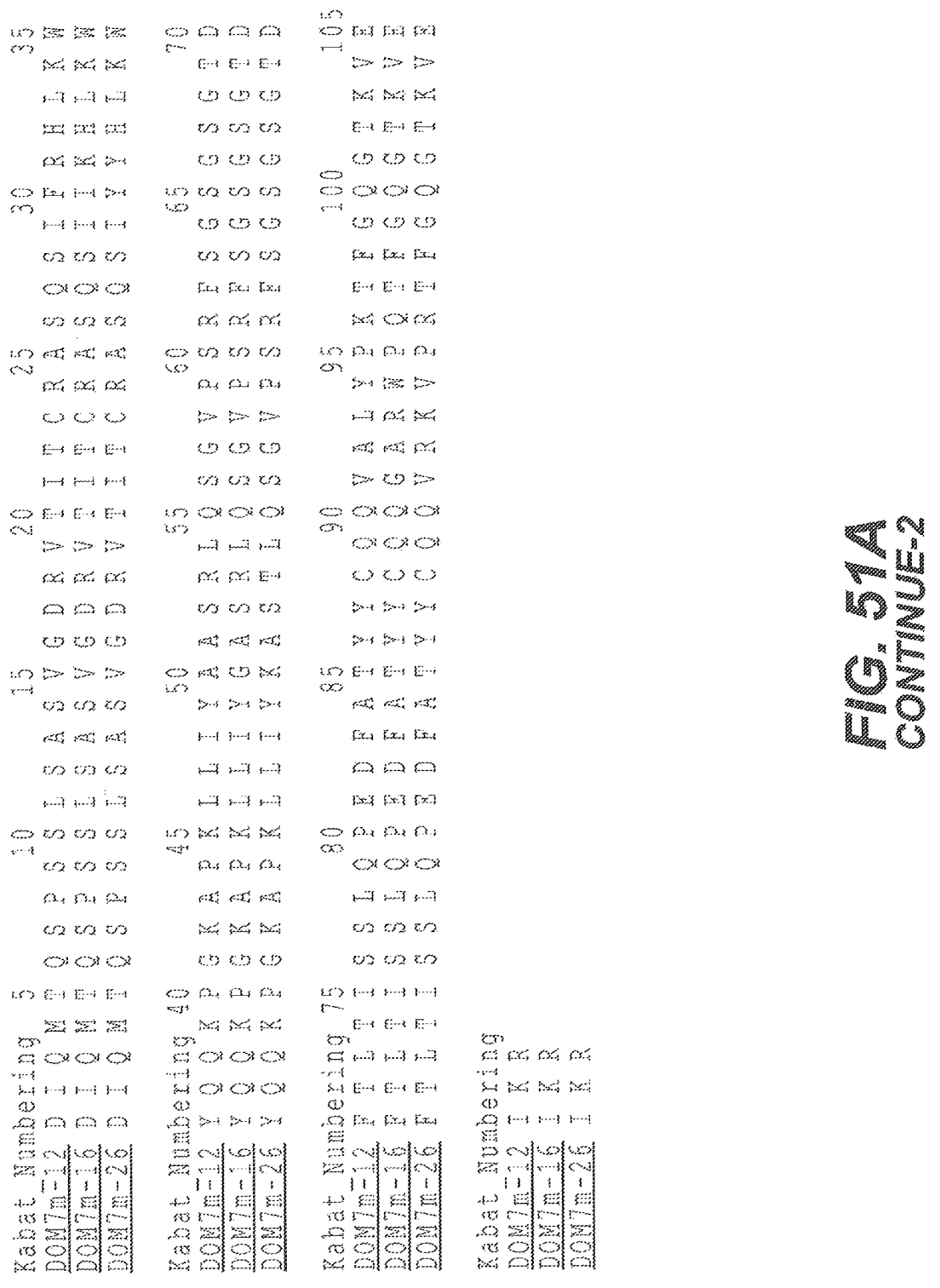
Figure 51A:
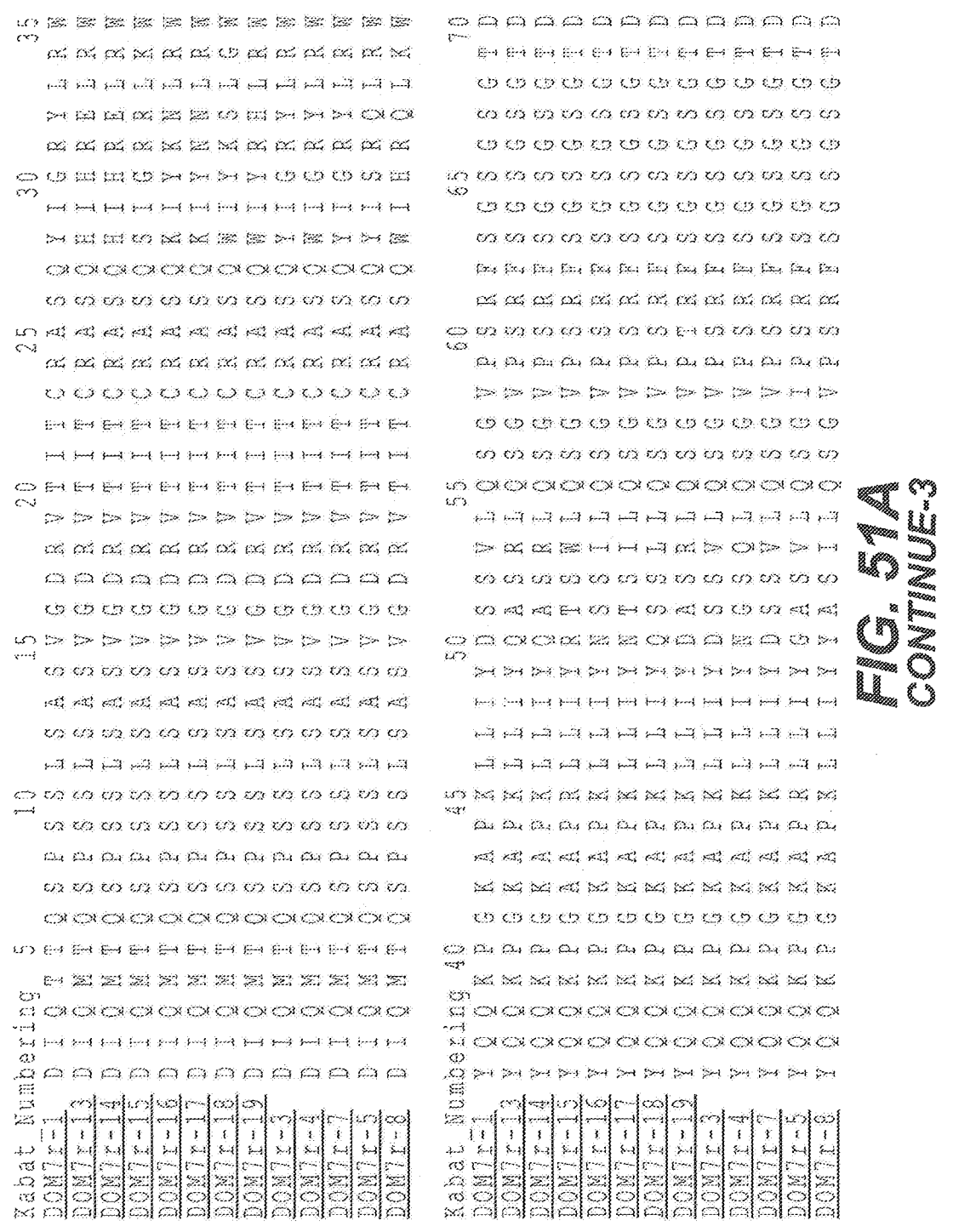
Figure 51A:
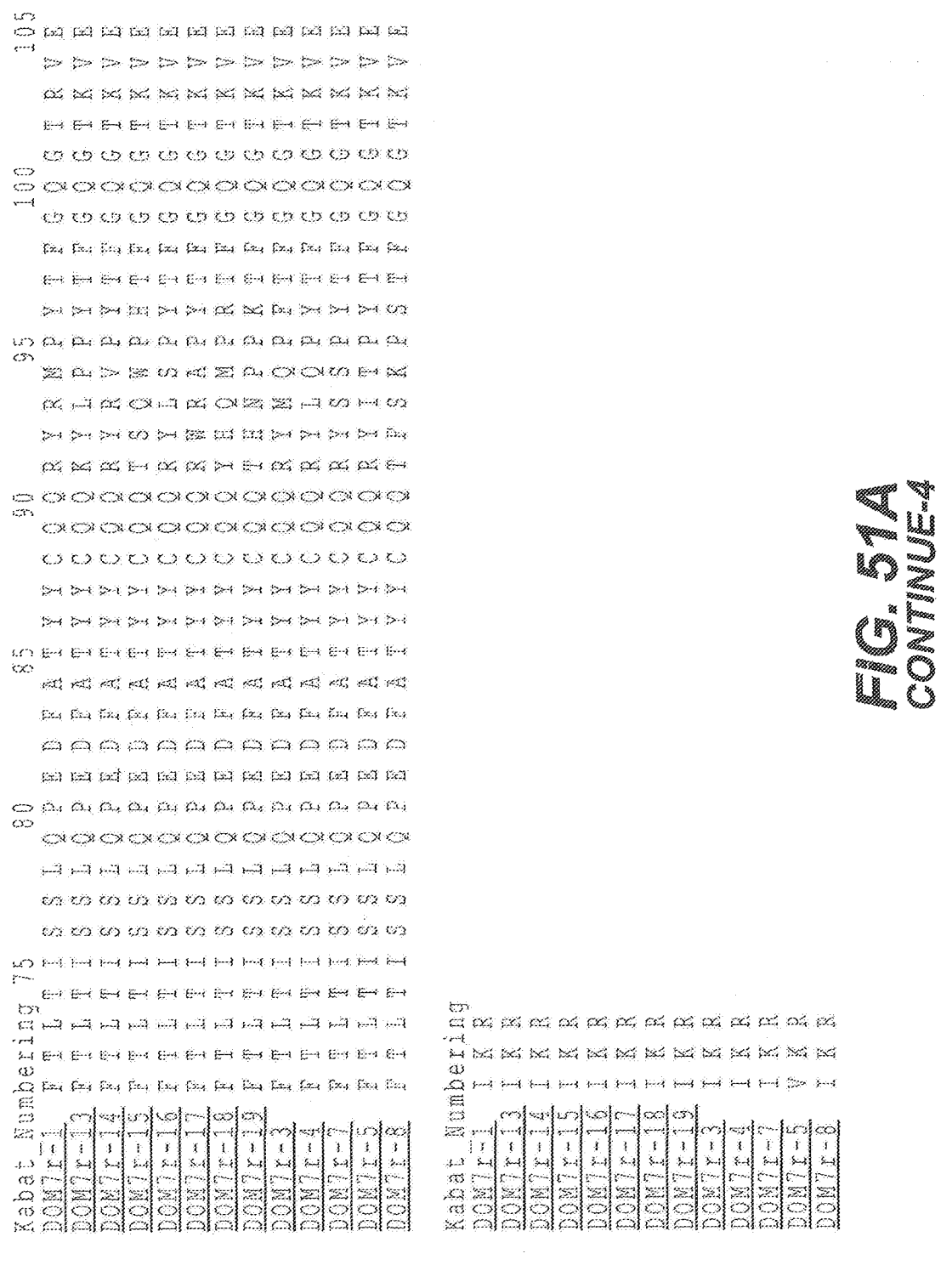
Figure 51A:
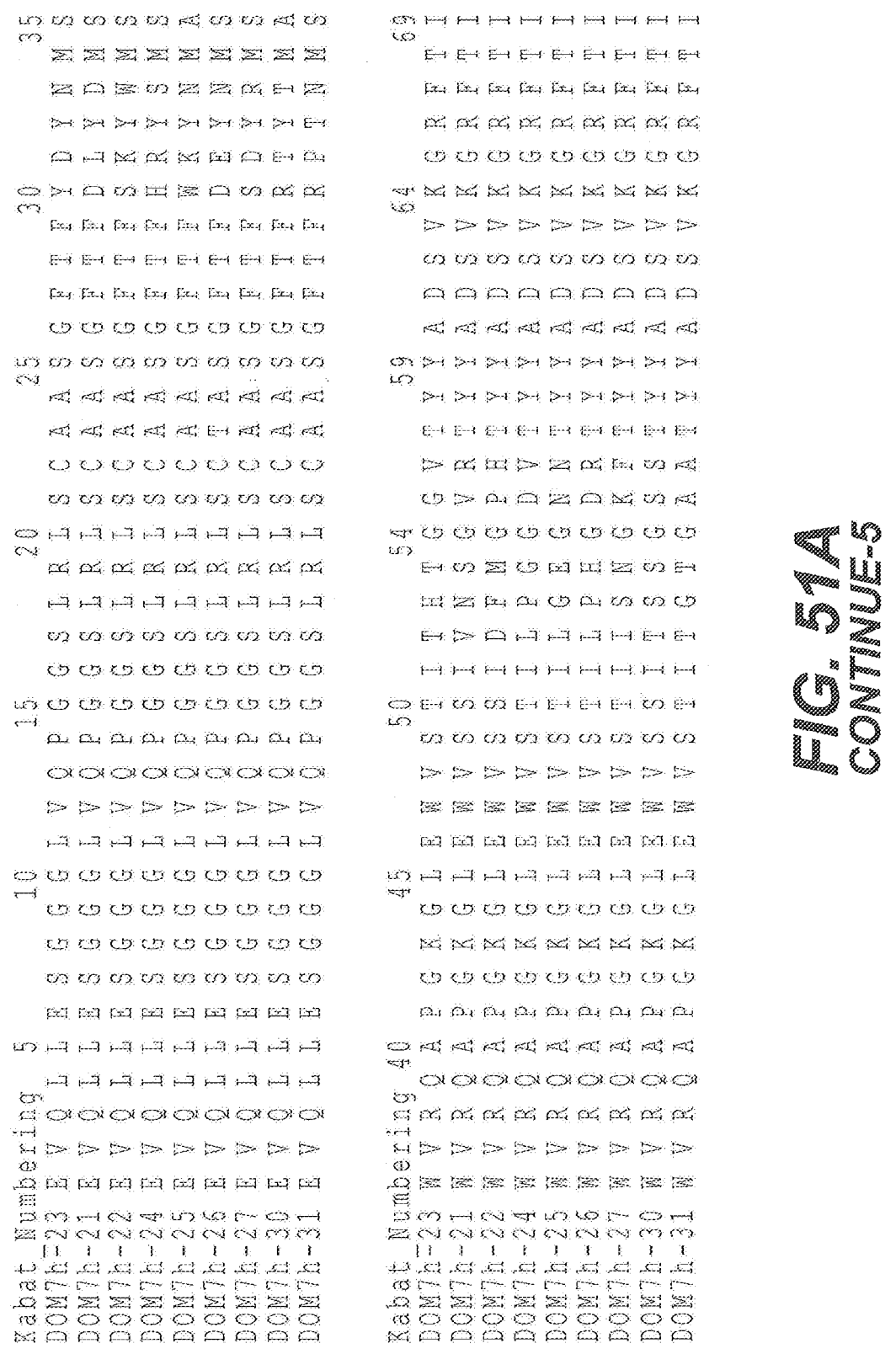
Figure 51A:
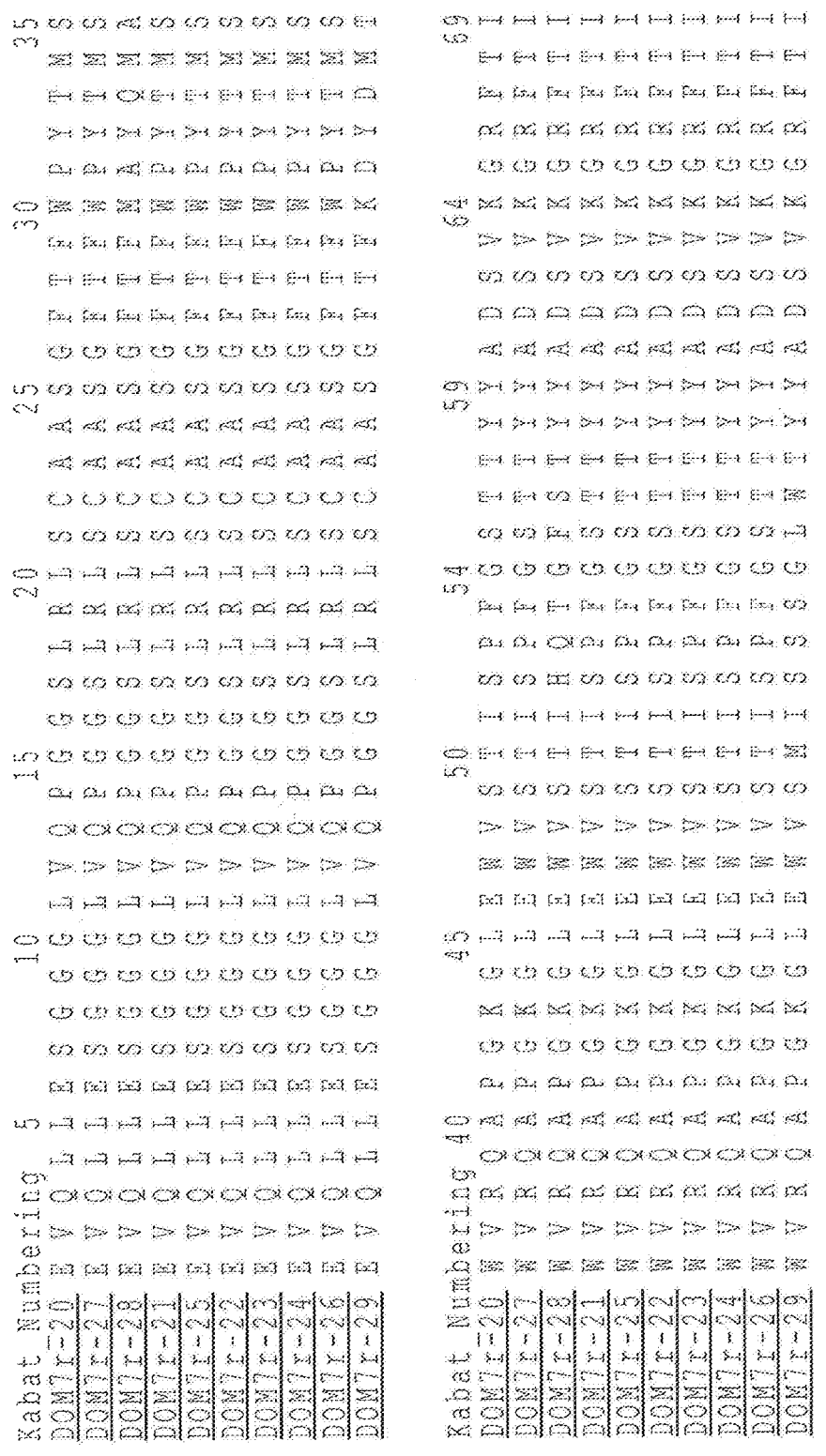
Figure 51A:
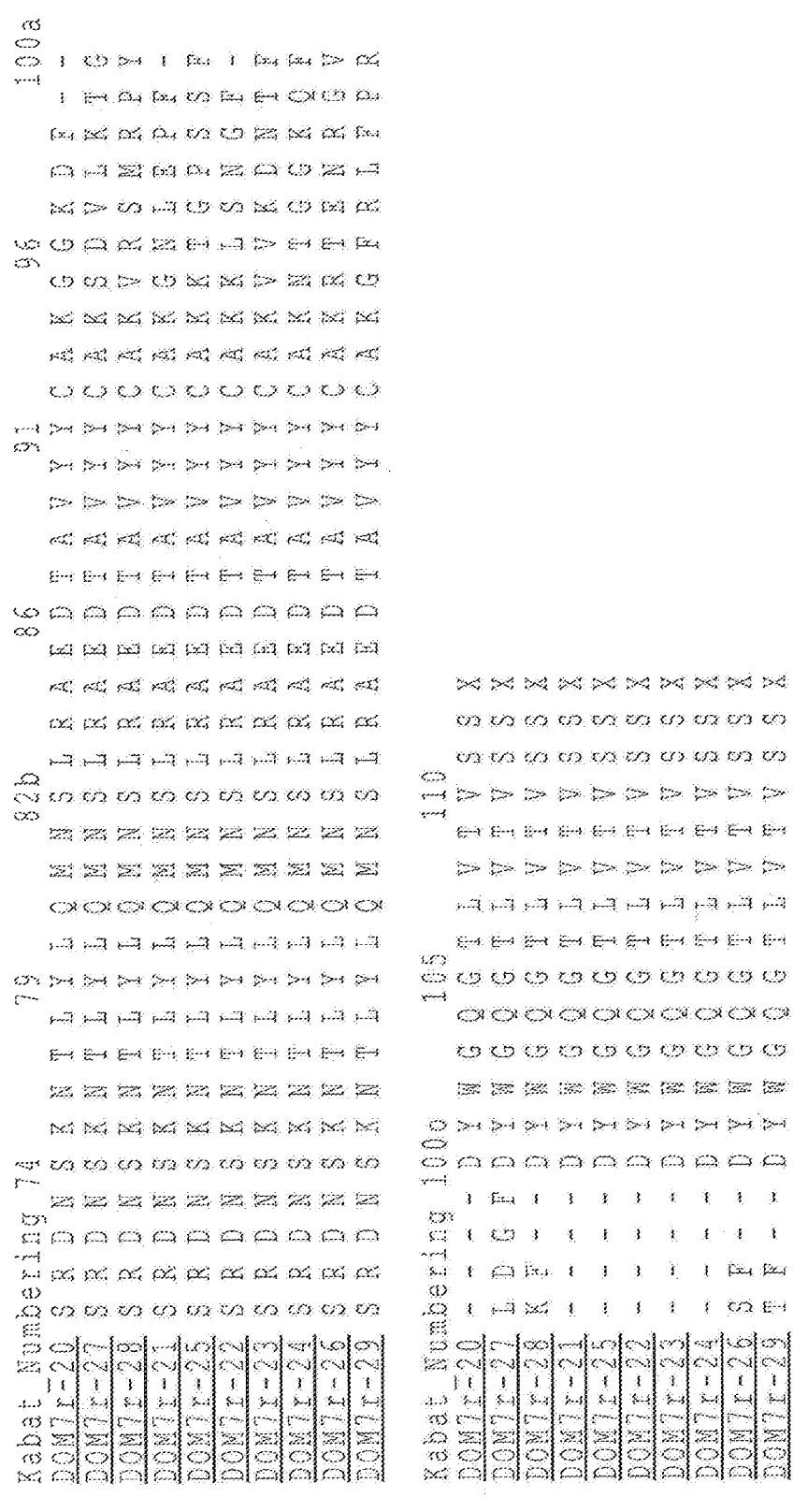

FIGS. 51A-51B: Depict sequences (amino acid and nucleotide as shown in SEQ ID NO:s 103-221 and 263) of DAB™s that bind serum albumin.

FIGS. 52A-52C: Depict the amino acid sequence of DOM15-26-593-Fc fusion (as shown in SEQ ID NO: 264), the amino acid sequence of the human IgG1 Fc portion (as shown in SEQ ID NO: 265) of the DOM15-26-593-Fc fusion and a nucleic acid sequence encoding the DOM15-26-593-Fc fusion (as shown in SEQ ID NO: 266).

FIG. 53: Codon Optimised Sequence 1

FIG. 54: Codon Optimised Sequence 2

FIG. 55: Codon Optimised Sequence 3

FIG. 56: Codon Optimised Sequence 4

FIG. 57: Codon Optimised Sequence 5

DETAILED DESCRIPTION OF THE INVENTION

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods.

As used herein, the term "antagonist of Tumor Necrosis Factor Receptor 1 (TNFR1)" or "anti-TNFR1 antagonist" or the like refers to an agent (e.g., a molecule, a compound) which binds TNFR1 and can inhibit a (i.e., one or more) function of TNFR1. For example, an antagonist of TNFR1 can inhibit the binding of TNFα to TNFR1 and/or inhibit signal transduction mediated through TNFR1. Accordingly, TNFR1-mediated processes and cellular responses (e.g., TNFα-induced cell death in a standard L929 cytotoxicity assay) can be inhibited with an antagonist of TNFR1.

As used herein, "peptide" refers to about two to about 50 amino acids that are joined together via peptide bonds.

As used herein, "polypeptide" refers to at least about 50 amino acids that are joined together by peptide bonds. Polypeptides generally comprise tertiary structure and fold into functional domains.

As used herein, a peptide or polypeptide (e.g. a domain antibody (DAB™)) that is "resistant to protease degradation" is not substantially degraded by a protease when incubated with the protease under conditions suitable for protease activity. A polypeptide (e.g., a DAB™) is not substantially degraded when no more than about 25%, no more than about 20%, no more than about 15%, no more than about 14%, no more than about 13%, no more than about 12%, no more than about 11%, no more than about 10%, no more than about 9%, no more than about 8%, no more than about 7%, no more than about 6%, no more than about 5%, no more than about 4%, no more than about 3%, no more that about 2%, no more than about 1%, or substantially none of the protein is degraded by protease after incubation with the protease for about one hour at a temperature suitable for protease activity. For example at 37 or 50 degrees C. Protein degradation can be assessed using any suitable method, for example, by SDS-PAGE or by functional assay (e.g., ligand binding) as described herein.

As used herein, "display system" refers to a system in which a collection of polypeptides or peptides are accessible for selection based upon a desired characteristic, such as a physical, chemical or functional characteristic. The display system can be a suitable repertoire of polypeptides or peptides (e.g., in a solution, immobilized on a suitable support). The display system can also be a system that employs a cellular expression system (e.g., expression of a library of nucleic acids in, e.g., transformed, infected, transfected or transduced cells and display of the encoded polypeptides on the surface of the cells) or an acellular expression system (e.g., emulsion compartmentalization and display). Exemplary display systems link the coding function of a nucleic acid and physical, chemical and/or functional characteristics of a polypeptide or peptide encoded by the nucleic acid. When such a display system is employed, polypeptides or peptides that have a desired physical, chemical and/or functional characteristic can be selected and a nucleic acid encoding the selected polypeptide or peptide can be readily isolated or recovered. A number of display systems that link the coding function of a nucleic acid and physical, chemical and/or functional characteristics of a polypeptide or peptide are known in the art, for example, bacteriophage display (phage display, for example phagemid display), ribosome display, emulsion compartmentalization and display, yeast display, puromycin display, bacterial display, display on plasmid, covalent display and the like. (See, e.g., EP 0436597 (Dyax), U.S. Pat. No. 6,172,197 (McCafferty et al.), U.S. Pat. No. 6,489,103 (Griffiths et al.).)

As used herein, "repertoire" refers to a collection of polypeptides or peptides that are characterized by amino acid sequence diversity. The individual members of a repertoire can have common features, such as common structural features (e.g., a common core structure) and/or common functional features (e.g., capacity to bind a common ligand (e.g., a generic ligand or a target ligand, TNFR1)).

As used herein, "functional" describes a polypeptide or peptide that has biological activity, such as specific binding activity. For example, the term "functional polypeptide" includes an antibody or antigen-binding fragment thereof that binds a target antigen through its antigen-binding site.

As used herein, "generic ligand" refers to a ligand that binds a substantial portion (e.g., substantially all) of the functional members of a given repertoire. A generic ligand (e.g., a common generic ligand) can bind many members of a given repertoire even though the members may not have binding specificity for a common target ligand. In general, the presence of a functional generic ligand-binding site on a polypeptide (as indicated by the ability to bind a generic ligand) indicates that the polypeptide is correctly folded and functional. Suitable examples of generic ligands include superantigens, antibodies that bind an epitope expressed on a substantial portion of functional members of a repertoire, and the like.

"Superantigen" is a term of art that refers to generic ligands that interact with members of the immunoglobulin superfamily at a site that is distinct from the target ligand-binding sites of these proteins. Staphylococcal enterotoxins are examples of superantigens which interact with T-cell receptors. Superantigens that bind antibodies include Protein G, which binds the IgG constant region (Bjorck and Kronvall, *J. Immunol.*, 133:969 (1984)); Protein A which binds the IgG constant region and $V_H$ domains (Forsgren and Sjoquist, *J. Immunol.*, 97:822 (1966)); and Protein L which binds $V_L$ domains (Bjorck, *J. Immunol.*, 140:1194 (1988)).

As used herein, "target ligand" refers to a ligand which is specifically or selectively bound by a polypeptide or peptide. For example, when a polypeptide is an antibody or antigen-binding fragment thereof, the target ligand can be any desired antigen or epitope. Binding to the target antigen is dependent upon the polypeptide or peptide being functional.

As used herein an antibody refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a DAB™, $V_H$, $V_{HH}$, $V_L$), and modified versions of any of the foregoing (e.g., modified by the covalent attachment of polyethylene glycol or other suitable polymer or a humanized $V_{HH}$).

The phrase "immunoglobulin single variable domain" refers to an antibody variable domain ($V_H$, $V_{HH}$, $V_L$) that specifically binds an antigen or epitope independently of other V regions or domains. An immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "DAB™" is the same as an "immunoglobulin single variable domain" as the term is used herein. A "single immunoglobulin variable domain" is the same as an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ DAB™s. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The term "library" refers to a mixture of heterogeneous polypeptides or nucleic acids. The library is composed of members, each of which has a single polypeptide or nucleic acid sequence. To this extent, "library" is synonymous with "repertoire." Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. In one embodiment, each individual organism or cell contains only one or a limited number of library members. In one embodiment, the nucleic acids are incorporated into expression vectors, in order to allow expression of the polypeptides encoded by the nucleic acids. In an aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of diverse polypeptides.

A "universal framework" is a single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, (1987) *J. Mol. Biol.* 196:910-917. Libraries and repertoires can use a single framework, or a set of such frameworks, which has been found to permit the derivation of virtually any binding specificity though variation in the hypervariable regions alone.

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds target antigen) administered to a subject over the course of one day (24 hours) (daily dose), two days, one week, two weeks, three weeks or one or more months (e.g., by a single administration, or by two or more administrations). The interval between doses can be any desired amount of time.

The phrase, "half-life," refers to the time taken for the serum concentration of the ligand (eg, DAB™, polypeptide or antagonist) to reduce by 50%, in vivo, for example due to degradation of the ligand and/or clearance or sequestration of the ligand by natural mechanisms. The ligands of the invention may be stabilized in vivo and their half-life increased by binding to molecules which resist degradation and/or clearance or sequestration. Typically, such molecules are naturally occurring proteins which themselves have a long half-life in vivo. The half-life of a ligand is increased if its functional activity persists, in vivo, for a longer period than a similar ligand which is not specific for the half-life increasing molecule. For example, a ligand specific for human serum albumin (HAS) and a target molecule is compared with the same ligand wherein the specificity to HSA is not present, that is does not bind HSA but binds another molecule. For example, it may bind a third target on the cell. Typically, the half-life is increased by 10%, 20%, 30%, 40%, 50% or more. Increases in the range of 2×, 3×, 4×, 5×, 10×, 20×, 30×, 40×, 50× or more of the half-life are possible. Alternatively, or in addition, increases in the range of up to 30×, 40×, 50×, 60×, 70×, 80×, 90×, 100×, 150× of the half-life are possible.

As used herein, "hydrodynamic size" refers to the apparent size of a molecule (e.g., a protein molecule, ligand) based on the diffusion of the molecule through an aqueous solution. The diffusion, or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein.

As referred to herein, the term "competes" means that the binding of a first target to its cognate target binding domain is inhibited in the presence of a second binding domain that is specific for said cognate target. For example, binding may be inhibited sterically, for example by physical blocking of a binding domain or by alteration of the structure or environment of a binding domain such that its affinity or avidity for a target is reduced. See WO2006038027 for details of how to perform competition ELISA and competition BIA-CORE™ experiments to determine competition between first and second binding domains.

Calculations of "homology" or "identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In an embodiment, the length of a reference sequence aligned for comparison purposes is at least 30%, or at least 40%, or at least 50%, or at least 60%, or at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences. Amino acid and nucleotide sequence alignments and homology, similarity or identity, as defined herein may be prepared and determined using the algorithm BLAST 2 Sequences, using default parameters (Tatusova, T. A. et al., *FEMS Microbiol Lett,* 174:187-188 (1999)).

Selection Methods

The invention in one embodiment relates to polypeptides and DAB™s selected by a method of selection of protease resistant peptides and polypeptides that have a desired biological activity. Two selective pressures are used in the method to produce an efficient process for selecting polypeptides that are highly stable and resistant to protease degradation, and that have desired biological activity. As described herein, protease resistant peptides and polypeptides generally retain biological activity. In contrast, protease sensitive peptides and polypeptides are cleaved or digested by protease in the methods described herein, and therefore, lose their biological activity. Accordingly, protease resistant peptides or polypeptides are generally selected based on their biological activity, such as binding activity.

The methods described herein provide several advantages. For example, as disclosed and exemplified herein, variable domains, antagonists, peptides or polypeptides that are selected for resistance to proteolytic degradation by one protease (e.g., trypsin), are also resistant to degradation by other proteases (e.g., elastase, leucozyme). In one embodiment protease resistance correlates with a higher melting temperature (Tm) of the peptide or polypeptide. Higher melting temperatures are indicative of more stable variable domains, antagonists, peptides and polypeptides. Resistance to protease degradation also correlates in one embodiment with high affinity binding to target ligands. Thus, the methods described herein provide an efficient way to select, isolate and/or recover variable domains, antagonists, peptides, polypeptides that have a desired biological activity and that are well suited for in vivo therapeutic and/or diagnostic uses because they are protease resistant and stable. In one embodiment protease resistance correlates with an improved PK, for example improved over n variable domain, antagonist, peptide or polypeptide that is not protease resistant. Improved PK may be an improved AUC (area under the curve) and/or an improved half-life. In one embodiment protease resistance correlates with an improved stability of the variable domain, antagonist, peptide or polypeptide to shear and/or thermal stress and/or a reduced propensity to aggregate during nebulisation, for example improved over an variable domain, antagonist, peptide or polypeptide that is not protease resistant. In one embodiment protease resistance correlates with an improved storage stability, for example improved over an variable domain, antagonist, peptide or polypeptide that is not protease resistant. In one aspect, one, two, three, four or all of the advantages are provided, the advantages being resistance to protease degradation, higher Tm and high affinity binding to target ligand.

In one aspect, there is provided a method for selecting, isolating and/or recovering a peptide or polypeptide from a library or a repertoire of peptides and polypeptides (e.g., a display system) that is resistant to degradation by a protease (e.g., one or more proteases). In one embodiment, the method is a method for selecting, isolating and/or recovering a polypeptide from a library or a repertoire of peptides and polypeptides (e.g., a display system) that is resistant to degradation by a protease (e.g., one or more proteases). Generally, the method comprises providing a library or repertoire of peptides or polypeptides, combining the library or repertoire with a protease (e.g., trypsin, elastase, leucozyme, pancreatin, sputum) under conditions suitable for protease activity, and selecting, isolating and/or recovering a peptide or polypeptide that is resistant to degradation by the protease and has a desired biological activity. Peptides or polypeptides that are degraded by a protease generally have reduced biological activity or lose their biological activity due to the activity of protease. Accordingly, peptides or polypeptides that are resistant to protease degradation can be selected, isolated and/or recovered using the method based on their biological activity, such as binding activity (e.g., binding a general ligand, binding a specific ligand, binding a substrate), catalytic activity or other biological activity.

The library or repertoire of peptides or polypeptides is combined with a protease (e.g., one or more proteases) under conditions suitable for proteolytic activity of the protease. Conditions that are suitable for proteolytic activity of protease, and biological preparations or mixtures that contain proteolytic activity, are well-known in the art or can be readily determined by a person of ordinary skill in the art. If desired, suitable conditions can be identified or optimized, for example, by assessing protease activity under a range of pH conditions, protease concentrations, temperatures and/or by varying the amount of time the library or repertoire and the protease are permitted to react. For example, in some embodiments, the ratio (on a mole/mole basis) of protease, eg trypsin, to peptide or polypeptide (eg, variable domain) is 800 to 80,00 (eg, 8,000 to 80,000) protease:peptide or polypeptide, eg when 10 micrograms/ml of protease is used, the ratio is 800 to 80,000 protease:peptide or polypeptide; or when 100 micrograms/ml of protease is used, the ratio is 8,000 to 80,000 protease:peptide or polypeptide. In one embodiment the ratio (on a weight/weight, eg microgram/microgram basis) of protease (eg, trypsin) to peptide or polypeptide (eg, variable domain) is 1,600 to 160,000 (eg, 16,000 to 160,000) protease:peptide or polypeptide eg when 10 micrograms/ml of protease is used, the ratio is 1,600 to 160,000 protease:peptide or polypeptide; or when 100 micrograms/ml of protease is used, the ratio is 16,000 to 160,000 protease:peptide or polypeptide. In one embodiment, the protease is used at a concentration of at least 100 or 1000 micrograms/ml and the protease:peptide ratio (on a mole/mole basis) of protease, eg trypsin, to peptide or polypeptide (eg, variable domain) is 8,000 to 80,000 protease:peptide or polypeptide. In one embodiment, the protease is used at a concentration of at least 10 micrograms/ml and the protease:peptide ratio (on a mole/mole basis) of protease, eg trypsin, to peptide or polypeptide (eg, variable domain) is 800 to 80,000 protease:peptide or polypeptide. In one embodiment the ratio (on a weight/weight, eg microgram/microgram basis) of protease (eg, trypsin) to peptide or polypeptide (eg, variable domain) is 1600 to 160,000 protease:peptide or polypeptide eg when C is 10 micrograms/ml; or when C or C' is 100 micrograms/ml, the ratio is 16,000 to 160,000 protease:peptide or polypeptide. In one embodiment, the concentration (c or c') is at least 100 or 1000 micrograms/ml protease. For testing an individual or isolated peptide or polypeptide (eg, an immunoglobulin variable domain), eg one that has already been isolated from a repertoire or library, a protease can be added to a solution of peptide or polypeptide in a suitable buffer (e.g., PBS) to produce a peptide or polypeptide/protease solution, such as a solution of at least about 0.01% (w/w) protease/peptide or polypeptide, about 0.01% to about 5% (w/w) protease/peptide or polypeptide, about 0.05% to about 5% (w/w) protease/peptide or polypeptide, about 0.1% to about 5% (w/w) protease/peptide or polypeptide, about 0.5% to about 5% (w/w) protease/peptide or polypeptide, about 1% to about 5% (w/w) protease/peptide or polypeptide, at least about 0.01% (w/w) protease/peptide or polypeptide, at least about 0.02% (w/w) protease/peptide or polypeptide, at least about 0.03% (w/w) protease/peptide or polypeptide, at least about 0.04% (w/w) protease/peptide or polypeptide, at least about 0.05% (w/w) protease/peptide or polypeptide, at least about 0.06% (w/w) protease/peptide or polypeptide, at least about 0.07% (w/w) protease/peptide or polypeptide, at least about 0.08% (w/w) protease/peptide or polypeptide, at least about 0.09% (w/w) protease/peptide or polypeptide, at least about 0.1% (w/w) protease/peptide or polypeptide, at least about 0.2% (w/w) protease/peptide or polypeptide, at least about 0.3% (w/w) protease/peptide or polypeptide, at least about 0.4% (w/w) protease/peptide or polypeptide, at least about 0.5% (w/w) protease/peptide or polypeptide, at least about 0.6% (w/w) protease/peptide or polypeptide, at least about 0.7% (w/w) protease/peptide or polypeptide, at least about 0.8% (w/w) protease/peptide or polypeptide, at least about 0.9% (w/w) protease/peptide or polypeptide, at least about 1% (w/w) protease/peptide or polypeptide, at least about 2% (w/w) protease/peptide or polypeptide, at least about 3% (w/w) protease/peptide or polypeptide, at least about 4% (w/w) protease/peptide or polypeptide, or about 5% (w/w) protease/peptide or polypeptide. The mixture can be incubated at a suitable temperature for protease activity (e.g., room temperature, about 37° C.) and samples can be taken at time intervals (e.g., at 1 hour, 2 hours, 3 hours, etc.). The samples can be analyzed for protein degradation using any suitable method, such as SDS-PAGE analysis or ligand binding, and the results can be used to establish a time course of degradation.

Any desired protease or proteases can be used in the methods described herein. For example, a single protease, any desired combination of different proteases, or any biological preparation, biological extract, or biological homogenate that contains proteolytic activity can be used. It is not necessary that the identity of the protease or proteases that are used be known. Suitable examples of proteases that can be used alone or in any desired combination include serine protease, cysteine protease, aspartate proteases, thiol proteases, matrix metalloprotease, carboxypeptidase (e.g., carboxypeptidase A, carboxypeptidase B), trypsin, chymotrypsin, pepsin, papain, elastase, leukozyme, pancreatin, thrombin, plasmin, cathepsins (e.g., cathepsin G), proteinase (e.g., proteinase 1, proteinase 2, proteinase 3), thermolysin, chymosin, enteropeptidase, caspase (e.g., caspase 1, caspase 2, caspase 4, caspase 5, caspase 9, caspase 12, caspase 13), calpain, ficain, clostripain, actinidain, bromelain, separase and the like. Suitable biological extracts, homogenates and preparations that contains proteolytic activity include sputum, mucus (e.g., gastric mucus, nasal mucus, bronchial mucus), bronchoalveolar lavage, lung homogenate, lung extract, pancreatic extract, gastric fluid, saliva, tears and the like. The protease is used in an amount suitable for proteolytic degradation to occur. For example, as described herein, protease can be used at about 0.01% to about 5% (w/w, protease/peptide or polypeptide). When protease is combined with a display system that comprises the repertoire of peptides or polypeptides (e.g., a phage display system), for example, the protease can be used at a concentration of about 10 µg/ml to about 3 mg/ml, about 10 µg/ml, about 20 µg/ml, about 30 µg/ml, about 40 µg/ml, about 50 µg/ml, about 60 µg/ml, about 70 µg/ml, about 80 µg/ml, about 90 µg/ml, about 100 µg/ml, about 200 µg/ml, about 300 µg/ml, about 400 µg/ml, about 500 µg/ml, about 600 µg/ml, about 700 µg/ml, about 800 µg/ml, about 900 µg/ml, about 1000 µg/ml, about 1.5 mg/ml, about 2 mg/ml, about 2.5 mg/ml or about 3 mg/ml.

The protease is incubated with the collection of peptides or polypeptides (library or repertoire) at a temperature that is suitable for activity of the protease. For example, the protease and collection of peptides or polypeptides can be incubated at a temperature of about 20° C. to about 40° C. (e.g., at room temperature, about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C.). The protease and the collection of peptides or polypeptides are incubated together for a period of time sufficient for proteolytic degradation to occur. For example, the collection of peptides or polypeptides can be incubated together with protease for about 30 minutes to about 24 or about 48 hours. In some examples, the collection of peptides or polypeptides is incubated together with protease overnight, or for at least about 30 minutes, about 1 hour, about 1.5 hours, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, or longer.

It is generally desirable, at least in early selection rounds (e.g. when a display system is used), that the protease results in a reduction in the number of clones that have the desired biological activity that is selected for by at least one order of magnitude, in comparison to selections that do not include incubation with protease. In particular examples, the amount of protease and conditions used in the methods are sufficient to reduce the number of recovered clones by at least about one log (a factor of 10), at least about 2 logs (a factor of 100), at least about 3 logs (a factor of 1000) or at least about 4 logs (a factor of 10,000). Suitable amounts of protease and incubation conditions that will result in the desired reduction in recovered clones can be easily determined using conventional methods and/or the guidance provided herein.

The protease and collection of peptides or polypeptides can be combined and incubated using any suitable method (e.g., in vitro, in vivo or ex vivo). For example, the protease and collection of peptides or polypeptides can be combined in a suitable container and held stationary, rocked, shaken, swirled or the like, at a temperature suitable for protease activity. If desired, the protease and collection of peptides or polypeptides can be combined in an in vivo or ex vivo system, such as by introducing the collection of polypeptides (e.g., a phage display library or repertoire) into a suitable animal (e.g., a mouse), and after sufficient time for protease activity has passed, recovering the collection of peptides or polypeptides. In another example, an organ or tissue is perfused with the collection of polypeptides (e.g., a phage display library or repertoire), and after sufficient time for protease activity has passed, the collection of polypeptides is recovered.

Following incubation, a protease resistant peptide or polypeptide can be selected based on a desired biological activity, such as a binding activity. If desired, a protease inhibitor can be added before selection. Any suitable protease inhibitor (or combination of two or more protease inhibitors) that will not substantially interfere with the selection method can be used. Examples of suitable protease inhibitors include, α1-anti-trypsin, α2-macroglobulin, amastatin, antipain, antithrombin III, aprotinin, 4-(2-Aminoethyl) benzenesulfonyl fluoride hydrochloride (AEBSF), (4-amidino-phenyl)-methane-sulfonyl fluoride (APMSF), bestatin, benzamidine, chymostatin, 3,4-dichloroisocoumarin, diisoproply fluorophosphate (DIFP), E-64, ethylenediamine tetraacedic acid (EDTA), elastatinal, leupeptin, N-ethylmaleimide, phenylmethyl sulfonylfluoride (PMSF), pepstatin, 1,10-phenanthroline, phosphoramidon, serine protease inhibitors, N-tosyl-L-lysine-chloromethyl ketone (TLCK), Na-tosyl-Phe-chloromethylketone (TPCK) and the like. In addition, many preparations that contain inhibitors of several classes of proteases are commercially available (e.g., ROCHE COMPLETE PROTEASE INHIBITOR COCKTAIL TABLETS™ (Roche Diagnostics Corporation; Indianapolis, Ind., USA), which inhibits chymotrypsin, thermolysin, papain, pronase, pancreatic extract and trypsin).

A protease resistant peptide or polypeptide can be selected using a desired biological activity selection method, which allows peptides and polypeptides that have the desired biological activity to be distinguished from and selected over peptides and polypeptides that do not have the desired biological activity. Generally, peptides or polypeptides that have been digested or cleaved by protease loose their biological activity, while protease resistant peptides or polypeptides remain functional. Thus, suitable assays for biological activity can be used to select protease resistant peptides or polypeptides. For example, a common binding function (e.g., binding of a general ligand, binding of a specific ligand, or binding of a substrate) can be assessed using a suitable binding assay (e.g., ELISA, panning). For example, polypeptides that bind a target ligand or a generic ligand, such as protein A, protein L or an antibody, can be selected, isolated, and/or recovered by panning or using a suitable affinity matrix. Panning can be accomplished by adding a solution of ligand (e.g., generic ligand, target ligand) to a suitable vessel (e.g., tube, petri dish) and allowing the ligand to become deposited or coated onto the walls of the vessel. Excess ligand can be washed away and polypeptides (e.g., a phage display library) can be added to the vessel and the vessel maintained under conditions suitable for the polypeptides to bind the immobilized ligand. Unbound polypeptide can be washed away and bound polypeptides can be recovered using any suitable method, such as scraping or lowering the pH, for example.

When a phage display system is used, binding can be tested in a phage ELISA. Phage ELISA may be performed according to any suitable procedure. In one example, populations of phage produced at each round of selection can be screened for binding by ELISA to the selected target ligand or generic ligand, to identify phage that display protease resistant peptides or polypeptides. If desired, soluble peptides and polypeptides can be tested for binding to target ligand or generic ligand, for example by ELISA using reagents, for example, against a C- or N-terminal tag (see for example Winter et al. (1994) *Ann. Rev. Immunology* 12, 433-55 and references cited therein). The diversity of the selected phage may also be assessed by gel electrophoresis of PCR products (Marks et al. 1991, supra; Nissim et al. 1994 supra), probing (Tomlinson et al., 1992) *J. Mol. Biol.* 227, 776) or by sequencing of the vector DNA.

In addition to specificity for TNFR1, an antagonist or polypeptide (eg, a dual specific ligand) comprising an anti-TNFR1 protease resistant polypeptide (e.g., single antibody variable domain) can have binding specificity for a generic ligand or any desired target ligand, such as human or animal proteins, including cytokines, growth factors, cytokine receptors, growth factor receptors, enzymes (e.g., proteases), co-factors for enzymes, DNA binding proteins, lipids and carbohydrates.

In some embodiments, the protease resistant peptide or polypeptide (eg, DAB™) or antagonist binds TNFR1 in pulmonary tissue. In one embodiment, the antagonist or polypeptide also binds a further target in pulmonary tissue.

When a display system (e.g., a display system that links coding function of a nucleic acid and functional characteristics of the peptide or polypeptide encoded by the nucleic acid) is used in the methods described herein it may be frequently advantageous to amplify or increase the copy number of the nucleic acids that encode the selected peptides or polypeptides. This provides an efficient way of obtaining sufficient quantities of nucleic acids and/or peptides or polypeptides for additional rounds of selection, using the methods described herein or other suitable methods, or for preparing additional repertoires (e.g., affinity maturation repertoires). Thus, in some embodiments, the methods comprise using a display system (e.g., that links coding function of a nucleic acid and functional characteristics of the peptide or polypeptide encoded by the nucleic acid, such as phage display) and further comprises amplifying or increasing the copy number of a nucleic acid that encodes a selected peptide or polypeptide. Nucleic acids can be amplified using any suitable methods, such as by phage amplification, cell growth or polymerase chain reaction.

The methods described herein can be used as part of a program to isolate protease resistant peptides or polypeptides, eg DAB™s, that can comprise, if desired, other suitable selection methods. In these situations, the methods described herein can be employed at any desired point in the program, such as before or after other selection methods are used. The methods described herein can also be used to provide two or more rounds of selection, as described and exemplified herein.

In one example, the method is for selecting a peptide or polypeptide, eg a DAB™, that is resistant to degradation by elastase, comprising providing a library or repertoire of peptides or polypeptides, combining the library or repertoire with elastase (or a biological preparation, extract or homogenate comprising elastase) under conditions suitable for proteolytic digestion by elastase, and selecting, isolating and/or recovering a peptide or polypeptide that is resistant to degradation by elastase and has TNFR1 binding activity.

In particular embodiments, there is provided a method for selecting an immunoglobulin single variable domain (a DAB™) that is resistant to degradation by elastase and binds TNFR1. In these embodiments, a library or repertoire comprising DAB™s is provided and combined with elastase (or a biological preparation, extract or homogenate comprising elastase) under conditions suitable for proteolytic digestion by elastase. Elastase resistant DAB™s are selected that specifically bind TNFR1. For example, the elastase resistant DAB™ is not substantially degraded when incubated at 37° C. in a 0.04% (w/w) solution of elastase for a period of at least about 2 hours. In one embodiment, the elastase resistant DAB™ is not substantially degraded when incubated at 37° C. in a 0.04% (w/w) solution of elastase for a period of at least about 12 hours. In one embodiment, the elastase resistant DAB™ is not substantially degraded when incubated at 37° C. in a 0.04% (w/w) solution of elastase for a period of at least about 24 hours, at least about 36 hours, or at least about 48 hours.

In an embodiment, there is provided a method for selecting an immunoglobulin single variable domain (a DAB™) that is resistant to degradation by elastase and binds TNFR1. The method comprises providing a phage display system comprising a repertoire of polypeptides that comprise an immunoglobulin single variable domain, combining the phage display system with elastase (about 100 µg/ml) and incubating the mixture at about 37° C., for example, overnight (e.g., about 12-16 hours), and then selecting phage that display a DAB™ that specifically bind TNFR1.

In one example, there is provided a method for selecting a peptide or polypeptide (eg, a DAB™) that is resistant to degradation by leucozyme, comprising providing a library or repertoire of peptides or polypeptides, combining the library or repertoire with leucozyme (or a biological preparation, extract or homogenate comprising leucozyme) under conditions suitable for proteolytic digestion by leucozyme, and selecting, isolating and/or recovering a peptide or polypeptide that is resistant to degradation by leucozyme and has specific TNFR1 binding activity.

In particular embodiments, there is provided a method for selecting an immunoglobulin single variable domain (a DAB™) that is resistant to degradation by leucozyme and binds TNFR1. In these embodiments, a library or repertoire comprising DAB™s is provided and combined with leucozyme (or a biological preparation, extract or homogenate comprising leucozyme) under conditions suitable for proteolytic digestion by leucozyme. Leucozyme resistant DAB™s are selected that specifically bind TNFR1. For example, the leucozyme resistant DAB™ is not substantially degraded when incubated at 37° C. in a 0.04% (w/w) solution of leucozyme for a period of at least about 2 hours. In one embodiment, the leucozyme resistant DAB™ is not substantially degraded when incubated at 37° C. in a 0.04% (w/w) solution of leucozyme for a period of at least about 12 hours. In one embodiment, the leucozyme resistant DAB™ is not substantially degraded when incubated at 37° C. in a 0.04% (w/w) solution of leucozyme for a period of at least about 24 hours, at least about 36 hours, or at least about 48 hours.

In an embodiment, there is provided a method for selecting an immunoglobulin single variable domain (a DAB™) that is resistant to degradation by leucozyme and specifically binds TNFR1. The method comprises providing a phage display system comprising a repertoire of polypeptides that comprise an immunoglobulin single variable domain, combining the phage display system with leucozyme (about 100 µg/ml) and incubating the mixture at about 37° C., for example, overnight (e.g., about 12-16 hours), and then selecting phage that display a DAB™ that specifically bind TNFR1.

In another example, there is provided a method for selecting a peptide or polypeptide (eg, a DAB™) that is resistant to degradation by trypsin, comprising providing a library or repertoire of peptides or polypeptides, combining the library or repertoire with trypsin under conditions suitable for proteolytic digestion by trypsin, and selecting, isolating and/or recovering a peptide or polypeptide that is resistant to degradation by trypsin and specifically binds TNFR1.

In particular embodiments, there is provided a method for selecting an immunoglobulin single variable domain (a DAB™) that is resistant to degradation by trypsin and specifically binds TNFR1. In these embodiments, a library or repertoire comprising DAB™s is provided and combined with trypsin (or a biological preparation, extract or homogenate comprising trypsin) under conditions suitable for proteolytic digestion by trypsin. Trypsin resistant DAB™s are selected that bind TNFR1. For example, the trypsin resistant DAB™ is not substantially degraded when incubated at 37° C. in a 0.04% (w/w) solution of trypsin for a period of at least about 2 hours. In one embodiment, the trypsin resistant DAB™ is not substantially degraded when incubated at 37° C. in a 0.04% (w/w) solution of trypsin for a period of at least about 3 hours. In one embodiment, the trypsin resistant DAB™ is not substantially degraded when incubated at 37° C. in a 0.04% (w/w) solution of trypsin for a period of at least about 4 hours, at least about 5 hours, at least about 6 hours, at least about 7 hours, at least about 8 hours, at least about 9 hours, at least about 10 hours, at least about 11 hours, or at least about 12 hours.

In an exemplary embodiment, there is provided a method for selecting an immunoglobulin single variable domain (a DAB™) that is resistant to degradation by trypsin and specifically binds TNFR1. The method comprises providing a phage display system comprising a repertoire of polypeptides that comprise an immunoglobulin single variable domain, combining the phage display system with trypsin (100 µg/ml) and incubating the mixture at about 37° C., for example overnight (e.g., about 12-16 hours), and then selecting phage that display a dAb that specifically bind TNFR1.

In another aspect, there is provided a method of producing a repertoire of protease resistant peptides or polypeptides (eg, DAB™s). The method comprises providing a repertoire of peptides or polypeptides; combining the repertoire of peptides or polypeptides and a protease under suitable conditions for protease activity; and recovering a plurality of peptides or polypeptides that specifically bind TNFR1, whereby a repertoire of protease resistant peptides or polypeptides is produced. Proteases, display systems, conditions for protease activity, and methods for selecting peptides or polypeptides that are suitable for use in the method are described herein with respect to the other methods.

In some embodiments, a display system (e.g., a display system that links coding function of a nucleic acid and functional characteristics of the peptide or polypeptide encoded by the nucleic acid) that comprises a repertoire of peptides or polypeptides is used, and the method further comprises amplifying or increasing the copy number of the nucleic acids that encode the plurality of selected peptides or polypeptides. Nucleic acids can be amplified using any suitable method, such as by phage amplification, cell growth or polymerase chain reaction.

In particular embodiment, there is provided a method of producing a repertoire of protease resistant polypeptides that comprise anti-TNFR1 DAB™s. The method comprises providing a repertoire of polypeptides that comprise DAB™s; combining the repertoire of peptides or polypeptides and a protease (e.g., trypsin, elastase, leucozyme) under suitable conditions for protease activity; and recovering a plurality of polypeptides that comprise DAB™s that have binding specificity for TNFR1. The method can be used to produce a naïve repertoire, or a repertoire that is biased toward a desired binding specificity, such as an affinity maturation repertoire based on a parental DAB™ that has binding specificity for TNFR1.

Polypeptide Display Systems

In one embodiment, the repertoire or library of peptides or polypeptides provided for use in the methods described herein comprise a suitable display system. The display system may resist degradation by protease (e.g., a single protease or a combination of proteases, and any biological extract, homogenate or preparation that contains proteolytic activity (e.g., sputum, mucus (e.g., gastric mucus, nasal mucus, bronchial mucus), bronchoalveolar lavage, lung homogenate, lung extract, pancreatic extract, gastric fluid, saliva, tears and the like). The display system and the link between the display system and the displayed polypeptide is in one embodiment at least as resistant to protease as the most stable peptides or polypeptides of the repertoire. This allows a nucleic acid that encodes a selected displayed polypeptide to be easily isolated and/or amplified.

In one example, a protease resistant peptide or polypeptide, eg a DAB™, can be selected, isolated and/or recovered from a repertoire of peptides or polypeptides that is in solution, or is covalently or noncovalently attached to a suitable surface, such as plastic or glass (e.g., microtiter plate, polypeptide array such as a microarray). For example an array of peptides on a surface in a manner that places each distinct library member (e.g., unique peptide sequence) at a discrete, predefined location in the array can be used. The identity of each library member in such an array can be determined by its spatial location in the array. The locations in the array where binding interactions between a target ligand, for example, and reactive library members occur can be determined, thereby identifying the sequences of the reactive members on the basis of spatial location. (See, e.g., U.S. Pat. No. 5,143,854, WO 90/15070 and WO 92/10092.)

In one embodiment, the methods employ a display system that links the coding function of a nucleic acid and physical, chemical and/or functional characteristics of the polypeptide encoded by the nucleic acid. Such a display system can comprise a plurality of replicable genetic packages, such as bacteriophage or cells (bacteria). In one embodiment, the display system comprises a library, such as a bacteriophage display library.

A number of suitable bacteriophage display systems (e.g., monovalent display and multivalent display systems) have been described. (See, e.g., Griffiths et al., U.S. Pat. No. 6,555,313 B1 (incorporated herein by reference); Johnson et al., U.S. Pat. No. 5,733,743 (incorporated herein by reference); McCafferty et al., U.S. Pat. No. 5,969,108 (incorporated herein by reference); Mulligan-Kehoe, U.S. Pat. No. 5,702,892 (Incorporated herein by reference); Winter, G. et al., *Annu. Rev. Immunol.* 12:433-455 (1994); Soumillion, P. et al., *Appl. Biochem. Biotechnol.* 47(2-3):175-189 (1994); Castagnoli, L. et al., *Comb. Chem. High Throughput Screen*, 4(2):121-133 (2001).) The peptides or polypeptides displayed in a bacteriophage display system can be displayed on any suitable bacteriophage, such as a filamentous phage (e.g., fd, M13, F1), a lytic phage (e.g., T4, T7, lambda), or an RNA phage (e.g., MS2), for example.

Generally, a library of phage that displays a repertoire of peptides or phage polypeptides, as fusion proteins with a suitable phage coat protein (e.g., fd pIII protein), is produced or provided. The fusion protein can display the peptides or polypeptides at the tip of the phage coat protein, or if desired at an internal position. For example, the displayed peptide or polypeptide can be present at a position that is amino-terminal to domain 1 of pIII. (Domain 1 of pIII is also referred to as N1.) The displayed polypeptide can be directly fused to pIII (e.g., the N-terminus of domain 1 of pIII) or fused to pIII using a linker. If desired, the fusion can further comprise a tag (e.g., myc epitope, His tag). Libraries that comprise a repertoire of peptides or polypeptides that are displayed as fusion proteins with a phage coat protein can be produced using any suitable methods, such as by introducing a library of phage vectors or phagemid vectors encoding the displayed peptides or polypeptides into suitable host bacteria, and culturing the resulting bacteria to produce phage (e.g., using a suitable helper phage or complementing plasmid if desired). The library of phage can be recovered from the culture using any suitable method, such as precipitation and centrifugation.

The display system can comprise a repertoire of peptides or polypeptides that contains any desired amount of diversity. For example, the repertoire can contain peptides or polypeptides that have amino acid sequences that correspond to naturally occurring polypeptides expressed by an organism, group of organisms (eg, a repertoire of sequences of $V_{HH}$ DAB's isolated from a Camelid), desired tissue or desired cell type, or can contain peptides or polypeptides that have random or randomized amino acid sequences. If desired, the polypeptides can share a common core or scaffold. The polypeptides in such a repertoire or library can comprise defined regions of random or randomized amino acid sequence and regions of common amino acid sequence. In certain embodiments, all or substantially all polypeptides in a repertoire are of a desired type, such as a desired enzyme (e.g., a polymerase) or a desired antigen-binding fragment of an antibody (e.g., human $V_H$ or human $V_L$). In embodiments, the polypeptide display system comprises a repertoire of polypeptides wherein each polypeptide comprises an antibody variable domain. For example, each polypeptide in the repertoire can contain a $V_H$, a $V_L$ or an Fv (e.g., a single chain Fv).

Amino acid sequence diversity can be introduced into any desired region of a peptide or polypeptide or scaffold using any suitable method. For example, amino acid sequence diversity can be introduced into a target region, such as a complementarity determining region of an antibody variable domain or a hydrophobic domain, by preparing a library of nucleic acids that encode the diversified polypeptides using any suitable mutagenesis methods (e.g., low fidelity PCR, oligonucleotide-mediated or site directed mutagenesis, diversification using NNK codons) or any other suitable method. If desired, a region of a polypeptide to be diversified can be randomized.

The size of the polypeptides that make up the repertoire is largely a matter of choice and uniform polypeptide size is not required. In one embodiment, the polypeptides in the repertoire have at least tertiary structure (form at least one domain).

Selection/Isolation/Recovery

A protease resistant peptide or polypeptide (e.g., a population of protease resistant polypeptides) can be selected, isolated and/or recovered from a repertoire or library (e.g., in a display system) using any suitable method. In one embodiment, a protease resistant polypeptide is selected or isolated based on a selectable characteristic (e.g., physical characteristic, chemical characteristic, functional characteristic). Suitable selectable functional characteristics include biological activities of the peptides or polypeptides in the repertoire, for example, binding to a generic ligand (e.g., a superantigen), binding to a target ligand (e.g., an antigen, an epitope, a substrate), binding to an antibody (e.g., through an epitope expressed on a peptide or polypeptide), and catalytic activity. (See, e.g., Tomlinson et al., WO 99/20749; WO 01/57065; WO 99/58655). In one embodiment, the selection is based on specific binding to TNFR1. In another embodiment, selection is on the basis of the selected functional characteristic to produce a second repertoire in which members are protease resistant, followed by selection of a member from the second repertoire that specifically binds TNFR1.

In some embodiments, the protease resistant peptide or polypeptide is selected and/or isolated from a library or repertoire of peptides or polypeptides in which substantially all protease resistant peptides or polypeptides share a common selectable feature. For example, the protease resistant peptide or polypeptide can be selected from a library or repertoire in which substantially all protease resistant peptides or polypeptides bind a common generic ligand, bind a common target ligand, bind (or are bound by) a common antibody, or possess a common catalytic activity. This type of selection is particularly useful for preparing a repertoire of protease resistant peptides or polypeptides that are based on a parental peptide or polypeptide that has a desired biological activity, for example, when performing affinity maturation of an immunoglobulin single variable domain.

Selection based on binding to a common generic ligand can yield a collection or population of peptides or polypeptides that contain all or substantially all of the protease resistant peptides or polypeptides that were components of the original library or repertoire. For example, peptides or polypeptides that bind a target ligand or a generic ligand, such as protein A, protein L or an antibody, can be selected, isolated and/or recovered by panning or using a suitable affinity matrix. Panning can be accomplished by adding a solution of ligand (e.g., generic ligand, target ligand) to a suitable vessel (e.g., tube, petri dish) and allowing the ligand to become deposited or coated onto the walls of the vessel. Excess ligand can be washed away and peptides or polypeptides (e.g., a repertoire that has been incubated with protease) can be added to the vessel and the vessel maintained under conditions suitable for peptides or polypeptides to bind the immobilized ligand. Unbound peptides or polypeptides can be washed away and bound peptides or polypeptides can be recovered using any suitable method, such as scraping or lowering the pH, for example.

Suitable ligand affinity matrices generally contain a solid support or bead (e.g., agarose) to which a ligand is covalently or noncovalently attached. The affinity matrix can be combined with peptides or polypeptides (e.g., a repertoire that has been incubated with protease) using a batch process, a column process or any other suitable process under conditions suitable for binding of peptides or polypeptides to the ligand on the matrix. Peptides or polypeptides that do not bind the affinity matrix can be washed away and bound peptides or polypeptides can be eluted and recovered using any suitable method, such as elution with a lower pH buffer, with a mild denaturing agent (e.g., urea), or with a peptide that competes for binding to the ligand. In one example, a biotinylated target ligand is combined with a repertoire under conditions suitable for peptides or polypeptides in the repertoire to bind the target ligand (TNFR1). Bound peptides or polypeptides are recovered using immobilized avidin or streptavidin (e.g., on a bead).

In some embodiments, the generic ligand is an antibody or antigen binding fragment thereof. Antibodies or antigen binding fragments that bind structural features of peptides or polypeptides that are substantially conserved in the peptides or polypeptides of a library or repertoire are particularly useful as generic ligands. Antibodies and antigen binding fragments suitable for use as ligands for isolating, selecting and/or recovering protease resistant peptides or polypeptides can be monoclonal or polyclonal and can be prepared using any suitable method.

Libraries/Repertoires

In other aspects, there are provided repertoires of protease resistant peptides and polypeptides, to libraries that encode protease resistant peptides and polypeptides, and to methods for producing such libraries and repertoires.

Libraries that encode and/or contain protease resistant peptides and polypeptides can be prepared or obtained using any suitable method. The library can be designed to encode protease resistant peptides or polypeptides based on a peptide or polypeptide of interest (e.g., an anti-TNFR1 peptide or polypeptide selected from a library) or can be selected from another library using the methods described herein. For example, a library enriched in protease resistant polypeptides can be prepared using a suitable polypeptide display system.

In one example, a phage display library comprising a repertoire of displayed polypeptides comprising immunoglobulin single variable domains (e.g., $V_H$, Vk, Vλ) is combined with a protease under conditions suitable for protease activity, as described herein. Protease resistant polypeptides are recovered based on a desired biological activity, such as a binding activity (e.g., binding generic ligand, binding target ligand) thereby yielding a phage display library enriched in protease resistant polypeptides. In one embodiment, the recovery is on the basis of binding generic ligand to yield an enriched library, followed by selection of an anti-TNFR1 member of that library based on specific binding to TNFR1.

In another example, a phage display library comprising a repertoire of displayed polypeptides comprising immunoglobulin single variable domains (e.g., $V_H$, VK, Vλ) is first screened to identify members of the repertoire that have binding specificity for a desired target antigen (TNFR1). A collection of polypeptides having the desired binding specificity are recovered and the collection is combined with protease under conditions suitable for proteolytic activity, as described herein. A collection of protease resistant polypeptides that have the desired target binding specificity is recovered, yielding a library enriched in protease resistant and high affinity polypeptides. As described herein in an embodiment, protease resistance in this selection method correlates with high affinity binding.

Libraries that encode a repertoire of a desired type of polypeptides can readily be produced using any suitable method. For example, a nucleic acid sequence that encodes a desired type of polypeptide (e.g., a polymerase, an immunoglobulin variable domain) can be obtained and a collection of nucleic acids that each contain one or more mutations can be prepared, for example by amplifying the nucleic acid using an error-prone polymerase chain reaction (PCR) system, by chemical mutagenesis (Deng et al., *J. Biol. Chem.*, 269:9533 (1994)) or using bacterial mutator strains (Low et al., *J. Mol. Biol.*, 260:359 (1996)).

In other embodiments, particular regions of the nucleic acid can be targeted for diversification. Methods for mutating selected positions are also well known in the art and include, for example, the use of mismatched oligonucleotides or degenerate oligonucleotides, with or without the use of PCR. For example, synthetic antibody libraries have been created by targeting mutations to the antigen binding loops. Random or semi-random antibody H3 and L3 regions have been appended to germline immunoblulin V gene segments to produce large libraries with unmutated framework regions (Hoogenboom and Winter (1992) supra; Nissim et al. (1994) supra; Griffiths et al. (1994) supra; DeKruif et al. (1995) supra). Such diversification has been extended to include some or all of the other antigen binding loops (Crameri et al. (1996) *Nature Med.,* 2:100; Riechmann et al. (1995) *Bio/Technology,* 13:475; Morphosys, WO 97/08320, supra). In other embodiments, particular regions of the nucleic acid can be targeted for diversification by, for example, a two-step PCR strategy employing the product of the first PCR as a "mega-primer." (See, e.g., Landt, O. et al., *Gene* 96:125-128 (1990).) Targeted diversification can also be accomplished, for example, by SOE PCR. (See, e.g., Horton, R. M. et al., *Gene* 77:61-68 (1989).)

Sequence diversity at selected positions can be achieved by altering the coding sequence which specifies the sequence of the polypeptide such that a number of possible amino acids (e.g., all 20 or a subset thereof) can be incorporated at that position. Using the IUPAC nomenclature, the most versatile codon is NNK, which encodes all amino acids as well as the TAG stop codon. The NNK codon may be used in order to introduce the required diversity. Other codons which achieve the same ends are also of use, including the NNN codon, which leads to the production of the additional stop codons TGA and TAA. Such a targeted approach can allow the full sequence space in a target area to be explored.

The libraries can comprise protease resistant antibody polypeptides that have a known main-chain conformation. (See, e.g., Tomlinson et al., WO 99/20749.)

Libraries can be prepared in a suitable plasmid or vector. As used herein, vector refers to a discrete element that is used to introduce heterologous DNA into cells for the expression and/or replication thereof. Any suitable vector can be used, including plasmids (e.g., bacterial plasmids), viral or bacteriophage vectors, artificial chromosomes and episomal vectors. Such vectors may be used for simple cloning and mutagenesis, or an expression vector can be used to drive expression of the library. Vectors and plasmids usually contain one or more cloning sites (e.g., a polylinker), an origin of replication and at least one selectable marker gene. Expression vectors can further contain elements to drive transcription and translation of a polypeptide, such as an enhancer element, promoter, transcription termination signal, signal sequences, and the like. These elements can be arranged in such a way as to be operably linked to a cloned insert encoding a polypeptide, such that the polypeptide is expressed and produced when such an expression vector is maintained under conditions suitable for expression (e.g., in a suitable host cell).

Cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV40, adenovirus) are useful for cloning vectors in mammalian cells. Generally, the origin of replication is not needed for mammalian expression vectors, unless these are used in mammalian cells able to replicate high levels of DNA, such as COS cells.

Cloning or expression vectors can contain a selection gene also referred to as selectable marker. Such marker genes encode a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal or leader sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for procaryotic (e.g., the β-lactamase and lactose promoter systems, alkaline phosphatase, the tryptophan (trp) promoter system, lac, tac, T3, T7 promoters for *E. coli*) and eucaryotic (e.g., simian virus 40 early or late promoter, Rous sarcoma virus long terminal repeat promoter, cytomegalovirus promoter, adenovirus late promoter, EG-1a promoter) hosts are available.

In addition, expression vectors typically comprise a selectable marker for selection of host cells carrying the vector, and, in the case of a replicable expression vector, an origin of replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

Suitable expression vectors for expression in prokaryotic (e.g., bacterial cells such as *E. coli*) or mammalian cells include, for example, a pET vector (e.g., pET-12a, pET-36, pET-37, pET-39, pET-40, Novagen and others), a phage vector (e.g., pCANTAB 5 E, Pharmacia), pRIT2T (Protein A fusion vector, Pharmacia), pCDM8, pCDNA1.1/amp, pcDNA3.1, pRc/RSV, pEF-1 (Invitrogen, Carlsbad, Calif.), pCMV-SCRIPT, pFB, pSG5, pXT1 (Stratagene, La Jolla, Calif.), pCDEF3 (Goldman, L. A., et al., *Biotechniques,* 21:1013-1015 (1996)), pSVSPORT (GibcoBRL, Rockville, Md.), pEF-Bos (Mizushima, S., et al., *Nucleic Acids Res.,* 18:5322 (1990)) and the like. Expression vectors which are suitable for use in various expression hosts, such as prokaryotic cells (*E. coli*), insect cells (*Drosophila* Schnieder S2 cells, Sf9), yeast (*P. methanolica, P. pastoris, S. cerevisiae*) and mammalian cells (eg, COS cells) are available.

Examples of vectors are expression vectors that enable the expression of a nucleotide sequence corresponding to a polypeptide library member. Thus, selection with generic and/or target ligands can be performed by separate propagation and expression of a single clone expressing the polypeptide library member. As described above, the selection display system may be bacteriophage display. Thus, phage or phagemid vectors may be used. Example vectors are phagemid vectors which have an *E. coli.* origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector can contain a β-lactamase gene to confer selectivity on the phagemid and a lac promoter upstream of an expression cassette that can contain a suitable leader sequence, a multiple cloning site, one or more peptide tags, one or more TAG stop codons and the phage protein pIII. Thus, using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only or product phage, some of which contain at least one copy of the polypeptide-pIII fusion on their surface.

The libraries and repertoires described herein can contain antibody formats. For example, the polypeptide contained within the libraries and repertoires can be whole separate $V_H$ or $V_L$ domains, any of which are either modified or unmodified. scFv fragments, as well as other antibody polypeptides, can be readily produced using any suitable method. A number of suitable antibody engineering methods are well known in the art. For example, a scFv can be formed by linking nucleic acids encoding two variable domains with a suitable oligonucleotide that encodes an appropriate linker peptide, such as (Gly-Gly-Gly-Gly-Ser (SEQ ID NO: 222))$_3$ or other suitable linker peptides. The linker bridges the C-terminal end of the first V region and the N-terminal end of the second V region. Similar techniques for the construction of other antibody formats, such as Fv, Fab and F(ab')$_2$ fragments can be used. To format Fab and F(ab')$_2$ fragments, $V_H$ and $V_L$ polypeptides can be combined with constant region segments, which may be isolated from rearranged genes, germline C genes or synthesized from antibody sequence data. A library or repertoire described herein can be a $V_H$ or $V_L$ library or repertoire.

The polypeptides comprising a protease resistant variable domain may comprise a target ligand (TNFR1) binding site and a generic ligand binding site. In certain embodiments, the generic ligand binding site is a binding site for a superantigen, such as protein A, protein L or protein G. The variable domains can be based on any desired variable domain, for example a human VH (e.g., $V_H$ 1a, $V_H$ 1b, $V_H$ 2, $V_H$ 3, $V_H$ 4, $V_H$ 5, $V_H$ 6), a human Vλ(e.g., VλI, VλII, VλIII, VλIV, VλV, VλVI or Vκ1) or a human Vκ (e.g., Vκ2, Vκ3, Vκ4, Vκ5, Vκ6, Vκ7, Vκ8, Vκ9 or Vκ10) or a Camelid $V_{HH}$, optionally that has been humanized.

Nucleic Acids, Host Cells and Methods for Producing Protease Resistant Polypeptides The invention relates to isolated and/or recombinant nucleic acids encoding protease resistant peptides or polypeptides e.g., that are selectable or selected by the methods described herein.

Nucleic acids referred to herein as "isolated" are nucleic acids which have been separated away from other material (e.g., other nucleic acids such as genomic DNA, cDNA and/or RNA) in its original environment (e.g., in cells or in a mixture of nucleic acids such as a library). An isolated nucleic acid can be isolated as part of a vector (e.g., a plasmid).

Nucleic acids referred to herein as "recombinant" are nucleic acids which have been produced by recombinant DNA methodology, including methods which rely upon artificial recombination, such as cloning into a vector or chromosome using, for example, restriction enzymes, homologous recombination, viruses and the like, and nucleic acids prepared using the polymerase chain reaction (PCR).

The invention also relates to a recombinant host cell which comprises a (one or more) recombinant nucleic acid or expression construct comprising a nucleic acid encoding a protease resistant peptide or polypeptide, e.g., a peptide or polypeptide selectable or selected by the methods described herein. There is also provided a method of preparing a protease resistant peptide or polypeptide, comprising maintaining a recombinant host cell of the invention under conditions appropriate for expression of a protease resistant peptide or polypeptide. The method can further comprise the step of isolating or recovering the protease resistant peptide or polypeptide, if desired.

For example, a nucleic acid molecule (i.e., one or more nucleic acid molecules) encoding a protease resistant peptide or polypeptide, or an expression construct (i.e., one or more constructs) comprising such nucleic acid molecule(s), can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable animal, in suitable culture media supplemented with appropriate salts, growth factors, antibiotics, nutritional supplements, etc.), whereby the encoded peptide or polypeptide is produced. If desired, the encoded peptide or polypeptide can be isolated or recovered (e.g., from the animal, the host cell, medium, milk). This process encompasses expression in a host cell of a transgenic animal (see, e.g., WO 92/03918, GenPharm International).

The protease resistant peptide or polypeptide selected by the method described herein can also be produced in a suitable in vitro expression system, by chemical synthesis or by any other suitable method. Thus, the present invention provides for protease resistant peptides and polypeptides.

Polypeptides, DAB™s & Antagonists

As described and exemplified herein, protease resistant DAB™s of the invention generally bind their target ligand with high affinity. Thus, in another aspect, there is provided a method for selecting, isolating and/or recovering a polypeptide or DAB™ of the invention that binds TNFR1 with high affinity. Generally, the method comprises providing a library or repertoire of peptides or polypeptides (eg DAB™s), combining the library or repertoire with a protease (e.g., trypsin, elastase, leucozyme, pancreatin, sputum) under conditions suitable for protease activity, and selecting, isolating and/or recovering a peptide or polypeptide that binds a ligand (e.g., target ligand). Because the library or repertoire has been exposed to protease under conditions where protease sensitive peptides or polypeptides will be digested, the activity of protease can eliminate the less stable polypeptides that have low binding affinity, and thereby produce a collection of high affinity binding peptides or polypeptides. For example, the polypeptide or DAB™ of the invention can bind TNFR1 with an affinity ($K_D$; $K_D=K_{off}$ (kd)/$K_{on}$(ka) as determined by surface plasmon resonance) of 1 µM or stronger, or about 500 nM to about 0.5 pM. For example, the polypeptide or DAB™ of the invention can bind TNFR1 with an affinity of about 500 nM, about 100 nM, about 10 nM, about 1 nM, about 500 pM, about 100 pM, about 10 pM, about 1 pM or about 0.5 pM. Although we are not bound by any particular theory, peptides and polypeptides that are resistant to proteases are believed to have a lower entropy and/or a higher stabilization energy. Thus, the correlation between protease resistance and high affinity binding may be related to the compactness and stability of the surfaces of the peptides and polypeptides and DAB™s selected by the method described herein.

In one embodiment, the polypeptide, DAB™ or antagonist of the invention inhibits binding of TNF alpha to TNF alpha Receptor I (p55 receptor) with an inhibitory concentration 50 (IC50) of or about 500 nM to 50 pM, or 100 nM to 50 pM, or 10 nM to 100 pM, or 1 nM to 100 pM; for example 50 nM or less, or 5 nM or less, or 500 pM or less, or 200 pM or less, or 100 pM or less.

In certain embodiments, the polypeptide, DAB™ or antagonist specifically binds TNFR1, eg, human TNFR1, and dissociates from human TNFR1 with a dissociation constant ($K_D$) of 300 nM to 1 pM or 300 nM to 5 pM or 50 nM to 1 pM or 50 nM to 5 pM or 50 nM to 20 pM or about 10 pM or about 15 pM or about 20 pM as determined by surface plasmon resonance. In certain embodiments, the polypeptide, DAB™ or antagonist specifically binds TNFR1, eg, human TNFR1, and dissociates from human TNFR1 with a $K_{off}$ rate constant of $5\times10^{-1}$ $s^{-1}$ to $1\times10^{-7}$ $s^{-1}$ or $1\times10^{-3}$ $s^{-1}$ to $1\times10^{-7}$ $s^{-1}$ or $1\times10^{-4}$ $s^{-1}$ to $1\times10^{-7}$ $s^{-1}$ or $1\times10^{-5}$ $s^{-1}$ to $1\times10^{-7}$ $s^{-1}$ or $1\times10^{-4}$ $s^{-1}$ or $1\times10^{-5}$ $s^{-1}$ as determined by surface plasmon resonance. In certain embodiments, the polypeptide, DAB™ or antagonist specifically binds TNFR1, eg, human TNFR1, with a $K_{on}$ of $1\times10^{-3}$ $M^{-1}$ $s^{-1}$ to $1\times10^{-7}$ $M^{-1}$ $s^{-1}$ or $1\times10^{-3}$ $M^{-1}$ $s^{-1}$ to $1\times10^{-6}$ $M^{-1}$ $s^{-1}$ or about $1\times10^{-4}$ $M^{-1}$ $s^{-1}$ or about $1\times10^{-5}$ $M^{-1}$ $s^{-1}$. In one embodiment, the polypeptide, DAB™ or antagonist specifically binds TNFR1, eg, human TNFR1, and dissociates from human TNFR1 with a dissociation constant ($K_D$) and a $K_{off}$ as defined in this paragraph. In one embodiment, the polypeptide, DAB™ or antagonist specifically binds TNFR1, eg, human TNFR1, and dissociates from human TNFR1 with a dissociation constant ($K_D$) and a $K_{on}$ as defined in this paragraph. In some embodiments, the polypeptide or DAB™ specifically binds TNFR1 (eg, human TNFR1) with a $K_D$ and/or $K_{off}$ and/or $K_{on}$ as recited in this paragraph and comprises an amino acid sequence that is at least or at least about 80%, 85%, 90%, 91%, 92%, 93%, 94%, 95%, 96%, 97%, 98%, or 99% identical to the amino acid sequence of DOM1h-131-206 (shown in FIG. 3).

The polypeptide, DAB™ or antagonist can be expressed in *E. coli* or in *Pichia* species (e.g., *P. pastoris*). In one embodiment, the ligand or DAB™ monomer is secreted in a quantity of at least about 0.5 mg/L when expressed in *E. coli* or in *Pichia* species (e.g., *P. pastoris*). Although, the ligands and DAB™ monomers described herein can be secretable when expressed in *E. coli* or in *Pichia* species (e.g., *P. pastoris*), they can be produced using any suitable method, such as synthetic chemical methods or biological production methods that do not employ *E. coli* or *Pichia* species.

In some embodiments, the polypeptide, DAB™ or antagonist does not comprise a Camelid immunoglobulin variable domain, or one or more framework amino acids that are unique to immunoglobulin variable domains encoded by Camelid germline antibody gene segments, eg at position 108, 37, 44, 45 and/or 47.

Antagonists of TNFR1 according to the invention can be monovalent or multivalent. In some embodiments, the antagonist is monovalent and contains one binding site that interacts with TNFR1, the binding site provided by a polypeptide or DAB™ of the invention. Monovalent antagonists bind one TNFR1 and may not induce cross-linking or clustering of TNFR1 on the surface of cells which can lead to activation of the receptor and signal transduction.

In other embodiments, the antagonist of TNFR1 is multivalent. Multivalent antagonists of TNFR1 can contain two or more copies of a particular binding site for TNFR1 or contain two or more different binding sites that bind TNFR1, at least one of the binding sites being provided by a polypeptide or DAB™ of the invention. For example, as described herein the antagonist of TNFR1 can be a dimer, trimer or multimer comprising two or more copies of a particular polypeptide or DAB™ of the invention that binds TNFR1, or two or more different polypeptides or DAB™s of the invention that bind TNFR1. In one embodiment, a multivalent antagonist of TNFR1 does not substantially agonize TNFR1 (act as an agonist of TNFR1) in a standard cell assay (i.e., when present at a concentration of 1 nM, 10 nM, 100 nM, 1 µM, 10 µM, 100 µM, 1000 µM or 5,000 µM, results in no more than about 5% of the TNFR1-mediated activity induced by TNFα (100 µg/ml) in the assay).

In certain embodiments, the multivalent antagonist of TNFR1 contains two or more binding sites for a desired epitope or domain of TNFR1. For example, the multivalent antagonist of TNFR1 can comprise two or more binding sites that bind the same epitope in Domain 1 of TNFR1.

In other embodiments, the multivalent antagonist of TNFR1 contains two or more binding sites provided by polypeptides or DAB™s of the invention that bind to different epitopes or domains of TNFR1. In one embodiment, such multivalent antagonists do not agonize TNFR1 when present at a concentration of about 1 nM, or about 10 nM, or about 100 nM, or about 1 µM, or about 10 µM, in a standard L929 cytotoxicity assay or a standard HeLa IL-8 assay as described in WO2006038027.

Other antagonists of TNFR1 do no inhibit binding of TNF to TNFR1. Such ligands (and antagonists) may have utility as diagnostic agents, because they can be used to bind and detect, quantify or measure TNFR1 in a sample and will not compete with TNF in the sample for binding to TNFR1. Accordingly, an accurate determination of whether or how much TNFR1 is in the sample can be made.

In other embodiments, the polypeptide, DAB™ or antagonist specifically binds TNFR1 with a $K_D$ described herein and inhibits lethality in a standard mouse LPS/D-galactosamine-induced septic shock model (i.e., prevents lethality or reduces lethality by at least about 10%, as compared with a suitable control). In one embodiment, the polypeptide, DAB™ or antagonist inhibits lethality by at least about 25%, or by at least about 50%, as compared to a suitable control in a standard mouse LPS/D-galactosamine-induced septic shock model when administered at about 5 mg/kg or more, for example about 1 mg/kg.

In other embodiments, the polypeptide, DAB™ or antagonist binds TNFR1 and antagonizes the activity of the TNFR1 in a standard cell assay with an $ND_{50}$ of ≤100 nM, and at a concentration of ≤10 µM the DAB™ agonizes the activity of the TNFR1 by ≤5% in the assay.

In particular embodiments, the polypeptide, DAB™ or antagonist does not substantially agonize TNFR1 (act as an agonist of TNFR1) in a standard cell assay (i.e., when present at a concentration of 1 nM, 10 nM, 100 nM, 1 µM, 10 µM, 100 µM, 1000 µM or 5,000 µM, results in no more than about 5% of the TNFR1-mediated activity induced by TNFα (100 µg/ml) in the assay).

In certain embodiments, the polypeptide, DAB™ or antagonist of the invention are efficacious in models of chronic inflammatory diseases when an effective amount is administered. Generally an effective amount is about 1 mg/kg to about 10 mg/kg (e.g., about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg). The models of chronic inflammatory disease (see those described in WO2006038027) are recognized by those skilled in the art as being predictive of therapeutic efficacy in humans.

In particular embodiments, the polypeptide, DAB™ or antagonist is efficacious in the standard mouse collagen-induced arthritis model (see WO2006038027 for details of the model). For example, administering an effective amount of the polypeptide, DAB™ or antagonist can reduce the average arthritic score of the summation of the four limbs in the standard mouse collagen-induced arthritis model, for example, by about 1 to about 16, about 3 to about 16, about 6 to about 16, about 9 to about 16, or about 12 to about 16, as compared to a suitable control. In another example, administering an effective amount of the polypeptide, DAB™ or antagonist can delay the onset of symptoms of arthritis in the standard mouse collagen-induced arthritis model, for example, by about 1 day, about 2 days, about 3 days, about 4 days, about 5 days, about 6 days, about 7 days, about 10 days, about 14 days, about 21 days or about 28 days, as compared to a suitable control. In another example, administering an effective amount of the polypeptide, DAB™ or antagonist can result in an average arthritic score of the summation of the four limbs in the standard mouse collagen-induced arthritis model of 0 to about 3, about 3 to about 5, about 5 to about 7, about 7 to about 15, about 9 to about 15, about 10 to about 15, about 12 to about 15, or about 14 to about 15.

In other embodiments, the polypeptide, DAB™ or antagonist is efficacious in the mouse ΔARE model of arthritis (see WO2006038027 for details of the model). For example, administering an effective amount of the polypeptide, DAB™ or antagonist can reduce the average arthritic score in the mouse ΔARE model of arthritis, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the polypeptide, DAB™ or antagonist can delay the onset of symptoms of arthritis in the mouse ΔARE model of arthritis by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the polypeptide, DAB™ or antagonist can result in an average arthritic score in the mouse ΔARE model of arthritis of 0 to about 0.5, about 0.5 to about 1, about 1 to about 1.5, about 1.5 to about 2, or about 2 to about 2.5.

In other embodiments, the polypeptide, DAB™ or antagonist is efficacious in the mouse ΔARE model of inflammatory bowel disease (IBD) (see WO2006038027 for details of the model). For example, administering an effective amount of the polypeptide, DAB™ or antagonist can reduce the average acute and/or chronic inflammation score in the mouse ΔARE model of IBD, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the polypeptide, DAB™ or antagonist can delay the onset of symptoms of IBD in the mouse ΔARE model of IBD by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the polypeptide, DAB™ or antagonist can result in an average acute and/or chronic inflammation score in the mouse ΔARE model of IBD of 0 to about 0.5, about 0.5 to about 1, about 1 to about 1.5, about 1.5 to about 2, or about 2 to about 2.5.

In other embodiments, the polypeptide, DAB™ or antagonist is efficacious in the mouse dextran sulfate sodium (DSS) induced model of IBD (see WO2006038027 for details of the model). For example, administering an effective amount of the polypeptide, DAB™ or antagonist can reduce the average severity score in the mouse DSS model of IBD, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the polypeptide, DAB™ or antagonist can delay the onset of symptoms of IBD in the mouse DSS model of IBD by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the polypeptide, DAB™ or antagonist can result in an average severity score in the mouse DSS model of IBD of 0 to about 0.5, about 0.5 to about 1, about 1 to about 1.5, about 1.5 to about 2, or about 2 to about 2.5.

In particular embodiments, the polypeptide, DAB™ or antagonist is efficacious in the mouse tobacco smoke model of chronic obstructive pulmonary disease (COPD) (see WO2006038027 and WO2007049017 for details of the model). For example, administering an effective amount of the ligand can reduce or delay onset of the symptoms of COPD, as compared to a suitable control.

Animal model systems which can be used to screen the effectiveness of the antagonists of TNFR1 (e.g, ligands, antibodies or binding proteins thereof) in protecting against or treating the disease are available. Methods for the testing of systemic lupus erythematosus (SLE) in susceptible mice are known in the art (Knight et al. (1978) *J. Exp. Med.*, 147: 1653; Reinersten et al. (1978) *New Eng. J. Med.*, 299: 515). Myasthenia Gravis (MG) is tested in SJL/J female mice by inducing the disease with soluble AchR protein from another species (Lindstrom et al. (1988) *Adv. Immunol.*, 42: 233). Arthritis is induced in a susceptible strain of mice by injection of Type II collagen (Stuart et al. (1984) *Ann. Rev. Immunol.*, 42: 233). A model by which adjuvant arthritis is induced in susceptible rats by injection of mycobacterial heat shock protein has been described (Van Eden et al. (1988) *Nature*, 331: 171). Thyroiditis is induced in mice by administration of thyroglobulin as described (Maron et al. (1980) *J. Exp. Med.*, 152: 1115). Insulin dependent diabetes mellitus (IDDM) occurs naturally or can be induced in certain strains of mice such as those described by Kanasawa et al. (1984) *Diabetologia*, 27: 113. EAE in mouse and rat serves as a model for MS in human. In this model, the demyelinating disease is induced by administration of myelin basic protein (see Paterson (1986) *Textbook of Immunopathology*, Mischer et al., eds., Grune and Stratton, New York, pp. 179-213; McFarlin et al. (1973) *Science*, 179: 478: and Satoh et al. (1987) *J. Immunol.*, 138: 179).

Generally, the present ligands (e.g., antagonists) will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences*, 16th Edition). A variety of suitable formulations can be used, including extended release formulations.

The ligands (e.g., antagonits) of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the ligands of the present invention, or even combinations of ligands according to the present invention having different specificities, such as ligands selected using different target antigens or epitopes, whether or not they are pooled prior to administration.

The route of administration of pharmaceutical compositions according to the invention may be any of those commonly known to those of ordinary skill in the art. For therapy, including without limitation immunotherapy, the selected ligands thereof of the invention can be administered to any patient in accordance with standard techniques.

The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician. Administration can be local (e.g., local delivery to the lung by pulmonary administration, e.g., intranasal administration) or systemic as indicated.

The ligands of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the present ligands (e.g., antagonists) or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of ligand, e.g. DAB™ or antagonist per kilogram of body weight, with doses of 0.05 to 2.0 mg/kg/dose being more commonly used. For prophylactic applications, compositions containing the present ligands or cocktails thereof may also be administered in similar or slightly lower dosages, to prevent, inhibit or delay onset of disease (e.g., to sustain remission or quiescence, or to prevent acute phase). The skilled clinician will be able to determine the appropriate dosing interval to treat, suppress or prevent disease. When an ligand of TNFR1 (e.g., antagonist) is administered to treat, suppress or prevent a chronic inflammatory disease, it can be administered up to four times per day, twice weekly, once weekly, once every two weeks, once a month, or once every two months, at a dose off, for example, about 10 µg/kg to about 80 mg/kg, about 100 µg/kg to about 80 mg/kg, about 1 mg/kg to about 80 mg/kg, about 1 mg/kg to about 70 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 1 mg/kg to about 10 mg/kg, about 10 µg/kg to about 10 mg/kg, about 10 µg/kg to about 5 mg/kg, about 10 µg/kg to about 2.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg. In particular embodiments, the ligand of TNFR1 (e.g., antagonist) is administered to treat, suppress or prevent a chronic inflammatory disease once every two weeks or once a month at a dose of about 10 µg/kg to about 10 mg/kg (e.g., about 10 µg/kg, about 100 µg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg.)

Treatment or therapy performed using the compositions described herein is considered "effective" if one or more symptoms are reduced (e.g., by at least 10% or at least one point on a clinical assessment scale), relative to such symptoms present before treatment, or relative to such symptoms in an individual (human or model animal) not treated with such composition or other suitable control. Symptoms will obviously vary depending upon the disease or disorder targeted, but can be measured by an ordinarily skilled clinician or technician. Such symptoms can be measured, for example, by monitoring the level of one or more biochemical indicators of the disease or disorder (e.g., levels of an enzyme or metabolite correlated with the disease, affected cell numbers, etc.), by monitoring physical manifestations (e.g., inflammation, tumor size, etc.), or by an accepted clinical assessment scale, for example, the Expanded Disability Status Scale (for multiple sclerosis), the Irvine Inflammatory Bowel Disease Questionnaire (32 point assessment evaluates quality of life with respect to bowel function, systemic symptoms, social function and emotional status—score ranges from 32 to 224, with higher scores indicating a better quality of life), the Quality of Life Rheumatoid Arthritis Scale, or other accepted clinical assessment scale as known in the field. A sustained (e.g., one day or more, or longer) reduction in disease or disorder symptoms by at least 10% or by one or more points on a given clinical scale is indicative of "effective" treatment. Similarly, prophylaxis performed using a composition as described herein is "effective" if the onset or severity of one or more symptoms is delayed, reduced or abolished relative to such symptoms in a similar individual (human or animal model) not treated with the composition.

A composition containing a ligand (e.g., antagonist) or cocktail thereof according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the ligands whereby the undesired cells are killed or otherwise removed from the blood for return to the mammal in accordance with standard techniques.

A composition containing a ligand (e.g., antagonist) according to the present invention may be utilised in prophylactic and therapeutic settings to aid in the alteration, inactivation, killing or removal of a select target cell population in a mammal.

The ligands (e.g., anti-TNFR1 antagonists, DAB™ monomers) can be administered and or formulated together with one or more additional therapeutic or active agents. When a ligand (eg, a DAB™) is administered with an additional therapeutic agent, the ligand can be administered before, simultaneously with or subsequent to administration of the additional agent. Generally, the ligand and additional agent are administered in a manner that provides an overlap of therapeutic effect.

In one embodiment, the invention is a method for treating, suppressing or preventing a chronic inflammatory disease, comprising administering to a mammal in need thereof a therapeutically-effective dose or amount of a polypeptide, DAB™ or antagonist of TNFR1 according to the invention.

In one embodiment, the invention is a method for treating, suppressing or preventing arthritis (e.g., rheumatoid arthritis, juvenile rheumatoid arthritis, ankylosing spondylitis, psoriatic arthritis) comprising administering to a mammal in need thereof a therapeutically-effective dose or amount of a polypeptide, DAB™ or antagonist of TNFR1 according to the invention.

In another embodiment, the invention is a method for treating, suppressing or preventing psoriasis comprising administering to a mammal in need thereof a therapeutically-effective dose or amount of a polypeptide, DAB™ or antagonist of TNFR1 according to the invention.

In another embodiment, the invention is a method for treating, suppressing or preventing inflammatory bowel disease (e.g., Crohn's disease, ulcerative colitis) comprising administering to a mammal in need thereof a therapeutically-effective dose or amount of a polypeptide, DAB™ or antagonist of TNFR1 according to the invention.

In another embodiment, the invention is a method for treating, suppressing or preventing chronic obstructive pulmonary disease (e.g., chronic bronchitis, chronic obstructive bronchitis, emphysema), comprising administering to a mammal in need thereof a therapeutically-effective dose or amount of a polypeptide, DAB™ or antagonist of TNFR1 according to the invention.

In another embodiment, the invention is a method for treating, suppressing or preventing pneumonia (e.g., bacterial pneumonia, such as Staphylococcal pneumonia) comprising administering to a mammal in need thereof a therapeutically-effective dose or amount of a polypeptide, DAB™ or antagonist of TNFR1 according to the invention.

The invention provides a method for treating, suppressing or preventing other pulmonary diseases in addition to chronic obstructive pulmonary disease, and pneumonia. Other pulmonary diseases that can be treated, suppressed or prevented in accordance with the invention include, for example, cystic fibrosis and asthma (e.g., steroid resistant asthma). Thus, in another embodiment, the invention is a method for treating, suppressing or preventing a pulmonary disease (e.g., cystic fibrosis, asthma) comprising administering to a mammal in need thereof a therapeutically-effective dose or amount of a polypeptide, DAB™ or antagonist of TNFR1 according to the invention.

In particular embodiments, an antagonist of TNFR1 is administered via pulmonary delivery, such as by inhalation (e.g., intrabronchial, intranasal or oral inhalation, intranasal drops) or by systemic delivery (e.g., parenteral, intravenous, intramuscular, intraperitoneal, subcutaneous).

In another embodiment, the invention is a method treating, suppressing or preventing septic shock comprising administering to a mammal in need thereof a therapeutically-effective dose or amount of a polypeptide, DAB™ or antagonist of TNFR1 according to the invention.

In a further aspect of the invention, there is provided a composition comprising a a polypeptide, DAB™ or antagonist of TNFR1 according to the invention and a pharmaceutically acceptable carrier, diluent or excipient.

Moreover, the present invention provides a method for the treatment of disease using a polypeptide, DAB™ or antagonist of TNFR1 or a composition according to the present invention. In an embodiment the disease is cancer or an inflammatory disease, eg rheumatoid arthritis, asthma or Crohn's disease.

Formats

Increased half-life is useful in in vivo applications of immunoglobulins, especially antibodies and most especially antibody fragments of small size. Such fragments (Fvs, disulphide bonded Fvs, Fabs, scFvs, DAB™s) suffer from rapid clearance from the body; thus, whilst they are able to reach most parts of the body rapidly, and are quick to produce and easier to handle, their in vivo applications have been limited by their only brief persistence in vivo. One embodiment of the invention solves this problem by providing increased half-life of the ligands in vivo and consequently longer persistence times in the body of the functional activity of the ligand.

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Half lives (t ½ alpha and t ½ beta) and AUC can be determined from a curve of serum concentration of ligand against time. The WINNONLIN™ analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The t alpha half life is the half life of the first phase and the t beta half life is the half life of the second phase. Thus, in one embodiment, the present invention provides a ligand or a composition comprising a ligand according to the invention having a tα half-life in the range of 15 minutes or more. In one embodiment, the lower end of the range is 30 minutes, 45 minutes, 1 hour, 2 hours, 3 hours, 4 hours, 5 hours, 6 hours, 7 hours, 10 hours, 11 hours or 12 hours. In addition, or alternatively, a ligand or composition according to the invention will have a to half life in the range of up to and including 12 hours. In one embodiment, the upper end of the range is 11, 10, 9, 8, 7, 6 or 5 hours. An example of a suitable range is 1 to 6 hours, 2 to 5 hours or 3 to 4 hours.

In one embodiment, the present invention provides a ligand (polypeptide, DAB™ or antagonist) or a composition comprising a ligand according to the invention having a tβ half-life in the range of 2.5 hours or more. In one embodiment, the lower end of the range is 3 hours, 4 hours, 5 hours, 6 hours, 7 hours, 10 hours, 11 hours, or 12 hours. In addition, or alternatively, a ligand or composition according to the invention has a tβ half-life in the range of up to and including 21 days. In one embodiment, the upper end of the range is 12 hours, 24 hours, 2 days, 3 days, 5 days, 10 days, 15 days or 20 days. In one embodiment a ligand or composition according to the invention will have a tβ half life in the range 12 to 60 hours. In a further embodiment, it will be in the range 12 to 48 hours. In a further embodiment still, it will be in the range 12 to 26 hours.

In addition, or alternatively to the above criteria, the present invention provides a ligand or a composition comprising a ligand according to the invention having an AUC value (area under the curve) in the range of 1 mg·min/ml or more. In one embodiment, the lower end of the range is 5, 10, 15, 20, 30, 100, 200 or 300 mg·min/ml. In addition, or alternatively, a ligand or composition according to the invention has an AUC in the range of up to 600 mg·min/ml. In one embodiment, the upper end of the range is 500, 400, 300, 200, 150, 100, 75 or 50 mg·min/ml. In one embodiment a ligand according to the invention will have a AUC in the range selected from the group consisting of the following: 15 to 150 mg·min/ml, 15 to 100 mg·min/ml, 15 to 75 mg·min/ml, and 15 to 50 mg·min/ml.

Polypeptides and DAB™s of the invention and antagonists comprising these can be formatted to have a larger hydrodynamic size, for example, by attachment of a PEG group, serum albumin, transferrin, transferrin receptor or at least the transferrin-binding portion thereof, an antibody Fc region, or by conjugation to an antibody domain. For example, polypeptides DAB™s and antagonists formatted as a larger antigen-binding fragment of an antibody or as an antibody (e.g., formatted as a Fab, Fab', F(ab)$_2$, F(ab')$_2$, IgG, scFv).

Hydrodynamic size of the ligands (e.g., DAB™ monomers and multimers) of the invention may be determined using methods which are well known in the art. For example, gel filtration chromatography may be used to determine the hydrodynamic size of a ligand. Suitable gel filtration matrices for determining the hydrodynamic sizes of ligands, such as cross-linked agarose matrices, are well known and readily available.

The size of a ligand format (e.g., the size of a PEG moiety attached to a DAB™ monomer), can be varied depending on the desired application. For example, where ligand is intended to leave the circulation and enter into peripheral tissues, it is desirable to keep the hydrodynamic size of the ligand low to facilitate extravazation from the blood stream. Alternatively, where it is desired to have the ligand remain in the systemic circulation for a longer period of time the size of the ligand can be increased, for example by formatting as an Ig like protein.

Half-Life Extension by Targeting an Antigen or Epitope that Increases Half-Live In Vivo The hydrodynaminc size of a ligand and its serum half-life can also be increased by conjugating or associating a TNFR1 binding polypeptide, DAB™ or antagonist of the invention to a binding domain (e.g., antibody or antibody fragment) that binds an antigen or epitope that increases half-live in vivo, as described herein. For example, the TNFR1 binding agent (e.g., polypeptide) can be conjugated or linked to an anti-serum albumin or anti-neonatal Fc receptor antibody or antibody fragment, eg an anti-SA or anti-neonatal Fc receptor DAB™, Fab, Fab' or scFv, or to an anti-SA affibody or anti-neonatal Fc receptor Affibody or an anti-SA avimer, or an anti-SA binding domain which comprises a scaffold selected from, but preferably not limited to, the group consisting of CTLA-4, lipocallin, SpA, an affibody, an avimer, GroEl and fibronectin (see PCT/GB2008/000453 filed 8 Feb. 2008 for disclosure of these binding domain, which domains and their sequences are incorporated herein by reference and form part of the disclosure of the present text). Conjugating refers to a composition comprising polypeptide, DAB™ or antagonist of the invention that is bonded (covalently or noncovalently) to a binding domain that binds serum albumin.

Suitable polypeptides that enhance serum half-life in vivo include, for example, transferrin receptor specific ligand-neuropharmaceutical agent fusion proteins (see U.S. Pat. No. 5,977,307, the teachings of which are incorporated herein by reference), brain capillary endothelial cell receptor, transferrin, transferrin receptor (e.g., soluble transferrin receptor), insulin, insulin-like growth factor 1 (IGF 1) receptor, insulin-like growth factor 2 (IGF 2) receptor, insulin receptor, blood coagulation factor X, α1-antitrypsin and HNF 1α. Suitable polypeptides that enhance serum half-life also include alpha-1 glycoprotein (orosomucoid; AAG), alpha-1 antichymotrypsin (ACT), alpha-1 microglobulin (protein HC; AIM), antithrombin III (AT III), apolipoprotein A-1 (Apo A-1), apolipoprotein B (Apo B), ceruloplasmin (Cp), complement component C3 (C3), complement component C4 (C4), C1 esterase inhibitor (C1 INH), C-reactive protein (CRP), ferritin (FER), hemopexin (HPX), lipoprotein(a) (Lp(a)), mannose-binding protein (MBP), myoglobin (Myo), prealbumin (transthyretin; PAL), retinol-binding protein (RBP), and rheumatoid factor (RF).

Suitable proteins from the extracellular matrix include, for example, collagens, laminins, integrins and fibronectin. Collagens are the major proteins of the extracellular matrix. About 15 types of collagen molecules are currently known, found in different parts of the body, e.g. type I collagen (accounting for 90% of body collagen) found in bone, skin, tendon, ligaments, cornea, internal organs or type II collagen found in cartilage, vertebral disc, notochord, and vitreous humor of the eye.

Suitable proteins from the blood include, for example, plasma proteins (e.g., fibrin, α-2 macroglobulin, serum albumin, fibrinogen (e.g., fibrinogen A, fibrinogen B), serum amyloid protein A, haptoglobin, profilin, ubiquitin, uteroglobulin and β-2-microglobulin), enzymes and enzyme inhibitors (e.g., plasminogen, lysozyme, cystatin C, alpha-1-antitrypsin and pancreatic trypsin inhibitor), proteins of the immune system, such as immunoglobulin proteins (e.g., IgA, IgD, IgE, IgG, IgM, immunoglobulin light chains (kappa/lambda)), transport proteins (e.g., retinol binding protein, α-1 microglobulin), defensins (e.g., beta-defensin 1, neutrophil defensin 1, neutrophil defensin 2 and neutrophil defensin 3) and the like.

Suitable proteins found at the blood brain barrier or in neural tissue include, for example, melanocortin receptor, myelin, ascorbate transporter and the like.

Suitable polypeptides that enhance serum half-life in vivo also include proteins localized to the kidney (e.g., polycystin, type IV collagen, organic anion transporter K1, Heymann's antigen), proteins localized to the liver (e.g., alcohol dehydrogenase, G250), proteins localized to the lung (e.g., secretory component, which binds IgA), proteins localized to the heart (e.g., HSP 27, which is associated with dilated cardiomyopathy), proteins localized to the skin (e.g., keratin), bone specific proteins such as morphogenic proteins (BMPs), which are a subset of the transforming growth factor β superfamily of proteins that demonstrate osteogenic activity (e.g., BMP-2, BMP-4, BMP-5, BMP-6, BMP-7, BMP-8), tumor specific proteins (e.g., trophoblast antigen, herceptin receptor, oestrogen receptor, cathepsins (e.g., cathepsin B, which can be found in liver and spleen)).

Suitable disease-specific proteins include, for example, antigens expressed only on activated T-cells, including LAG-3 (lymphocyte activation gene), osteoprotegerin ligand (OPGL; see *Nature* 402, 304-309 (1999)), OX40 (a member of the TNF receptor family, expressed on activated T cells and specifically up-regulated in human T cell leukemia virus type-I (HTLV-I)-producing cells; see *Immunol.* 165 (1):263-70 (2000)). Suitable disease-specific proteins also include, for example, metalloproteases (associated with arthritis/cancers) including CG6512 *Drosophila*, human paraplegin, human FtsH, human AFG3L2, murine ftsH; and angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF α), tumor necrosis factor-alpha (TNF-α), angiogenin, interleukin-3 (IL-3), interleukin-8 (IL-8), platelet-derived endothelial growth factor (PD-ECGF), placental growth factor (PlGF), midkine platelet-derived growth factor-BB (PDGF), and fractalkine.

Suitable polypeptides that enhance serum half-life in vivo also include stress proteins such as heat shock proteins (HSPs). HSPs are normally found intracellularly. When they are found extracellularly, it is an indicator that a cell has died and spilled out its contents. This unprogrammed cell death (necrosis) occurs when as a result of trauma, disease or injury, extracellular HSPs trigger a response from the immune system. Binding to extracellular HSP can result in localizing the compositions of the invention to a disease site.

Suitable proteins involved in Fc transport include, for example, Brambell receptor (also known as FcRB). This Fc receptor has two functions, both of which are potentially useful for delivery. The functions are (1) transport of IgG from mother to child across the placenta (2) protection of IgG from degradation thereby prolonging its serum half-life. It is thought that the receptor recycles IgG from endosomes. (See, Holliger et al, *Nat Biotechnol* 15(7):632-6 (1997).)

DAB™s that Bind Serum Albumin

The invention in one embodiment provides a polypeptide or antagonist (e.g., dual specific ligand comprising an anti-TNFR1 DAB™ (a first DAB™)) that binds to TNFR1 and a second DAB™ that binds serum albumin (SA), the second DAB™ binding SA with a $K_D$ as determined by surface plasmon resonance of 1 nM to 1, 2, 3, 4, 5, 10, 20, 30, 40, 50, 60, 70, 100, 200, 300, 400 or 500 μM (i.e., $\times 10^{-9}$ to $5 \times 10^{-4}$), or 100 nM to 10 μM, or 1 to 5 μM or 3 to 70 nM or 10 nM to 1, 2, 3, 4 or 5 M. For example 30 to 70 nM as determined by surface plasmon resonance. In one embodiment, the first DAB™ (or a DAB™ monomer) binds SA (e.g., HSA) with a $K_D$ as determined by surface plasmon resonance of approximately 1, 50, 70, 100, 150, 200, 300 nM or 1, 2 or 3 μM. In one embodiment, for a dual specific ligand comprising a first anti-SA DAB™ and a second DAB™ to TNFR1, the affinity (eg $K_D$ and/or $K_{off}$ as measured by surface plasmon resonance, eg using BIACORE™) of the second DAB™ for its target is from 1 to 100000 times (eg, 100 to 100000, or 1000 to 100000, or 10000 to 100000 times) the affinity of the first DAB™ for SA. In one embodiment, the serum albumin is human serum albumin (HSA). For example, the first DAB™ binds SA with an affinity of approximately 10 μM, while the second DAB™ binds its target with an affinity of 100 μM. In one embodiment, the serum albumin is human serum albumin (HSA). In one embodiment, the first DAB™ binds SA (eg, HSA) with a $K_D$ of approximately 50, for example 70, 100, 150 or 200 nM. Details of dual specific ligands are found in WO03002609, WO04003019 and WO04058821.

The ligands of the invention can in one embodiment comprise a DAB™ that binds serum albumin (SA) with a $K_D$ as determined by surface plasmon resonance of 1 nM to 1, 2, 3, 4, 5, 10, 20, 30, 40, 50, 60, 70, 100, 200, 300, 400 or 500 μM (i.e., $\times 10^{-9}$ to $5 \times 10^{-4}$), or 100 nM to 10 μM, or 1 to 5 μM or 3 to 70 nM or 10 nM to 1, 2, 3, 4 or 5 μM. For example 30 to 70 nM as determined by surface plasmon resonance. In one embodiment, the first DAB™ (or a DAB™ monomer) binds SA (e.g., HSA) with a $K_D$ as determined by surface plasmon resonance of approximately 1, 50, 70, 100, 150, 200, 300 nM or 1, 2 or 3 μM. In one embodiment, the first and second DAB™s are linked by a linker, for example a linker of from 1 to 4 amino acids or from 1 to 3 amino acids, or greater than 3 amino acids or greater than 4, 5, 6, 7, 8, 9, 10, 15 or 20 amino acids. In one embodiment, a longer linker (greater than 3 amino acids) is used to enhance potency ($K_D$ of one or both DAB™s in the antagonist).

In particular embodiments of the ligands and antagonists, the DAB™ binds human serum albumin and competes for binding to albumin with a DAB™ selected from the group consisting of MSA-16, MSA-26 (See WO04003019 for disclosure of these sequences, which sequences and their nucleic acid counterpart are incorporated herein by reference and form part of the disclosure of the present text), DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO:

515), DOM7r-32 (SEQ ID NO: 516), DOM7r-33 (SEQ ID NO: 517) (See WO2007080392 for disclosure of these sequences, which sequences and their nucleic acid counterpart are incorporated herein by reference and form part of the disclosure of the present text; the SEQ ID NO:s in this paragraph are those that appear in WO2007080392), dAb8 (dAb 10), dAb 10, dAb36, dAb7r20 (DOM7r20), dAb7r21 (DOM7r21), dAb7r22 (DOM7r22), dAb7r23 (DOM7r23), dAb7r24 (DOM7r24), dAb7r25 (DOM7r25), dAb7r26 (DOM7r26), dAb7r27 (DOM7r27), dAb7r28 (DOM7r28), dAb7r29 (DOM7r29), dAb7r29 (DOM7r29), dAb7r31 (DOM7r31), dAb7r32 (DOM7r32), dAb7r33 (DOM7r33), dAb7r33 (DOM7r33), dAb7h22 (DOM7h22), dAb7h23 (DOM7h23), dAb7h24 (DOM7h24), dAb7h25 (DOM7h25), dAb7h26 (DOM7h26), dAb7h27 (DOM7h27), dAb7h30 (DOM7h30), dAb7h31 (DOM7h31), dAb2 (dAbs 4,7,41), dAb4, dAb7, dAb11, dAb12 (dAb7m12), dAb13 (dAb 15), dAb15, dAb16 (dAb21, dAb7m16), dAb17, dAb18, dAb19, dAb21, dAb22, dAb23, dAb24, dAb25 (dAb26, dAb7m26), dAb27, dAb30 (dAb35), dAb31, dAb33, dAb34, dAb35, dAb38 (dAb54), dAb41, dAb46 (dAbs 47, 52 and 56), dAb47, dAb52, dAb53, dAb54, dAb55, dAb56, dAb7m12, dAb7m16, dAb7m26, dAb7r1 (DOM7r1), dAb7r3 (DOM7r3), dAb7r4 (DOM7r4), dAb7r5 (DOM7r5), dAb7r7 (DOM7r7), dAb7r8 (DOM7r8), dAb7r13 (DOM7r13), dAb7r14 (DOM7r14), dAb7r15 (DOM7r15), dAb7r16 (DOM7r16), dAb7r17 (DOM7r17), dAb7r18 (DOM7r18), dAb7r19 (DOM7r19), dAb7h1 (DOM7h1), dAb7h2 (DOM7h2), dAb7h6 (DOM7h6), dAb7h7 (DOM7h7), dAb7h8 (DOM7h8), dAb7h9 (DOM7h9), dAb7h10 (DOM7h10), dAb7h11 (DOM7h11), dAb7h12 (DOM7h12), dAb7h13 (DOM7h13), dAb7h14 (DOM7h14), dAb7p1 (DOM7p1), and dAb7p2 (DOM7p2) (see PCT/GB2008/000453 filed 8 Feb. 2008 for disclosure of these sequences, which sequences and their nucleic acid counterpart are incorporated herein by reference and form part of the disclosure of the present text). Alternative names are shown in brackets after the dAb, e.g. dAb8 has an alternative name which is dAb10 i.e. dAb8 (dAb 10). These sequences are also set out in FIGS. 51a and b.

In certain embodiments, the DAB™ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a DAB™ selected from the group consisting of

MSA-16, MSA-26,

DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), DOM7r-33 (SEQ ID NO: 517) (the SEQ ID NO:s in this paragraph are those that appear in WO2007080392), dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, Ab7h24, Ab7h25, Ab7h26, dAb7h27, dAb7h30, dAb7h31, dAb2, dAb4, dAb7, dAb 11, dAb 12, dAb 13, dAb 15, dAb 16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2.

For example, the DAB™ that binds human serum albumin can comprise an amino acid sequence that has at least about 90%, or at least about 95%, or at least about 96%, or at least about 97%, or at least about 98%, or at least about 99% amino acid sequence identity with DOM7h-2 (SEQ ID NO:482), DOM7h-3 (SEQ ID NO:483), DOM7h-4 (SEQ ID NO:484), DOM7h-6 (SEQ ID NO:485), DOM7h-1 (SEQ ID NO:486), DOM7h-7 (SEQ ID NO:487), DOM7h-8 (SEQ ID NO:496), DOM7r-13 (SEQ ID NO:497), DOM7r-14 (SEQ ID NO:498), DOM7h-22 (SEQ ID NO:489), DOM7h-23 (SEQ ID NO:490), DOM7h-24 (SEQ ID NO:491), DOM7h-25 (SEQ ID NO:492), DOM7h-26 (SEQ ID NO:493), DOM7h-21 (SEQ ID NO:494), DOM7h-27 (SEQ ID NO:495) (the SEQ ID NO:s in this paragraph are those that appear in WO2007080392), dAb8, dAb 10, dAb36, dAb7h21, dAb7h22, dAb7h23, Ab7h24, Ab7h25, Ab7h26, dAb7h27, dAb7h30, dAb7h31, dAb2, dAb4, dAb7, dAb 11, dAb 12, dAb 13, dAb 15, dAb 16, dAb 17, dAb 18, dAb 19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7h1, dAb7h2, dAb7h6, dAb7h7, dAb7h8, dAb7h9, dAb7h10, dAb7h11, dAb7h12, dAb7h13 and dAb7h14.

In certain embodiments, the DAB™ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a DAB™ selected from the group consisting of DOM7h-2 (SEQ ID NO:482), DOM7h-6 (SEQ ID NO:485), DOM7h-1 (SEQ ID NO:486), DOM7h-7 (SEQ ID NO:487), DOM7h-8 (SEQ ID NO:496), DOM7h-22 (SEQ ID NO:489), DOM7h-23 (SEQ ID NO:490), DOM7h-24 (SEQ ID NO:491), DOM7h-25 (SEQ ID NO:492), DOM7h-26 (SEQ ID NO:493), DOM7h-21 (SEQ ID NO:494), DOM7h-27 (SEQ ID NO:495) (the SEQ ID NO:s in this paragraph are those that appear in WO2007080392), dAb7h21, dAb7h22, dAb7h23, Ab7h24, Ab7h25, Ab7h26, dAb7h27, dAb7h30, dAb7h31, dAb2, dAb4, dAb7, dAb38, dAb41, dAb7h1, dAb7h2, dAb7h6, dAb7h7, dAb7h8, dAb7h9, dAb7h10, dAb7h11, dAb7h12, dAb7h13 and dAb7h14.

In more particular embodiments, the DAB™ is a $V_\kappa$ DAB™ that binds human serum albumin and has an amino acid sequence selected from the group consisting of DOM7h-2 (SEQ ID NO:482), DOM7h-6 (SEQ ID NO:485), DOM7h-1 (SEQ ID NO:486), DOM7h-7 (SEQ ID NO:487), DOM7h-8 (SEQ ID NO:496) (the SEQ ID NO:s in this paragraph are those that appear in WO2007080392), dAb2, dAb4, dAb7, dAb38, dAb41, dAb54, dAb7h1, dAb7h2, dAb7h6, dAb7h7, dAb7h8, dAb7h9, dAb7h10, dAb7h11, dAb7h12, dAb7h13 and dAb7h14.

In more particular embodiments, the DAB™ is a $V_H$ DAB™ that binds human serum albumin and has an amino acid sequence selected from dAb7h30 and dAb7h31.

In more particular embodiments, the DAB™ is dAb7h11 or dAb7h 14.

In other embodiments, the DAB™, ligand or antagonist binds human serum albumin and comprises one, two or three of the CDRs of any of the foregoing amino acid sequences, eg one, two or three of the CDRs of dAb7h 11 or dAb7h14.

Suitable Camelid $V_{HH}$ that bind serum albumin include those disclosed in WO 2004/041862 (Ablynx N.V.) and in WO2007080392 (which $V_{HH}$ sequences and their nucleic acid counterpart are incorporated herein by reference and form part of the disclosure of the present text), such as Sequence A (SEQ ID NO:518), Sequence B (SEQ ID NO:519), Sequence C (SEQ ID NO:520), Sequence D (SEQ ID NO:521), Sequence E (SEQ ID NO:522), Sequence F (SEQ ID NO:523), Sequence G (SEQ ID NO:524), Sequence H (SEQ ID NO:525), Sequence I (SEQ ID NO:526), Sequence J (SEQ ID NO:527), Sequence K (SEQ ID NO:528), Sequence L (SEQ ID NO:529), Sequence M (SEQ ID NO:530), Sequence N (SEQ ID NO:531), Sequence O (SEQ ID NO:532), Sequence P (SEQ ID NO:533), Sequence Q (SEQ ID NO:534), these sequence numbers correspond to those cited in WO2007080392 or WO 2004/041862 (Ablynx N.V.). In certain embodiments, the Camelid $V_{HH}$ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with ALB1 disclosed in WO2007080392 or any one of SEQ ID NOS: 518-534, these sequence numbers corresponding to those cited in WO2007080392 or WO 2004/041862.

In some embodiments, the ligand or antagonist comprises an anti-serum albumin DAB™ that competes with any anti-serum albumin DAB™ disclosed herein for binding to serum albumin (e.g., human serum albumin).

In an alternative embodiment, the antagonist or ligand comprises a binding moiety specific for TNFR1 (eg, human TNFR1), wherein the moiety comprises non-immunoglobulin sequences as described in co-pending application PCT/GB2008/000453 filed 8 Feb. 2008, the disclosure of these binding moieties, their methods of production and selection (eg, from diverse libraries) and their sequences are incorporated herein by reference as part of the disclosure of the present text)

Conjugation to a Half-Life Extending Moiety (Eg, Albumin)

In one embodiment, a (one or more) half-life extending moiety (eg, albumin, transferrin and fragments and analogues thereof) is conjugated or associated with the TNFR1-binding polypeptide, DAB™ or antagonist of the invention. Examples of suitable albumin, albumin fragments or albumin variants for use in a TNFR1-binding format are described in WO 2005077042, which disclosure is incorporated herein by reference and forms part of the disclosure of the present text. In particular, the following albumin, albumin fragments or albumin variants can be used in the present invention:

SEQ ID NO:1 (as disclosed in WO 2005077042, this sequence being explicitly incorporated into the present disclosure by reference);

Albumin fragment or variant comprising or consisting of amino acids 1-387 of SEQ ID NO:1 in WO 2005077042;

Albumin, or fragment or variant thereof, comprising an amino acid sequence selected from the group consisting of: (a) amino acids 54 to 61 of SEQ ID NO:1 in WO 2005077042; (b) amino acids 76 to 89 of SEQ ID NO:1 in WO 2005077042; (c) amino acids 92 to 100 of SEQ ID NO: 1 in WO 2005077042; (d) amino acids 170 to 176 of SEQ ID NO:1 in WO 2005077042; (e) amino acids 247 to 252 of SEQ ID NO: 1 in WO 2005077042; (f) amino acids 266 to 277 of SEQ ID NO: 1 in WO 2005077042; (g) amino acids 280 to 288 of SEQ ID NO:1 in WO 2005077042; (h) amino acids 362 to 368 of SEQ ID NO: 1 in WO 2005077042; (i) amino acids 439 to 447 of SEQ ID NO: 1 in WO 2005077042 (j) amino acids 462 to 475 of SEQ ID NO: 1 in WO 2005077042; (k) amino acids 478 to 486 of SEQ ID NO: 1 in WO 2005077042; and (l) amino acids 560 to 566 of SEQ ID NO: 1 in WO 2005077042.

Figure 3:
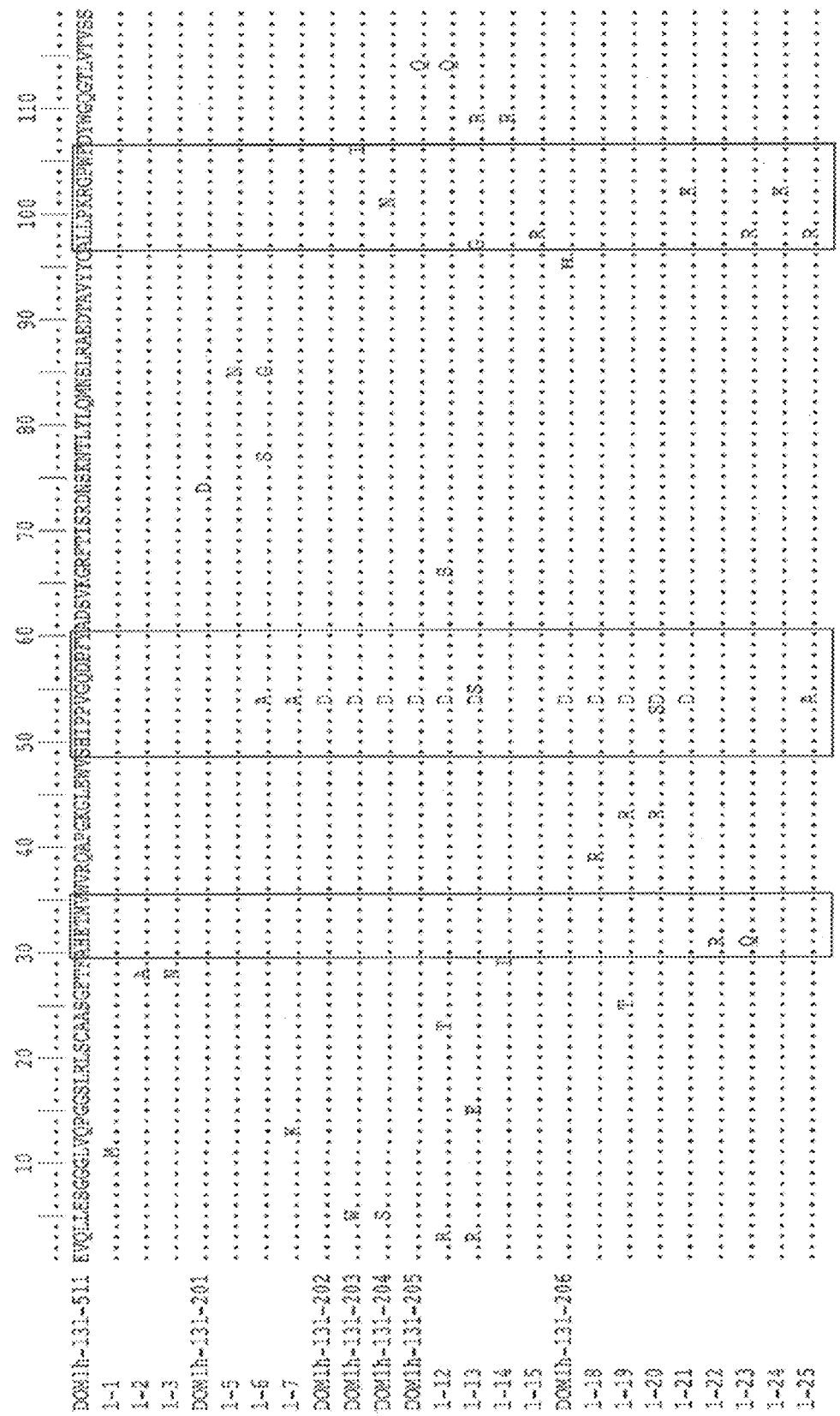
FIG. 3 is an illustration of the amino acid sequences of DOM1h-131-511 (SEQ ID NO: 3) and 24 selected variants including DOM1h-131-206 (SEQ ID NO: 3). The amino acids that differ from the parent sequence in selected clones are highlighted (those that are identical are marked by dots). The loops corresponding to CDR1, CDR2 and CDR3 are outlined with boxes.

Further examples of suitable albumin, fragments and analogs for use in a TNFR1-binding format are described in WO 03076567, which disclosure is incorporated herein by reference and which forms part of the disclosure of the present text. In particular, the following albumin, fragments or variants can be used in the present invention:

Human serum albumin as described in WO 03076567, eg, in FIG. 3 (this sequence information being explicitly incorporated into the present disclosure by reference);

Human serum albumin (HA) consisting of a single non-glycosylated polypeptide chain of 585 amino acids with a formula molecular weight of 66,500 (See, Meloun, et al., *FEBS Letters* 58:136 (1975); Behrens, et al., *Fed. Proc.* 34:591 (1975); Lawn, et al., *Nucleic Acids Research* 9:6102-6114 (1981); Minghetti, et al., *J. Biol. Chem.* 261:6747 (1986));

A polymorphic variant or analog or fragment of albumin as described in Weitkamp, et al., *Ann. Hum. Genet.* 37:219 (1973);

An albumin fragment or variant as described in EP 322094, eg, HA(1-373, HA(1-388), HA(1-389), HA(1-369), and HA(1-419) and fragments between 1-369 and 1-419;

An albumin fragment or variant as described in EP 399666, eg, HA(1-177) and HA(1-200) and fragments between HA(1-X), where X is any number from 178 to 199.

Where a (one or more) half-life extending moiety (eg, albumin, transferrin and fragments and analogues thereof) is used to format the TNFR1-binding polypeptides, DAB™s and antagonists of the invention, it can be conjugated using any suitable method, such as, by direct fusion to the TNFR1-binding moiety (eg, anti-TNFR1 DAB™), for example by using a single nucleotide construct that encodes a fusion protein, wherein the fusion protein is encoded as a single polypeptide chain with the half-life extending moiety located N- or C-terminally to the TNFR1 binding moiety. Alternatively, conjugation can be achieved by using a peptide linker between moeities, eg, a peptide linker as described in WO 03076567 or WO 2004003019 (these linker disclosures being incorporated by reference in the present disclosure to provide examples for use in the present invention). Typically, a polypeptide that enhances serum half-life in vivo is a polypeptide which occurs naturally in vivo and which resists degradation or removal by endogenous mechanisms which remove unwanted material from the organism (e.g., human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport.

In embodiments of the invention described throughout this disclosure, instead of the use of an anti-TNFR1 "DAB™" in an antagonist or ligand of the invention, it is contemplated that the skilled addressee can use a polypeptide or domain that comprises one or more or all 3 of the CDRs of a DAB™ of the invention that binds TNFR1 (e.g., CDRs grafted onto a suitable protein scaffold or skeleton, eg an affibody, an SpA scaffold, an LDL receptor class A domain or an EGF domain) The disclosure as a whole is to be construed accordingly to provide disclosure of antagonists using such domains in place of a DAB™. In this respect, see PCT/GB2008/000453 filed 8 Feb. 2008, the disclosure of which is incorporated by reference).

In one embodiment, therefore, an antagonist of the invention comprises an immunoglobulin single variable domain or domain antibody (DAB™) that has binding specificity for TNFR1 or the complementarity determining regions of such a DAB™ in a suitable format. The antagonist can be a polypeptide that consists of such a DAB™, or consists essentially of such a DAB™. The antagonist can be a polypeptide that comprises a DAB™ (or the CDRs of a DAB™) in a suitable format, such as an antibody format (e.g., IgG-like format, scFv, Fab, Fab', F(ab')$_2$), or a dual specific ligand that comprises a DAB™ that binds TNFR1 and a second DAB™ that binds another target protein, antigen or epitope (e.g., serum albumin).

Polypeptides, DAB™s and antagonists according to the invention can be formatted as a variety of suitable antibody formats that are known in the art, such as, IgG-like formats, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single variable domain (e.g., $V_H$, $V_L$), a DAB™, and modified versions of any of the foregoing (e.g., modified by the covalent attachment of polyalkylene glycol (e.g., polyethylene glycol, polypropylene glycol, polybutylene glycol) or other suitable polymer).

In some embodiments, the invention provides a ligand (eg, an anti-TNFR1 antagonist) that is an IgG-like format. Such formats have the conventional four chain structure of an IgG molecule (2 heavy chains and two light chains), in which one or more of the variable regions ($V_H$ and or $V_L$) have been replaced with a DAB™ of the invention. In one embodiment, each of the variable regions (2 $V_H$ regions and 2 $V_L$ regions) is replaced with a DAB™ or single variable domain, at least one of which is an anti-TNFR1 DAB™ according to the invention. The DAB™(s) or single variable domain(s) that are included in an IgG-like format can have the same specificity or different specificities. In some embodiments, the IgG-like format is tetravalent and can have one (anti-TNFR1 only), two (eg, anti-TNFR1 and anti-SA), three or four specificities. For example, the IgG-like format can be monospecific and comprises 4 DAB™s that have the same specificity; bispecific and comprises 3 DAB™s that have the same specificity and another DAB™ that has a different specificity; bispecific and comprise two DAB™s that have the same specificity and two DAB™s that have a common but different specificity; trispecific and comprises first and second DAB™ s that have the same specificity, a third DAB™ with a different specificity and a fourth DAB™ with a different specificity from the first, second and third DAB™ s; or tetraspecific and comprise four DAB™s that each have a different specificity. Antigen-binding fragments of IgG-like formats (e.g., Fab, F(ab')$_2$, Fab', Fv, scFv) can be prepared. In one embodiment, the IgG-like formats or antigen-binding fragments thereof do not crosslink TNFR1, for example, the format may be monovalent for TNFR1. If complement activation and/or antibody dependent cellular cytotoxicity (ADCC) function is desired, the ligand can be an IgG1-like format. If desired, the IgG-like format can comprise a mutated constant region (variant IgG heavy chain constant region) to minimize binding to Fc receptors and/or ability to fix complement. (see e.g. Winter et al, GB 2,209,757 B; Morrison et al., WO 89/07142; Morgan et al., WO 94/29351, Dec. 22, 1994).

The ligands of the invention (polypeptides, DAB™s and antagonists) can be formatted as a fusion protein that contains a first immunoglobulin single variable domain that is fused directly to a second immunoglobulin single variable domain. If desired such a format can further comprise a half-life extending moiety. For example, the ligand can comprise a first immunoglobulin single variable domain that is fused directly to a second immunoglobulin single variable domain that is fused directly to an immunoglobulin single variable domain that binds serum albumin.

Generally the orientation of the polypeptide domains that have a binding site with binding specificity for a target, and whether the ligand comprises a linker, is a matter of design choice. However, some orientations, with or without linkers, may provide better binding characteristics than other orientations. All orientations (e.g., dAb 1-linker-dAb2; dAb2-linker-dAb1) are encompassed by the invention are ligands that contain an orientation that provides desired binding characteristics can be easily identified by screening.

Polypeptides and DAB™s according to the invention, including DAB™ monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides.

The invention moreover provides dimers, trimers and polymers of the aforementioned DAB™ monomers.

Codon Optimised Sequences

As described above, embodiments of the invention provide codon optimized nucleotide sequences encoding polypeptides and variable domains of the invention. As shown in the following illustration, codon optimized sequences of about 70% identity can be produced that encode for the same variable domain (in this case the variable domain amino acid sequence is identical to DOM1h-131-206). In this instance, the sequences were optimized for expression by *Pichia pastoris* (codon optimized sequences 1-3) or *E. coli* (codon optimized sequences 4 and 5).

We performed a calculation taking into account the degeneracy in the genetic code and maximised the number of nucleotide changes within each degenerate codon encoded by the nucleotide sequence of DOM1h-131-206 as shown in FIG. 19 and a theoretical nucleotide sequence which still encodes a variable domain that is identical to DOM1h-131-206. The calculation revealed that the theoretical sequence would have only 57% identity to the nucleotide sequence of DOM1h-131-206 as shown in FIG. 19. Codon optimized sequences are shown in FIGS. 53-57.

EXEMPLIFICATION

Example A: Lead Selection & Characterisation of Domain Antibodies to Human TNFR1

Domain antibodies generated were derived from phage libraries. Both soluble selections and panning to passively absorbed human TNFR1 were performed according to the relevant standard methods. Human TNFR1 was purchased as a soluble recombinant protein either from R&D systems (Cat No 636-R1-025/CF) or Peprotech (Cat no. 310-07) and either used directly (in the case of passive selections) or after biotinylation using coupling via primary amines followed by quality control of its activity in a biological assay and analysis of its MW and extent of biotinylation by mass spectrometry. Typically 3 rounds of selection were performed utilising decreasing levels of antigen in every next round.

Outputs from selections were screened by phage ELISA for the presence of anti-TNFR1 binding clones. DNA was isolated from these phage selections and subcloned into a expression vector for expression of soluble DAB™ fragments. Soluble DAB™ fragments were expressed in 96-well plates and the supernantants were used to screen for the presence of anti-TNFR1 binding DAB™s, either using a direct binding ELISA with anti-c-myc detection or BIACORE™ using a streptavidin/biotinylated TNFR1 BIACORE™ chip and ranked according to off-rates.

The lead molecules, described below, were derived from the parental DAB™, designated DOM1h-131 (disclosed in WO2006038027). This molecule was selected from the phage display library after 3 rounds of selections using 60 nM of biotinylated antigen. Streptavidin or NEUTRAVIDIN™ coated DYNABEADS™ were alternated as capture reagents in each round of selection to prevent selection of binders against either streptavidin or NEUTRAVIDIN™. The potency of the lead DOM1h-131 at this stage was in the low micromolar range as determined in the MRC-5 fibroblast/IL-8 release cell assay. The binding kinetics as determined by BIACORE™ typically displayed fast-on/fast-off rates. *E. coli* expression levels of this DOM1h-131 lead molecule, as a C-terminally myc tagged monomer were in the region of 8 mg/l.

Affinity Maturation of Leads:

DOM1h-131 was taken forward into affinity maturation to generate mutants with higher potency and improved biophysical characteristics (see FIG. 3 for amino acid sequences of DOM1h-131 derived leads). After generation of an error-prone library (average number of 1 amino acid change per DAB™ sequence, library size 8×10$^7$) using an error-prone PCR polymerase (GENEMORPH II™, Stratagene), seven rounds of selection utilising these error-prone libraries were performed. This strategy led to the isolation of clone DOM1h-131-8, a molecule where 4 amino acid changes (one in framework 1 (FR 1), one in CDR1, one in CDR3 and one in FR4) gave an approximate 100-fold improvement in potency as measured by the MRC-5 cell assay (~4 nM). In this assay MRC-5 cells were incubated with the test samples for one hour then TNF-α (200 µg/ml) was added. After an overnight incubation IL-8 release was determined using an IL-8 ABI 8200™ cellular detection assay (FMAT™). A TNF-α dose curve was included in each experiment. The concentration of TNF-α used to compete with DAB™ binding to TNFR1 (200 µg/ml) was approximately 70% of the maximum TNF-α response in this assay.

In order to further improve potency, single amino acid positions were diversified by oligo-directed mutagenesis at key positions suggested by the error-prone lead consensus information. During this process an improved version of the DOM1h-131-8 clone, DOM1h-131-24 (originally named DOM1h-131-8-2 prior to correction) was isolated through BIACORE™ screening that had a single K94R amino acid mutation (amino acid numbering according to Kabat) and an RBA potency of 200-300 µM.

Further error-prone libraries based on this lead and the NNS library from which it was derived were generated and subjected to three rounds of phage selections using heat treatment (for method see Jespers L, et al., Aggregation-resistant domain antibodies selected on phage by heat denaturation. *Nat Biotechnol.* 2004 September; 22(9):1161-5). During this selection, libraries were pooled and clones derived from round two of the selection yielded DAB™s such as DOM1h-131-53 which were considered to be more heat stable. It was hypothesised that these clones would possess better biophysical characteristics. Some framework mutations in clone DOM1h-131-53 were germlined to generate clone DOM1h-131-83. This clone formed the basis for further diversification via oligo-directed individual CDR mutagenesis either using phage display selection as described above or using the in-vitro compartmentalization technology using emulsions. The phage display strategy generated leads DOM1h-131-117 and DOM1h-131-151. The in-vitro compartmentalization technology generated DOM1h-131-511.

Figure 50:
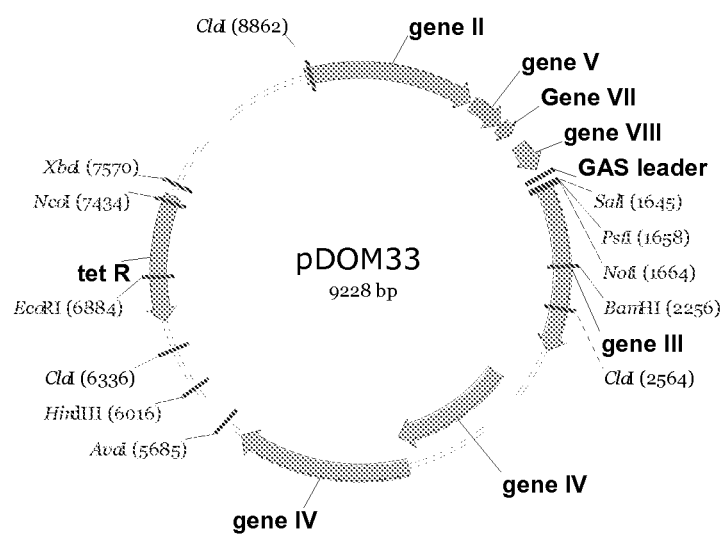

At this stage these three leads were compared in biophysical and biological assays and DOM1h-131-511 was the molecule with the best properties. Furthermore these molecules were tested for their resistance to proteolytic cleavage in the presence of trypsin or leucozyme. Leucozyme consists of pooled sputum from patients with cystic fibrosis and contains high levels of elastase and other proteases and was used as a surrogate for in vivo conditions in lung diseases. This data indicated that all three leads DOM1h-131-117, DOM1h-131-151 and DOM1h-131-511 were rapidly degraded in presence of trypsin or leucozyme. This finding raised concerns about the in vivo persistence of DOM1h-131-511 when in the patient and a strategy was developed to select for improved resistance to trypsin. It was hypothesised that such improved trypsin resistance could have a beneficial effect on other biophysical properties of the molecule. Essentially the standard phage selection method was modified to allow for selection in the presence of proteases prior to selection on antigen. To this end a new phage vector was engineered in which the c-myc tag was deleted to allow selections in the presence of trypsin without cleaving the displayed DAB™ off the phage. DOM1h-131-511 based error-prone libraries were generated and cloned in the pDOM33 vector (see FIG. 50 for pDOM33 vector map). Phage stocks generated from this library were pre-treated with either 1 mg/ml or 100 µg/ml trypsin at 37° C. for 24 hours, subsequently protease inhibitor which was ROCHE COMPLETE PROTEASE INHIBITORS™ (2×) was added to block the trypsin activity prior to selection on the relevant antigen. Four rounds of selection were performed. Soluble expressed TNFR1 binding DAB™s were assessed using the BIACORE™ for their ability to bind TNFR1 with or without the presence of proteases during one hour or overnight incubations at 37° C. in the presence or absence of trypsin (at 100 μg/ml or 1000 μg/ml final trypsin concentration).

This led to the isolation of two lead molecules DOM1h-131-202 and DOM1h-131-206 which demonstrated improved protease resistance as shown by BIACORE™ antigen binding experiments. It is interesting to note that DOM1h-131-202 contained only one mutation in CDR2 (V53D), all amino acid numbering according to Kabat) in comparison to DOM1h-131-511, whereas DOM1h-131-206 contained only two mutations: the first mutation is the same as in DOM1h-131-202 (V53D mutation in CDR2) and the second is a Y91H mutation in FR3 (see FIG. 3). This Y91H mutation in FR3 does occur in the 3-20 human germline gene indicating that this residue occurs in human antibodies. The three clones DOM1h-131-511, DOM1h-131-202 and DOM1h-131-206 have amino acid sequences as shown in FIG. 3.

Activity of the Molecules was Determined as Below:

BIACORE™ binding affinity assessment of DOM1H-131-202, DOM1H-131-511 and DOM1H-131-206 for binding to human TNFR1.

The binding affinities of DOM1H-131-202, DOM1H-131-511 and DOM1H-131-206 for binding to human recombinant *E. coli*-expressed human TNFR1 were assessed by BIACORE™ analysis. Analysis was carried out using biotinylated human TNFR1. 1400 RU of biotinylated TNFR1 was coated to a streptavidin (SA) chip. The surface was regenerated back to baseline using mild acid elution conditions. DOM1H-131-202, DOM1H-131-511 and DOM1H-131-206 were passed over this surface at defined concentrations using a flow rate of 50 μl/min. The work was carried out on a BIACORE™ 3000 machine and data were analysed and fitted to the 1:1 model of binding. The binding data fitted well to the 1:1 model for all tested molecules. All $K_D$ values were calculated from $k_{on}$ and $k_{off}$ rates. BIACORE™ runs were carried out at 25° C.

The data below were produced from three independent experiments. In each experiment the results were calculated by averaging a number of fits using highest DAB™ concentrations for kd and lower concentrations for ka. The data are presented as the mean and standard deviation (in brackets) of the results (Table 1).

TABLE 1

BIACORE ™ data for DOM1H-131-202, DOM1H-131-511 and DOM1H-131-206 binding to human TNFR1

|  | $k_{on}$ | $k_{off}$ | $K_D$ (nM) |
|---|---|---|---|
| DOM1H-131-511 (511) | 5.03E+05 (1.07E+05) | 5.06E−04 (1.01E−04) | 1.07 (0.44) |
| DOM1H-131-202 (202) | 1.02E+06 (2.69E+05) | 5.42E−04 (3.69E−05) | 0.55 (0.11) |
| DOM1H-131-206 (206) | 1.55E+06 (3.57E+05) | 7.25E−04 (1.95E−04) | 0.47 (0.06) |

DOM1H-131-202, DOM1H-131-511 and DOM1H-131-206 bound similarly and with high affinity to human TNFR1. DOM1H-131-202 and DOM1H-131-206 bind with average affinities of 0.55 nM and 0.47 nM respectively. Both DOM1H-131-202 and DOM1H-131-206 have a slightly better affinity in comparison to DOM1H-131-511 which has an average affinity of 1.07 nM.

Receptor Binding Assay:

The potency of the DAB™s was determined against human TNFR1 in a receptor binding assay. This assay measures the binding of TNF-alpha to TNFR1 and the ability of soluble DAB™ to block this interaction. The TNFR1-FC fusion is captured on a bead pre-coated with goat anti-human IgG (H&L). The receptor coated beads are incubated with TNF-alpha (10 ng/ml), DAB™, biotin conjugated anti-TNF-alpha and streptavidin ALEXA FLUOR™ 647 in a black sided clear bottomed 384 well plate. After 6 hours the plate is read on the ABI 8200™ cellular detection system and bead associated fluorescence determined. If the DAB™ blocks TNF-alpha binding to TNFR1 the fluorescent intensity will be reduced.

Figure 38:
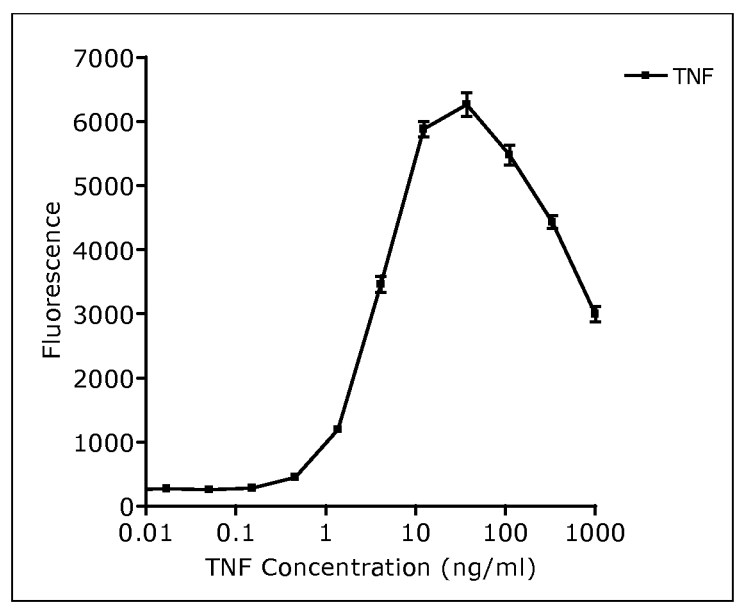
Figure 39:
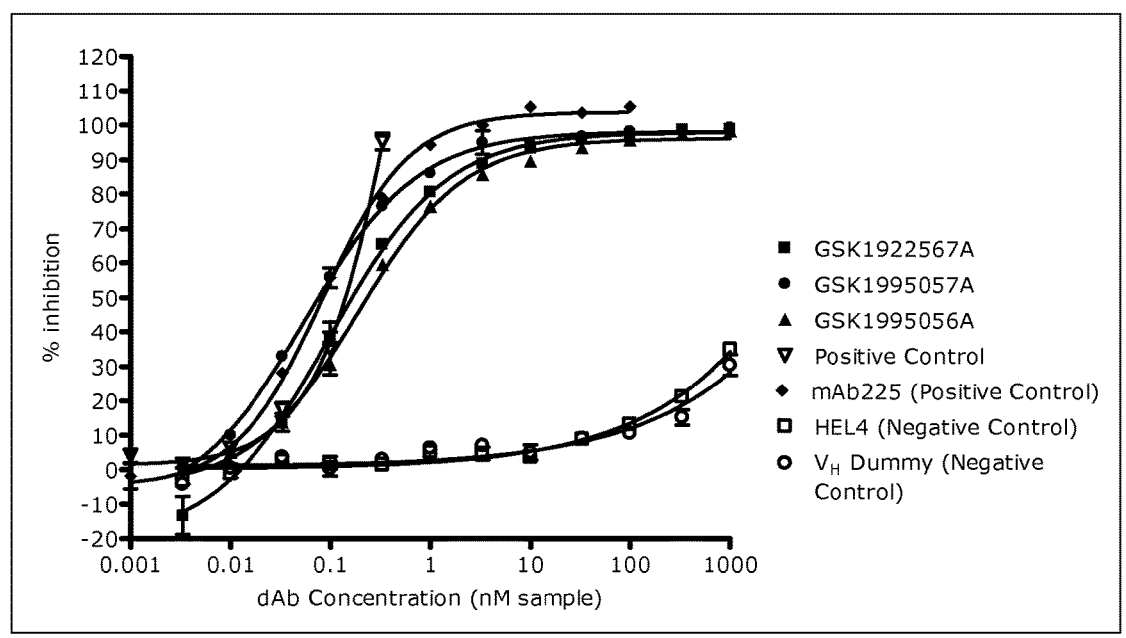

Data was analysed using the ABI 8200™ analysis software. Concentration effect curves and potency ($EC_{50}$) values were determined using GRAPHPAD PRISM™ and a sigmoidal dose response curve with variable slope. The assay was repeated on three separate occasions. A TNF-alpha dose curve was included in each experiment (FIGS. 38 and 39). The concentration of TNF-alpha used to compete with DAB™ binding to TNFR1 (10 ng/ml) is approximately 90% of the maximum TNF-alpha response in this assay.

A representative graph is shown in FIG. 39 showing the ability of DAB™s to inhibit the binding of TNF-alpha to TNFR1. In all three experiments the negative control samples (HEL4, an anti-hen egg white lysozyme DAB™ and $V_H$ dummy) weakly inhibit the interaction between TNF-alpha and TNFR1 at high concentrations. The average potency ($EC_{50}$) values for the test samples and positive controls (anti-TNFR1 mAb obtained from R&D Systems, mAb225) and ENBREL™ (etanercept; a dimeric fusion consisting of TNFR2 linked to the Fc portion of IgG1; licensed for the treatment of rheumatoid arthritis) are shown in Table 2.

TABLE 2

Potency ($EC_{50}$) values for DOM1H-131-202, DOM1H-131-206 and DOM1H-131-511 in a TNFR1 receptor binding assay for three repeat experiments.

| Sample | Average $EC_{50}$ (nM) | SEM |
|---|---|---|
| DOM1H-131-202 | 0.11 | 0.008 |
| DOM1H-131-206 | 0.07 | 0.01 |
| DOM1H-131-511 | 0.19 | 0.01 |
| ENBREL ™ (Etanercept) | 0.20 | 0.07 |
| Anti-TNFR1 mAb # mAb225 | 0.08 | 0.003 |

In this assay DOM1H-131-206 appears more potent than the other two DAB™s being tested and has a similar potency to the commercially available anti-TNFR1 mAb, MAB225 (R and D Systems).

Expression of lead clones from *Pichia pastoris* was carried out as described below: The primary amino acid sequence of the three lead molecules was used to produce codon optimised genes for secreted expression in *Pichia pastoris*. There is 75% sequence identity between the codon optimized and the non-codon optimized DOM1H-131-206. The three synthetic genes were cloned into the expression vector pPIC-Zα (from Invitrogen) and then transformed into two *Pichia* strains, X33 and KM71H. The transformed cells were plated out onto increasing concentrations of ZEOCIN™ (100, 300, 600 and 900 μg/ml) to select for clones with multiple integrants. Approximately 15 clones for each cell line and construct were selected for expression screening. As the correlation between high/low gene copy number and expression level is not fully understood in *Pichia pastoris*, several clones were picked from across the ZEOCIN™ concentration range. 5 L fermenter runs were carried out using clones that had not been extensively screened for high productivity. This allowed the production of significant amounts of material for further studies.

Material Production for Protein Characterisation:

Protein A based chromatography resins have been extensively used to purify $V_H$ DAB™s from microbial culture supernatants. Although this allows a single step purification method for producing high purity material, usually >90% in most cases, for some molecules the low pH elution conditions can result in the formation of aggregates. There is also the issue of the limited capacity of affinity resins for DAB™s; this would mean the use of significant quantities of resin to process from fermenters. In order to produce high quality material for characterisation and further stability and nebuliser studies, a downstream purification process was devised using a mixed modal charge induction resin as the primary capture step followed by anion exchange. Without significant optimisation, this allowed the recovery of ~70% of the expressed DAB™ at a purity of ~95%.

For the capture step on the mixed modal charge induction resin, CAPTO™ MMC from GE Healthcare, column equilibration is performed using 50 mM sodium phosphate pH6.0 and the supernatant is loaded without any need for dilution or pH adjustment. After washing the column, the protein is eluted by pH gradient using an elution buffer which is 50 mM Tris pH 9.0. The specific wash and gradient conditions will vary slightly depending on the pI of the protein being eluted.

The eluate peak is then further purified with a flow through step using anion exchange chromatography. This removes residual HMW contamination such as alcohol oxidase and reduces endotoxin. The resin is equilibrated with either PBS or phosphate buffer pH 7.4 without salt. Upon loading the eluate from CAPTO™ MMC onto the anion exchange resin the DAB™ does not bind and is recovered from the flow through. Endotoxin and other contaminants bind to the resin. The presence of salt if using PBS buffer improves protein recovery to 91% for this step rather than 86% recovery achieved without salt. However the presence of salt reduces the effectiveness of endotoxin removal such that a typical endotoxin level of DAB™ following this step with the inclusion of salt was measured as 58 EU/ml compared with a level of <1.0 EU/ml obtained when no salt was present.

Protein Characterisation:

The material produced from the 5 L fermenter runs was characterised for identity using electrospray mass spectrometry, amino terminal sequencing and isoelectric focusing and for purity using SDS-PAGE, SEC and GELCODE™ glycoprotein staining kit (Pierce).

Identity:

The amino terminal sequence analysis of the first five residues of each protein, was as expected (EVQLL . . . ) (SEQ ID NO: 259). Mass spectrometry was performed on samples of the proteins which had been buffer exchanged into 50:50 $H_2O$:acetonitrile containing 0.1% glacial acetic acid using C4 ZIP-TIPS™ (Millipore). The measured mass for each of the three proteins was within 0.5 Da of the theoretical mass based on the primary amino acid sequence (calculated using average masses) when allowing for a mass difference of −2 from the formation of the internal disulphide bond. IEF was used to identify the proteins based on their pI which was different for each protein.

Purity:

The three proteins were loaded onto non-reducing SDS-PAGE gels in 1 μg and 10 μg amounts in duplicate. A single band was observed in all instances. Size exclusion chromatography was also performed to demonstrate levels of purity. For size exclusion chromatography (SEC) 100 μg of each protein were loaded onto a TOSOH G2000 SWXL™ column flowing at 0.5 ml/min. Mobile phase was PBS/10% ethanol.

Investigation of DAB™ Stability for Candidate Selection:

For the indication of COPD, it would be necessary to deliver the DAB™ into the lung, eg using a nebuliser device. This would mean the protein could potentially experience a range of shear and thermal stresses depending on the type of nebuliser used and could be subjected to enzymatic degradation by proteases in the lung environment. It was determined if the protein could be delivered using this type of device, form the correct particle size distribution and remain functional following nebuliser delivery. Therefore the intrinsic stability of each molecule to a range of physical stresses was investigated to determine the baseline stability and the most sensitive stability indicating assays. As the stability of each protein will be dependent on the buffer solution it is solubilised in, some pre-formulation work was necessary. This information, such as buffer, pH, would also be useful for understanding the stability of the protein during the downstream purification process and subsequent storage. In order to characterise the changes in the molecules during exposure to a range of physical stresses, a range of analytical techniques were used such as size exclusion chromatography (SEC), SDS-PAGE and isoelectric focusing (IEF).

Assessment of Protease Stability of DOM1H-131-202, DOM1H-131-511 and DOM1H-131-206:

The protease stability of DOM1H-131-202, DOM1H-131-511 and DOM1H-131-206 was assessed by BIACORE™ analysis of the residual binding activity after pre-incubation for defined timepoints in excess of proteases. Approximately 1400 RU of biotinylated TNFR1 was coated to a streptavidin (SA) chip. 250 nM of DOM1H-131-202, DOM1H-131-511 and DOM1H-131-206 was incubated with PBS only or with 100 μg/ml of trypsin, elastase or leucozyme for 1, 3, and 24 hours at 30° C. The reaction was stopped by the addition of a cocktail of protease inhibitors. The DAB™/protease mixtures were then passed over the TNFR1 coated chip using reference cell subtraction. The chip surface was regenerated with 10 ul 0.1M glycine pH 2.2 between each injection cycle. The fraction of DOM1H-131-202, DOM1H-131-511 and DOM1H-131-206 bound to human TNFR1 (at 10 secs) pre-incubated with proteases was determined relative to DAB™ binding without proteases. BIACORE™ runs were carried out at 25° C.

The data was produced from three independent experiments. The bar graph indicates mean values and the error bars indicate standard deviation of the results (for results see FIG. 24).

It was found that DOM1H-131-202 and DOM1H-131-206 were shown to have greater resistance to proteolytic degradation by trypsin, elastase or leucozyme in comparison to DOM1H-131-511. The difference between DOM1H-131-202 and DOM1H-131-206 in comparison to DOM1H-131-511 is most pronounced after 1 hr with trypsin and after 3 hrs with elastase or leucozyme.

Thermal Stability as Determined Using DSC:

In order to determine at which pH the molecules had the greatest stability, differential scanning calorimeter (DSC) was used to measure the melting temperatures ($T_m$) of each DAB™ in Britton-Robinson buffer. As Britton-Robinson is made up of three component buffer systems (acetate, phosphate and borate), it is possible to produce a pH range from 3-10 in the same solution. The theoretical pI was determined from the proteins primary amino acid sequence. From the DSC, the pH at which the DAB™s had their greatest intrinsic thermal stability was found to be pH 7 for DOM1H-

131-202 (202), pH 7-7.5 for DOM1H-131-206 (206) and pH 7.5 for DOM1H-131-511 (511). For all subsequent stress and stability work the following pHs were used for each DAB™; for DOM1H-131-202 (202) and DOM1H-131-206 (206) pH 7.0 and for DOM1H-131-511 (511) pH 7.5 in Britton-Robinson buffer. The results are summarised in Table 3 below:

TABLE 3

Summary of the pH and $T_m$s of DOM1H-131-202 (202), DOM1H-131-206 (206) and DOM1H-131-511 (511) as determined by DSC in Britton-Robinson buffer at 1 mg/ml

| DAB ™ | pH that gives greatest intrinsic thermal stability | Tm (° C.) of the DAB ™ at the given pH |
|---|---|---|
| DOM1H-131-202 (202) | 7.0 | 68.6 |
| DOM1H-131-206 (206) | 7.0-7.5 | 65.8 |
| DOM1H-131-511 (511) | 7.5 | 58.0 |

Intrinsic Solubility Testing:

All the lead DAB™s were concentrated in centrifugal VIVASPIN™ concentrators (5K cut-off), to determine their maximum solubility and the levels of recovery upon concentration. Experiments were performed in Britton-Robinson buffer at the most stable pH. Sample volumes and concentrations were measured over a time course and deviation from expected concentration recorded as well as percent recovery of the sample.

It was found that all proteins could be concentrated to over 100 mg/ml in Britton-Robinson buffer. Both DOM1H-131-202 (202) and DOM1H-131-206 (206) showed lower recoveries than expected compared to DOM1H-131-511 (511), but still within acceptable levels.

Nebuliser Delivery of the Lead DAB™s:

By testing different nebulisers and formulation buffers it was demonstrated that the DAB™ could effectively be delivered using a wide range of nebulising devices. More importantly, it was shown for the first time that nebulisation of the DAB™ in the formulation buffer produced the desired particle size distribution (compared using the percentage of droplets <5 μm) for effective lung delivery whilst maintaining protein functionality. This is further described below.

Comparison of Performance in Various Devices:

DOM1H-131-511 (511) was tested in six nebuliser devices comprising two devices from each of the three main groups of nebulisers for liquid formulations i.e. ultrasonic nebulisers, jet nebulisers and vibrating mesh nebulisers. In each device the DAB™ was tested at 5 mg/ml with a range of PEG concentrations. For each sample the percentage of droplet size <5 μm was measured using a Malvern SPRAYTEC™ Device (Malvern Instruments Limited, UK) and the results are shown in FIG. 35. The stability of each sample after being nebulised was assessed using SEC to analyse the amount of sample which had dimerised both in the material remaining in the cup and in collected aerosol. The results may be seen in FIG. 36. The less the extent of dimer formation the greater the stability.

Most devices can deliver 40% or more of the liquid formulation in the correct size range but the EFLOW™ (a vibrating mesh nebuliser device) and PARI LC+™ (a jet nebuliser) devices perform better, with the PARI LC*™ (star) device delivering more than 80% when PEG is included in the buffer. This increase in delivery with PEG is also observed with the EFLOW™ and, to a lesser extent, with the PARI LC+™. Importantly activity of the DAB™ was also found to be retained after nebulisation (see results in FIG. 8)

Effect of Buffer Additives:

Due to the lower stability of DOM1H-131-511 (511), the 50 mM phosphate formulation buffer contained both PEG 1000 and sucrose (and has a viscosity which is within the range which is defined as about equal to the viscosity of a solution of about 2% to about 10% PEG 1000 in 50 mM phosphate buffer containing 1.2% (w/v sucrose) to help protect the DAB™ from both shear and thermal stress. As both DOM1H-131-202 (202) and DOM1H-131-206 (206) have higher $T_m$'s and showed considerably improved stability to thermal stress, all the molecules were tested in both the original formulation buffer and in Britton-Robinson buffer (which has a lower viscosity than the formulation buffer). The DAB™s were tested in both the EFLOW™ and PARI LC+™ devices with run time of 3.5 minutes at a protein concentration of 5 mg/ml and the particle size distribution determined using a Malvern SPRAYTEC™ Device. As a comparison, a marketed drug for cystic fiborosis (designated standard protein X) that is delivered using a nebuliser device, was tested in its own formulation buffer. The results are shown in FIG. 37. For good delivery and distribution into the deep lung, the ideal particle size is less than 6 microns, e.g. <5 μm. All the DAB™s give comparable levels of particle sizes that were less than 5 μm in both the Britton-Robinson buffer and formulation buffer (as described earlier). However, the higher viscosity of the formulation buffer could be particularly beneficial for producing particles within the correct size range, e.g. particles <5 μm.

The concentration of the DAB™ in the cup of the device was determined by A280 measurements before and after nebulisation. It was found that the protein concentration did not change significantly indicating that neither the protein nor vehicle is preferentially nebulised during delivery.

Conclusion:

It has been demonstrated as described above that polypeptides such as DAB™s can be nebulised in a range of commercially available nebuliser devices and importantly that they retain stability and biological activity after nebulisation and there is no significant aggregation observed following nebulisation. When viscosity enhancing excipients, such as PEG are added to the buffer formulation, particle size distribution and percentage droplet size less than 5 μm can be improved, thus potentially improving DAB™ delivery to the deep lung.

Delivery of DAB™ to the lung can also be improved by increasing the DAB™ concentration for example a concentration of up to about 40 mg/ml and delivery time without any reduction in DAB™ stability or activity.

Example 1

Phage Vector pDOM13

A filamentous phage (fd) display vector, pDOM13 was used. This vector produces fusion proteins with phage coat protein III. The multiple cloning site of pDOM13 is illustrated in FIG. 1. The genes encoding DAB's were cloned as SalI/NotI fragments.

Example 2

Test protease selections on phage-displayed domain antibodies (DAB™s) with a range of resistance to trypsin The genes encoding DAB™s DOM4-130-54 which binds IL-1R1, DOM1h-131-511 which binds TNFR1, and DOM15-10, DOM15-26 and DOM15-26-501, which bind VEGFA, were cloned in pDOM13 and phages displaying these DAB™s were produced according to standard techniques. Phages were purified by PEG precipitation, resuspended in PBS and titered.

The above DAB™s displayed a range of ability to resist degradation by trypsin when tested as isolated proteins. Resistance to degradation was assessed as follows: DAB™ (1 mg/ml) in PBS was incubated with trypsin at 40 µg/ml at 30° C., resulting in a molecular ratio of 25:1 DAB™:trypsin. Samples (30 µl) were taken immediately before addition of trypsin, and then at T=1 hour, 3 hours, and 24 hours. Protease activity was neutralized by addition of ROCHE COMPLETE PROTEASE INHIBITORS™ (2×) followed by immersion in liquid nitrogen and storage on dry ice. 15 µg of each DAB™ sample was subsequently analyzed by electrophoresis on a NOVEX™ 10-20% Tricine gel and proteins were stained with SUREBLUE™ (1×).

Figure 2:
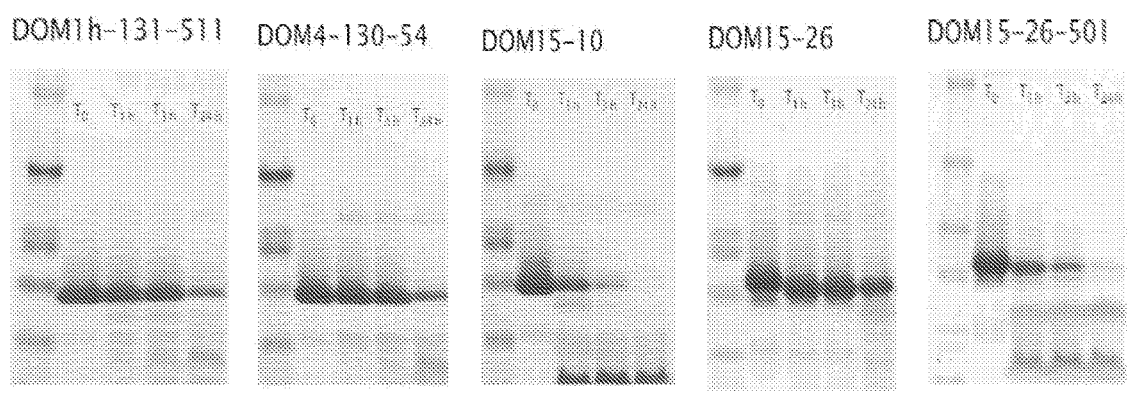
FIG. 2 shows several NOVEX™ 10-20% TRICENE™ gels run with samples from different time points of DAB™s that were incubated with trypsin at 40 ug/ml at 30° C. Samples were taken immediately before the addition of trypsin, and then at one hour, three hours and 24 hours after the addition of trypsin. The proteins were stained with 1× SUREBLUE™. The gels illustrate that both DOM15-10 and DOM15-26-501 were significantly digested during the first three hours of incubation with trypsin. Digestion of DOM15-26, DOM4-130-54 and DOM1h-131-511 only became apparent after 24 hours of incubation with trypsin.

Both DOM15-10 and DOM15-26-501 were significantly digested during the first three hours. DOM15-26, DOM4-130-54 and DOM1h-131-511 were more stable, with digestion of the DAB™s only becoming apparent after 24 hours (FIG. 2).

The phage-displayed DAB™s were also incubated in the presence of trypsin to evaluate if trypsin resistance of phage-displayed DAB™s correlated with the results obtained with the isolated soluble DAB™s. Various concentrations of trypsin and incubation times were tested. In all cases, after neutralization of trypsin with ROCHE COMPLETE PROTEASE INHIBITORS™, the phages were tested for their ability to bind a generic ligand:protein A, which binds all $V_H$ domain antibodies (e.g., DOM1h-131, DOM15-26, DOM15-26-501) or protein L, which binds all VK domain antibodies (e.g., DOM4-130-54, DOM15-10). Phage were also tested for binding to target antigens. In both cases, binding was assumed to correlate with retention of the DAB™ structural integrity through resistance to proteolysis. The binding activity was measured either by ELISA (using conjugated antibodies against phage) or by elution of bound phages and titre analysis following infection of exponentially growing E. coli TG1 cells.

Tests with DOM15-10, DOM15-26 and DOM15-26-501 on Phage

Each DAB™ was treated for one hour at room temperature with a range of trypsin concentrations (100 µg/ml, 10 µg/ml and 0 µg/ml). Trypsin activity was blocked with ROCHE COMPLETE PROTEASE INHIBITORS™ (IX) and then the phages were diluted in 2% MARVELL™ in PBS, incubated with 50 nM of biotinylated antigen (recombinant human VEGF (R&D systems)) for one hour at room temperature. Strepavidin-coated beads (DYNABEADS™ M-280 (Invitrogen)) that were pre-blocked for one hour at room temperature with 2% MARVELL™ in PBS were added, and the mixture was then incubated for five minutes at room temperature. All of the incubation steps with DYNABEADS™ were carried out on a rotating wheel. Unbound phages were washed away by washing the beads eight times with 1 ml of 0.1% TWEEN-20™ in PBS. Bound phages were eluted with 0.5 ml of 0.1M Glycine pH2.2 and neutralized with 100 µl of 1M Tris-HCL pH 8.0. Eluted phage were used to infect exponentially growing TG1 cells (one hour at 37° C.) and plated on tetracycline plates. Plates were incubated overnight at 37° C. and colony counts were made (see Table 4). The best results were observed from selection with incubation with 100 µg/ml trypsin. There was about a 10-fold increase in the yield of DOM15-26 in comparison to DOM15-10 and DOM15-26-501.

A second experiment was done to further confirm these results under more severe incubation conditions. Phage displayed DAB™s were treated for 1 hour or 2 hours at 37° C. with agitation (250 rpm). The best results were observed from selections with 2 hour incubation with 100 ug/ml trypsin. The yield of DOM15-26 was 200-fold higher than the yield of DOM15-26-501 and 1000-fold higher than the yield of DOM15-10.

In a third experiment, phages displaying DOM15-26 and DOM15-26-501 were mixed 1:1 at the start. They were then either incubated with trypsin (1000 µg/ml) or without trypsin for two hours at 37° C. with agitation (250 rpm), and then selected for antigen binding as described above. Sequencing of ten colonies from each selection revealed a mixed population of clones for selection without trypsin pre-treatment (DOM15-26: 4/10; DOM15-26-501: 6/10), whereas all clones from the selection with trypsin encoded for DOM15-26 as expected.

These experiments indicate that a selection pressure can be obtained by adding a protease to phages displaying DAB™s, such that phages displaying the most proteolytically stable DAB™s are preferentially selected (following panning on a generic ligand or the antigen).

TABLE 4

| Experiment | Length of incubation | Temp. | Trypsin concentration | DOM15-26 titre | DOM15-26-501 titre | 1:1 mixed titre | DOM15-10 titre |
|---|---|---|---|---|---|---|---|
| 1 input $10^{10}$ | 1 hr | Room temp | 100 µg/ml | $1.6 \times 10^8$ | $6.3 \times 10^7$ | | $1.1 \times 10^7$ |
| | 1 hr | Room temp | 10 µg/ml | $3 \times 10^8$ | $4.4 \times 10^8$ | | $2.4 \times 10^8$ |
| | 1 hr | Room temp | 0 µg/ml | $0.9 \times 10^8$ | $2 \times 10^8$ | | $0.7 \times 10^8$ |
| 2 input $10^9$ | 1 hr, 250 rpm | 37° C. | 100 µg/ml | $2 \times 10^7$ | $1 \times 10^6$ | | $1 \times 10^5$ |
| | 2 hr, 250 rpm | 37° C. | 100 µg/ml | $1 \times 10^7$ | $6 \times 10^4$ | | $1 \times 10^4$ |
| | 2 hr, 250 rpm | 37° C. | 0 µg/ml | $5.4 \times 10^7$ | $4.1 \times 10^7$ | | $3 \times 10^8$ |
| 3 input $10^{10}$ | 2 h, 250 rpm | 37° C. | 100 µg/ml | $2.3 \times 10^8$ | $8 \times 10^5$ | $6.8 \times 10^7$ | |
| | 2 h, 250rpm | 37° C. | 0 µg/ml | $3.9 \times 10^8$ | $4.4 \times 10^8$ | $4.8 \times 10^8$ | |

Tests with DOM4-130-54 on Phage

DOM4-130-54 was tested in a similar protocol as described above. The parameters that were varied were: concentration of trypsin, temperature and length of incubation. Biopanning was done against IL-RI-Fc (a fusion of IL-1RI and Fc) at 1 nM concentration in PBS. Significant reductions in phage titre were only observed after incubation of the phage with 100 μg/ml trypsin overnight at 37° C. (see Table 5).

TABLE 5

| Length of incubation | Temperature | Trypsin concentration | Titre |
|---|---|---|---|
| 1 hr | Room temp | 100 μg/ml | $1.8 \times 10^{10}$ |
| 1 hr | Room temp | 10 μg/ml | $7.2 \times 10^{9}$ |
| 1 hr | Room temp | 0 μg/ml | $6.6 \times 10^{9}$ |
| Overnight | Room temp | 100 μg/ml | $2.16 \times 10^{9}$ |
| Overnight | Room temp | 10 μg/ml | $7.2 \times 10^{9}$ |
| Overnight | Room temp | 0 μg/ml | $7.8 \times 10^{9}$ |
| Overnight | 37° C. | 100 μg/ml | $2.04 \times 10^{6}$ |
| Overnight | 37° C. | 10 μg/ml | $3.84 \times 10^{8}$ |
| Overnight | 37° C. | 0 μg/ml | $7.2 \times 10^{9}$ |

Tests with DOM1 h-131 Phage

DOM1h-131 phage (closely related to DOM1h-131-511 by amino acid sequence) were treated with 0 μg/ml, 10 μg/ml, 100 μg/ml and 1000 μg/ml trypsin for one hour at room temperature. Digestion was inhibited by the addition of 25× ROCHE COMPLETE PROTEASE INHIBITORS™. Serial 2-fold dilutions of the phage were carried out down an ELISA plate coated with 1 nM TNFR1, and binding phage were detected with anti-M13-HRP. The results are shown below in Table 6.

TABLE 6

| DOM1h-131 Trypsin concentration | | | | |
|---|---|---|---|---|
| 1 mg/ml | 100 μg/ml | 10 μg/ml | 0 μg/ml | Phage input |
| 0.284 | 0.418 | 0.784 | 0.916 | 4.51E+10 |
| 0.229 | 0.377 | 0.802 | 0.944 | 2.26E+10 |
| 0.183 | 0.284 | 0.860 | 0.949 | 1.13E+10 |
| 0.133 | 0.196 | 0.695 | 0.962 | 5.64E+09 |
| 0.114 | 0.141 | 0.573 | 0.946 | 2.82E+09 |
| 0.089 | 0.115 | 0.409 | 0.850 | 1.41E+09 |
| 0.084 | 0.084 | 0.286 | 0.705 | 7.05E+08 |
| 0.080 | 0.084 | 0.213 | 0.577 | 3.52E+08 |

These test experiments clearly show that 100 μg/ml of trypsin and a temperature of 37° C. are appropriate to apply a selection pressure on phages displaying DAB™s of various degrees of resistance to proteolysis by trypsin. Incubation time with the protease can be optimized for each phage-displayed DAB™, if desired.

Example 3

Protease Selection of Phage-Displayed Repertoires of Domain Antibodies

Four repertoires were created using the following DAB™s as parent molecules: DOM4-130-54, DOM1h-131-511, DOM15-10 and DOM15-26-555. Random mutations were introduced in the genes by PCR using the STRATAGENE MUTAZYME II™ kit, biotinylated primers and 5-50 μg of template for a 50 μl reaction. After digestion with SalI and NotI, the inserts were purified from undigested products with streptavidin-coated beads and ligated into pDOM13 at the corresponding sites. E. coli TB1 cells were transformed with the purified ligation mix resulting in large repertoires of tetracycline-resistant clones: $8.5 \times 10^{8}$ (DOM4-130-54), $1.5 \times 10^{9}$ (DOM1h-131-511), $6 \times 10^{8}$ (DOM15-10) and $3 \times 10^{9}$ (DOM15-26-555).

Phage libraries were prepared by double precipitation with PEG and resuspended in PBS.

The rates of amino acid mutations were 2.3 and 4.4 for the DOM1h-131-511 and DOM4-130-54 repertoires, respectively. The functionality was assessed by testing 96 clones in phage ELISA using wells coated with protein A or protein L (at 1 μg/ml). 62.5% and 27% of the clones exhibited functional display of DAB™s in the DOM1h-131-511 and DOM4-130-54 repertoires, respectively.

The rates of amino acid mutations were 2.5 and 4.6 for the DOM15-10 and DOM15-26-555 repertoires, respectively. The functionality was assessed by testing 96 clones in phage ELISA using wells coated with protein A or protein L (at 1 μg/ml). 31.3% and 10.4% of the clones exhibited functional display of DAB™s in the DOM15-10 and DOM15-26-555 repertoires, respectively.

DOM4-130-54 and DOM1h-131-511 Repertoires

Four rounds of selection were carried out with these libraries to select for DAB™s with improved protease resistance.

The first round of selection was by antigen binding (1 nM or 10 nM antigen) without protease treatment to clean-up the library to remove any clones that no longer bound antigen with high affinity. The outputs from round 1 were in the $10^{8}$-$10^{10}$ range (compared to an input of $10^{11}$ phage) indicating that the majority of the library bound antigen with high affinity.

In round 2, protease treatment with 100 μg/ml trypsin was introduced, and the outputs are as shown below in Table 7:

TABLE 7

| Trypsin incubation conditions | DOM1h-131-511 library | DOM4-130-54 library |
|---|---|---|
| 37° C. overnight | $1.86 \times 10^{6}$ | $2.1 \times 10^{6}$ |
| 37° C. 2 hrs | $4.8 \times 10^{8}$ | $5.1 \times 10^{8}$ |
| Room temperature 2 hrs | $1.2 \times 10^{9}$ | $4.62 \times 10^{9}$ |
| No trypsin | $\sim 1 \times 10^{9}$ | $\sim 4 \times 10^{9}$ |
| No antigen | $1.8 \times 10^{4}$ | $< 6 \times 10^{3}$ |

There was significant selection when the DAB™s were treated with trypsin at 37° C. overnight. This output was taken forward to round 3, where the phage were treated with either 1 mg/ml or 100 μg/ml trypsin at 37° C. for 24 hours. The titres of the trypsin treated phage from round 3 were $10^{5}$-$10^{6}$ for the DOM1h-131-511 repertoire and $10^{7}$-$10^{8}$ for the DOM4-130-154 repertoire.

All outputs from round 3 (DOM1h-131-511 and DOM4-130-154 with 1 mg/ml and 100 μg/ml) underwent a fourth round of selection against 1 nM antigen with 100 μg/ml trypsin. The titres were in the range of $10^{6}$-$10^{8}$, similar to that seen in round 3. Some enrichment was seen for the DOM1h-131-511 repertoire, but no enrichment was seen for the DOM4-130-54 repertoire.

DOM15-10 and DOM15-26-555 Repertoires

The first round of selection was carried out with 2 nM biotinylated hVEGF (human vascular endothelial growth factor) concentration and without protease treatment to clean-up the library to remove any clones that no longer bound antigen with high affinity. The outputs from round 1 were about $10^{8}$ (compared to an input of $10^{10}$ phage for DOM15-10 and $10^{11}$ phage for DOM15-26-555) indicating that the majority of the library bound antigen with high affinity.

The second and third rounds of selection were performed with 2 nM biotinylated hVEGF. Prior to panning on hVEGF, the phages were incubated in the presence of trypsin (100

µg/ml) at 37° C. in a shaker (250 rpm). Incubation time was one hour for the DOM15-10 repertoire and two hours for the DOM15-26-555 repertoire.

The outputs were as follows: $1.5 \times 10^6$ and $9 \times 10^5$ for the second and third rounds of selection with the DOM15-10 repertoire; $2.2 \times 10^8$ and $3.9 \times 10^9$ for the second and third rounds of selection with the DOM15-26-555.

Example 4

Analysis of Selection Outputs: DOM4-130-54 and DOM1h-131-511 Repertoires

Figure 4:
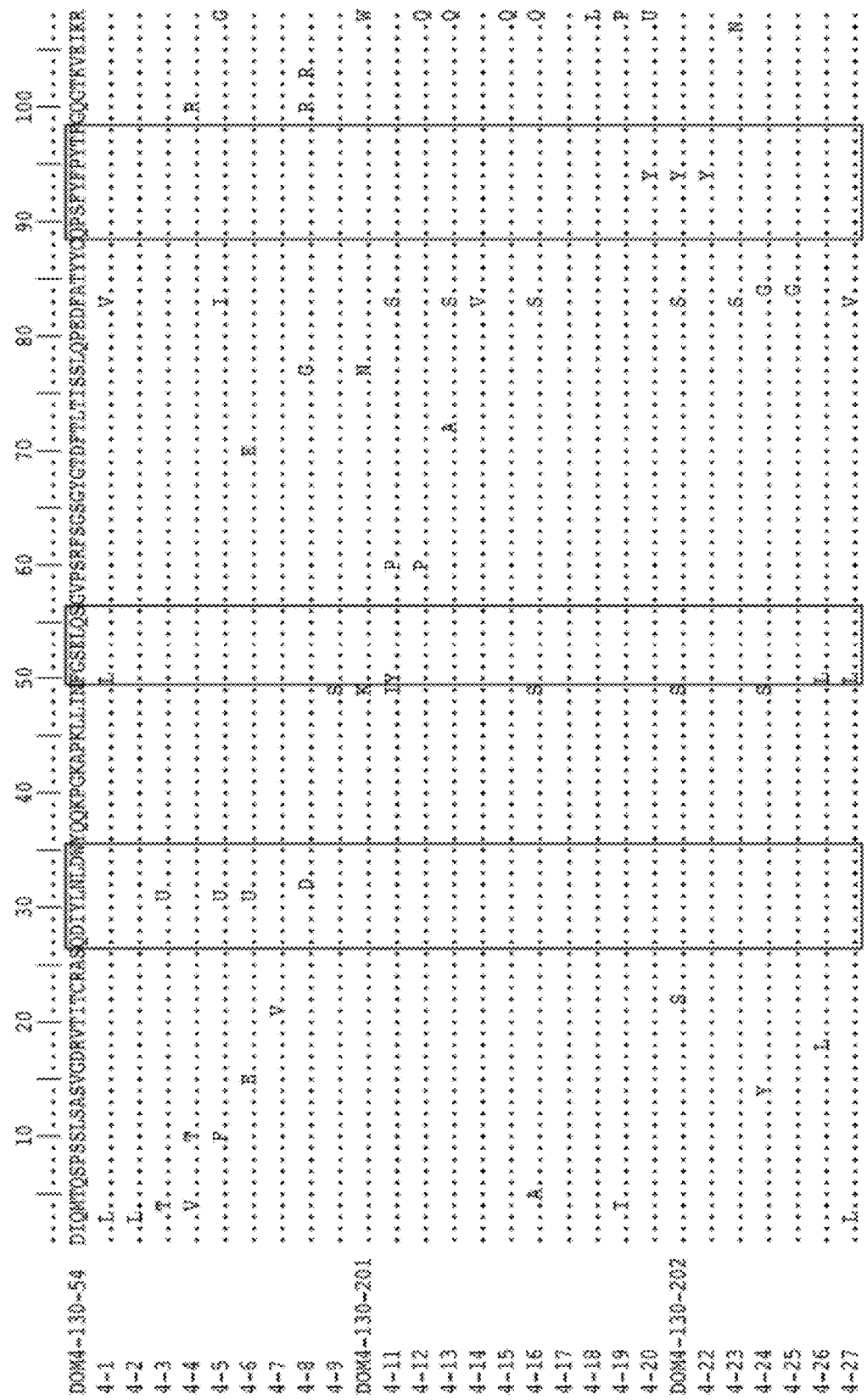
FIG. 4 is an illustration of the amino acid sequences of DOM4-130-54 (SEQ ID NO: 5) and 27 selected variants. The amino acids that differ from the parent sequence in selected clones are highlighted (those that are identical are marked by dots). The loops corresponding to CDR1, CDR2 and CDR3 are outlined with boxes.

All outputs from round 3 and round 4 were subcloned into the pDOM5 vector and transformed into JM83 cells. The pDOM5 vector is a pUC119-based vector. Expression of proteins is driven by the Plac promoter. A GAS1 leader sequence (see WO 2005/093074) ensured secretion of isolated, soluble DAB™s into the periplasm and culture supernatant of *E. coli* JM83. 96 and 72 individual colonies from round 3 and round 4 were randomly picked for expression 12-24 clones were sequenced from each round 3 and round 4 output. Consensus mutations were observed in both selections and approximately 25 clones harboring consensus motifs were chosen for further characterization. The amino acid sequences of these clones are shown in FIG. 3 (DOM1h-131-511 selected variants) and FIG. 4 (DOM4-130-54 selected variants) and listed as DNA sequences in FIGS. 19A-19L. The amino acids that differ from the parent sequence in selected clones are highlighted (those that are identical are marked by dots). The loops corresponding to CDR1, CDR2 and CDR3 are outlined with boxes.

These clones were expressed in a larger amount, purified on protein L (for DOM4-130-54 variants) and protein A (for DOM1h-131-511 variants) and tested for antigen binding on BIACORE™ after one hour or overnight incubation at 37° C. in the presence or absence of trypsin (100 µg/ml or 1000 µg/ml final concentration).

Generally, the outputs from the DOM4-130-54 selections were more stable with most clones remaining resistant to trypsin for one hour and the best clones resistant overnight. In comparison, a small number of clones from the DOM1h-131-511 selections were resistant to trypsin for one hour, whilst none of the clones were resistant overnight.

Example 5

Analysis of Selection Outputs: DOM15-10 and DOM15-26-555 Repertoires

The effectiveness of selection with trypsin pre-treatment was first tested on monoclonal phage ELISA with and without trypsin digestion. Eighteen colonies from the second round of selection and 24 colonies from the third round of selection of each library were picked. Clones DOM15-10, DOM15-26-501 and DOM15-26 were used as controls. Additional controls included amplified and purified phage solution from each library after second and third rounds of trypsin selection.

Each phage sample was divided into two fractions, the first was treated with 100 ug/ml trypsin, the second was not treated with trypsin. Incubation of both fractions was carried out for one hour at 37° C. with agitation (250 rpm) and blocked by adding ROCHE COMPLETE PROTEASE INHIBITORS™ (1×).

Phage ELISA was performed using the trypsin-digested and undigested samples. ELISA wells were coated with NEUTRAVIDIN™ in 0.1M bicarbonate buffer at a concentration of 1 µg/ml. After the washing steps with PBS and blocking of the antigen-coated wells with 1% TWEEN-20™ in PBS for one hour at room temperature, the wells were coated with biotinylated hVEGF diluted in 1% TWEEN-20™ in PBS at a concentration of 100 ng/ml. Next, the wells were washed with PBS and treated or untreated phage supernatants diluted 1:1 with 1% TWEEN-20™/PBS, were added. After 30 minutes of incubation at 37° C., the wells were washed with 1% TWEEN-20™/PBS, followed by a 30 minute incubation at 37° C. with anti-M13 phage-HRP conjugate (diluted 1/5000 in 1% TWEEN-20™/PBS). The wells were then washed with PBS and peroxidase. Reaction was initiated by adding SUREBLUE™ reagent. After about ten minutes, the reaction was stopped with an equivalent volume of 1M HCl and the wells were read at $OD_{450\ nM}$.

ELISA read-outs of unstable controls DOM15-10 and DOM15-26-501 treated with trypsin gave an $OD_{450}$ lower than 0.404 and this value was assumed as a border value of an unstable clone. All samples that gave an OD lower than 0.404 were considered to be unstable. All samples above that value were considered to be stable.

TABLE 8

| Library | Trypsin | | No trypsin | |
| --- | --- | --- | --- | --- |
| | 2nd selection | 3rd selection | 2nd selection | 3rd selection |
| DOM15-10 | 33% | 89% | 100% | 100% |
| DOM15-26-555 | 94.4% | 100% | 100% | 100% |

Table 8 shows the percentage of stable clones after the second and third rounds of trypsin selection of each library. The enrichment of trypsin resistant clones is visible in both libraries after the third round of selection. The values of control ELISA wells containing amplified purified phage mix after each selection were much higher than 0.404 in each case after trypsin digestion. Moreover, a small increase in signal was observed when comparing trypsin-treated phage from the third round of selection with trypsin-treated phage from the second round of selection. The DOM15-10 phage library showed an increase of about 14% of the starting value. DOM15-26-555 phage library showed an increase that represents about 2% of the starting value.

Overall these results show that selection with trypsin pre-treatment was effective to select trypsin-resistant phage clones from the DOM15-10 and DOM15-26-555 repertoires.

All outputs from the second and third rounds of selection (DOM15-26-555) and from the third round of selection only (DOM15-10) were subcloned into the pDOM5 vector and transformed into HB2151 electrocompetent cells. The pDOM5 vector is a pUC119-based vector. Expression of proteins is driven by the Plac promoter. A GAS1 leader sequence ensured secretion of isolated, soluble DAB™s into the periplasm and culture supernatant of *E. coli* HB2151. 184 individual colonies from each round of selection (3 and 4) were randomly picked for expression in 1 ml culture volumes.

Bacterial supernatants were diluted in HBS-EP BIACORE™ buffer (1:1 volume ratio) and split to duplicates. Trypsin was added to only one vial at a final concentration of 20 µg/ml. Incubation was carried out for 40 minutes at 37° C. with agitation (250 rpm). After blocking the reaction with ROCHE COMPLETE PROTEASE INHIBITORS™ (1×), both trypsin treated and untreated phage supernatants were tested on BIACORE™ 3000 for antigen binding (2,000 RU of biotinylated hVEGF on a SA sensorchip).

Figure 5:
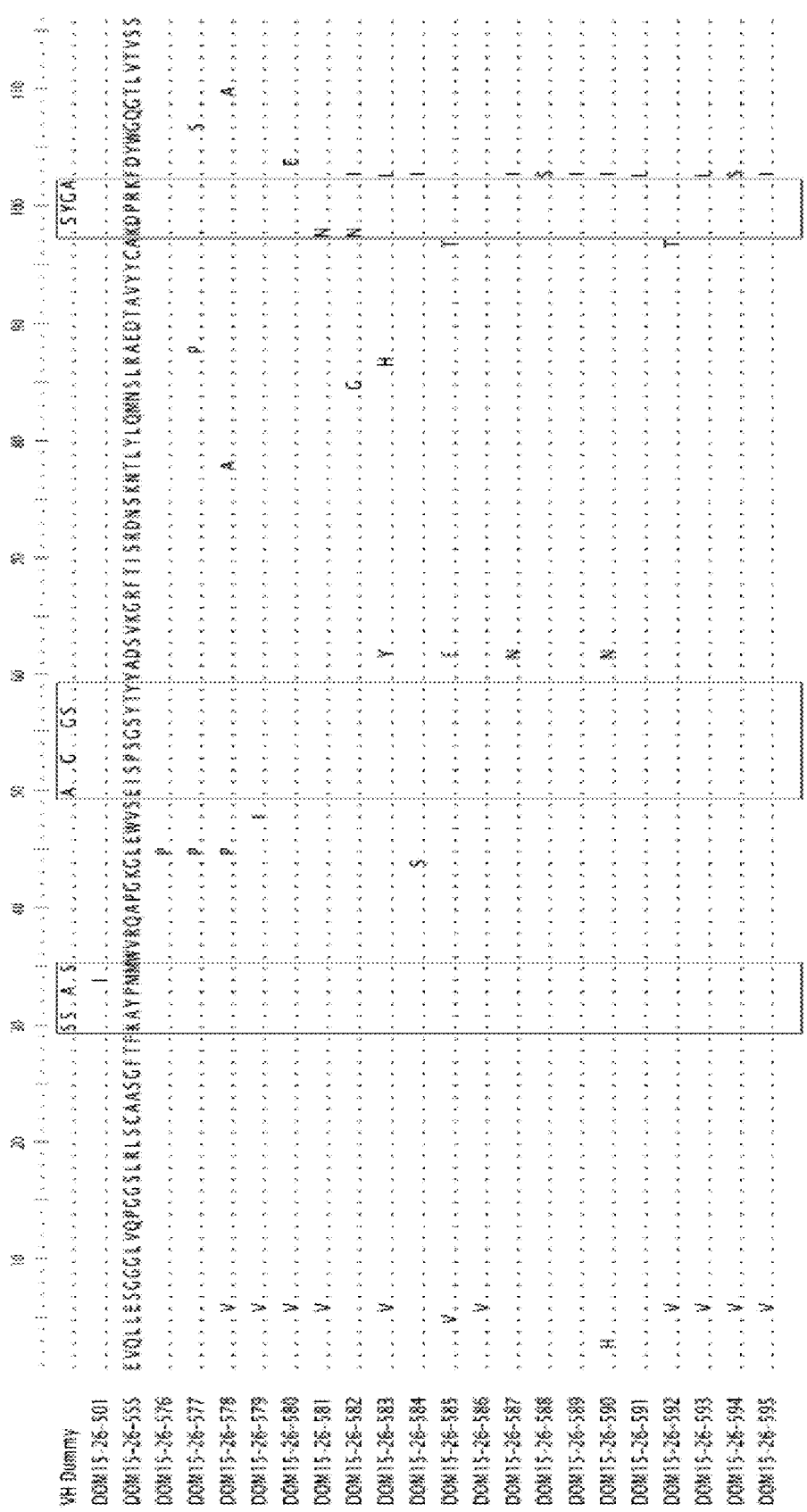
FIG. 5 is an illustration of the amino acid sequence of DOM15-26-555 (SEQ ID NO: 7) and 21 selected variants. The amino acids that differ from the parent sequence in selected clones are highlighted (those that are identical are marked by dots). The loops corresponding to CDR1, CDR2 and CDR3 are outlined with boxes. SYGA (SEQ ID NO: 6) is also shown.
Figure 6:
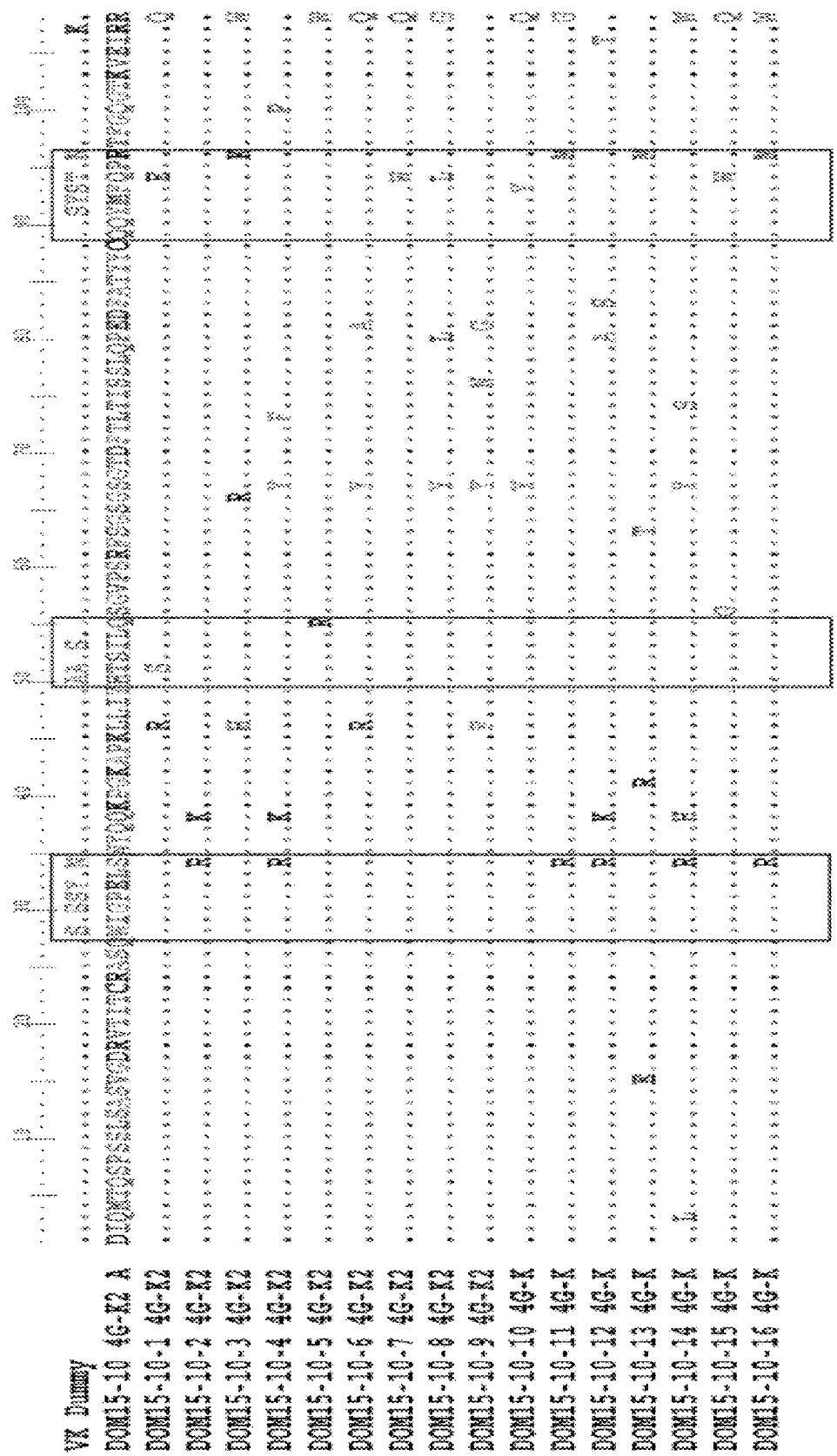
FIG. 6 is an illustration of the amino acid sequence of DOM15-10 (SEQ ID NO: 10) and 16 selected variants. The amino acids that differ from the parent sequence in selected clones are highlighted (those that are identical are marked by dots). The loops corresponding to CDR1, CDR2 and CDR3 are outlined with boxes. SYST (SEQ ID NO: 9) is also shown.
Figure 7A:
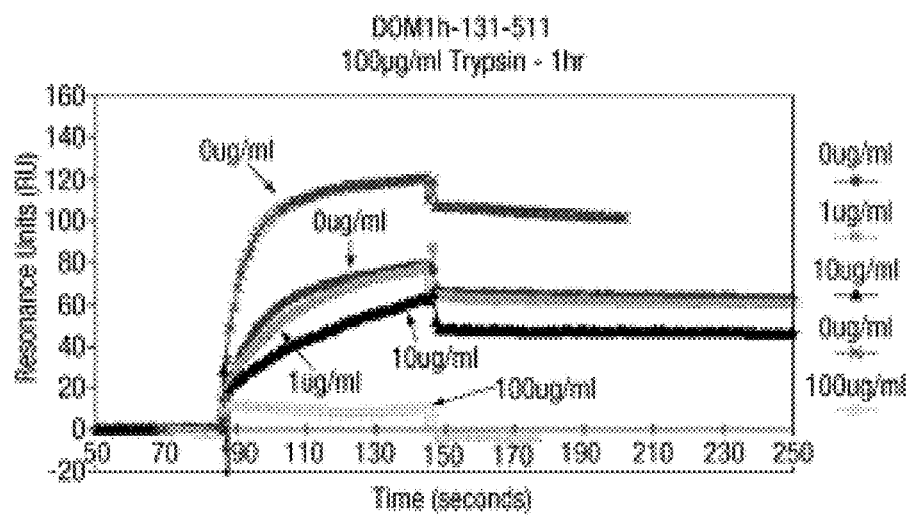
FIGS. 7A-7D are BIACORE™ traces showing bind of a parent DAB™, DOM1h-131-511 (FIG. 7A) and three variant DAB™s, DOM1h-131-203 (FIG. 7B), DOM1h-131-204 (FIG. 7C) and DOM1h-131-206 (FIG. 7D), to immobilized TNFR1 after incubation with different concentrations of trypsin (ranging from 0 to 100 μg/ml) overnight at 37° C. The results show that all three variants are more resistant than the parent to proteolysis at high concentrations of trypsin (100 ug/ml).
Figure 7B:
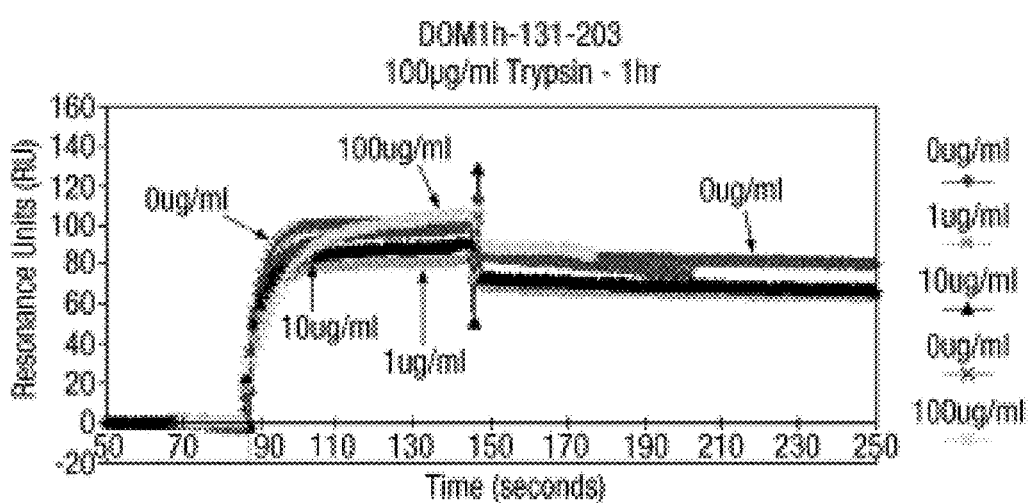
Figure 7C:
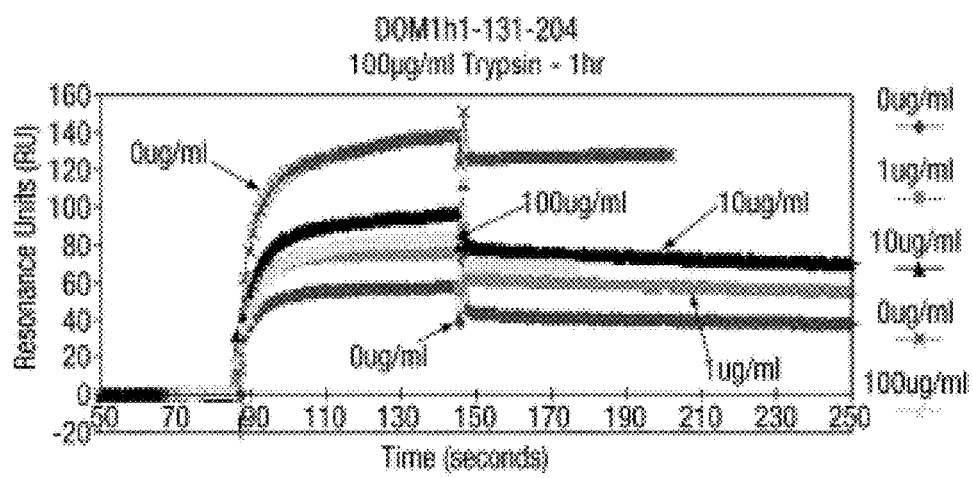
Figure 7D:
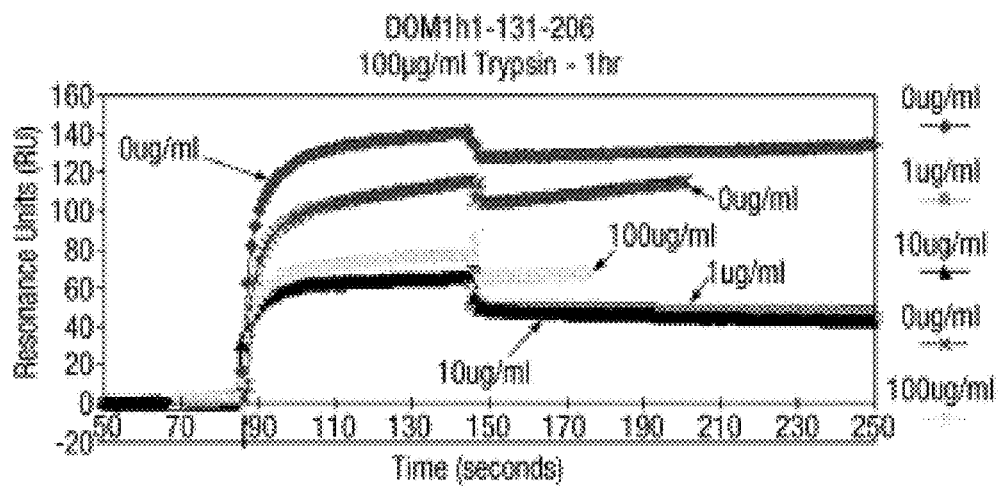

The criteria for picking clones were: a decrease in antigen binding of <15% of DAB™s treated with trypsin relative to untreated DAB™s (based on max RU reached on selected time point), which would reflect DAB™s stability to protease treatment in general; and off-rate decrease of <40% between two time points during dissociation of a DAB™ from the antigen. Based on these values, 60 clones from both the second and third rounds of selection of the DOM15-26-555 library and 17 clones from the third round of selection of the DOM15-10 library were sequenced. Consensus mutations were observed in both libraries' outputs and 17 clones from each library harboring consensus motifs were chosen for further characterization. The amino acid sequences of these clones are shown in FIG. 5 (DOM15-26-555 selected variants) and FIG. 6 (DOM15-10 selected variants) and listed as DNA sequences in FIGS. 20A-20E. The amino acids that differ from the parent sequence in selected clones are highlighted (those that are identical are marked by dots). The loops corresponding to CDR1, CDR2 and CDR3 are outlined by boxes.

These clones were expressed in 50 ml expression cultures, purified on protein A (for DOM15-26-555 variants) or protein L (for DOM15-10 variants) diluted to 100 nM concentration in HBS-EP buffer and tested for antigen binding on BIACORE™ after 1.5 hours of incubation at 37° C. with agitation (250 rpm) in the presence or absence of trypsin (20 µg/ml final concentration).

These clones were also tested for trypsin resistance using the method described in Example 2. Proteins were buffer exchanged to PBS and concentrated to 1 mg/ml. 25 µg of protein was mixed with 1 µg of trypsin (Promega) and incubated for 0 hours and 24 hours at 30° C. After this time, the reaction was blocked with ROCHE COMPLETE PROTEASE INHIBITORS™ (1x) and DTT, as well as loading agent, was added Samples were denatured for five minutes at 100° C. Then 15 µg of each sample was analyzed by electrophoresis on NOVEX™ 10-20% Tricine gels and proteins were stained with SUREBLUE™ (1x).

Generally, the outputs from the DOM15-26-555 selections were more stable, with most clones remaining resistant to trypsin for 1.5 hours when tested on BIACORE™ and overnight when run on SDS-PAGE. In comparison, only a small number of clones from the DOM15-10 selections were resistant to trypsin for overnight treatment when run on SDS-PAGE.

Example 6

Identification of DOM1h-131-511 Variants

Figure 8A:
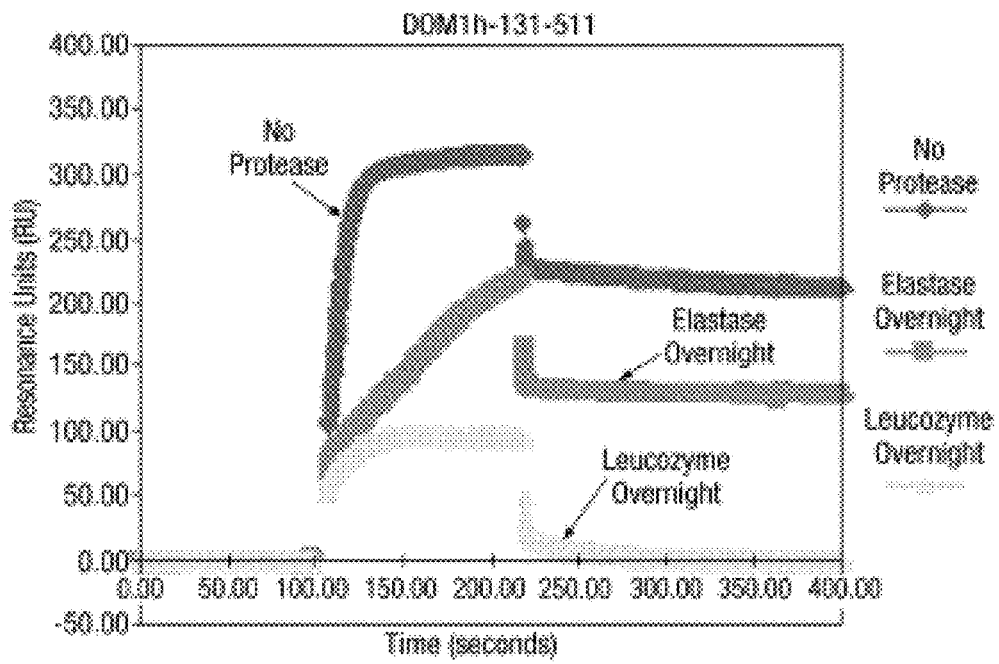
FIGS. 8A-8C are BIACORE™ traces showing binding of DAB™s DOM1h-131-511 (FIG. 8A), DOM1h-131-202 (FIG. 8B) and DOM1h-131-206 (FIG. 8C) to immobilized TNFR1 after incubation with elastase and leucozyme overnight. The DAB™s showed increased resistance to proteolysis compared to the parent against both elastase and leucozyme.
Figure 8B:
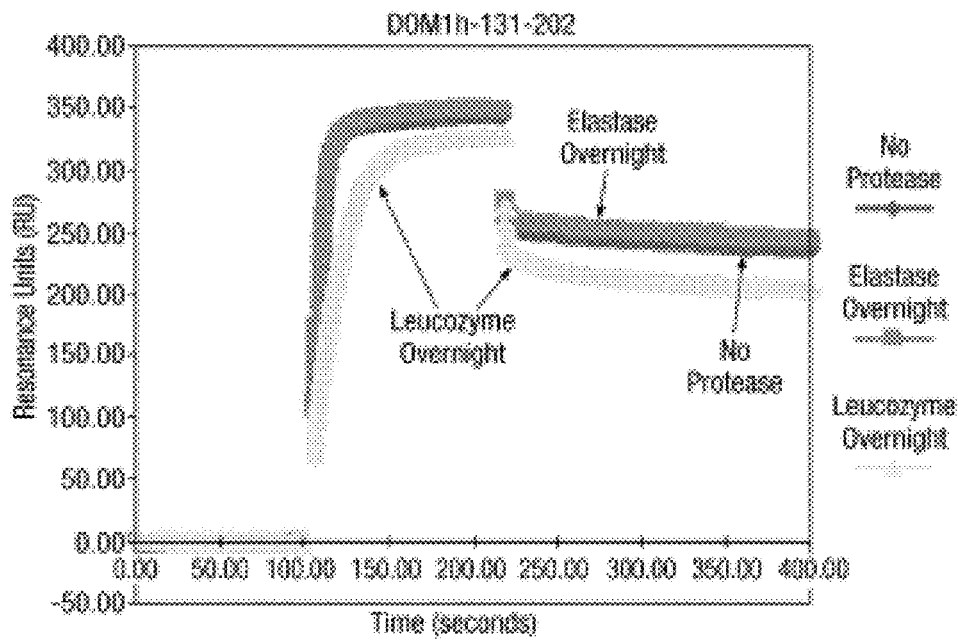
Figure 8C:
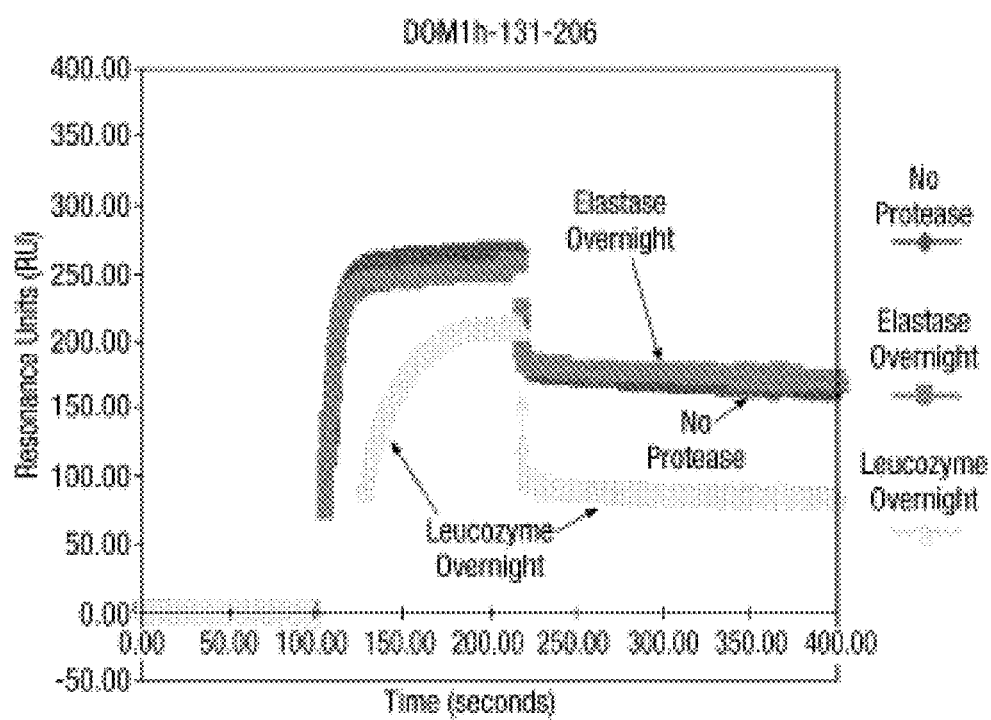

DOM1h-131-203, DOM1h-131-204 and DOM1h-131-206 were analyzed in further detail. They were compared on the BIACORE™ at a DAB™ concentration of 500 nM after incubation with different concentrations of trypsin (ranging from 0 to 100 µg/ml) overnight at 37° C. The BIACORE™ traces are shown in FIG. 7. The results clearly show that both variants are more resistant than their parent to proteolysis at high concentration of trypsin (100 µg/ml). Two of the DAB™s, DOM1h-131-202 and DOM1h-131-206, were also compared along with their parent against a range of other proteases including leucozyme, elastase and pancreatin under the conditions described above, with a protease concentration of 100 µg/ml. The DAB™s showed increased resistance to proteolysis compared to the parent against all proteases tested. The BIACORE™ traces for elastase and leucozyme are shown in FIG. 8.

Figure 9:
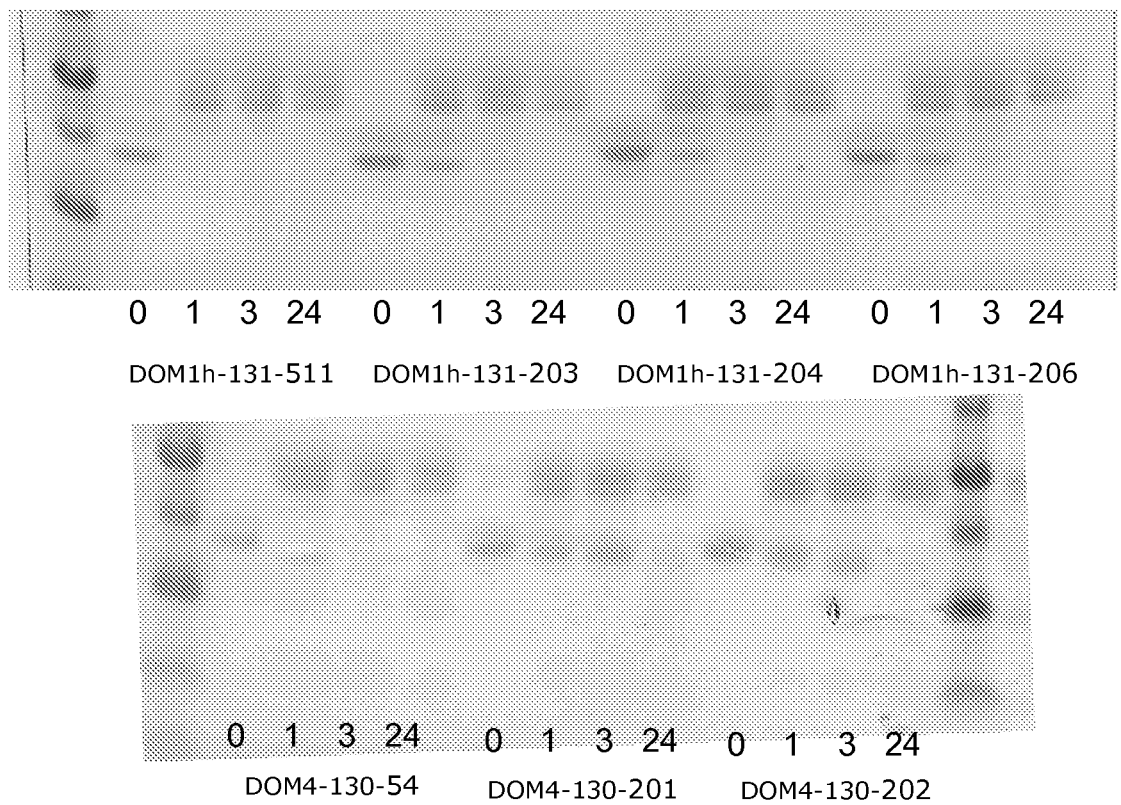
FIG. 9 shows two 4-12% NOVEX™ Bis-Tris gels run with samples of DAB™s DOM1h-131-511, DOM1h-131-203, DOM1h-131-204, DOM1h-131-206, DOM1h-131-54, DOM1h-131-201, and DOM1h-131-202 before incubation with trypsin and samples after incubation with 100 μg/ml of trypsin for 1 hour, 3 hours and 24 hours.

5 µM of each DAB™ was treated with 100 µg/ml sequencing grade trypsin for 0, 1, 3 and 24 hours. The reaction was inhibited with 25x ROCHE COMPLETE PROTEASE INHIBITOR™ and the reactions were run on a 4-12% NOVEX™ Bis-Tris gel. The gels are shown in FIG. 9.

Example 7

Identification of DOM4-130-54 Variants

Figure 10A:
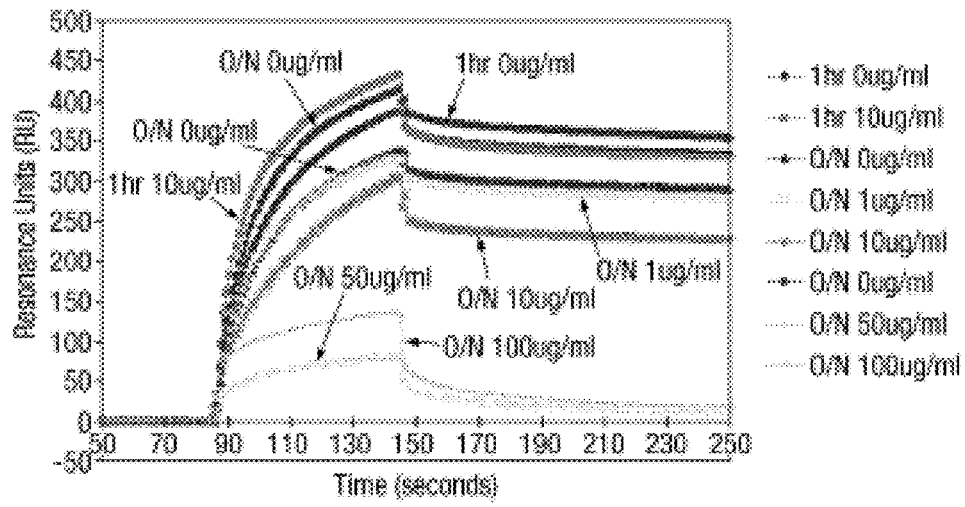
FIGS. 10A-10C are BIACORE™ traces showing binding of DOM4-130-54 (FIG. 10A), DOM4-130-201 (FIG. 10B) and DOM4-130-202 (FIG. 10C) to immobilized IL-1R1 fusion protein after incubation with different concentrations of trypsin (ranging from 0 to 100 μg/ml) overnight at 37° C. The results show that both variants are more resistant than their parent to proteolysis at high concentrations of trypsin (100 μg/ml).
Figure 10B:
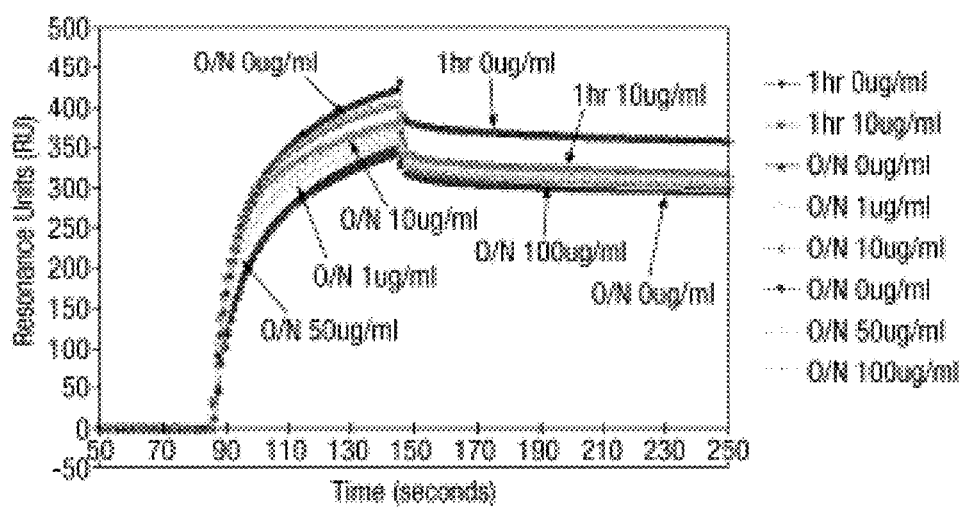
Figure 10C:
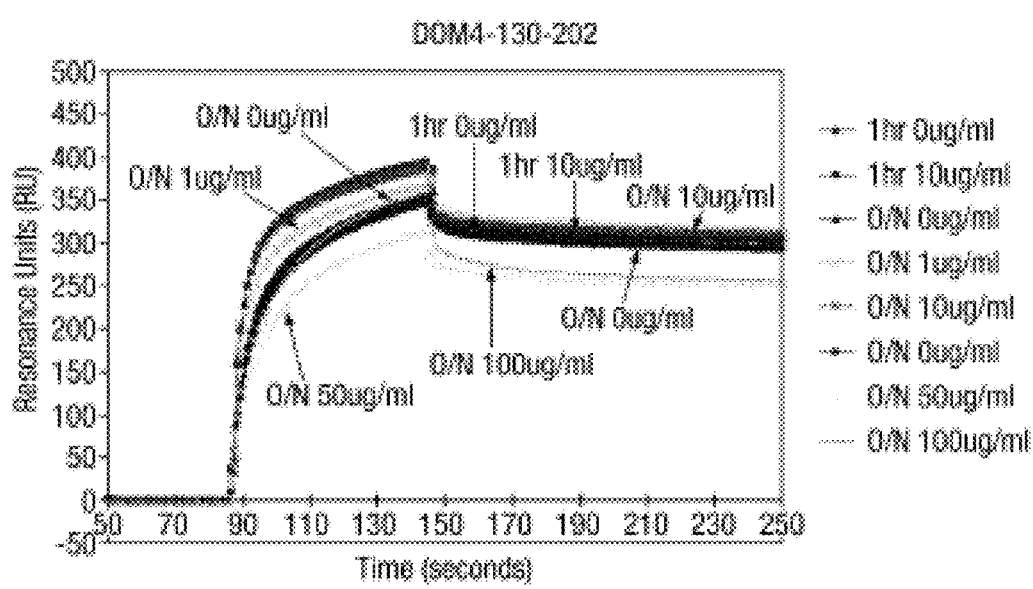
Figure 11A:
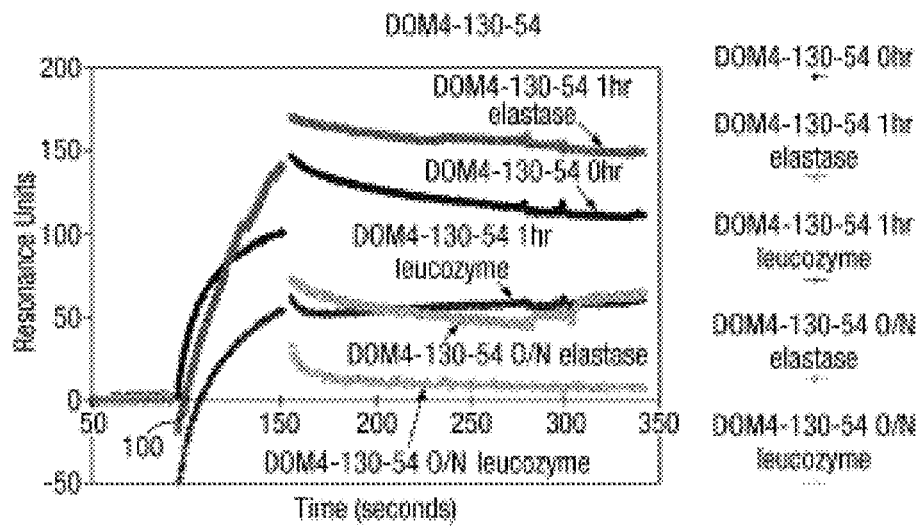
FIGS. 11A-11C are BIACORE™ traces showing binding of DOM4-130-54 (FIG. 11A), DOM4-130-201 (FIG. 11B) and DOM4-130-202 (FIG. 11C) to immobilized IL-1R1 fusion protein after incubation with elastase and leucozyme overnight. The DAB™s showed increased resistance to proteolysis compared to parent against both proteases tested.
Figure 11B:
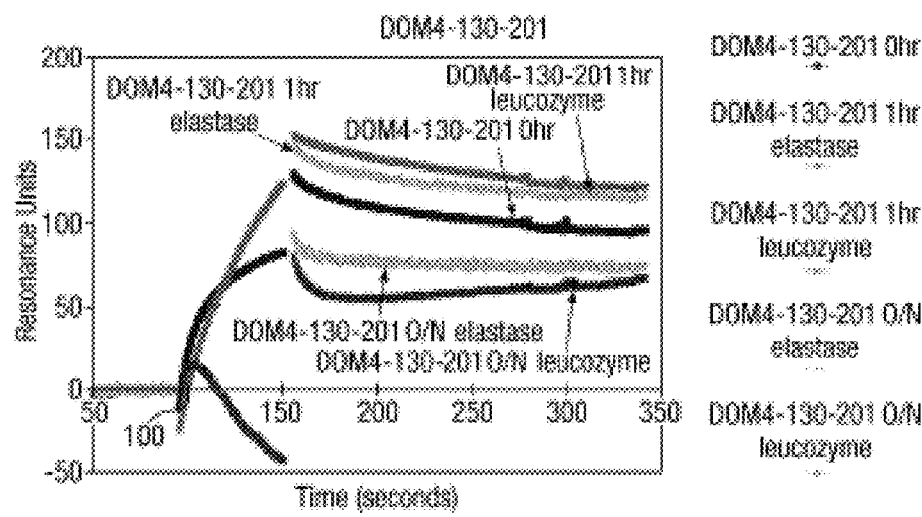
Figure 11C:
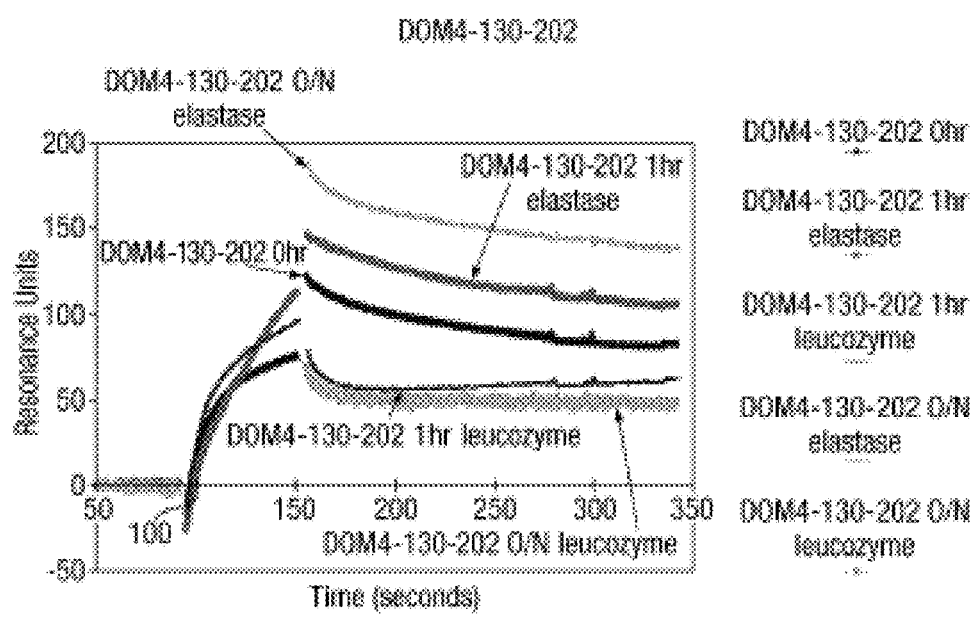
Figure 12:
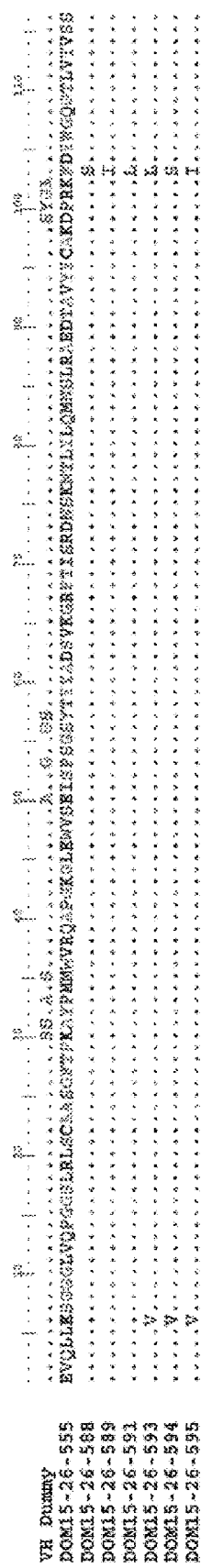
FIG. 12 is an illustration of the amino acid sequence of DOM15-26-555 SEQ ID NO: 12 and 6 variants. The amino acids that differ from the parent sequence in selected clones are highlighted (those that are identical are marked by dots). SYGA (SEQ ID NO: 11) is also shown.
Figure 13A:
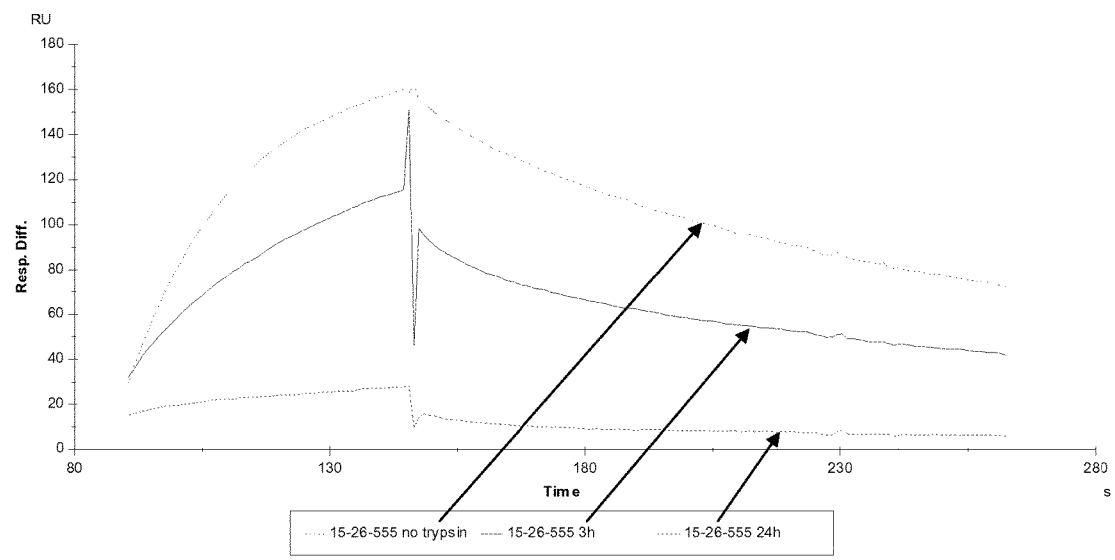
FIGS. 13A and 13B are BIACORE™ traces showing binding of the parent DAB™, DOM15-26-555 (FIG. 13A) and the most protease resistant variant, DOM15-26-593 (FIG. 13B) to immobilized VEGF. The parent and the variant were compared on the BIACORE™ for hVEGF binding at the DAB™ concentration of 100 nM after incubation with trypsin at a concentration of 200 μg/ml. The reaction was carried out for three hours or 24 hours at 37° C. The results show that the variant is more resistant than the parent to proteolysis after 24 hours of trypsin treatment.
Figure 13B:
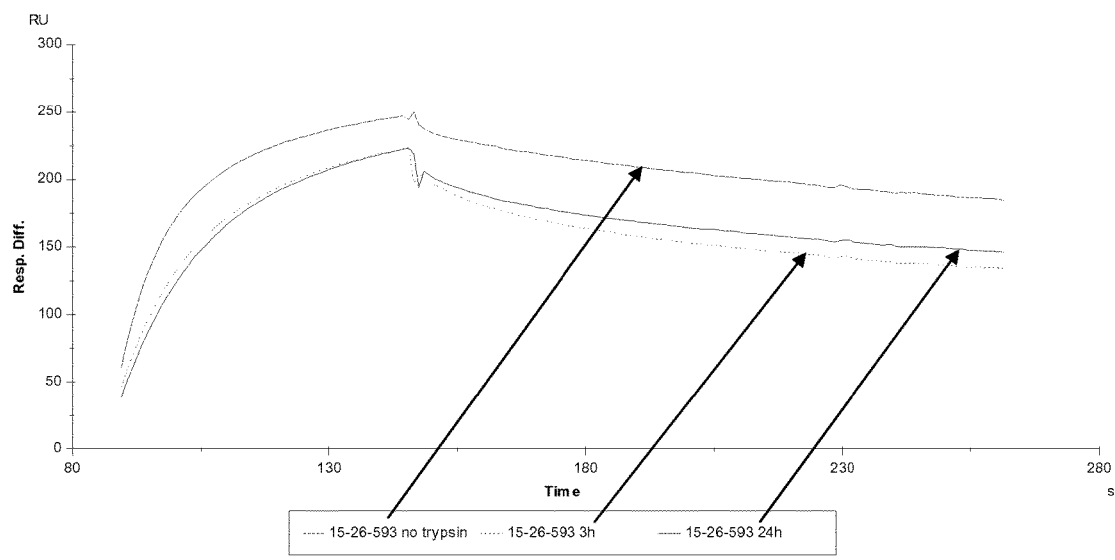
Figure 14:
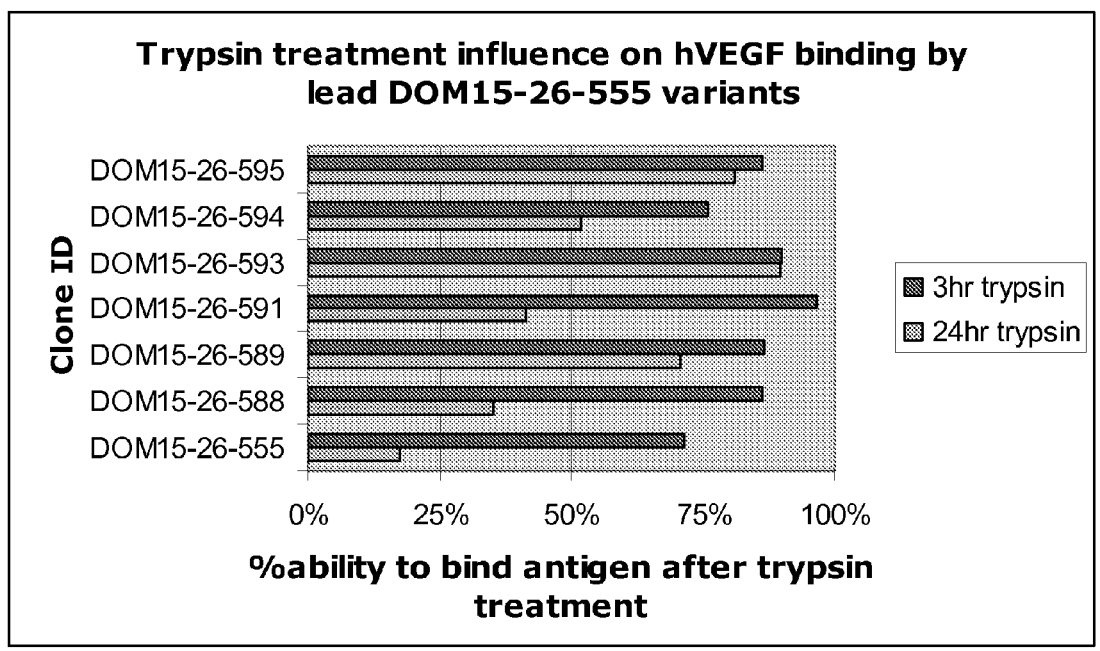
FIG. 14 is a graph showing effects of trypsin treatment on hVEGF binding by DOM15-26-555 variants. The results clearly show that all variants are more resistant than the parent (DOM15-26-555) to proteolysis after 24 hours of trypsin treatment.
Figure 15:
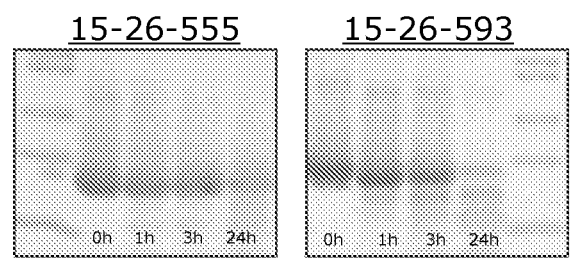
FIG. 15 shows two NOVEX™ 10-20% Tricine gels that were loaded with 15 μg of treated and untreated samples of DOM15-26-555 or DOM15-26-593. Samples were taken immediately before the addition of trypsin, and then at one hour, three hours and 24 hours after the addition of trypsin. The proteins were stained with 1× SUREBLUE™. The gels illustrate that the trypsin resistance profile of DOM15-26-593 varied from the profile shown by the BIACORE™ experiment.
Figure 17A:
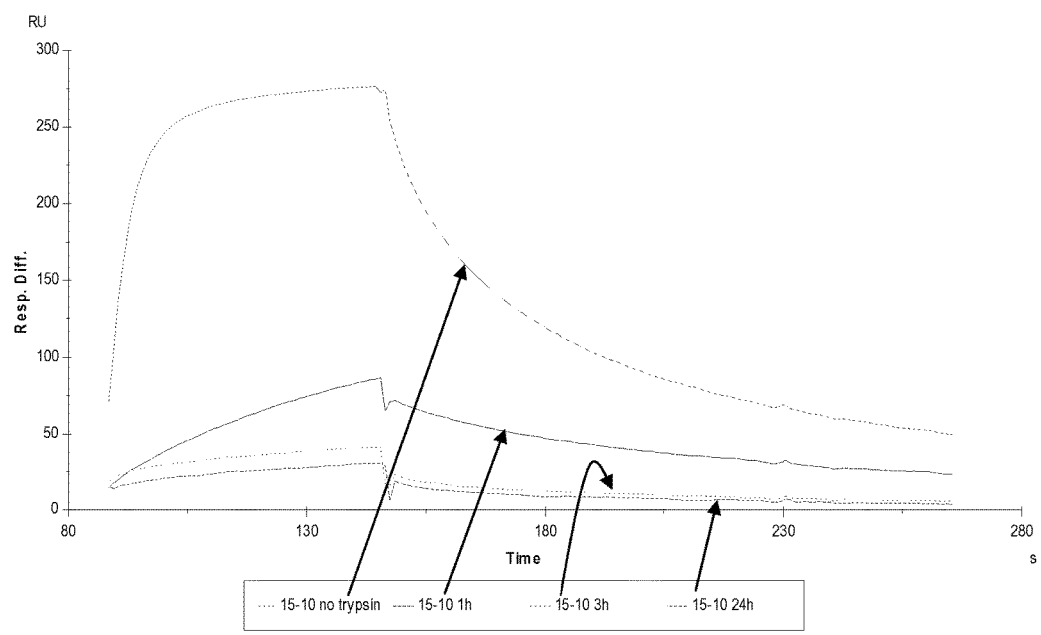
FIGS. 17A and 17B are BIACORE™ traces showing binding of the parent, DOM15-10 (FIG. 17A) and the variant, DOM15-10-11 (FIG. 17B), to immobilized VEGF. The parent and the variant were compared on the BIACORE™ for hVEGF binding at the DAB™ concentration of 100 nM after incubation with trypsin at a concentration of 200 μg/ml. The reaction was carried out for one hour, three hours and 24 hours at 37° C. The results show that the variant is more resistant than the parent to proteolysis after 24 hours of trypsin treatment.
Figure 17B:
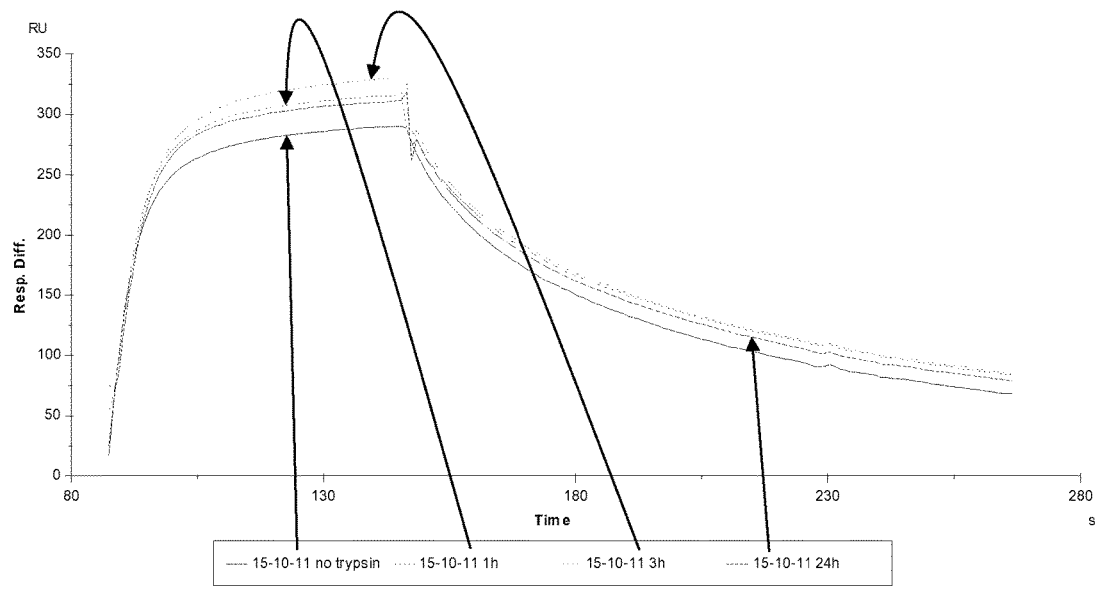
Figure 18:
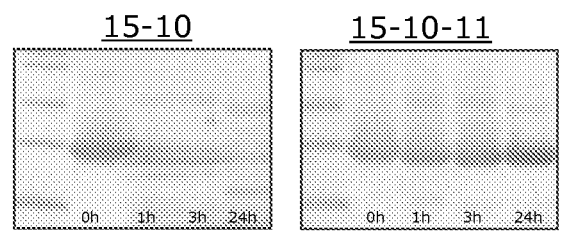
FIG. 18 shows two NOVEX™ 10-20% TRICENE™ gels that were loaded with 15 μg of samples of DOM15-10 and DOM15-10-11. Samples were taken immediately before the addition of trypsin, and then at one hour, three hours, and 24 hours after the addition of trypsin. The proteins were stained with SUREBLUE™ (1×). The results show that the binding activity seen in the BIACORE™ study directly reflects the protein's integrity.

DOM4-130-201 and DOM4-130-202 were analyzed in further detail. They were compared on the BIACORE™ at a DAB™ concentration of 500 nM after incubation with different concentrations of trypsin (ranging from 0 to 100 µg/ml) overnight at 37° C. The BIACORE™ traces are shown in FIG. 10. The results clearly show that all three variants are more resistant than their parent to proteolysis at high concentrations of trypsin (100 µg/ml). DOM4-130-201 and DOM4-130-202 were also compared with the parent against a range of other proteases including leucozyme, elastase and pancreatin under the conditions described above with a protease concentration of 100 µg/ml. Although the results were less apparent than with trypsin, the lead DAB™s showed increased resistance to proteolysis compared to parent against all proteases tested. The BIACORE™ traces for elastase and leucozyme are shown in FIG. 11.

5 µM of each DAB™ was treated with 100 ug/ml sequencing grade trypsin for 0, 1, 3 and 24 hours. The reaction was inhibited with 25x ROCHE COMPLETE PROTEASE INHIBITOR™ and the reactions were run on a 4-12% NOVEX™ Bis-Tris gel. The gels are shown in FIG. 9.

Example 8

Further Characterization of DOM1h-131-511 and DOM4-130-54 Variants

The DAB™s were first analyzed using Differential Scanning Calorimetry (DSC) to determine whether the increase in trypsin resistance correlated with an increase in melting temperature (Tm). An increase in trypsin stability does correlate with an increase in Tm (see Table 9)

TABLE 9

| Name | Tm, ° C. |
|---|---|
| DOM1h-131-511 | 57.9 |
| DOM1h-131-202 | 67.5 |
| DOM1h-131-203 | 65.7 |
| DOM1h-131-204 | 62.3 |
| DOM1h-131-206 | 64.9 |
| DOM4-130-54 | 54.1 |
| DOM4-130-201 | 64.7 |
| DOM4-130-202 | 64.5 |

The DOM1h-131-511 derived DAB™s were also compared in a MRC-5 cell-based assay (see Table 10). In this assay, the ability of the DAB's to neutralize TNFα stimulated IL-8 release was measured to determine whether the increase in trypsin stability had led to a decrease in efficacy. However, the activity of the trypsin-resistant DAB™s in the assay was substantially unaffected.

TABLE 10

| Sample | ND50 nM |
|---|---|
| DOM1h-131-511 | 1.98 |
| DOM1h-131-511 | 1.71 |

TABLE 10-continued

| Sample | ND50 nM |
|---|---|
| DOM1h-131-511 (230307CE) | 1.89 |
| DOM1h-131-203 (230307CE) | 2.28 |
| DOM1h-131-204 (230307CE) | 1.89 |
| DOM1h-131-511 | 1.46 |
| DOM1h-131-206 (230307CE) | 0.71 |

The DOM4-130-54 derived DAB™s were tested in a Receptor Binding Assay to see if they still had the same ability to inhibit the binding of IL-1 to IL-RI (see Table 11). The activity of the trypsin resistant DAB™s was unaffected in this assay.

TABLE 11

| DAB ™ | IC50 (nM) |
|---|---|
| DOM4-130-54 | 280 pM |
| DOM4-130-201 | 257 pM |
| DOM4-130-202 | 254 pM |

Example 9

Identification of DOM15-26-555 Variants

DOM15-26-588, DOM15-26-589, DOM15-26-591, and DOM15-26-593 were analyzed in further detail together with their parent and two additional DAB™s, DOM15-26-594 and DOM15-26-595, which were created by mutagenesis to combine mutations that would have the greatest impact on potency and stability (E6V and F100S/I). Sequences are shown in FIG. 12. Clones were compared on the BIACORE™ for hVEGF binding at the DAB™ concentration of 100 nM after incubation with trypsin at a concentration of 200 μg/ml. The reaction was carried out for three hours and 24 hours at 37° C. with agitation (250 rpm). The BIACORE™ traces of the best clone, DOM15-26-593, and the parent are shown in FIG. 13. Other results are presented as a chart in FIG. 14. The results clearly show that all variants are more resistant than the parent to proteolysis after 24 hours of trypsin treatment.

Trypsin resistance of DOM15-26-593 and the parent was also examined by running treated and un-treated samples on SDS-PAGE. Briefly, proteins were buffer exchanged to PBS and concentrated to 1 mg/ml. 25 ug of protein was mixed with 1 μg of sequencing grade trypsin (Promega) and incubated for 0 hours, 1 hour, 3 hours and 24 hours at 30° C. After this time, the reaction was blocked with ROCHE COMPLETE PROTEASE INHIBITOR™ (1×) and DTT, as well as loading agent, was added. Samples were denatured for five minutes at 100° C. 15 ug of each sample was loaded on NOVEX™ 10-20% Tricine gels and proteins were stained with SUREBLUE™ (1×). The results are shown in FIG. 15. The trypsin resistance profile of DOM15-26-593 in this experiment varied from the profile shown by the BIACORE™ experiment, suggesting that differences in reaction conditions may influence the final result of trypsin cleavage. Nonetheless, DOM15-26-593 has better biophysical properties, as well as affinity, than other selected clones, as shown below. A summary of the properties of the DOM15-26-555 variants is also shown in Table 12 below.

TABLE 12

| | Attribute | | | | | |
|---|---|---|---|---|---|---|
| | SEC-MALLS | | | | | Trypsin Stability |
| DAB ™ | % monomer | Est. mw | DSC Tm ° C. | RBA nM | BIACORE ™ KD nM | % binding @ +24 hrs |
| 15-26 | 0 | 37-136 | 64 | 10 | 28.2 | 30 |
| 15-26-501 | 0-40 | 18-290 | 51 | 1.14 | 9.1 | 5 |
| 15-26-555 | 0 | 28-78 | 63 | 11.7 | 26.1 | 10 |
| 15-26-588 | 10 | 33 | 70 | 27 | 59.1 | 15 |
| 15-26-589 | 90 | 17 | 63 | 1.94 | 9.6 | 65 |
| 15-26-591 | 20 | 21-234 | 63 | 16 | 38 | 35 |
| 15-26-593 | 80 | 17 | 65 | 0.323 | 3.2 | 80 |
| 15-26-595 | 60 | 17 | 65 | 0.828 | 5 | 70 |

Example 10

Identification of DOM15-10 Variants

DOM15-10-11 was analyzed in further detail, together with its parent, DOM15-10. Sequences are shown in FIG. 16. The DAB™s were compared on the BIACORE™ for hVEGF binding at the DAB™ concentration of 100 nM after incubation with trypsin at a concentration of 200 μg/ml. The reaction was carried out for 1 hour, 3 hours and 24 hours at 37° C. with agitation (250 rpm). The BIACORE™ traces of these DAB™s are shown in FIG. 17. The result clearly shows that the selected variant is more resistant than the parent to proteolysis after 24 hours of trypsin treatment.

Trypsin resistance of the lead and the parent was also examined by running treated and un-treated samples of SDS-PAGE. Briefly, proteins were buffer exchanged to PBS and concentrated to 1 mg/ml. 25 μg of protein was mixed with 1 μg of sequencing grade trypsin (Promega) and incubated for 0 hours, 1 hour, 3 hours and 24 hours at 30° C. After this time, the reaction was blocked with ROCHE COMPLETE PROTEASE INHIBITOR™ (1×) and DTT, as well as loading agent, was added. Samples were denatured for five minutes at 100° C. 15 μg of each sample was loaded on NOVEX™ 10-20% TRICENE™ gels and proteins were stained with SUREBLUE™ (1×). The results are presented in FIG. 18. In this case, the trypsin resistant profile correlates well with the BIACORE™ trypsin test, showing that the binding activity directly reflects the protein's integrity.

Example 11

Further Characterization of DOM15-26-555 and DOM15-10 Variants

The DAB™s were analyzed using Differential Scanning Calorimetry (DSC) to determine whether the increase in trypsin resistance correlated with an increase in Tm. The results are shown in Table 13. There is a correlation between the trypsin resistance of DOM15-26-555 variants and melting temperature. The lead DOM15-26-588 and DOM15-26-593 showed improved Tm, but the other clones did not. It is worth noting that both DOM15-26-555 and DOM15-10 parent molecules have much higher Tm at the start (63.3-63.7° C.) than the DOM4-130-54 and DOM1h-131-511 parent molecules (Tm at start: 57.9-54.1° C.), but overall the protease resistant clones reach a Tm in a similar range (average Tm of 65.1° C. for the DOM1h-131-511/DOM4-130-54 variants and average Tm of 64.9° C. for the DOM15-26-55/DOM15-10 variants).

TABLE 13

| Name | Tm ° C. |
|---|---|
| DOM15-26-555 | 63.3 |
| DOM15-26-588 | 70.1 |
| DOM15-26-589 | 63 |
| DOM15-26-591 | 63 |
| DOM15-26-593 | 65 |
| DOM15-10 | 63.7 |
| DOM15-10-11 | 63.3 |

The DAB's were also compared in a receptor binding assay and BIACORE™ kinetics were measured to determine whether the increase in trypsin stability had led to a decrease in efficacy. However, the activity of the DAB™s in the assay was substantially unaffected or even improved. The results are presented in Table 14.

TABLE 14

| Clone ID | $EC_{50}$ (nM) | $K_D$ (nM) |
|---|---|---|
| DOM15-26-555 | 11.7 | 26.1 |
| DOM15-26-588 | 27 | 59.1 |
| DOM15-26-589 | 1.94 | 9.6 |
| DOM15-26-591 | 16 | 38 |
| DOM15-26-593 | 0.323 | 3.2 |
| DOM15-26-594 | 4.09 | 15.1 |
| DOM15-26-595 | 0.828 | 5 |
| DOM15-10 | 10.23 | 23.6 |
| DOM15-10-11 | 3.58 | 14.6 |

Advantages of an Enhanced Tm

Most proteins—including domain antibodies—exist in two states: a folded state (which leads to a biologically active molecule) and an unfolded state (which does not bear functional activity). These two states co-exist at all temperatures and the relative proportion of each state is usually determined by a constant K that is a function of the kinetic constants of folding and unfolding. The melting temperature is usually defined as the temperature at which K=1, i.e. the temperature at which the fraction of folded protein is equal to be fraction of unfolded protein. The constant K is determined by the stabilizing and destabilizing intramolecular interactions of a protein and therefore is primarily determined by the amino acid sequence of the protein. Extrinsic parameters such as temperature, pH, buffer composition, pressure influence K and therefore the melting temperature.

Unfolded proteins are easy targets for degradation mechanisms: (i) exposure of disulfide bonds increase risks of oxidation or reduction depending on the circumstances, (ii) enhanced backbone flexibility favours auto-proteolytic reactions, (iii) exposure of peptide segments offers targets to proteases in vivo, to proteases during production processes and to carry-over proteases during downstream processing and long-term storage, and (iv) exposure of aggregation-prone segments leads to inter-molecular aggregation and protein precipitation. In all cases, a loss of protein integrity, protein content and protein activity happens, thereby compromising efforts to (i) ensure batch reproducibility, (ii) ensure long-term stability on shelf, and (iii) in vivo efficacy.

In nature proteins have been designed by evolution to adequately perform at body temperature and to be readily replaced via homeostatic mechanisms. Therapeutic proteins manufactured through biotechnogical processes face a different environment: they are frequently produced by recombinant DNA technology in a foreign host, are expressed at higher amount in large vessels, undergo very important changes in pH or buffer composition throughout downstream processes and finally are stored at high concentrations in non-physiological buffers for prolonged period of time. New delivery techniques (e.g. inhalation, sc patch, slow delivery nanoparticles) are also adding on the stress undergone by therapeutic proteins. Finally the advent of protein engineering techniques has resulted in the production of enhanced or totally novel therapeutic proteins. Because most engineering techniques are in-vitro based techniques aimed at altering or creating new amino acid sequences, evolution processes that have gradually improved biological proteins do not take place, hence resulting in proteins of sub-optimal performances with regards to stress resistance.

The technique of the present invention aims at reproducing one of the conditions faced by proteins throughout Darwinian evolution. Peptides or polypeptides, eg immunoglobulin single variable domains are infused with proteases that play a major role in tissue remodelling and protein homeostasis. Any particular mutation that may result in a protein with an improved fit to its function is also tested for its ability to fit within the environment it is performing in. This process is reproduced in one embodiment of the present invention: a repertoire of peptide or polypeptide variants is created and exposed to a protease. In a second step, the repertoire of variants is contacted with a specific target. Only those protein variants that have sustained degradation by the protease are able to engage with the target and therefore recovered, eg, by a simple affinity purification process named 'biopanning'. The system offers a number of advantages in comparison to in vivo processes: the protein repertoire can be faced with a wider range of conditions, eg a range of proteases, at higher concentrations, for longer times, in different buffers or pHs and at different temperatures. Thus this in vitro technology offers a means to design proteins that may perform and remain stable in a wider range of environments than those they originate from. Clearly this offers multiple advantages for the biotechnological industry and for the area of therapeutic proteins in particular.

Example 12: PK Correlation Data for Protease Resistant Leads

The parent DAB™ and a protease-resistant DAB™ in each of the four DAB™ lineages, were further evaluated in vivo (see Table 15 below for list and details)

TABLE 15

| Lineage | DAB ™ ID | Resistance to trypsin | Tm (° C.) | Activity (nM) | ID as Fc fusion |
|---|---|---|---|---|---|
| DOM4-130 | DOM4-130-54 | Good | 54 | 0.128* | DMS1541 |
| | DOM4-130-202 | Very high | 64 | 0.160* | DMS1542 |
| DOM1h-131 | DOM1h-131-511 | Good | 57 | 0.048† | DMS1543 |
| | DOM1h-131-206 | Very high | 64 | 0.047† | DMS1544 |
| DOM15-10 | DOM15-10 | Low | 64 | 0.913† | DMS1546 |
| | DOM15-10-11 | High | 63 | 0.577† | DMS1531 |

TABLE 15-continued

| Lineage | DAB ™ ID | Resistance to trypsin | Tm (° C.) | Activity (nM) | ID as Fc fusion |
|---|---|---|---|---|---|
| DOM15-26 | DOM15-26-501(*) | Low | 52 | 0.330† | DMS1545 |
| | DOM15-26-593 | High | 65 | 0.033† | DMS1529 |

*as determined by MRC5/IL-a bioassay;
†as determined by RBA assay

Note:
DOM15-26-501 is a parent version of DOM15-26-555 exemplified above in this patent application.
DOM15-26-555 has one germline amino acid mutation in CDR1 (I34M).
DOM15-26-501 has a lower melting temperature than DOM15-26-555 (52 C. v 63.3 C.) and an increased susceptibility to digestion by trypsin.
DOM15-26-501 was chosen over DOM15-26-555 for the PK study as it is a better representative for poor stability in comparison to DOM15-26-593.

We can translate the resistance as follows:
1 is low
2 is moderate
3 is good
4 is high
5 is very high Then this means that the trypsin resistance of the parent molecules is:
DOM4-130-54 is Good
DOM1h-131-511 is Good
DOM15-10 is Low
DOM15-26-501 is Low As for the selected leads:
DOM4-130-202 is Very high
DOM1h-131-206 is Very high
DOM15-10-11 is High
DOM15-26-593 is High Because domain antibodies are small in size (12-15 kDa) they are rapidly cleared from the circulation upon iv or sc injection. Indeed the renal glomerular filtration cut-off is above 50 kDa and therefore small proteins such as DAB™s are not retained in the circulation as they pass through the kidneys. Therefore, in order to evaluate the long term effects of resistance to proteases in vivo, we tag domain antibodies with a moiety that increases systemic residence. Several approaches (e.g. PEG, Fc fusions, albumin fusion, etc) aiming at extending half-life have been reported in the literature. In this application the domain antibodies have been tagged (or formatted) with the Fc portion of the human IgG1 antibody. This format offers two advantages: (i) the molecular size of the resulting dAb-Fc is ~75 kDa which is large enough to ensure retention in circulation, (ii) the antibody Fc moiety binds to the FcRn receptor (also know as "Brambell" receptor). This receptor is localized in epithelial cells, endothelial cells and hepatocytes and is involved in prolonging the life-span of antibodies and albumin: indeed upon pinocytosis of antibodies and other serum proteins, the proteins are directed to the acidified endosome where the FcRn receptor intercepts antibodies (through binding to the Fc portion) before transit to the endosome and return these to the circulation. Thus by tagging the Fc portion to the DAB™, it is ensured that the DAB™s will exposed for long period to two at least compartments—the serum and the pre-endosomal compartments, each of which containing a specific set of proteolytic enzymes. In addition, the FcRn receptor mediates transcytosis whereby Fc-bearing proteins migrate to and from the extravascular space.

Formatting with Fc was accomplished by fusing the gene encoding the $V_H$ and VK DAB™s to the gene encoding the human IgG1 Fc, through a short intervening peptide linker (in bold):

For a VH DAB ™ (underlined):
(SEQ ID NO: 260)
EVQ...GQGTLVTVSSASTHTCPPCPAPELLGGP...(hIgG1Fc)...PGK*

For a VK DAB ™ (underlined):
(SEQ ID NO: 261)
DIQ...GQGTKVEIKRTVAAPSTHTCPPCPAPELLGGP...(hIgG1Fc)...PGK*

Figure 21:
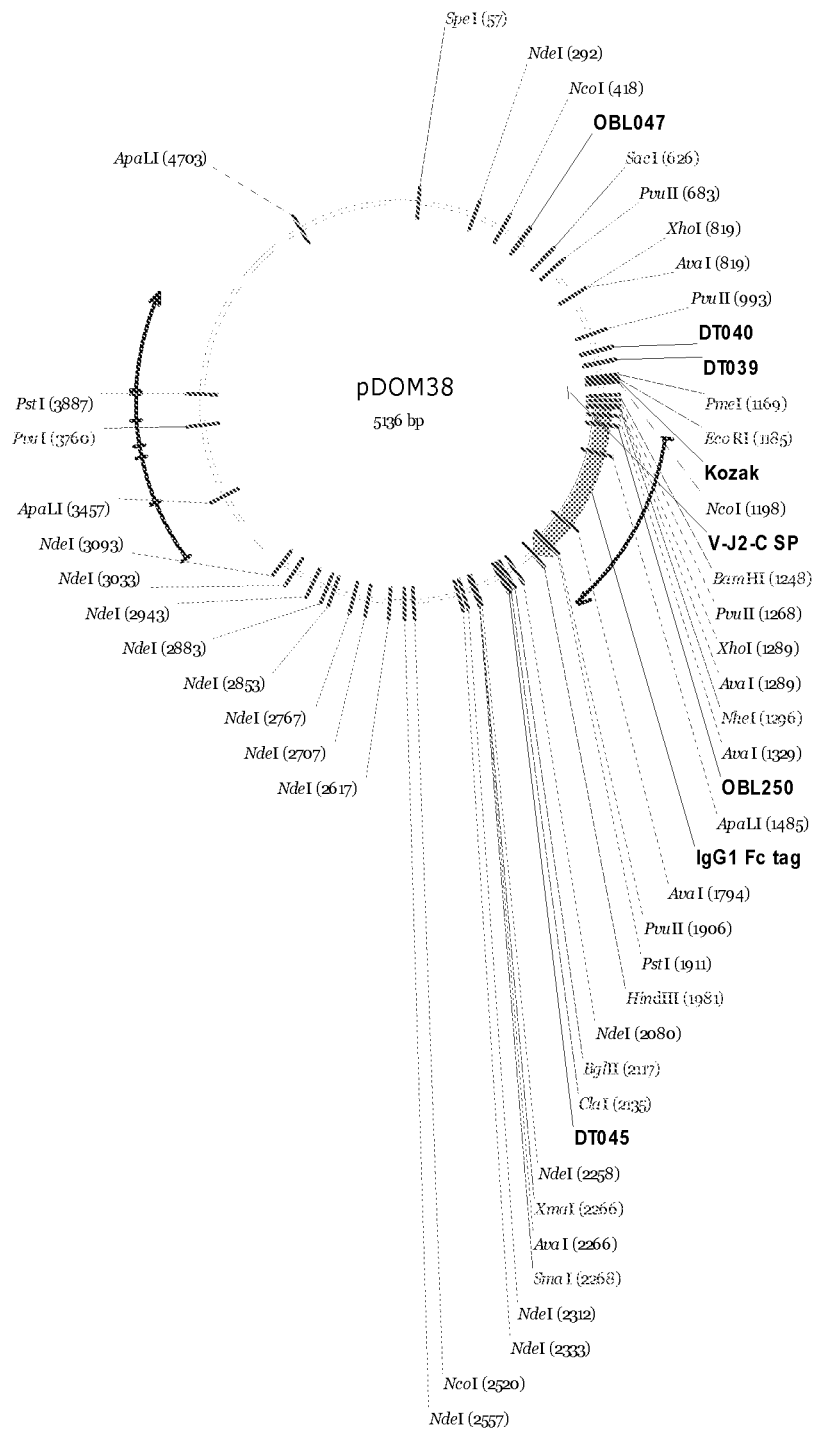
FIG. 21 shows a vector map of pDOM 38.

Material was produced by transient transfection of HEK293/6E cells using 293-FECTIN™ (Invitrogen) according to standard protocols. These cells are designed for high-level transient expression when used in conjunction with the pTT series of vectors (Durocher et al 2002). Thus the DAB™ genes were cloned into a modified pTT5 vector (pDOM38) to generate the Fc fusion expression vector (see FIG. 21). The supernatant from the transfected cells was harvested at 5 days post-transfection, clarified by centrifugation and filtered through a 0.2 μm filter. The dAb-Fc fusion proteins were purified by capture onto Protein-A STREAMLINE™ resin (GE Healthcare). Protein was eluted from the column in 10 mM sodium citrate pH3, followed by the addition of and 1M sodium citrate pH6, to achieve a final composition of 100 mM sodium citrate pH6.

The dAb-Fc molecules were tested for in vivo half life in the rat at a target dose of 5 mg/kg into female Sprague-Dawley rats (n=3 per group). It should be noted that the target dose vastly exceeds target concentration in rats, so it is expected that differences in affinities between parent DAB™s and trypsin-resistant DAB™s (see example 11) will not impact on the fate of the molecules in vivo. Hence differences in PK profiles between DAB™s are expected to reflect on an antigen-independent elimination process.

Blood samples were taken after 0.03, 1, 4, 8, 24, 48, 72, 96, 120 and 168 hours post administration. After clot formation, serum was withdrawn and then tested in hIL-1R1, TNFR1 or VEGF antigen capture assays:

hIL-1R1 Antigen Capture Assays:
Coat with 4 ug/mL anti-hIL-1R1
Block
Add 500 ng/mL shIL-1R1
Add samples
Detect with anti-human Fc HRP @ 1:10,000
TNFR1 Antigen Capture Assays:
Coat with 0.1 ug/mL sTNFR1
Block
Add samples
Detect with anti-human Fc HRP @ 1:10,000
VEGF Antigen Capture Assays:
Coat with 0.25 ug/mL VEGF
Block
Add samples
Detect with anti-human Fc HRP @ 1:10,000

Raw data from the assays were converted into concentrations of drug in each serum sample. The mean μg/mL values at each time point were then analysed in WINNONLIN™ using non-compartmental analysis (NCA). The PK profiles of each dAb-Fc pair are shown in Table 16 which summarises the determined PK parameters.

TABLE 16

| ID | DAB ™ | Half Life (hr) | AUC/D (0-inf) (hr * μg/mL)/(mg/kg) | % AUC Extrapolated |
|---|---|---|---|---|
| DMS1541 | 4-130-54 | 93.2 | 691.5 | 22.7 |
| DMS1542 | 4-130-202 | 176.8 | 710.1 | 49 |

TABLE 16-continued

| ID | DAB™ | Half Life (hr) | AUC/D (0-inf) (hr * µg/mL)/(mg/kg) | % AUC Extrapolated |
|---|---|---|---|---|
| DMS1543 | 1h-131-511 | 140.8 | 1807.5 | 40 |
| DMS1544 | 1h-131-206 | 158.6 | 2173.0 | 43.6 |
| DMS1546 | 15-10 | 43.2 | 324.6 | 3.8 |
| DMS1531 | 15-10-11 | 56.6 | 770.5 | n.d. |
| DMS1545 | 15-26-501 | 12.9 | 89 | 5.1 |
| DMS1529 | 15-26-593 | 86.2 | 804.7 | 21.0 |

The results clearly indicate that—whilst the PK profiles of the dAb-Fc pairs 4-130-54 to 1h-131-206 are almost superimposable—the profiles vary widely with the other pairs. The effects are mostly visible when AUC/D is considered: the AUC/D of 15-10 is only 42% of that of 15-10-11. The AUC/D of 15-26-501 is only 11% of that of 15-26-593. These important differences also impact (to a lesser extent) half-lives: 43.2 h versus 56.6 h for 15-10 and 15-10-11, respectively. A greater difference is seen with the DOM15-26 lineage: 12.9 h versus 86.2 h for 15-26-501 and 15-26-593, respectively. Indeed for a good PK analysis using non-compartmental analysis, there should be at least 4 data points used to fit the linear regression slope and the period of time over which the half life is estimated should be at least 3 times that of the calculated half life.

In light of the biophysical properties described in the examples herein, it appears that the ability of any given DAB™ to resist degradation by trypsin is correlated with the ability of the dAb-Fc fusion to circulate for longer period in the rat serum. Indeed as shown in the examples, such as Example 10, DOM15-10 and DOM15-26-501 are the most degradable DAB™s: incubation of 25 ug DAB™ in the presence of 1 ug of trypsin at 30° C. for ~3h resulted in complete degradation. All other DAB™s in this study (whether they had been selected with trypsin (ie. DOM15-10-11, DOM15-26-593, DOM4-130-202 and DOM1h-131-206) or whether they already had some trypsin resistance as parent molecules (DOM4-130-54 and DOM1h-131-511)) have comparable PK profile in rats when re-formatted into dAb-Fc molecules. Thus, the present PK study suggests that susceptibility to proteolysis has its biggest impact on the in vivo stability of DAB™s when those DAB™s have very low resistance to proteolysis. It also shows that—beyond a certain level—further increments in resistance to degradation by trypsin (e.g. DOM4-130-206 v DOM4-130-54) do not significantly add up to the ability of the dAb-Fc molecule to further slow down elimination in vivo.

In three cases, selection in the presence of trypsin resulted in new molecules with increased thermal stability (defined by the melting temperature): DOM4-130-202, DOM1h-131-206 and DOM15-26-593. The PK study indicates that—in the present dataset—melting temperature is not an adequate parameter to rationalize the observed PK profiles: indeed DOM15-10 has a higher Tm than DOM15-10-11 and yet is more rapidly cleared than DOM15-10-11 from the circulation. Elsewhere, the two DAB™s of the DOM4-130 lineage have markedly different Tm (by 10° C.) and yet show almost identical stability in vivo when formatted into dAb-Fc molecules. It should be noted that melting temperature is not per se excluded as key parameter to predict in vivo stability. It just happens that with the present dataset, large Tm differences (from 54° C. and above) have not a significant impact on the fate of DAB's in vivo. This doesn't exclude the possibility that at melting temperature lower than 54° C., the in vivo stability of DAB™s may correlate with thermal stability, or perhaps even with thermal stability and resistance to proteases altogether.

Example 13

Trypsin Selections on DOM10-53-474
Trypsin Stability of Purified DOM10-53-474:
DOM10-53-474 is a domain antibody which binds to IL-13 with a high potency. To assess the stability of this DAB™ in the presence of trypsin, purified DAB™ was digested with trypsin for increased time points and run on a gel to examine any possible protein degradation. 25 µl of purified DOM10-53-474 at 1 mg/ml was incubated with 1 µl of sequencing grade trypsin at 1 mg/ml at 30° C., resulting in molecular ratio of 25:1 DAB™:trypsin. DAB™ was incubated with trypsin for 1 h, 4 h and 24 h and the protease activity was neutralised by addition of 4 µl of ROCHE COMPLETE PROTEASE INHIBITORS™ followed by incubation on ice. Time 0 sample was made by adding protease inhibitors to DAB™ without adding trypsin. 2 µl of sample was subsequently analysed by electrophoresis using LABCHIP™ according to manufacturers instructions.

Figure 22:
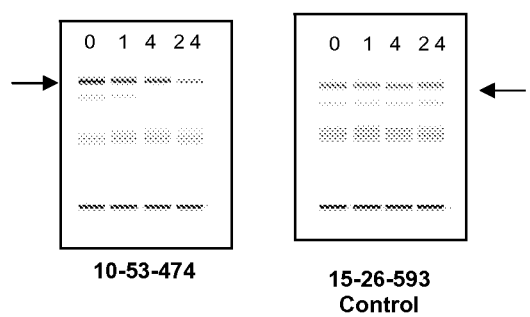
FIG. 22: Shows a gel run on LABCHIP™ of DOM10-53-474 and DOM15-26-593 proteins treated with trypsin at 25:1 DAB™:trypsin ratio at 30° C. for different time points. Arrows show full length protein.

FIG. 22 shows a gel run with DOM10-53-474 incubated with typsin for increased time points. For comparison one of the trypsin stable DAB™s, DOM15-26-593 was also treated with trypsin as explained above and was run alongside. As shown in the figure, DOM15-26-593 looks stable even after 24 h incubation with trypsin. However, DOM10-53-474 is degraded to a certain extent after 24 h, but looking stable at 1 h and 4 h time points. These data suggests that DOM10-53-474 is resistant to degradation by trypsin to a certain extent, but is not as stable as one of the most trypsin stable DAB™s DOM15-26-593.

Trypsin Stability of Phage-Displayed DOM10-53-474:
To assess the trypsin stability of phage displayed DOM10-53-474, the gene encoding DOM10-53-474 was cloned into Sal/Not sites of pDOM33 (FIG. 50) and phage produced according to standard techniques. Phage was purified by PEG precipitation, resuspended in PBS and titered.

Phage displayed DAB™s were incubated with trypsin for different time points to evaluate trypsin resistance. Following incubation with trypsin, stability was measured by titre analysis following infection of exponentially growing E. coli TG1 cells.

100 µl of phage was incubated in 100 µg/ml trypsin for 1 h, 2 h, 4 h and overnight at 37 C, in a shaking incubator. Trypsin activity was blocked with ROCHE COMPLETE PROTEASE INHIBITOR™ (×2) and then phage was diluted in 2% marvel in PBS, incubated with 10 nM biotinylated IL-13 for one hour at room temperature. Streptavidin-coated beads (DYNABEADS™ M-280 (Invitrogen) that were pre-blocked for one hour at room temperature with 2% MARVEL™ in PBS was added, and the mixture was then incubated for 5 minutes at room temperature. All of the incubation steps with DYNABEADS™ were carried out on a rotating wheel. Unbound phage was washed away by washing the beads eight times with 1 ml of 0.1% TWEEN-20™ in PBS. Bound phage was eluted with 0.5 ml of 0.1M Glycine pH 2.2 and neutralized with 100 µl of 1M Tris-HCL pH 8.0. Eluted phage was used to infect exponentially growing TG1 (1 h at 37° C.) and plated on tetracycline plates. Plates were incubated at 37° C. overnight and colony counts were made. Phage output titres following digestion with trypsin is summarised in Table 17. Phage titres decreased when incubated with trypsin for increased time points. After 24 h incubation all phage was digested.

TABLE 17

Output titres of trypsin selections performed on phage displayed DOM-10-53-474 parent:

| Length of trypsin incubation | Trypsin concentration | Titre |
|---|---|---|
| No trypsin control | — | $3 \times 10^7$ |
| 1 h | 100 µg/ml | $1 \times 10^7$ |
| 2 h | 100 µg/ml | $7 \times 10^6$ |
| 4 h | 100 µg/ml | $5 \times 10^6$ |
| overnight | 100 µg/ml | 0 |

Selection of DAB™s More Resistant to Trypsin:

In order to select for DAB™s which are more resistant to degradation by trypsin, random mutations were introduced to gene encoding DOM10-53-474 by PCR using STRATA-GENE MUTAZYME II™ kit, biotinylated primers and 5-50 µg of template for 50 µl reaction. After digestion with Sal1 and Not1, inserts were purified from undigested products with streptavidin coated beads and ligated into pDOM33 at the corresponding sites. *E. Coli* TB1 cells were transformed with purified ligation mix resulting in an error prone library of DOM10-53-474. The size of the library was $1.9 \times 10^9$ and the rate of amino acid mutation was 1.3.

Three rounds of selections were performed with this library to select for DAB™s with improved protease resistance. First round of selection was performed only with antigen without trypsin treatment to clean up the library to remove any clones that no longer bound antigen with high affinity. Selection was carried out at 10 nM IL-13. The outputs from round one were $2 \times 10^9$ compared to input phage of $6 \times 10^{10}$ indicating that majority of library bound antigen with high affinity.

The second and third rounds of selections were performed with 1 nM biotinylated IL-13. Prior to panning on IL-13, phage was incubated with 100 µg/ml of trypsin at 37° C. in a shaker (250 rpm). For second round selection, trypsin incubation was carried out for 1 h either at room temperature or at 37° C. The outputs from round 2 selection is shown in Table 18:

TABLE 18

Output phage titres following second round selection.

| Trypsin treatment | Titre |
|---|---|
| No treatment | $1 \times 10^8$ |
| 1 h room temperature | $5 \times 10^7$ |
| 1 h 37° C. | $2 \times 10^7$ |

Phage outputs from round 2 selection with 1 h trypsin treatment at 37° C. was used as the input for $3^{rd}$ round selection. For $3^{rd}$ round selection, phage was treated with 100 µg/ml trypsin but for longer time points: 2 h at 37° C., 4 h at 37° C., overnight at room temperature or overnight at 37° C. The output titres for 3 round selection are summarised in Table 19:

TABLE 19

Output phage titres following third round selection

| Trypsin treatment | Titre |
|---|---|
| No trypsin | $1.3 \times 10^8$ |
| 2 h at 37° C. | $1.9 \times 10^7$ |
| 4 h at 37° C. | $2 \times 10^6$ |
| Overnight at room temperature | $4 \times 10^7$ |
| Overnight at 37° C. | $2.1 \times 10^6$ |

Several clones from each selection outputs from round 1, 2 and 3 were sequenced to assess the sequence diversity. Following first round of selection without trypsin treatment, 50% of the selection outputs had parent DOM10-53-474 sequence. After $2^{nd}$ round of selection, percentage of parent increased to 75%. After $3^{rd}$ round of selection, percentage of parent increased to 80%.

This data indicate that DOM10-53-474 is already resistant to degradation by trypsin and not many new clones can be selected from these trypsin selections. FIG. 22 showed that when purified protein was digested with trypsin, DOM10-53-474 was not completely digested even after overnight trypsin treatment. However to see whether there are any new clones that are more trypsin resistant than DOM10-53-474 in selection outputs, selection 3 output where phage was treated overnight with trypsin at 37° C. was sub-cloned into pDOM5. Hundred clones were then sequenced to look for any trypsin resistant clones. Out of hundred clones analysed, only 26 clones had new sequences, however none of these clones had mutations at trypsin cleavage sites (Lysine or Arginine) suggesting that these clones are not more resistant to trypsin than DOM10-53-474.

Example 14

Storage and Biophysical Improvements Introduced into the Lead DOM0101 (Anti-TNFR1) DAB™s by Phage Selections in the Presence of Trypsin:

To improve the protease resistance of the lead molecule DOM1h-131-511, phage selections in the presence of trypsin were carried out as described earlier. The method produced a range of clones with improved trypsin stability compared to the parental DOM1h-131-511 molecule. Two clones, DOM1h-131-202 and DOM1h-131-206 were selected for further characterisation as they showed the most significant improvement to the action of trypsin. Further work as outlined below shows that with the improved resistance to the action of trypsin there are other beneficial effects, primarily on the stability of the molecules to shear and thermal stress. These two parameters are central to increasing the storage and shelf life stability of biopharmaceutical products.

Production of Lead DOM0101 DAB's in *Pichia pastoris*:

The genes encoding the primary amino acid sequence of the three lead molecules was used to produce secreted protein in *Pichia pastoris*. The three synthetic genes (DOM1h-131-511, DOM1h-131-202 and DOM1h-131-206) were cloned into the expression vector pPIC-Zα and then transformed into two *Pichia* strain, X33 and KM71H. The transformed cells were plated out onto increasing concentrations of ZEOCIN™ (100, 300, 600 and 900 µg/ml) to select for clones with multiple integrants. Several clones were then screened in 2 L flasks to identify high expressing cell lines. The best expressing clones were then used to produce material at 5 L scale in fermenters.

Protein Purification and Material Characterization:

In order to produce high quality material for characterisation and further stability studies, a downstream purification process was devised using a mixed modal charge induction resin (CAPTO™ MMC) as the primary capture step followed by anion exchange (Q Sepharose). Without significant optimisation, this allowed the recovery of ~70% of the expressed DAB™ at a purity of ~95%. The material was characterised for identity using electrospray mass spectrometry, amino terminal sequencing and isoelectric focusing and for purity using SDS-PAGE and SEC (size exclusion chromatography).

Protein Identity:

The amino terminal sequence analysis of the first five residues of each protein, was as expected (EVQLL . . . ) (SEQ ID NO: 259). Mass spectrometry was performed on samples of the proteins which had been buffer exchanged into 50:50 $H_2O$:acetonitrile containing 0.1% glacial acetic acid using C4 ZIP-TIPS™ (Millipore). The measured mass for each of the three proteins was within 0.5 Da of the theoretical mass based on the primary amino acid sequence (calculated using average masses) when allowing for a mass difference of −2 from the formation of the internal disulphide bond. IEF was used to identify the proteins based on their pI which was different for each protein.

Protein Purity:

The three proteins were loaded onto non-reducing SDS-PAGE gels in 1 μg and 10 μg amounts in duplicate. A single band was observed in all instance.

Figure 23:
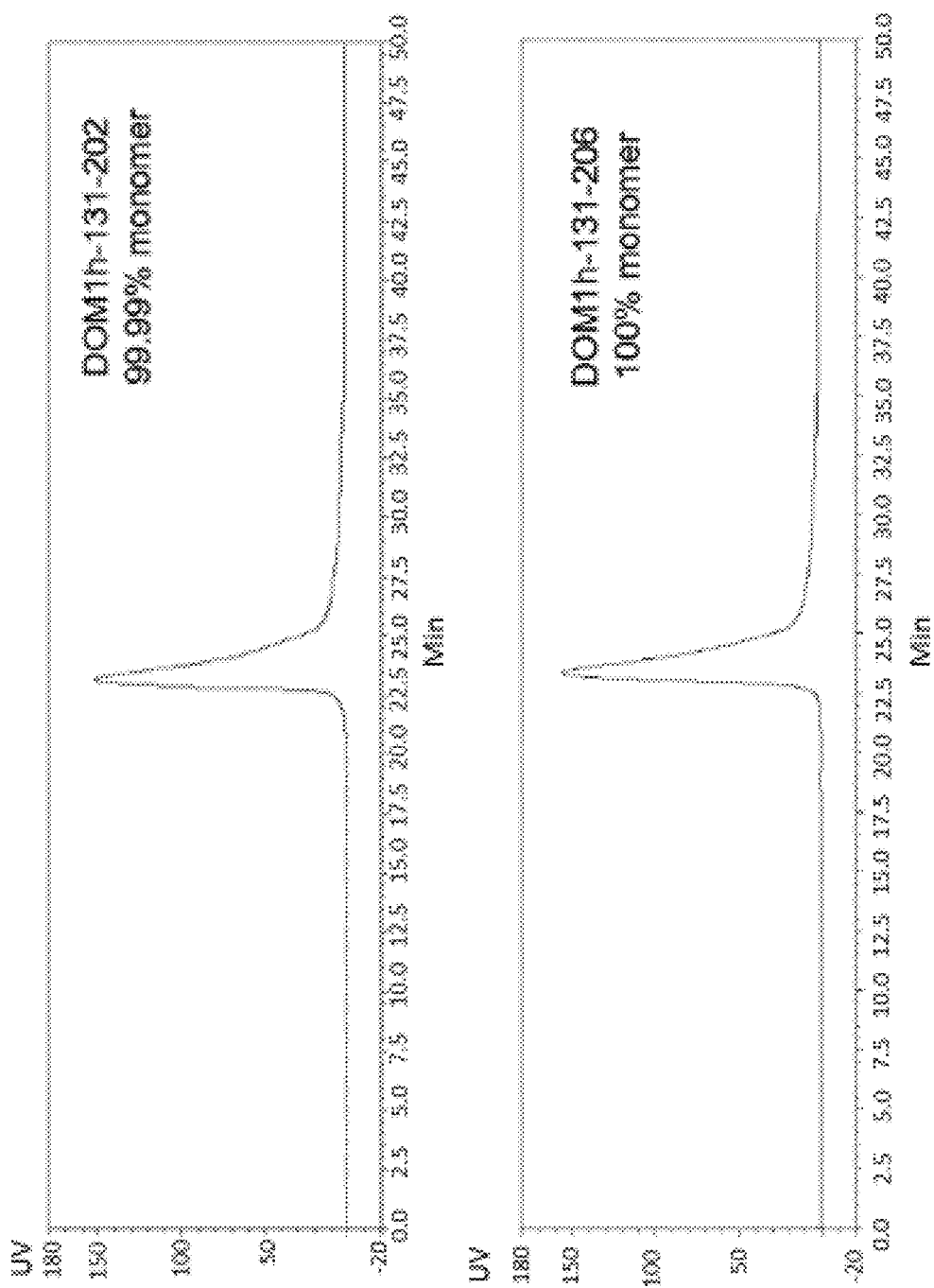
FIG. 23: Is a size exclusion chromatography trace showing the high level of purity obtained for each sample after purification by MMC chromatography followed by anion exchange. The UV was monitored at 225 nm and the column was run in 1×PBS with 10% ethanol (v/v). The percentage monomer was calculated by integration of the peak area with baseline correction.
Figure 23:
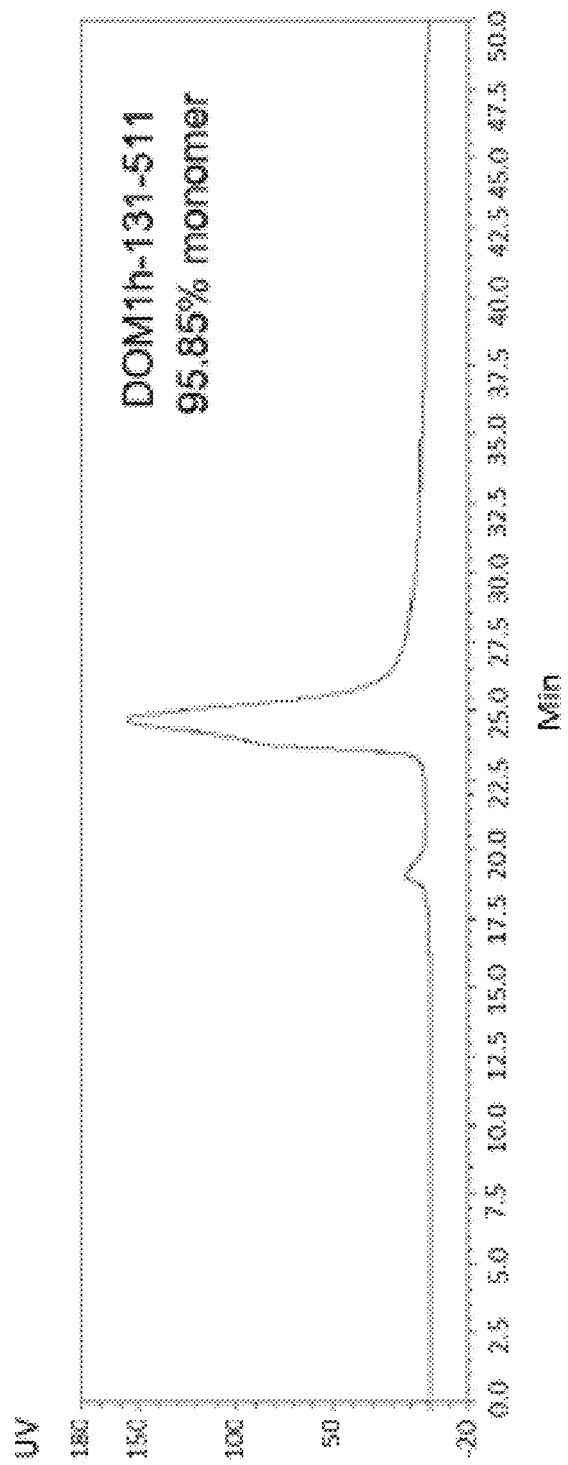

Size exclusion chromatography was also performed to demonstrate levels of purity. For size exclusion chromatography (SEC) 100 μg of each protein were loaded onto a TOSOH G2000 SWXL™ column flowing at 0.5 ml/min. Mobile phase was PBS/10% ethanol. The percentage of monomer was measured based on the area under the curve (see FIG. 23).

Comparison of Stability of DOM1h-131-511, -202 and -206

Figure 24:
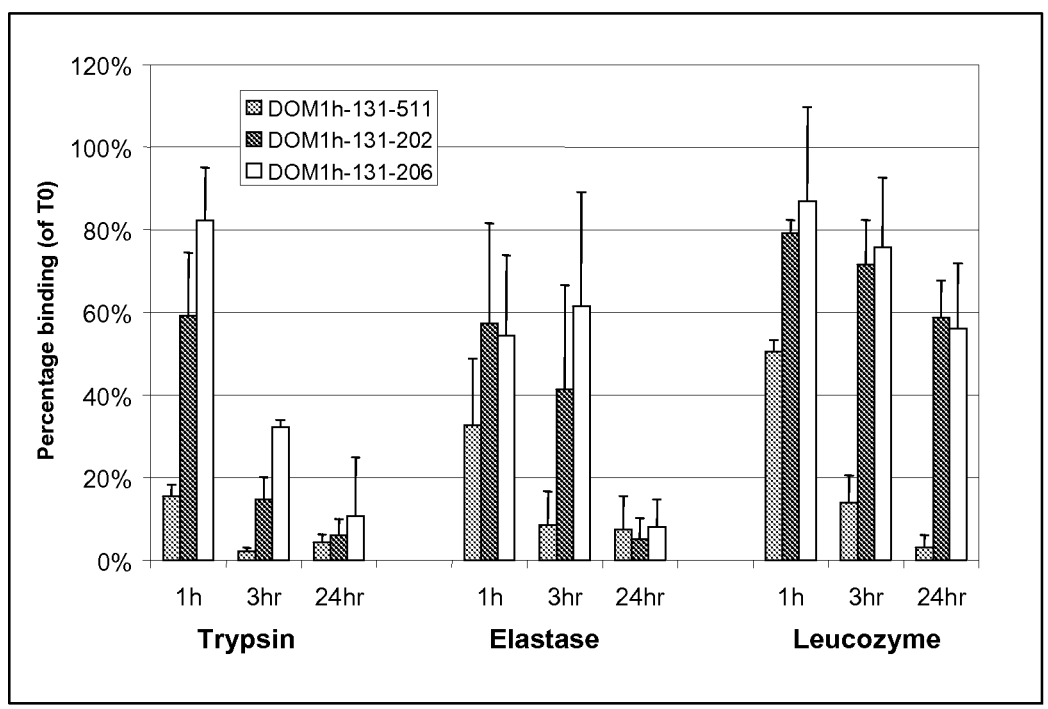
FIG. 24: Shows protease stability data for DOM1h-131-511, DOM1h-131-202 and DOM1h-131-206.

Assessment of Protease Stability:

The protease stability of DOM1h-131-511, DOM1h-131-202 and DOM1h-131-206 was assessed by BIACORE™ analysis of the residual binding activity after pre-incubation for defined timepoints in excess of proteases. Approximately 1400 RU of biotinylated TNFR1 was coated to a streptavidin (SA) chip. 250 nM of DOM1h-131-511, DOM1h-131-202 and DOM1h-131-206 was incubated with PBS only or with 100 ug/ml of trypsin, elastase or leucozyme for 1, 3, and 24 hour at 30° C. The reaction was stopped by the addition of a cocktail of protease inhibitors. The DAB™/protease mixtures were then passed over the TNFR1 coated chip using reference cell subtraction. The chip surface was regenerated with 10 ul 0.1 μM glycine pH 2.2 between each injection cycle. The fraction of DOM1h-131-511, DOM1h-131-202 and DOM1h-131-206 bound to human TNFR1 (at 10 secs) pre-incubated with proteases was determined relative to DAB™ binding without proteases. BIACORE™ runs were carried out at 25° C. The data below was produced from three independent experiments. The bar graph indicates mean values and the error bars indicate standard deviation of the results (FIG. 24).

It was found that DOM1 h-131-202 and DOM1 h-131-206 were shown to have greater resistance to proteolytic degradation by trypsin, elastase or leucozyme in comparison to DOM1h-131-511. The difference between DOM1h-131-202 and DOM1h-131-206 in comparison to DOM1h-131-511 is most pronounced after 1 hr with trypsin and after 3 hrs with elastase or leucozyme. There is a trend that DOM1h-131-206 is slightly more stable compared to DOM1h-131-202 in most of the conditions tested.

Thermal Stability of the DAB™s as Determined Using DSC:

In order to determine at which pH the lead molecules had the greatest stability, differential scanning calorimeter (DSC) was used to measure the melting temperatures ($T_m$) of each DAB™ in Britton-Robinson buffer. As Britton-Robinson is made up of three component buffer systems (40 mM of each of acetic, phosphoric and boric acid), it is possible to produce a pH range from 3-10 in the same solution. The theoretical pI was determined from the proteins primary amino acid sequence. From the DSC, the pH at which the DAB™s had their greatest intrinsic thermal stability was found to be pH 7 for DOM1h-131-202, pH 7-7.5 for DOM1h-131-206 and pH 7.5 for DOM1h-131-511. For all subsequent stress and stability work the following pHs were used for each DAB™; for DOM1h-131-202 and GSK1995057A DOM1h-131-206 pH 7.0 and for DOM1h-131-511 pH 7.5 in Britton-Robinson buffer. The results are summarised in Table 20.

TABLE 20

Summary of the pH and $T_m$s of DOM1h-131-202, DOM1h-131-206 and DOM1h-131-511 as determined by DSC in Britton-Robinson buffer at 1 mg/ml. The temperature was ramped at 180° C./hour.

| DAB ™ | pH that gives greatest intrinsic thermal stability | Tm (° C.) of the DAB ™ at the given pH |
|---|---|---|
| DOM1h-131-202 | 7.0 | 68.6 |
| DOM1h-131-206 | 7.0-7.5 | 65.8 |
| DOM1h-131-511 | 7.5 | 58.0 |

Two Week Thermal Stability Testing

The ability of a protein to endure prolonged periods of time at elevated temperatures is usually a good indication of its stability. Under these conditions, protein may undergo several physical processes such as aggregation or chemical modification. The DAB™s (at 1 mg/ml) were incubated at 37 and 50° C. for 14 days in Britton-Robinson buffer. SEC was used to determine how much monomer was left in solution over the 14 day period (FIG. 25).

Figure 25:
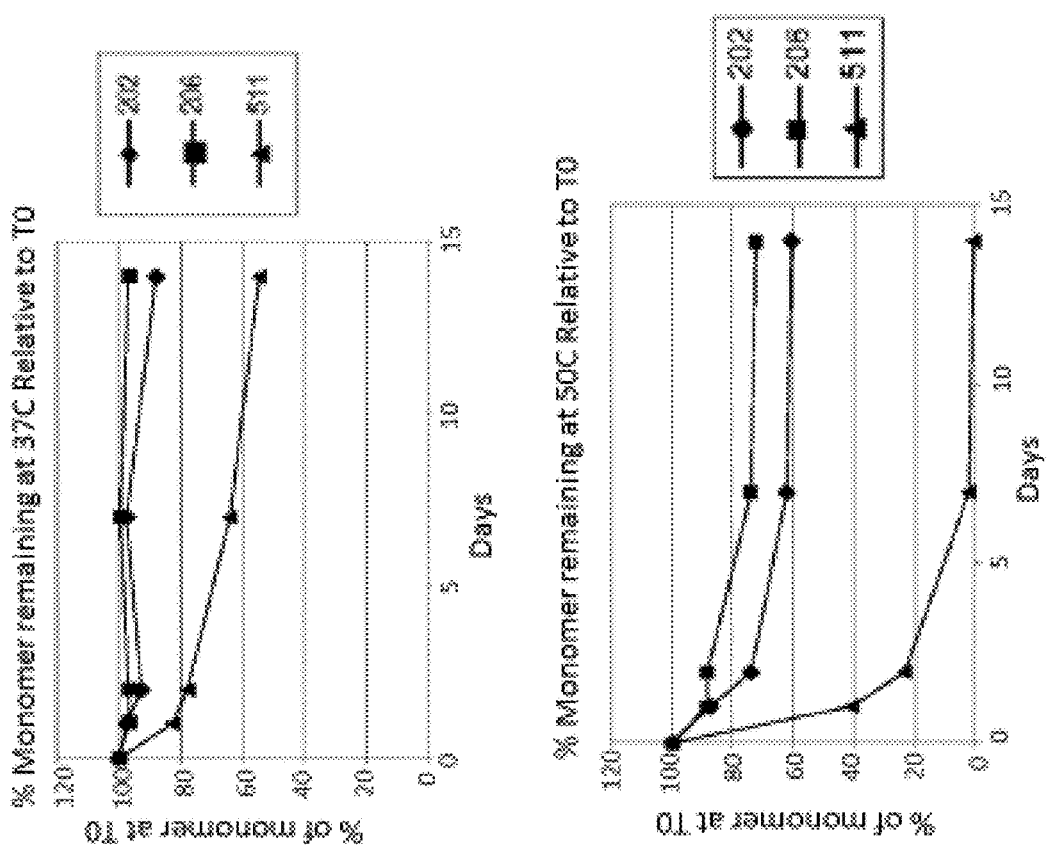
FIG. 25: Is an SEC which illustrates 14 day stability data of DOM1h-131-202, DOM1h-131-206 and DOM1h-131-511 in Britton-Robinson buffer at 37 and 50° C. The protein concentration for all the DAB™s was 1 mg/ml. SEC was used to determine if any changes had occurred in the protein during thermal stress and the amount of monomer left in solution relative to the time=0 (T0) sample.
Figure 26A:
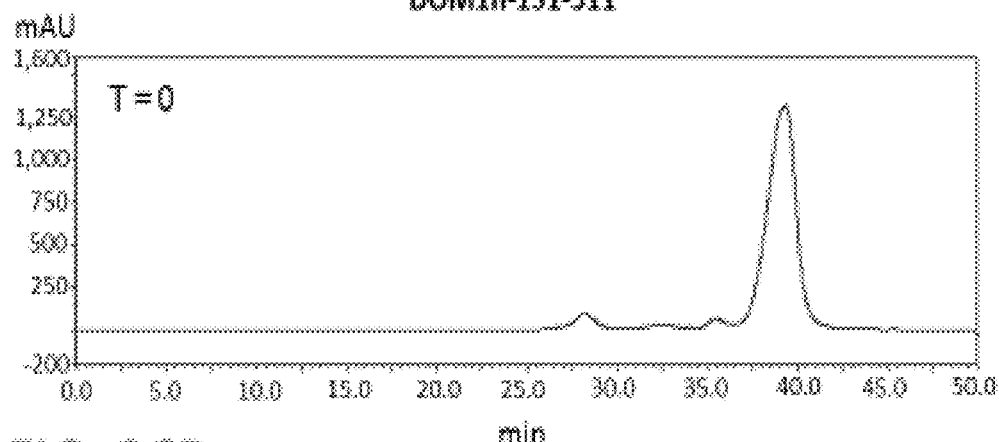
FIGS. 26A-26I: Show SEC traces showing the effect of thermal stress (37 and 50° C.) on DOM1h-131-511 (FIGS. 26A-26C), -202 (FIGS. 26D-26F) and -206 (FIGS. 26G-
Figure 26B:
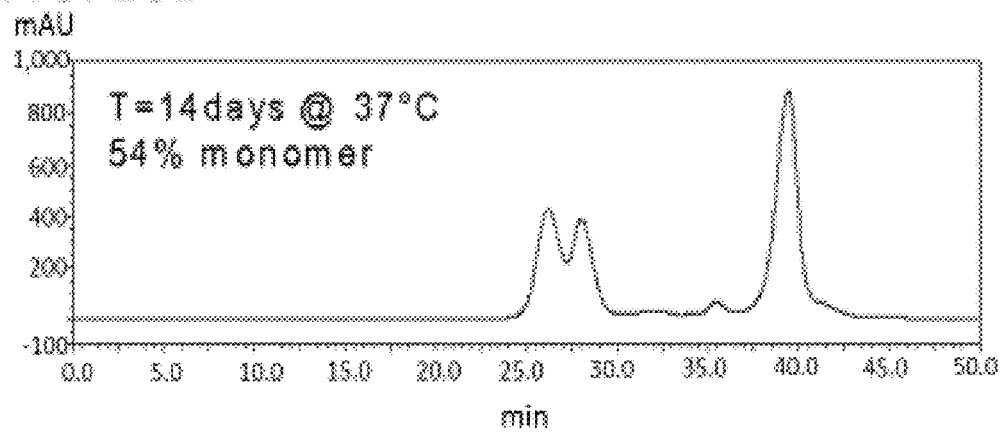
Figure 26C:
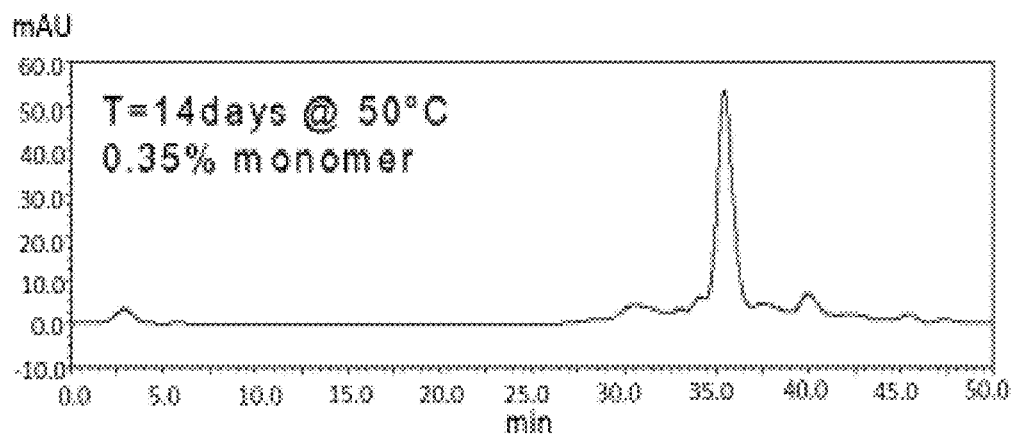
Figure 26D:
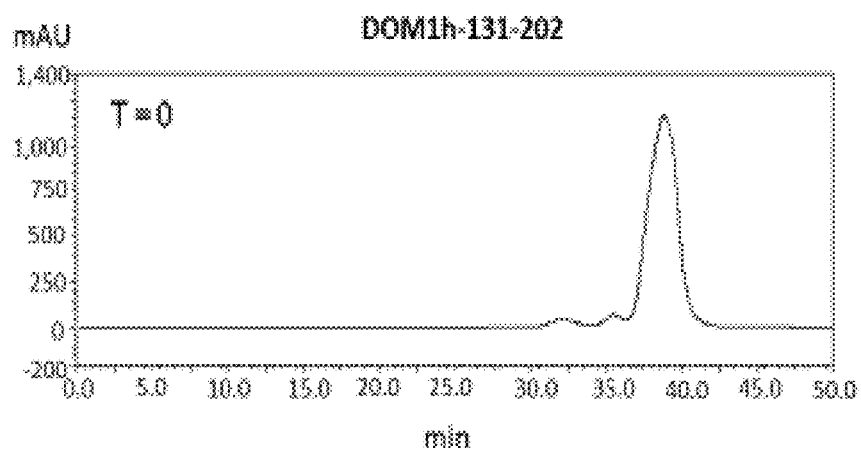
Figure 26E:
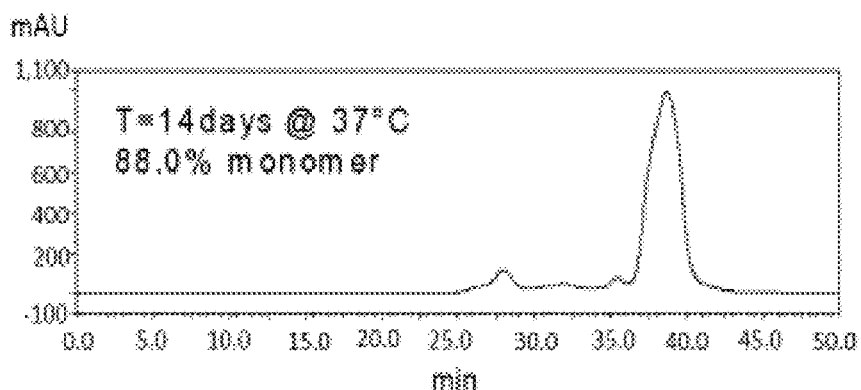
Figure 26F:
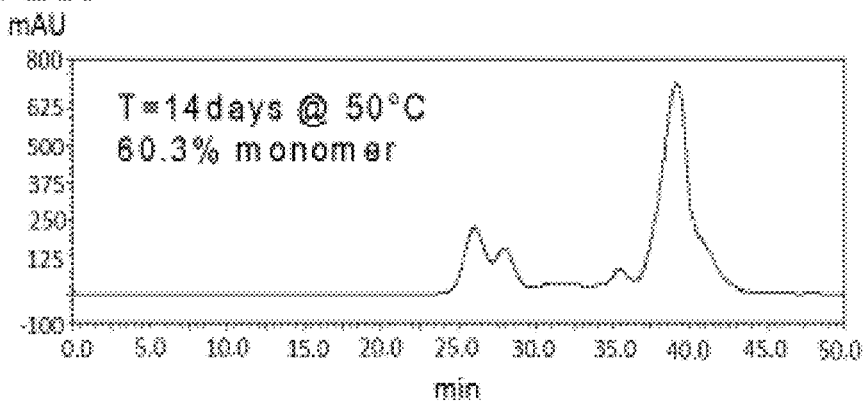
Figure 26G:
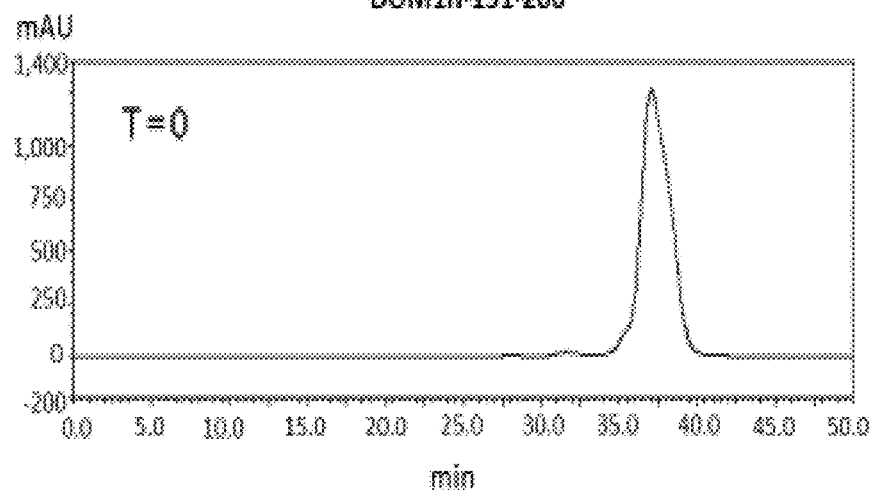
Figure 26H:
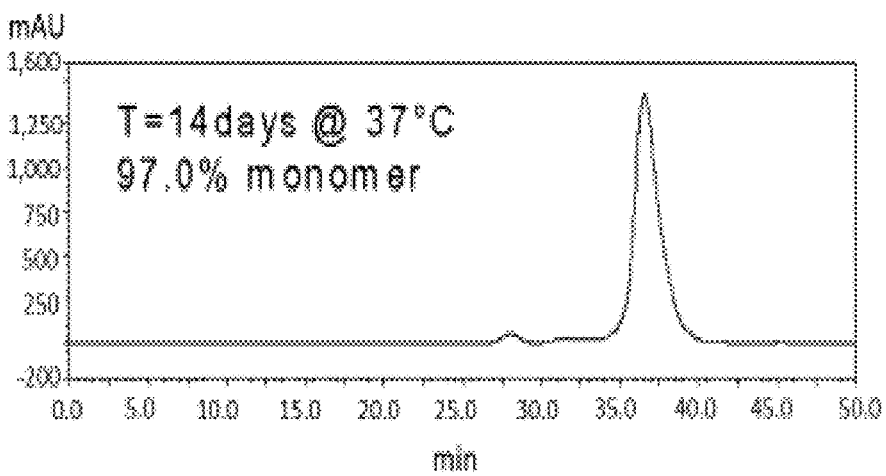
Figure 26I:
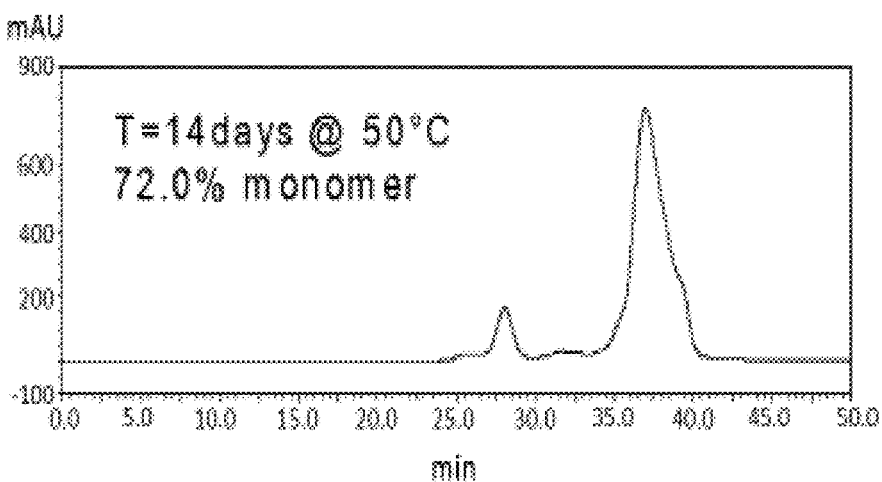

From FIG. 25 it can be seen that both DOM1h-131-202 and DOM1h-131-206 are significantly more stable than DOM1h-131-511 to thermal stress. Exposing proteins to elevated temperatures, such as 37 and 50° C., are routinely used to give an indication on a drug's long term shelf-life. These higher temperatures are used to accelerate the normal process associated with long term storage at room temperature such as deamidation, oxidation or aggregation. The level of aggregation formation in solution can also be monitored using SEC (FIG. 26A to I). After 14 days at 37° C., the loss of DOM1h-131-511 from solution can be attributed to both precipitation and the formation of higher ordered aggregates as determined by SEC (FIG. 26B). A significantly lower loss in protein is also seen with both DOM1h-131-202 and DOM1h-131-206 at 37° C. after 14 days with very little or no substantial increase in aggregate formation, especially in the case of DOM1h-131-206 (FIG. 26H). At 50° C., the difference between the molecules is even more pronounced, with DOM1h-131-206 showing better stability at the higher temperature than DOM1h-131-202 after 14 days, showing significantly reduced formation of higher molecular weight aggregates (FIG. 26). Relative to the t=0, DOM1h-131-206 shows only a small increased in aggregate formation after 14 days (FIG. 26I), whereas DOM1h-131-511 has all but precipitated out of solution (FIG. 26C).

This shows that the changes introduced into the DAB™ by the trypsin selections, e.g. the improved thermal stability, has significantly improved the protein storage stability at 37 and 50° C. Both DOM1h-131-202 and more significantly DOM1h-131-206, clearly have improved solution stability and lower tendency to form aggregates at elevated temperatures which can directly be translated to improved long term storage stability at more relevant temperatures such +4° C. and room temperature.

Samples from 24 hr, 48 hr, 7 days and 14 days time points from the thermal stress experiment were then analysed by IEF to see if the proteins had undergone any biophysical changes which would affect the overall charge of the protein (FIG. 27).

Again both DOM1h-131-202 and DOM1h-131-206 show no significant changes at 37° C. compared to DOM1h-131-511. With DOM1h-131-511 a faint second band appears at 37° C. after 24 hrs. It is believed this extra banding is due to dimerisation of the protein, thus masking charge and producing two populations of molecules. At 50° C. the difference between the molecules is more pronounced, DOM1h-131-206 clearly shows no significant changes at the elevated temperature whereas DOM1h-131-202 is showing some sign of modification after 24 hr. The majority of DOM1h-131-511 is lost by precipitation after 48 hr in Britton-Robinson.

The T=0, 7 and 14 day time points at 50° C. were analysed by the TNFR-1 RBA to determine the functionality of the protein after exposure to high temperatures (FIG. 28). The assay is currently not as sensitive as SEC or IEF at detecting subtle changes to the molecule due to stress, but it can be used show that the DAB™ can still bind to the antigen.

The shift in the curve to the left for DOM1h-131-511 reflects the fact that the majority of the DAB™ has been lost due to precipitation. The material that is left in solution is still able to bind antigen. As shown in FIG. 25, the majority of both DOM1h-131-202 and DOM1h-131-206 are able to be maintained in solution even after 14 days. The RBA shows that all the soluble protein is still functional and able to bind to TNFR1.

Storage Stability Testing at High Protein Concentrations:

Experiments were carried out to investigate the storage stability at +4° C. at very high protein concentrations to see how each molecule performed under these conditions. All the lead DAB™s were concentrated in centrifugal VIVASPIN™ concentrators (5K cut-off) in Britton-Robinson buffer at their most stable pH, to ~100 mg/ml. The samples at ~100 mg/ml were then left at +4° C. for 7 days and then analysed by SEC to see if any other physical changes had occurred to the samples during storage at high concentrations (FIG. 29). The samples were diluted to ~1 mg/ml before being run on the SEC column in 1×PBS 10% ethanol (v/v).

From the SEC traces it can be seen that neither DOM1h-131-202 nor DOM1h-131-206 show any significant increase in the formation of aggregates after 7 days, where as there is ~2% reduction in the monomer concentration for DOM1h-131-511.

Nebuliser Delivery of the Lead DAB™s:

For early stage toxicology and clinical work, the DAB™s will be formulated as a liquid and delivered via a nebulising device. Depending on the device (eg, ultrasonic, jet or vibrating mesh), the DAB™ will experience a degree of shear and thermal stress as it was nebulised to form a aerosol of defined particle size. As both DOM1h-131-202 and -206 have higher $T_m$'s and showed considerably improved stability to thermal stress compared to DOM1h-131-511, all the DAB™s were tested in two nebuliser devices to see how they responded to shear/thermal stress induced during nebulisation. Both the protein from the nebulised aerosol and the remaining DAB™ in the device (i.e. in the cup) were then analysed by SEC to determine the amount of aggregation generated during the process.

All the molecules were tested in Britton-Robinson buffer at their most stable pH. The DAB™s were tested in both the EFLOW RAPID™ (vibrating mesh) and PARI LC+™ (jet nebuliser) with run time of 3.5 minutes at a protein concentration of 5 mg/ml and the particle size distribution determined using a Malvern Spraytec. The results are shown in FIG. 30. For good delivery and distribution into the deep lung, the ideal particle size is <5 μm. All the DAB™s give comparable levels of particle sizes that were less than 5 μm in Britton-Robinson buffer. The concentration of the DAB™ in the cup of the device was determined by $A_{280}$ measurements before and after nebulisation (data not shown). It was found that the protein concentration did not change significantly indicating that neither the protein nor vehicle are preferentially nebulised during delivery.

Samples of the DAB™s nebulised in Britton-Robinson buffer were run on SEC to determine if during delivery the protein had undergone any physical changes. FIG. 31 shows the relative percentage change in either the cup or the aerosol as determined by SEC. It can be seen that both DOM1h-131-202 and DOM1h-131-206 undergo relative small changes in the concentration of monomer relative to DOM1h-131-511. This demonstrates that both DOM1h-131-202 and DOM1h-131-206 with their improved $T_m$'s have less propensity to aggregate during nebulisation.

FIG. 32 shows the actual SEC traces for DOM1h-131-206 and DOM1h-131-511 in Britton-Robinson buffer post nebulisation and demonstrates that the relative loss in monomer (FIG. 31) is due to dimer formation. This again provides further supporting evidence to the theory that the greater thermal stability shown by DOM1h-131-202 and DOM1h-131-206 can prevent significant aggregation even in an unoptimised formulation buffer.

For toxicology and safety assessment work, it is necessary to delivery the DAB™ at significantly higher levels into the animal than the therapeutic doses given to patients. This can only be achieved by using significantly higher protein concentrations and/or delivering the DAB™ over a prolonged period of time. As it had already been shown that DOM1h-131-511 forms aggregates on nebulisation at 5 mg/ml over 3.5 mins, DOM1h-131-206 was tested at 40 mg/ml in PBS and nebulised using the PARI LC+™ for up to 1 hour. Samples from the cup and aerosol were taken at the time points to throughout the run to see if the prolong nebulisation caused the DAB™s to aggregate due to shear or thermal stress as determined by SEC and the protein concentration (A280 nm measurements). Table 21 shows the protein concentration of the DAB™ both in the cup and aerosol as determined by A280.

TABLE 21

Measured protein concentration of DOM1h-131-206 as determined by A280 absorbance readings for both the cup and aerosol during nebulisation of the DAB ™ at ~40 mg/ml using the LC+ ™. Allowing for dilution errors and instrumental error the sample concentration does not change after nebulising the DAB ™ over 1 hr.

| Time (Mins) | Cup Sample (mg/ml) | Aerosol Sample (mg/ml) |
|---|---|---|
| 1 | 43.8 | 43.4 |
| 29 | 44.5 | 43.5 |
| 59 | 44.6 | 44.1 |

From Table 21 it can be seen that the concentration of the protein did not significantly change during the run, demonstrating that there was no significant loss of the protein due to aggregation. FIG. 33 shows that over the period of 1 hour of nebulisation, DOM1h-131-206 does not form any higher ordered aggregates such as dimers as determined by SEC. This clearly demonstrates that the improved biophysical properties, as introduced into the molecule by trypsin selections, significantly increases the DAB™s resistance to shear and thermal stress and that this can be directly correlated to improved storage shelf-life and the ability to nebulise the protein so that higher ordered aggregates do not form.

Solution State of the Lead DAB™s:

Since the major route of degradation for all the three lead DAB™s appears to be self-association leading initially to dimerisation followed by further aggregation and ultimately precipitation, the three lead molecules were investigated by Analytical Ultra-Centrifugation (AUC) to determine the degree of self-association. The proteins were investigated by two methods, sedimentation equilibrium and sedimentation velocity.

For the sedimentation equilibrium method the three samples were run at three different concentrations ranging from 0.5 mg/ml to 5 mg/ml with centrifugation effects using three different rotor speeds. By this method it was determined that DOM1h-131-511 is a stable dimer (26.1-34.4 kDa), DOM1h-131-202 is monomer/dimer equilibrium (22.7-27.8 kDa) with a relatively stable dimeric state at the concentrations measured with $K_d$=1.3 µM and DOM1h-131-206 is predominantly monomeric (15.4-17.9 kDa) with a $K_d$ for the monomer to dimer association of 360 µM.

Figure 34:
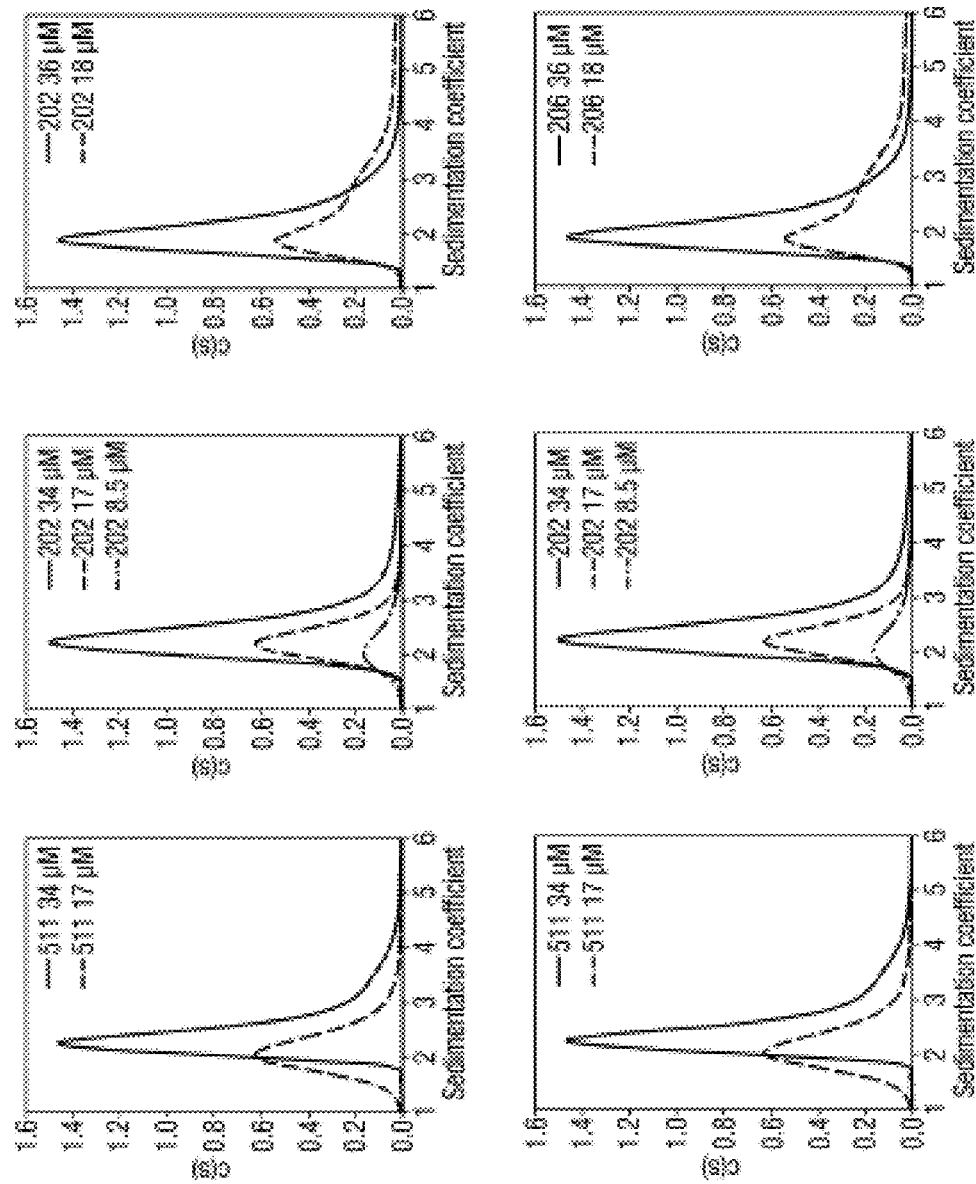
Figure 35:
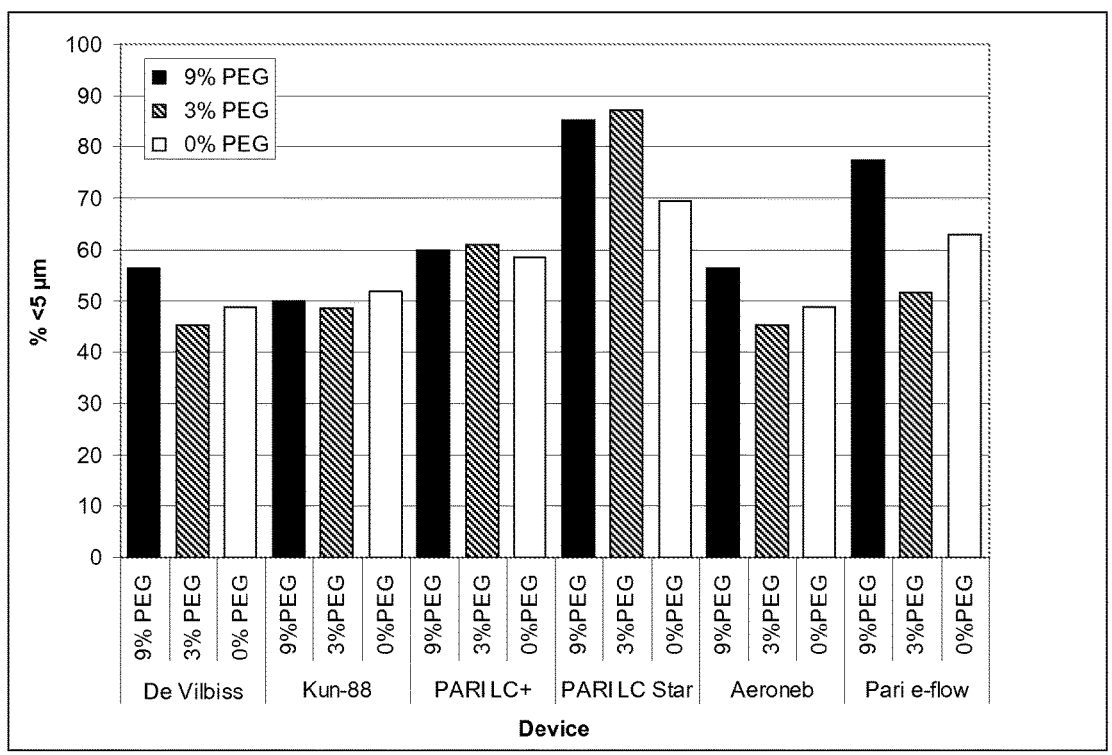
Figure 36:
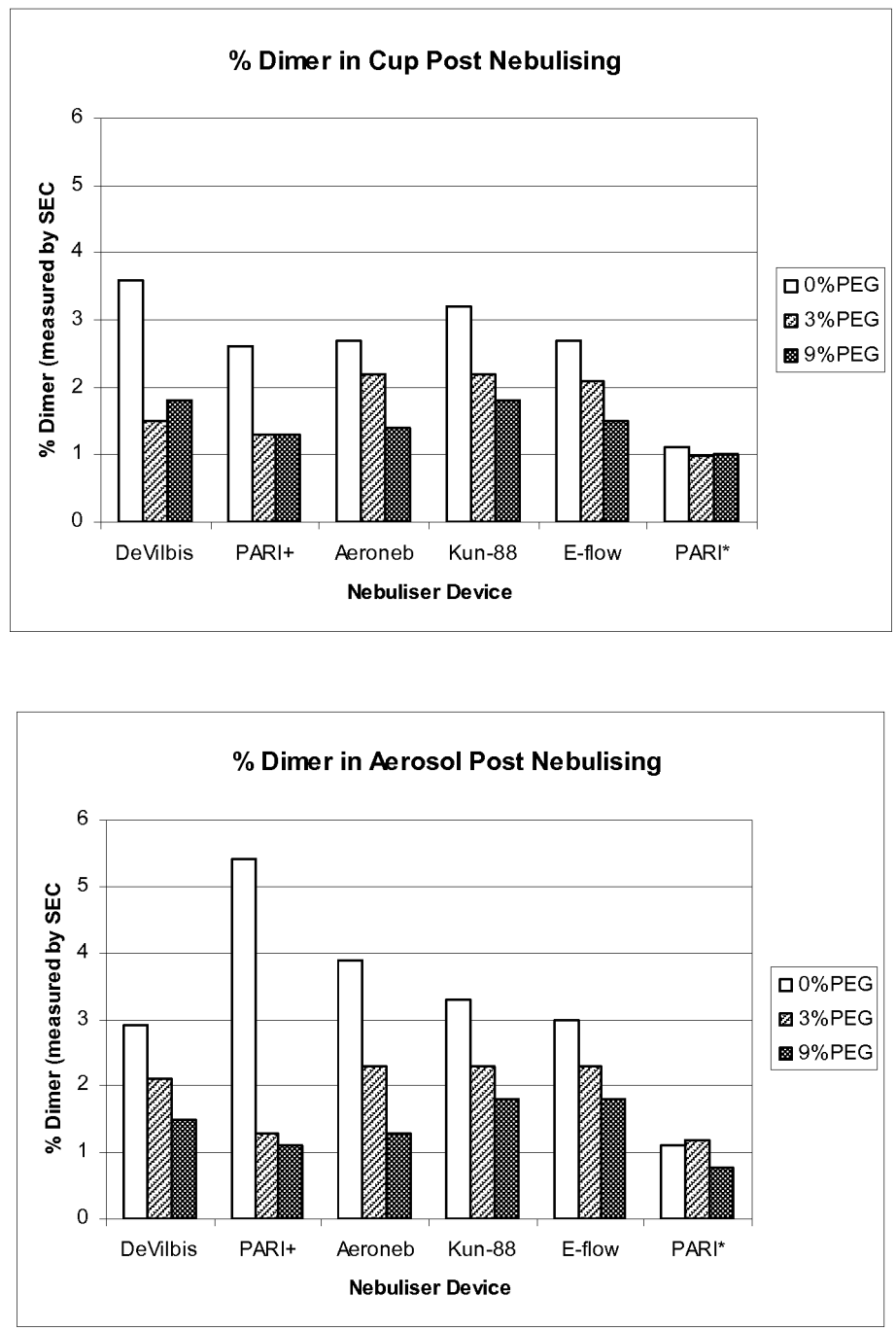
Figure 37:
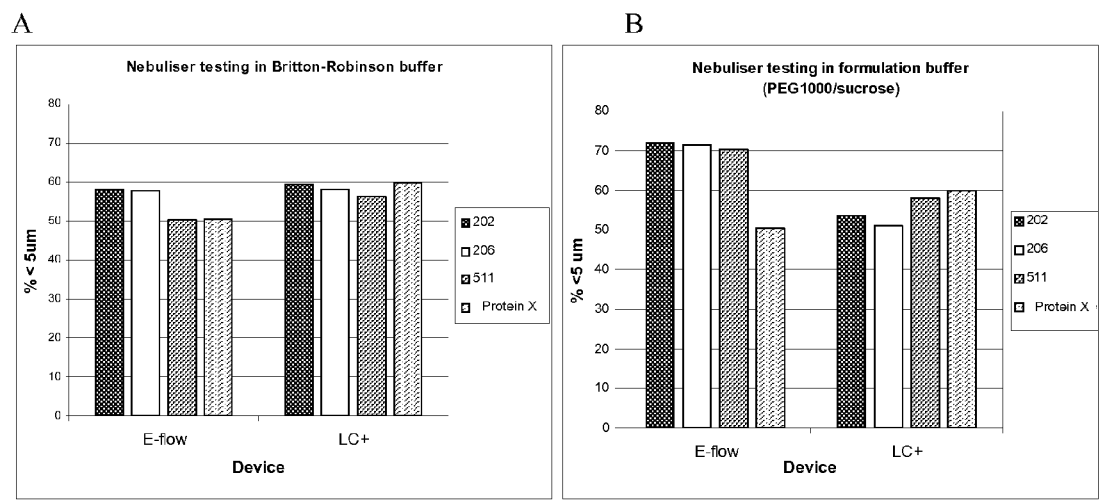

By the sedimentation velocity method all samples showed some degree of dissociation upon dilution. From the results obtained, shown in FIG. 34, the sedimentation coefficient observed for DOM1h-131-511 is indicative of higher order aggregates and the peak shift upon dilution is an indication of dissociation of these aggregates. The protein aggregation and dissociation cancel each other out which can give the impression of being a stable dimer as observed by sedimentation equilibrium. The sedimentation coefficients observed for DOM1h-131-202 are indicative of a rapid dynamic equilibrium and therefore the monomer and dimer peaks could not be separated from each other, giving the single peak with a higher sedimentation coefficient than is appropriate for the mass of the sample. This result agrees with the result obtained by the sedimentation equilibrium method and the dissociation constant was measured as being 1 µM. DOM1h-131-206 was determined to be more monomeric than the other two samples, having a sedimentation coefficient of 1.9 s as compared to 2.5 s for the other two samples. This data agrees well with the sedimentation equilibrium data. At the concentrations measured, ~10-fold below the $K_d$ of 360 M, the sample is predominantly monomeric.

Example 15

Figure 40:
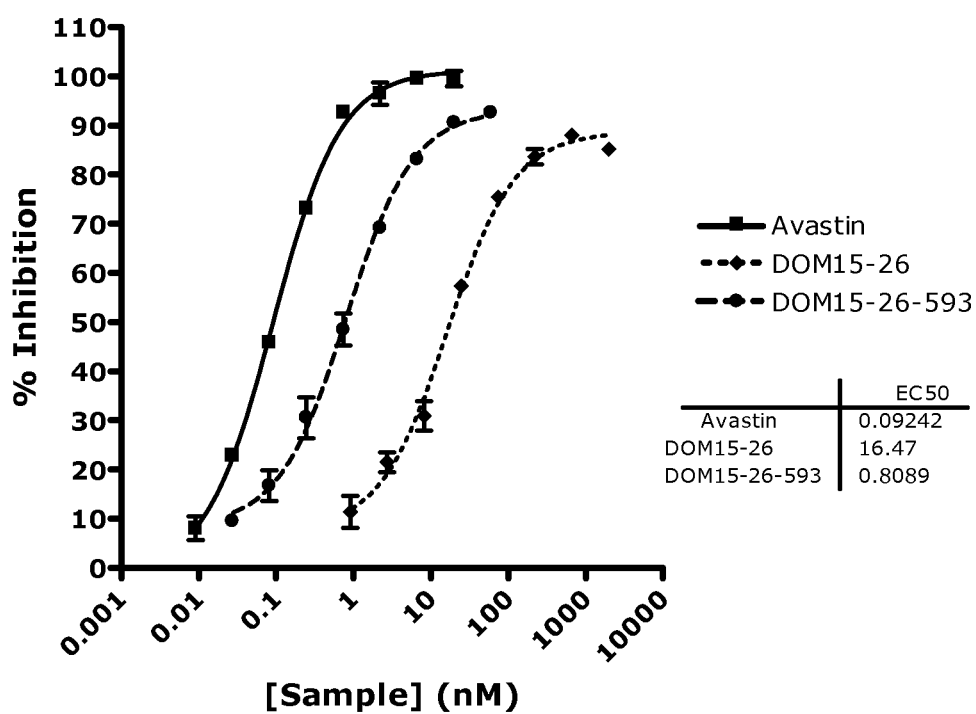

Potency enhancement of the DOM15-26-593 DAB™:

An example of the enhancement of potency in VEGFR2 Receptor Binding Assay of the DOM15-26-593 DAB™ over DOM15-26 parent is shown in FIG. 40. In this assay, the ability of a potential inhibitor to prevent binding of VEGF to VEGFR2 is measured in a plate-based assay. In this assay a VEGFR2-Fc chimera is coated on a 96-well ELISA plate, and to this is added a predetermined amount of VEGF that has been pre-incubated with a dilution series of the test DAB™. Following the washing-off of unbound protein, the amount of VEGF bound to the receptor is detected with an anti-VEGF antibody, the level of which is determined colorimetrically. A dose-response effect is plotted as percentage inhibition of VEGF binding as a function of test substance concentration. An effective inhibitor is therefore one that demonstrates substantial blocking of ligand binding at low concentrations.

FC Fusions potency and half life:

The therapeutic potential of VEGF blockade in the treatment of tumours has been realised for over 30 years. The chronic nature of cancer dictates that biopharmaceuticals require a long serum half life to mediate their effects, and this is not consistent with the rapid clearance of free DAB™s from the circulation by renal filtration. To assess the utility of the VEGF DAB™s as anti-angiogenics for the treatment of cancer, the lead domain antibodies were formatted as fusions with wild type human IgG1 Fc via a hybrid linker so as to form a bivalent molecule with a serum half life extended by the use of FcRn-mediated antibody salvage pathways.

In this Fc fusion format, the potency of the lead trypsin selected DAB™ DOM15-26-593 was compared with the initial parent DAB™ (DOM15-26) & the trypsin labile DAB™ (DOM15-26-501) using the assay described previously. The results are shown in the Table 22 below:

TABLE 22

Potency (RBA) & half life characteristics of DOM15-26 leads in the Fc fusion format

| DAB ™ | Fc | Potency (nM) | T½b (hrs) |
|---|---|---|---|
| DOM15-26 | hIgG1 | 0.506 | ND |
| DOM15-26-501 | hIgG1 | 0.323 | 12.9 |
| DOM15-26-593 | hIgG1 | 0.033 | 84.6 |

Figure 41:
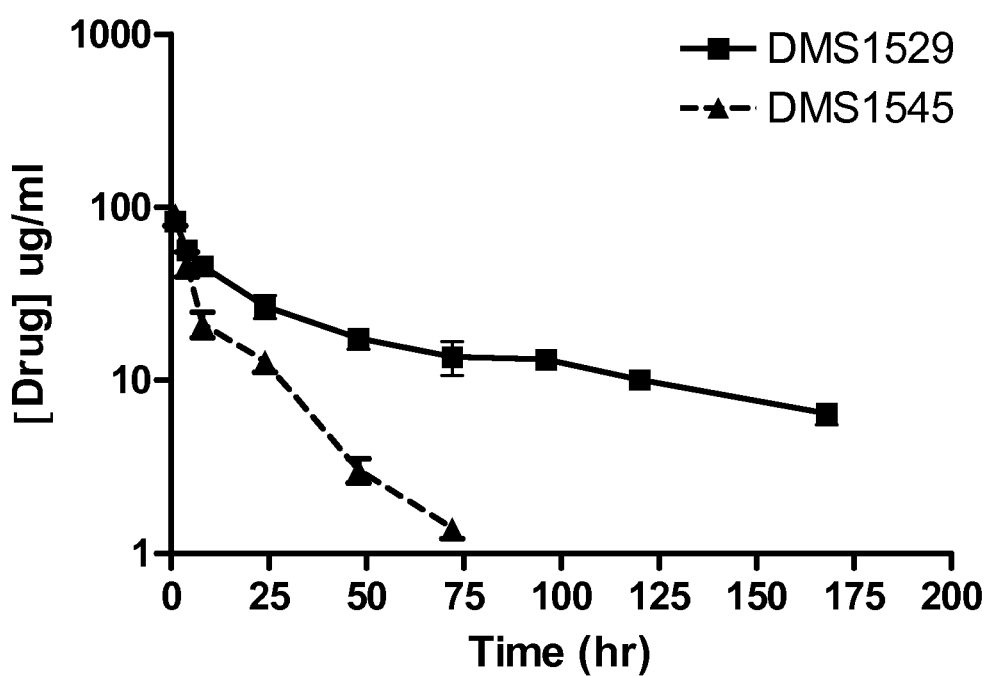

It can be seen from these results that in the dimeric Fc fusion format, affinity & potency are enhanced in relation to the free DAB™s due to the effect of avidity. It is clear that the potency enhancement obtained in DOM15-26-593 by virtue of trypsin selection is maintained and is even more pronounced in this Fc format. Furthermore, the improvements in thermal and protease stability translate into profound changes in the in vivo pharmacokinetic behaviour of the molecules. The improvement in the elimination half life (see FIG. 41) of DOM15-26-593 compared with DOM15-26-501 is likely to be a direct consequence of the increased stability of the DAB™, rendering it more resistant to the degradative processes that occur within the endosomal compartment. It is also to be expected, therefore, that DAB™s with enhanced protease stability are able to persist for longer in other biological compartments such as the serum, mucosal surfaces and various tissue compartments where proteolysis is an active process involved in the turnover of biological molecules.

Pharmacokinetic Clearance Profiles:

Pharmacokinetic clearance profiles of DOM15-26-593 and DOM15-26-501 were measured after i.v. administration DOM15-26-593 and DOM15-26-501 to 3 rats at concentrations of 5 mg/kg. Levels of DOM15-26-593 and DOM15-26-501 in the serum were then measured using a direct VEGF binding standard ELISA assay and an anti-human Fc antibody, therefore only intact drug in the serum samples were detected. The full pharmacokinetic profile is shown in the Table 23 below:

TABLE 23

Summary Pharmacokinetic parameters of the DOM15-26 & DOM15-26-593 Fc fusions in rat

| DAB ™ | Half Life (hr) | Cmax (µg/ml) | AUC (0-inf) (hr * µg/ml) | Clearance (ml/hr/kg) |
|---|---|---|---|---|
| DOM15-26-501 | 12.9 | 91.4 | 445.1 | 11.8 |
| DOM15-26-593 | 84.6 | 101.8 | 3810 | 1.3 |

It can be seen from these results that DOM15-26-593 has a significantly improved pharmacokinetic profile with e.g. an extended half life and reduce clearance rate.

The significantly improved potency and pharmacokinetic properties of the DOM15-26-593 resulted in analysis of the compound for a range of other biophysical attributes.

Figure 42A:
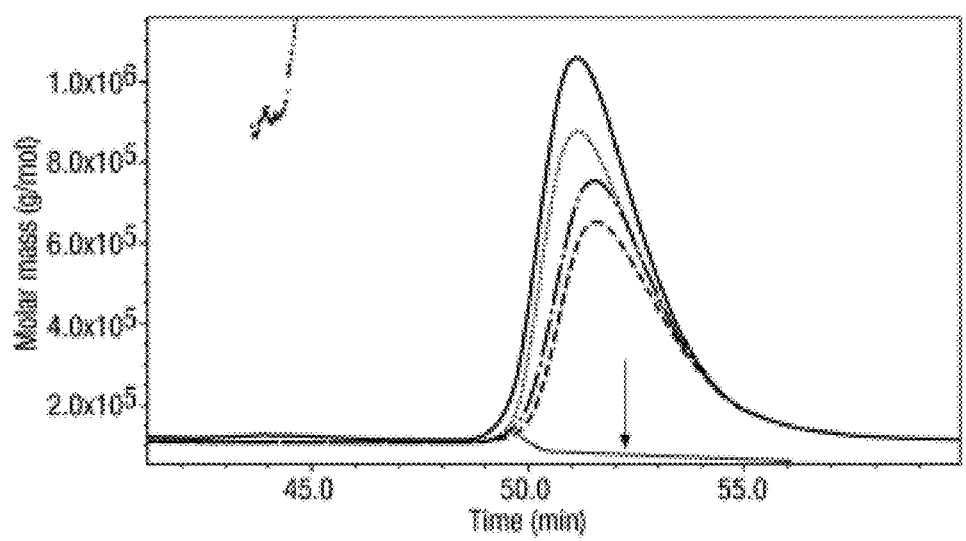

Solution State Properties: Analysis by SEC-MALLs & AUC:

Experiments were done with DOM15-26-593 as follows:

DOM15-26-593 behaves as a monomer in solution at concentrations of up to 2.5 mg/ml with a calculated molecular mass of 78-81 KDa, consistent with the calculated intact molecular mass of approx 76 kDa (FIG. 42a & 42b).

Thermal Melting Properties: Analysis by DSC

Figure 43:
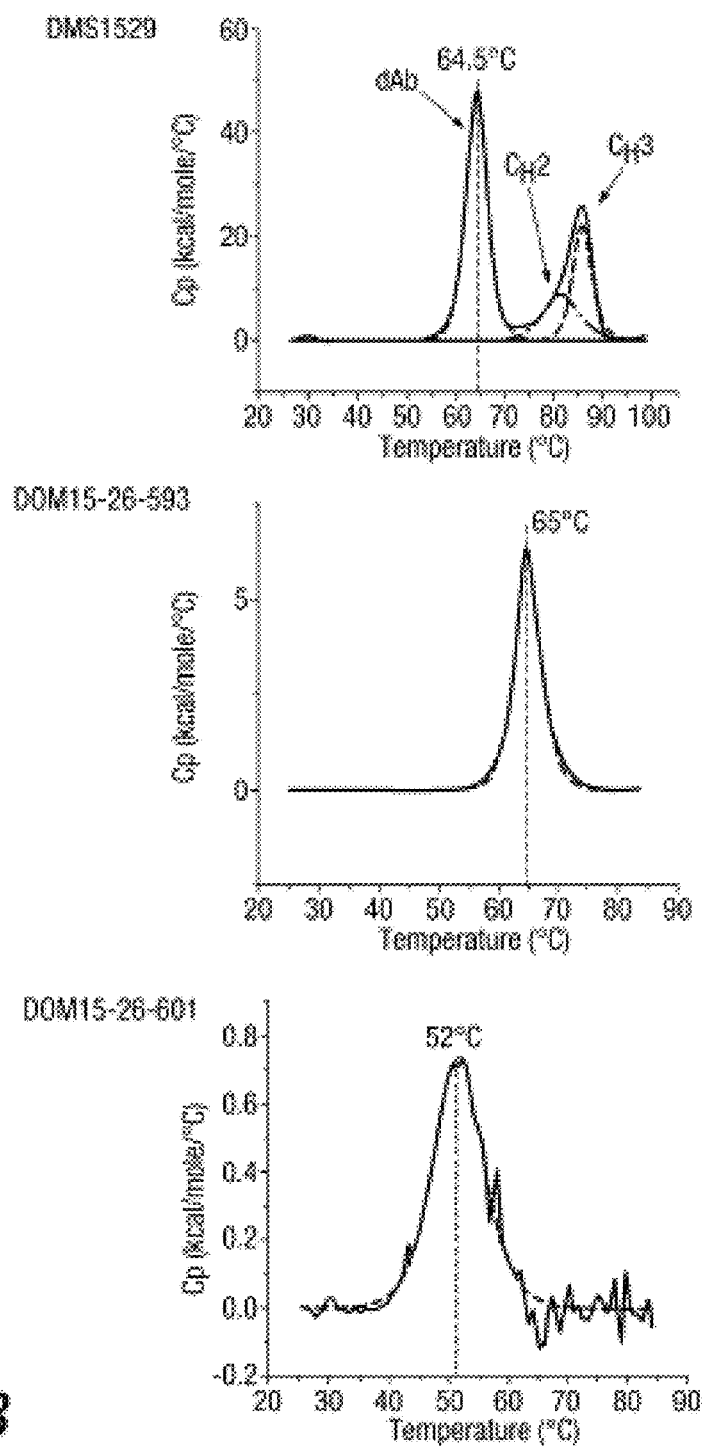

Experiments were done with DOM15-26-593 as follows:

The increased thermal stability of the trypsin selected DAB™ (65° C., FIG. 43 middle panel) is maintained in the Fc fusion (64.5° C., FIG. 43 upper panel). The Tm curve of the DOM15-26-501 DAB™ (52° C., FIG. 43 lower panel) is shown for comparison.

Stability to Freeze-Thaw, Temperature Stress and Serum Components

Figure 44:
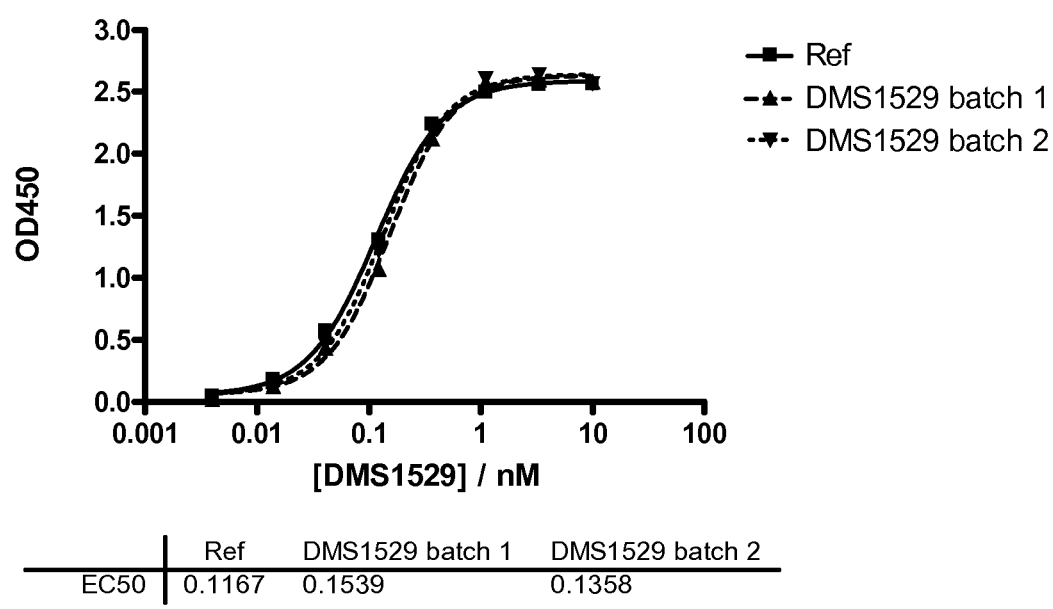
Figure 45:
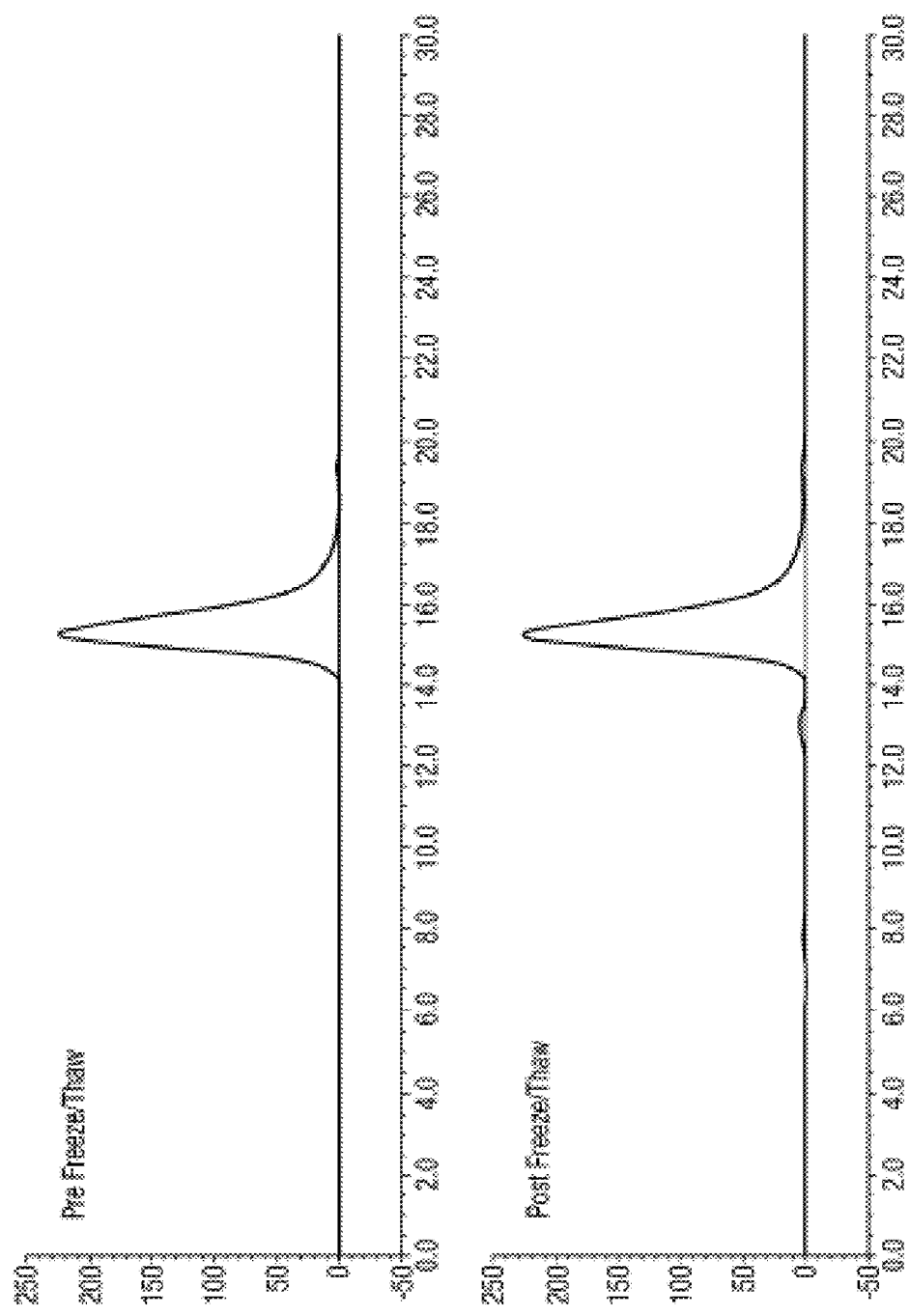
Figure 46:
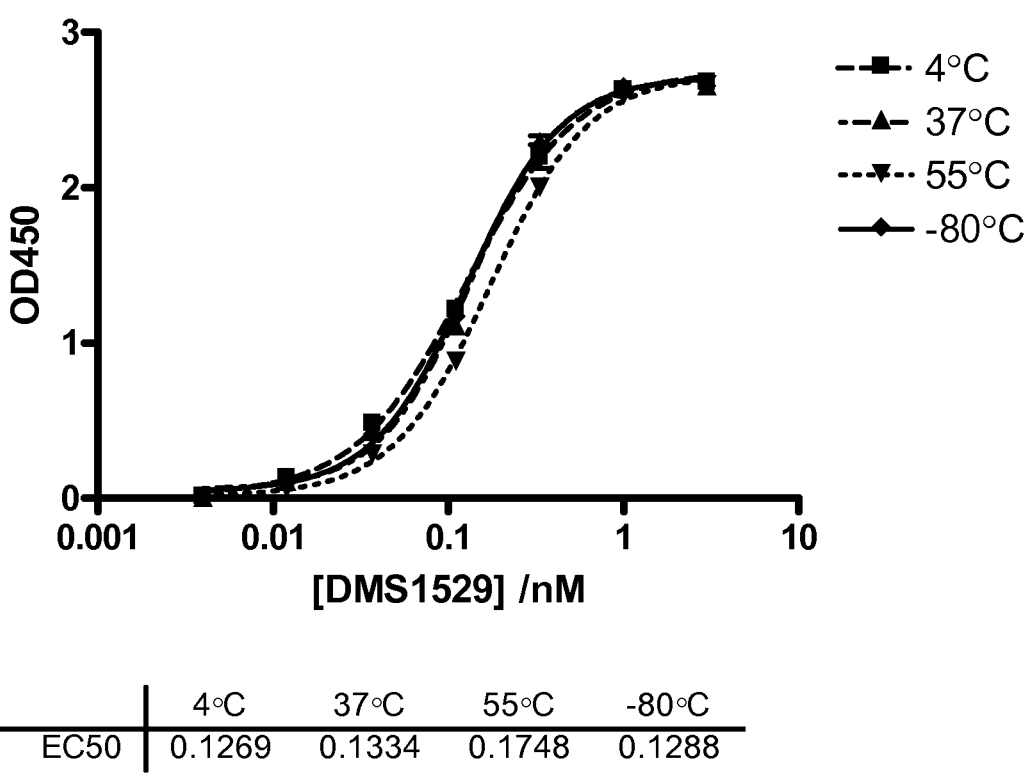
Figure 47:
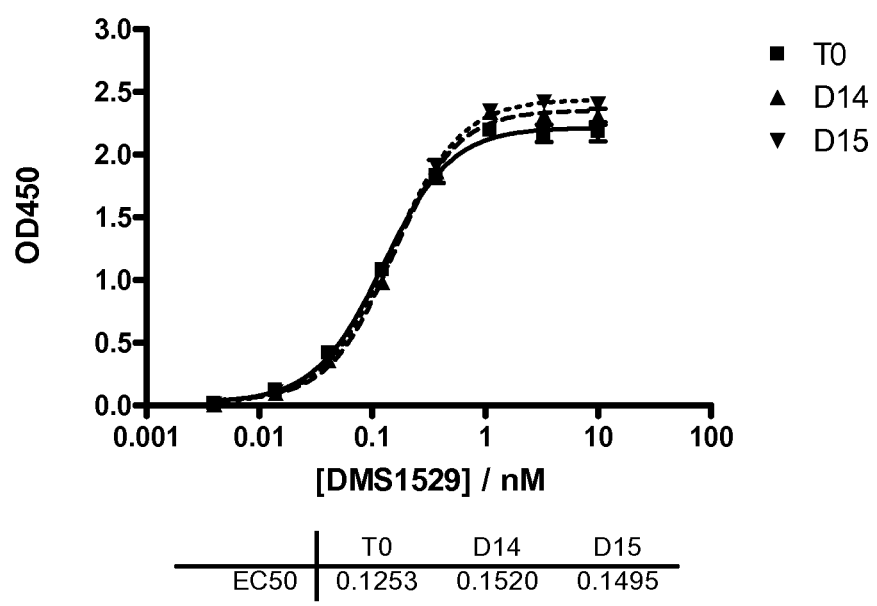
Figure 47B:
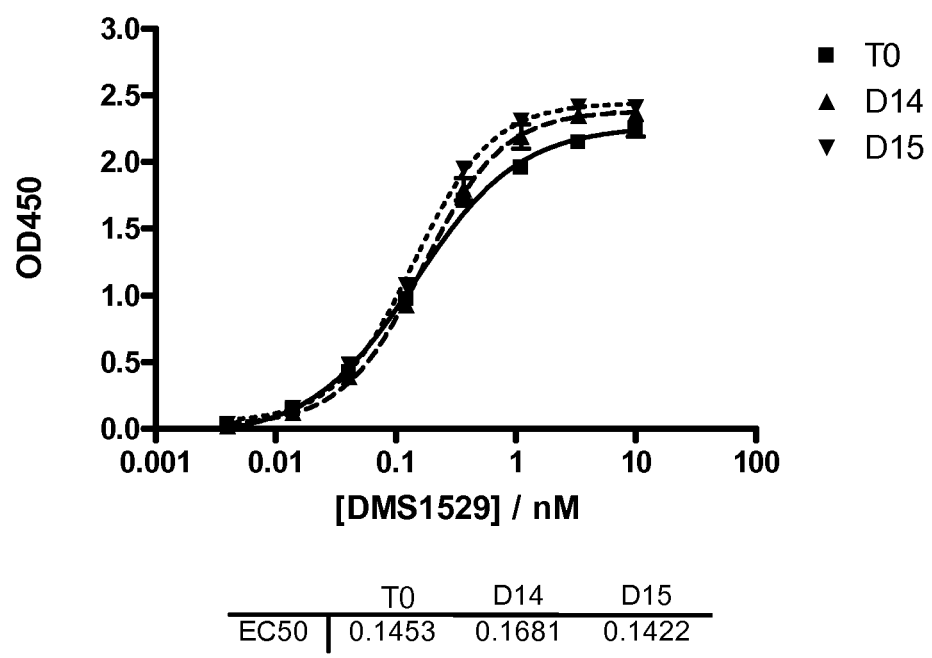
Figure 48:
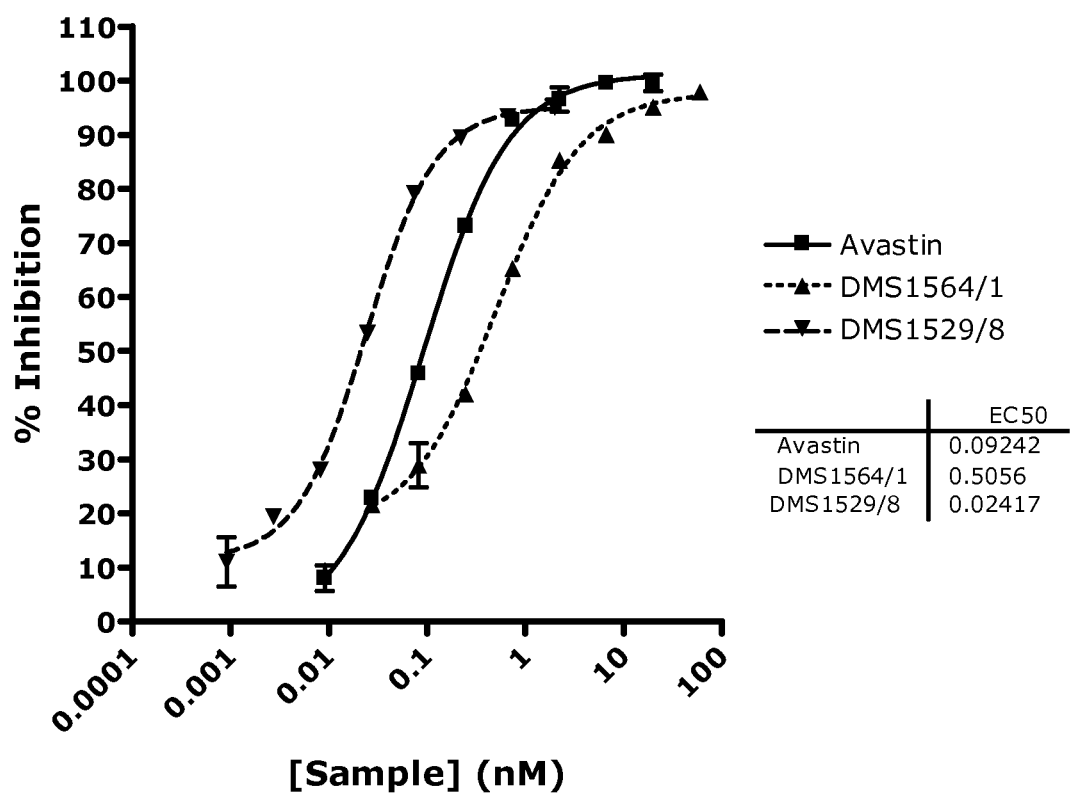
Figure 49:
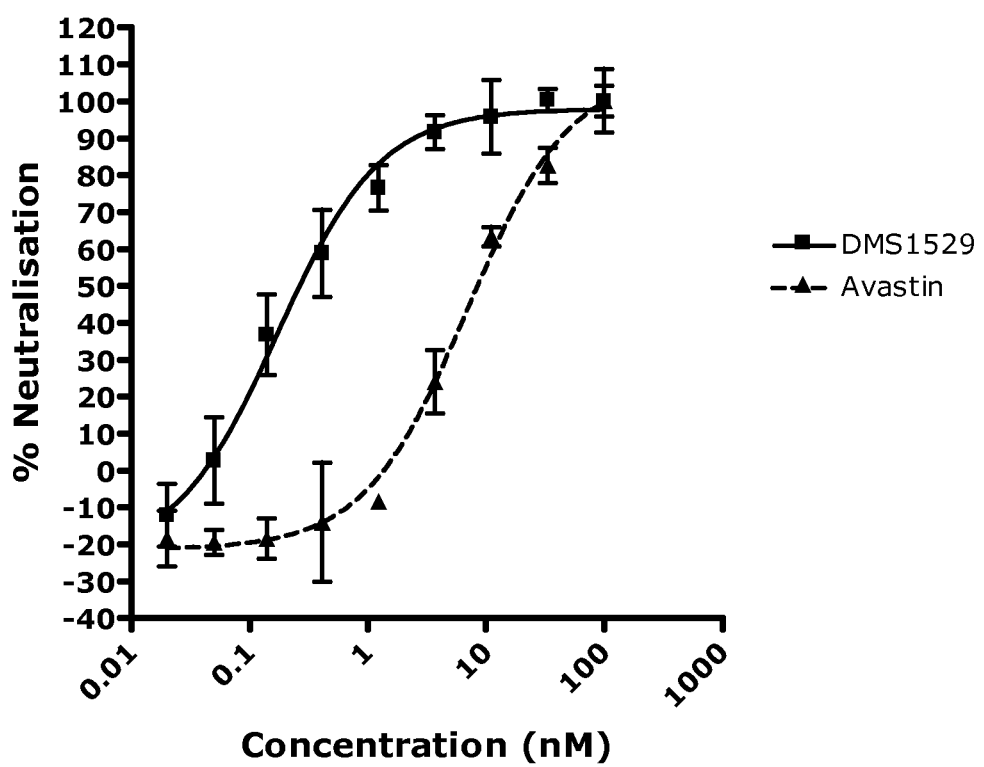

Experiments were done with DOM15-26-593 as follows:

The stability properties of the DOM15-26-593 DAB™ mean that the DOM15-26-593 DAB™ can be subjected to physical and biological stress with minimal effects on its ability to bind VEGF (FIGS. 44-47 (a and b)). For example, the molecule can be repeatedly freeze thawed from liquid nitrogen (−196° C.) to body temperature (37° C.) for 10 cycles without loss of binding activity as determined by ELISA (FIG. 44). This treatment also resulted in no obvious alterations in the molecule's aggregation state, as assessed by conventional size exclusion chromatography (FIG. 45). Further tests demonstrated that the molecule can be placed at a range of different temperatures from −80° C. to 55° C. with only a minor drop in antigen binding activity after 168 hours at only the highest incubation temperature (FIG. 46). Furthermore, incubation with serum from human or cynomolgus monkeys at 37° C. for 14 days caused no loss of antigen binding ability (FIGS. 47a and 47b), as determined by the VEGF binding ELISA Potency in VEGFR2 Receptor Binding Assay & HUVEC Cell Assay:

The receptor binding assays described above were carried out as follows:

The receptor binding assay described above was used to assess the potency of the Fc fusions (FIG. 48). It was found that the DOM15-26-593 DAB™ has enhanced potency in this assay, which establishes the ability of the DAB™ to block the binding of VEGF to VEGFR2 in vitro. The potency of the DMS 1529 was also demonstrated in a HUVEC (Human Umbilical Vein Endothelial Cell) assay, where the ability of VEGF antagonists to block the VEGF stimulated proliferation of HUVE cells is measured. Cell numbers are determined at the end of a fixed incubation period with a pre-determined amount of VEGF and a varying amount of test article. The more potent the antagonist, the lower the cell proliferation observed (FIG. 49).

The nucleotide sequence of DOM1h-131-511 is set out in this paragraph.

The Nucleotide Sequence of DOM1h-131-511:

```
                                                  (SEQ ID NO: 262)
GAGGTGCAGC TGTTGGAGTC TGGGGGAGGC TTGGTACAGC

CTGGGGGGTC CCTGCGTCTC TCCTGTGCAG CCTCCGGATT

CACCTTTGCG CATGAGACGA TGGTGTGGGT CCGCCAGGCT

CCAGGGAAGG GTCTAGAGTG GGTCTCACAT ATTCCCCCGG

TTGGTCAGGA TCCCTTCTAC GCAGACTCCG TGAAGGGCCG

GTTCACCATC TCCCGCGACA ATTCCAAGAA CACGCTATAT

CTGCAAATGA ACAGCCTGCG TGCCGAGGAC ACAGCGGTAT

ATTACTGTGC GCTGCTTCCT AAGAGGGGGC CTTGGTTTGA

CTACTGGGGT CAGGGAACCC TGGTCACCGT CTCGAGC
```

The material in the ASCII text file named "DB00056C1SeqList1April2013.txt [,]" created on Apr. 1, 2013 and having a size of 194,584 bytes is incorporated herein by reference in its entirety.

---

The invention claimed is:

1. A method of treating a respiratory disease selected from the group consisting of lung inflammation, chronic obstructive pulmonary disease (COPD), cystic fibrosis, acute respiratory distress syndrome (ARDS), asthma, hypersensitivity pneumonitis, idiopathic pulmonary fibrosis, interstitial lung disease, bronchiecstasis, environmental lung disease, and mesothelioma, in a human in need thereof, the method comprising:
   administering to the lung of said human a pulmonary formulation comprising an immunoglobulin single variable domain that comprises the amino acid sequence shown in SEQ ID NO: 224, in a particle having a size of 6 μm or less.

2. The method of claim 1, wherein the pulmonary formulation has a pH between 6.5 and 8.0.

3. The method of claim 2, wherein the pulmonary formulation further comprises a polyethylene glycol.

4. The method of claim 2, wherein the pulmonary formulation further comprises sucrose.

5. A method of treating a respiratory disease selected from the group consisting of lung inflammation, chronic obstructive pulmonary disease (COPD), cystic fibrosis, acute respiratory distress syndrome (ARDS), asthma, hypersensitivity pneumonitis, idiopathic pulmonary fibrosis, interstitial lung disease, bronchiecstasis, environmental lung disease, and mesothelioma, in a human in need thereof, the method comprising:
   administering to the lung of said human a pulmonary formulation comprising a polypeptide that comprises the amino acid sequence shown in SEQ ID NO: 224, in a particle having a size of 6 μm or less.

6. The method of claim 5, wherein the pulmonary formulation has a pH between 6.5 and 8.0.

7. The method of claim 6, wherein the pulmonary formulation further comprises a polyethylene glycol.

8. The method of claim 6, wherein the pulmonary formulation further comprises sucrose.

9. A method of treating a respiratory disease selected from the group consisting of lung inflammation, chronic obstructive pulmonary disease (COPD), cystic fibrosis, acute respiratory distress syndrome (ARDS), asthma, hypersensitivity pneumonitis, idiopathic pulmonary fibrosis, interstitial lung disease, bronchiecstasis, environmental lung disease, and mesothelioma, in a human in need thereof, the method comprising:
   administering to the lung of said human a pulmonary formulation comprising an immunoglobulin single variable domain that comprises the amino acid sequence shown in SEQ ID NO: 224 and a pharmaceutically acceptable carrier, in a particle having a size of 6 μm or less.

10. The method of claim 9, wherein the pulmonary formulation has a pH between 6.5 and 8.0.

11. The method of claim 10, wherein the pulmonary formulation further comprises a polyethylene glycol.

12. The method of claim 10, wherein the pulmonary formulation further comprises sucrose.

13. A method of treating a respiratory disease selected from the group consisting of lung inflammation, chronic obstructive pulmonary disease (COPD), cystic fibrosis, acute respiratory distress syndrome (ARDS), asthma, hypersensitivity pneumonitis, idiopathic pulmonary fibrosis, interstitial lung disease, bronchiecstasis, environmental lung disease, and mesothelioma, in a human in need thereof, the method comprising:
   administering to the lung of said human a pulmonary formulation comprising a polypeptide that comprises the amino acid sequence shown in SEQ ID NO: 224 and a pharmaceutically acceptable carrier, in a particle having a size of 6 μm or less.

14. The method of claim 13, wherein the pulmonary formulation has a pH between 6.5 and 8.0.

15. The method of claim 14, wherein the pulmonary formulation further comprises a polyethylene glycol.

16. The method of claim 14, wherein the pulmonary formulation further comprises sucrose.

17. The method of claim 1, wherein the respiratory disease is acute respiratory distress syndrome (ARDS).

18. The method of claim 5, wherein the respiratory disease is acute respiratory distress syndrome (ARDS).

19. The method of claim 9, wherein the respiratory disease is acute respiratory distress syndrome (ARDS).

20. The method of claim 13, wherein the respiratory disease is acute respiratory distress syndrome (ARDS).

* * * * *

SEQUENCE LISTING

```
<160> NUMBER OF SEQ ID NOS: 266

<210> SEQ ID NO 1
<211> LENGTH: 30
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

Met Leu Phe Lys Ser Leu Ser Lys Leu Ala Thr Ala Ala Ala Phe Phe
1               5                   10                  15

Ala Gly Val Ala Thr Ala Ala Ala Glu Thr Val Glu Ser
            20                  25                  30

<210> SEQ ID NO 2
<211> LENGTH: 109
<212> TYPE: DNA
<213> ORGANISM: Artificial Sequence
<220> FEATURE:
<223> OTHER INFORMATION: Nucleic acid sequence identified using
      molecular biology techniques.
```

```
<400> SEQUENCE: 2
taatgttatt taaatcatta tcaaaattag caaccgcagc agcattttttt gcaggcgtgg    60 caacagcgtc gacacactgc aggaggcggc cgcagaaact gttgaacgt              109

<210> SEQ ID NO 3
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 3

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Pro Pro Val Gly Gln Asp Pro Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 4
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 4

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Pro Pro Asp Gly Gln Asp Pro Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr His
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
            115

<210> SEQ ID NO 5
<211> LENGTH: 108
```

```
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Tyr Leu Asn
             20                  25                  30

Leu Asp Trp Tyr Gln Gln Lys Pro Gly Lys Ala Pro Lys Leu Leu Ile
         35                  40                  45

Asn Phe Gly Ser Glu Leu Gln Ser Gly Val Pro Ser Arg Phe Ser Gly
     50                  55                  60

Ser Gly Tyr Gly Thr Asp Phe Thr Leu Thr Ile Ser Ser Leu Gln Pro
 65                  70                  75                  80

Glu Asp Phe Ala Thr Tyr Tyr Cys Gln Pro Ser Phe Tyr Phe Pro Tyr
                 85                  90                  95

Thr Phe Gly Gln Gly Thr Lys Val Glu Ile Lys Arg
            100                 105

<210> SEQ ID NO 6
<211> LENGTH: 4
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 6

Ser Tyr Gly Ala
 1

<210> SEQ ID NO 7
<211> LENGTH: 116
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 7

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
            100                 105                 110

Thr Val Ser Ser
        115
```

<210> SEQ ID NO 8
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 8

Gly Gly Gly Gly Ser
1               5

<210> SEQ ID NO 9
<211> LENGTH: 4
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 9

Ser Tyr Ser Thr
1

<210> SEQ ID NO 10
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45

Tyr His Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Phe Gln Pro Arg
                85                  90                  95

Thr Phe Gly Gln Gly Thr Lys Val Glu Ile Arg Arg
            100                 105

<210> SEQ ID NO 11
<211> LENGTH: 4
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 11

Ser Tyr Gly Ala
1

<210> SEQ ID NO 12
<211> LENGTH: 116
<212> TYPE: PRT
<213> ORGANISM: Artificial Sequence
<220> FEATURE:

<223> OTHER INFORMATION: Amino acid sequence identified using molecular
       biology techniques.

<400> SEQUENCE: 12

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Ala Tyr
             20                  25                  30

Pro Met Met Trp Val Arg Gln Ala Pro Gly Lys Gly Leu Glu Trp Val
         35                  40                  45

Ser Glu Ile Ser Pro Ser Gly Ser Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Arg Lys Phe Asp Tyr Trp Gly Gln Gly Thr Leu Val
            100                 105                 110

Thr Val Ser Ser
            115
```

<210> SEQ ID NO 13
<211> LENGTH: 4
<212> TYPE: PRT
<213> ORGANISM: Artificial Sequence
<220> FEATURE:
<223> OTHER INFORMATION: Amino acid sequence identified using molecular
       biology techniques.

<400> SEQUENCE: 13

```
Ser Tyr Ser Thr
  1
```

<210> SEQ ID NO 14
<211> LENGTH: 108
<212> TYPE: PRT
<213> ORGANISM: Artificial Sequence
<220> FEATURE:
<223> OTHER INFORMATION: Amino acid sequence identified using molecular
       biology techniques.

<400> SEQUENCE: 14

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Pro Glu
             20                  25                  30

Leu Ser Trp Tyr Gln Gln Lys Pro Gly Lys Ala Pro Lys Leu Leu Ile
         35                  40                  45

Tyr His Thr Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Met Phe Gln Pro Arg
                 85                  90                  95

Thr Phe Gly Gln Gly Thr Lys Val Glu Ile Arg Arg
            100                 105
```

<210> SEQ ID NO 15
<211> LENGTH: 358
<212> TYPE: DNA

<213> ORGANISM: Artificial Sequence
<220> FEATURE:
<223> OTHER INFORMATION: Nucleic acid sequence identified using
      molecular biology techniques.

<400> SEQUENCE: 15
gaggtgcagc tgttggagtc tgggggaggc atggtacagc ctggggggtc cctgcgtctc    60
tcctgtgcag cctccggatt cacctttgcg catgagacga tggtgtgggt ccgccaggct   120
ccagggaagg gtctagagtg gtctcacat attcccccgg ttggtcagga tcccttctac    180
gcagactccg tgaagggccg gttcaccatc tcccgcgaca attccaagaa cacgctatat   240
ctgcaaatga acagcctgcg tgccgaggac acagcggtat attactgtgc gctgcttcct   300
aagagggggc cttggtttga ctactgggt cagggaaccc tggtcaccgt ctcgagcg     358

<210> SEQ ID NO 16
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 16
gaggtgcagc tgttggagtc tgggggaggc ttggtacagc ctggggggtc cctgcgtctc    60
tcctgtgcag cctccggatt cgcctttgcg catgagacga tggtgtgggt ccgccaggct   120
ccagggaagg gtctagagtg gtctcacat attcccccgg ttggtcagga tcccttctac    180
gcagactccg tgaagggccg gttcaccatc tcccgcgaca attccaagaa cacgctatat   240
ctgcaaatga acagcctgcg agccgaggac acagcggtat attactgtgc gctgcttcct   300
aagagggggc cttggtttga ctactgggt cagggaaccc tggtcaccgt ctcgagcg     358

<210> SEQ ID NO 17
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 17
gaggtgcagc tgttggagtc tgggggaggc ttggtacagc ctggggggtc cctgcgtctc    60
tcctgtgcag cctccggatt caactttgcg catgagacga tggtgtgggt ccgccaggct   120
ccagggaagg gtctagagtg gtctcacat attcccccgg ttggtcagga tcccttctac    180
gcagactccg tgaagggccg gttcaccatc tcccgcgaca attccaagaa cacgctatat   240
ctgcaaatga acagcctgcg tgccgaggac acagcggtat attactgtgc gctgcttcct   300
aagagggggc cttggtttga ctactgggt cagggaaccc tggtcaccgt ctcgagcg     358

<210> SEQ ID NO 18
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 18
gaggtgcagc tgttggagtc tgggggaggc ttggtacagc ctggggggtc cctgcgtctc    60
tcctgtgcag cctccggatt cacctttgcg catgagacga tggtgtgggt ccgccaggct   120

```
ccagggaagg gtctagagtg ggtctcacat attcccccgg ttggtcagga tcccttctac    180
gcagactccg tgaagggccg gttcaccatc tcccgcgacg attccaagaa cacgctatat    240
ctgcaaatga acagcctgcg tgccgaggac acagcggtat attactgtgc gctgcttcct    300 aagaggggc cttggtttga ctactggggt cagggaaccc tggtcaccgt ctcgagcg      358
```

<210> SEQ ID NO 19
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 19

```
gaggtgcagc tgttggagtc tgggggaggc ttggtacagc ctgggggtc cctgcgtctc     60 tcctgtgcag cctccggatt cacctttgcg catgagacga tggtgtgggt ccgccaggct   120
ccagggaagg gtctagagtg ggtctcacat attcccccgg ttggtcagga tcccttctat   180
gcagactccg tgaagggccg gttcaccatc tcccgcgaca attccaagaa cacgctatat   240
ctgcaaatga acaacctgcg cgccgaggac acagcggtat attactgtgc gctgcttcct   300 aagaggggc cttggtttga ctactggggt cagggaaccc tggtcaccgt ctcgagcg      358
```

<210> SEQ ID NO 20
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 20

```
gaggtgcagc tgttggagtc tgggggaggc ttggtacagc ctgggggtc cctgcgtctc     60 tcctgtgcag cctccggatt cacctttgcg catgagacga tggtgtgggt ccgccaggcc   120
ccagggaagg gtctagagtg ggtctcacat attcccccgg ctggtcagga tcccttctac   180
gcagactccg tgaagggccg gttcaccatc tcccgcgaca attccaagag cacgctatat   240
ctgcaaatga acggcctgcg tgccgaggac acagcggtat attactgtgc gctgcttcct   300 aagaggggc cttggtttga ctactggggt cagggaaccc tggtcaccgt ctcgagcg      358
```

<210> SEQ ID NO 21
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 21

```
gaggtgcagc tgttggagtc tgggggaggc ttggtaaagc ctgggggtc cctgcgtctc     60 tcctgtgcag cctccggatt cacctttgcg catgagacga tggtgtgggt ccgccaggct   120
cctgggaagg gtctagagtg ggtctcacat attcccccgg ctggtcagga tcccttctac   180
gcagactccg tgaagggccg gttcaccatc tcccgcgaca attccaagaa cacgctatat   240
ctgcaaatga acagcctgcg tgccgaggac acagcggtat attactgtgc gctgcttcct   300 aagaggggc cttggtttga ctactggggt cagggaaccc tggtcaccgt ctcgagcg      358
```

<210> SEQ ID NO 22
<211> LENGTH: 358
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 22

| gaggtgcagc tgttggagtc tggggagggc ttggtacagc ctgggggtc cctgcgtctc | 60 |
| tcctgtgcag cctccggatt cacctttgcg catgagacga tggtgtgggt ccgccaggcc | 120 |
| ccagggaagg gtctagagtg ggtctcacat attcccccgg acggtcaaga tcccttctac | 180 |
| gcagactccg tgaagggccg gttcaccatc tcccgcgaca attccaagaa cacgctatat | 240 |
| ctgcaaatga acagcctgcg tgccgaggac acagcggtat attactgtgc gctgcttcct | 300 |
| aagaggggc cttggtttga ctactgggt cagggaaccc tggtcaccgt ctcgagcg | 358 |

<210> SEQ ID NO 23
<211> LENGTH: 358
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 23

| gaggtgcagc tgtgggagtc tggggagggc ttggtacagc ctgggggtc cctgcgtctc | 60 |
| tcctgtgcag cctccggatt cacctttgcg catgagacga tggtgtgggt ccgccaggct | 120 |
| ccagggaagg gtctagagtg ggtctcacat attcccccgg atggtcagga tcccttctac | 180 |
| gcagactccg tgaagggccg gttcaccatc tcccgcgaca attccaagaa cacgctatat | 240 |
| ctgcaaatga acagcctgcg tgccgaggac acagcggtat attactgtgc gctgcttcct | 300 |
| aagaggggc cttggattga ctactgggt cagggaaccc tggtcaccgt ctcgagcg | 358 |

<210> SEQ ID NO 24
<211> LENGTH: 358
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 24

| gaggtgcagc tgtcggagtc tggggagggc ttggtacagc ctgggggtc cctgcgtctc | 60 |
| tcctgtgcag cctccggatt cacctttgcg catgagacga tggtgtgggt ccgccaggct | 120 |
| ccagggaagg gtctagagtg ggtctcacat attcccccag atggtcagga tcccttctac | 180 |
| gcagactccg tgaagggccg gttcaccatc tcccgcgaca attccaagaa cacgctatat | 240 |
| ctgcaaatga acagcctgcg tgccgaggac acagcggtat attactgtgc gctgcttcct | 300 |
| aataggggc cttggtttga ctactgggt cagggaaccc tggtcaccgt ctcgagcg | 358 |

<210> SEQ ID NO 25
<211> LENGTH: 358
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 25

```
gaggtgcagc tgttggagtc tggggaggc ttggtacagc ctgggggtc cctgcgtctc      60 tcctgtgcag cctccggatt cacctttgcg catgagacga tggtgtgggt ccgccaggct    120
ccagggaagg gtctagagtg gtctcacat attcccccgg atggtcagga tcccttctac     180
gcagactccg tgaagggccg gttcaccatc tcccgcgaca attccaagaa cacgctatat    240
ctgcaaatga acagcctgcg tgccgaggac acagcggtat attactgtgc gctgcttcct    300
aagagggggc cttggtttga ctactgggggt cagggaaccc aggtcaccgt ctcgagcg     358

<210> SEQ ID NO 26
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 26
gaggtgcggc tgttggagtc tggggaggc ttggtacagc ctgggggtc cctgcgtctc      60 tcctgtacag cctccggatt cacctttgcg catgagacga tggtgtgggt ccgccaggct    120
ccagggaagg gtctagagtg gtctcacat attcccccgg atggtcagga tcccttctac     180
gcagactccg tgaagagccg gttcaccatc tcccgcgaca attccaagaa cacgctatat    240
ctgcagatga acagcctgcg tgccgaggac acagcggtgt attactgtgc gctgcttcct    300
aagagagggc cttggtttga ctactgggggt cagggaaccc aggtcaccgt ctcgagcg     358

<210> SEQ ID NO 27
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 27
gaggtgcggc tgttggagtc tggggaggc ttggtacagc ctgaggggtc cctgcgtctc     60
tcctgtgcag cctccggatt cacctttgcg catgagacga tggtgtgggt ccgccaggct    120
ccagggaagg gtctagagtg gtctcacat attcccccgg atagccagga tcccttctac     180
gcagactccg tgaagggccg gttcaccatc tcccgcgaca attccaagaa cacgctatat    240
ctgcaaatga acagcctgcg tgccgaggac acagcggtat attactgtgg gctgcttcct    300
aagagggggc cttggtttga ctacagggggt cagggaaccc tggtcaccgt ctcgagcg     358

<210> SEQ ID NO 28
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 28
gaggtgcagc tgttggagtc tggggaggc ttggtacagc ctgggggtc cctgcgtctc      60 tcctgtgcag cctccggatt caccattgcg catgaaacga tggtgtgggt ccgccaggct    120
ccagggaagg gtctagagtg gtctcacat attcccccgg ttggtcagga tcccttctac     180
gcagactccg tgaagggccg gttcaccatc tcccgcgaca attccaagaa cacgctatat    240
ctgcaaatga acagcctgcg tgccgaggac acagcggtat attactgtgc gctgcttcct    300
```

```
aagagggggc cttggtttga ctaccgggt cagggaaccc tggtcaccgt ctcgagcg    358
```

<210> SEQ ID NO 29
<211> LENGTH: 358
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 29

```
gaggtgcagc tgttggagtc tgggggaggc ttggtacagc ctgggggtc cctgcgtctc    60
tcctgtgcag cctccggatt cacctttgcg catgagacga tggtgtgggt ccgccaggct   120
ccagggaagg gtctagagtg ggtctcacat attcctccgg ttggtcagga tcccttctac   180
gcagactccg tgaagggccg gttcaccatc tcccgcgaca attccaagaa cacgctatat   240
ctgcaaatga acagcctgcg tgccgaggac acagcggtat attactgtgc gcggcttcct   300
aagagggggc cttggtttga ctactgggt cagggaacct tggtcaccgt ctcgagcg    358
```

<210> SEQ ID NO 30
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 30

```
gaggtgcagc tgttggagtc tgggggaggc ttggtacagc ctgggggtc cctgcgtctc    60
tcctgtgcag cctccggatt cacctttgcg catgagacga tggtgtgggt ccgccaggca   120
ccagggaagg gtctagagtg ggtctcacat attccccggg atggtcagga tcccttctac   180
gcagactccg tgaagggccg gttcaccatc tcccgcgaca attccaagaa cacgctatat   240
ctgcaaatga acagcctgcg tgccgaggac acagcggtat atcactgtgc gctgcttcct   300
aagagggggc cttggtttga ctactgggt cagggaaccc tggtcaccgt ctcgagc      357
```

<210> SEQ ID NO 31
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 31

```
gaggtgcagc tgttggagtc tgggggaggc ttggtacagc ctgggggtc cctgcgtctc    60
tcctgtgcag cctccggatt cacctttgcg catgagacga tggtgtgggt ccgccgggct   120
ccagggaagg gtctagagtg ggtctcacat attccccggg atggtcagga tcccttctac   180
gcagactccg tgaagggccg gttcaccatc tcccgcgaca attccaagaa cacgctatat   240
ctgcaaatga acagcctgcg tgccgaggac acagcggtat attactgtgc gctgcttcct   300
aagagggggc cttggtttga ctactgggt cagggaaccc tggtcaccgt ctcgagc      357
```

<210> SEQ ID NO 32
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 32

```
gaggtgcagc tgttggagtc tgggggaggc ttggtacagc ctgggggtc cctgcgtctc      60 tcctgtgcag ccaccggatt cacctttgcg catgagacga tggtgtgggt ccgccaggct    120
ccagggaggg gtctagagtg gtctcacat attcccccgg atggtcagga tcccttctac     180
gcagactccg tgaagggccg gttcaccatc tcccgcgaca attccaagaa cacgctatat    240
ctgcaaatga acagcctgcg tgccgaggac acagcggtat attactgtgc gctgcttcct    300
aagagggggc cttggtttga ctactgggt cagggaaccc tggtcaccgt ctcgagc        357
```

<210> SEQ ID NO 33
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 33

```
gaggtgcagc tgttggagtc tgggggaggc ctggtacagc ctgggggtc cctgcgtctc     60 tcctgtgcag cctccggatt cacctttgcg catgagacga tggtgtgggt ccgccaggct   120
ccagggaggg gtctagagtg gtctcacat attccctcgg atggtcagga tcccttctac    180
gcagactccg tgaagggccg gttcaccatc tcccgcgaca attccaagaa cacgctatat   240
ctgcaaatga acagcctgcg tgccgaggac acagcggtat attactgtgc gctgcttcct   300
aagagggggc cttggttcga ctactgggt cagggaaccc tggtcaccgt ctcgagc       357
```

<210> SEQ ID NO 34
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 34

```
gaggtgcagc tgttggagtc tgggggaggc ttggtacagc ctgggggtc cctgcgtctc     60 tcctgtgcag cctccggatt cacctttgcg catgagacga tggtgtgggt ccgccaggct   120
ccagggaagg gtctagagtg gtctcacat attcccccgg atggtcagga tcccttctac    180
gcagactccg tgaagggccg gttcaccatc tcccgcgaca attccaagaa cacgctatat   240
ctgcaaatga acagcctgcg tgccgaggac acagcggtat attactgtgc gctgcttcct   300
aagaaggggc cttggtttga ctactgggt cagggaaccc tggtcaccgt ctcgagc       357
```

<210> SEQ ID NO 35
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 35

```
gaggtgcagc tgttggagtc tgggggaggc ttggtacagc ctgggggtc cctgcgtctc     60 tcctgtgcag cctccggatt cacctttgcg cgtgagacga tggtgtgggt ccgccaggct   120
ccagggaagg gtctagagtg gtctcacat attcccccgg ttggtcagga tcccttctac    180
gcagactccg tgaagggccg gttcaccatc tcccgcgaca attccaagaa cacgctatat   240
```
ctgcaaatga acagcctgcg tgccgaggac acagcggtat attactgtgc gctgcttcct    300
aagagggggc cttggtttga ctactggggt cagggaaccc tggtcaccgt ctcgagc      357

<210> SEQ ID NO 36
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 36
gaggtgcagc tgttggagtc tgggggaggc ttggtacagc ctggggggtc cctgcgtctc    60
tcctgtgcag cctccggatt cacctttgcg caagagacga tggtgtgggt ccgccaggct   120
ccagggaagg gtctagagtg ggtctcacat attcccccgg ttggtcagga tcccttctac   180
gcagactccg tgaagggccg gttcaccatc tcccgcgaca attccaagaa cacgctatat   240
ctgcaaatga acagcctgcg tgccgaagac acagcggtat attactgtgc gcggcttcct   300
aagagggggc cttggtttga ctactggggt cagggaaccc tggtcaccgt ctcgagc      357

<210> SEQ ID NO 37
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 37
gaggtgcagc tgttggagtc tgggggaggc ttggtacagc ctggggggtc cctgcgtctc    60
tcctgtgcag cttccggatt cacctttgcg catgagacga tggtgtgggt ccgccaggct   120
ccagggaagg gtctagagtg ggtctcacat attcccccgg ttggtcagga tcccttctac   180
gcagactccg tgaagggccg gttcaccatc tcccgcgaca attccaagaa cacgctatat   240
ctgcaaatga acagcctgcg tgccgaggac acagcggtat attactgtgc gctgcttcct   300
aagaaggggc cttggtttga ctactggggt cagggaaccc tggtcaccgt ctcgagc      357

<210> SEQ ID NO 38
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 38
gaggtgcagc tgttggagtc tgggggaggc ttggtacagc ctggggggtc cctgcgtctc    60
tcctgtgcag cctccggatt cacctttgcg catgagacga tggtgtgggt ccgccaggct   120
ccagggaagg gtctagagtg ggtctcacat attcccccgg ctggtcagga tcccttctac   180
gcagactccg tgaagggccg gttcaccatc tcccgcgaca attccaagaa cacgctatat   240
ctgcaaatga acagcctgcg tgccgaggac acagcggtat attactgtgc gcggcttcct   300
aagagggggc cttggtttga ctactggggt cagggaaccc tggtcaccgt ctcgagc      357

<210> SEQ ID NO 39
<211> LENGTH: 325
<212> TYPE: DNA
<213> ORGANISM: Artificial Sequence

```
<220> FEATURE:
<223> OTHER INFORMATION: Nucleic acid sequence identified using
      molecular biology techniques.

<400> SEQUENCE: 39
gacatcctga tgacccagtc tccatcctcc ctgtctgcat ctgtaggaga ccgtgtcacc    60
atcacttgcc gggcaagtca ggatatttac ctgaatttag actggtatca gcagaaacca   120
gggaaggccc ctaagctcct gatcaatctt ggttccgagt tgcaaagtgg tgtcccatca   180
cgtttcagtg gcagtggata tgggacagat ttcactctca ccatcagcag tctgcaacct   240
gaagatgtcg ctacgtacta ctgtcaaccg tcttttttact tcccttatac gttcggccaa   300
gggaccaagg tggaaatcaa acggg                                         325

<210> SEQ ID NO 40
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 40
gacatcctga tgacccagtc tccatcctcc ctgtctgcat ctgtaggaga ccgtgtcacc    60
atcacttgcc gggcaagtca ggatatttac ctgaatttag actggtatca gcagaaacca   120
gggaaagccc ctaagctcct gatcaattt ggctccgagt tgcaaagtgg tgtcccatca    180
cgtttcagtg gcagcggata tgggacagat ttcactctca ccatcagcag tctgcaacct   240
gaagatttcg ctacgtacta ctgtcaaccg tcttttttact tcccttatac gttcggccag   300
gggaccaagg tggaaatcaa acggg                                         325

<210> SEQ ID NO 41
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 41
gacatccaga cgacccagtc tccgtcctcc ctgtctgcat ctgtaggaga ccgtgtcacc    60
atcacttgcc gggcaagtca ggatatttac cagaatttag actggtatca gcagaaacca   120
gggaaagccc ctaagctcct gatcaattt ggttccgagt tgcaaagtgg tgtcccatct    180
cgtttcagtg gcagtggata tgggacagat ttcactctca ccatcagcag tctgcaacct   240
gaagatttcg ctacgtacta ctgtcaaccg tcttttttact tcccttatac gttcggccaa   300
gggaccaagg tggaaatcaa acggg                                         325

<210> SEQ ID NO 42
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 42
gacatccagg tgacccagtc tccatccacc ctgtctgcat ctgtaggaga ccgtgtcacc    60
atcacttgcc gggcaagtca ggatatttac ctgaatttag actggtatca gcagaaacca   120
```

```
gggaaagccc ctaagctcct gatcaacttt ggttccgagt tgcaaagtgg tgtcccatca     180
cgtttcagtg gcagtggata tgggacagat ttcactctca ccatcagcag tctgcaacct     240
gaagatttcg ctacgtacta ctgtcaaccg tcttttact tcccttatac gttcggccga     300
gggaccaagg tggaaatcaa acggg                                           325
```

```
<210> SEQ ID NO 43
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 43
gacatccaga tgacccagtc tccatccttc ctgtctgcat ctgtaggaga ccgtgtcacc      60
atcacttgcc gggcaagtca ggatatttac cagaatttag actggtatca gcagaaacca    120
gggaaagccc ctaagctcct gatcaatttt ggttccgagt tgcaaagtgg tgtcccatca    180
cgtttcagtg gcagtggata cgggacagat ttcactctca ccatcagcag tctgcaacct    240
gaagatatcg ctacgtacta ctgtcaaccg tcttttact tcccttatac gtttggccaa    300
gggaccaagg tggaaatcaa agggg                                          325
```

```
<210> SEQ ID NO 44
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 44
gacatccaga tgacccagtc tccatcctcc ctgtcggcat ctgaaggaga ccgtgtcacc      60
atcacttgcc gggcaagtca ggatatttac cagaatttag actggtatca gcagaaacca    120
gggaaagccc ctaagctcct gatcaatttt ggttccgagt tgcaaagtgg tgtcccatca    180
cgtttcagtg gcagtggata tgggacagaa ttcactctca ccatcagcag tctgcaacct    240
gaagacttcg ctacgtacta ctgtcaaccg tcttttact tcccttatac gttcggccaa    300
gggaccaagg tggaaatcaa acggg                                          325
```

```
<210> SEQ ID NO 45
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 45
gacatccaga tgacccagtc tccatcctcc ctgtctgcat ctgtaggaga ccgtgtcacc      60
gtcacttgcc gggcaagtca ggatatttac ctgaatttag actggtatca gcagaaacca    120
gggaaagccc ctaagctcct gatcaatttt ggttccgagt tgcaaagtgg tgtcccatca    180
cgtttcagtg gcagtggata tgggacagat ttcactctca ccatcagcag tctgcagcct    240
gaagatttcg ctacgtacta ctgtcaaccg tcttttact tcccttatac gttcggccaa    300
gggaccaagg tggaaatcaa acggg                                          325
```

```
<210> SEQ ID NO 46
```

```
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 46

Gly Gly Gly Gly Ser
  1               5

<210> SEQ ID NO 47
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 47

Gly Gly Gly Gly Ser
  1               5

<210> SEQ ID NO 48
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 48
gacatccaga tgacccagtc tccatcctcc ctgtctgcat ctgtaggaga ccgtgtcacc    60
atcacttgcc gggcaagtca ggatatttac ctggatttag actggtatca gcagaaacca   120
gggaaagccc ctaagctcct gatcaattttt ggttccgagt tgcaaagtgg tgtcccatca   180
cgtttcagtg gcagtggata tgggacagat ttcactctca ccatcagcgg tctgcaacct   240
gaagatttcg ctacgtacta ctgtcaaccg tcttttttact tcccttatac gttcggccga   300
gggaccaggg tggaaatcaa acggg                                          325

<210> SEQ ID NO 49
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 49
gacatccaga tgacccagtc tccatcctcc ctgtctgcat ctgtaggaga ccgtgtcacc    60
atcacttgcc gggcaagtca ggatatttac ctgaatttag actggtatca gcagaaacca   120
gggaaagccc ctaagctcct gatcagtttt ggttccgagt tgcaaagtgg tgtcccatca   180
cgtttcagtg gcagtggata tgggacagat ttcactctca ccatcagcag tctgcaacct   240
gaagatttcg ctacgtacta ctgtcaaccg tcttttttact tcccttacac gttcggccaa   300
gggaccaagg tggaaatcaa acggg                                          325

<210> SEQ ID NO 50
<211> LENGTH: 325
<212> TYPE: DNA
<213> ORGANISM: Artificial Sequence
<220> FEATURE:
<223> OTHER INFORMATION: Nucleic acid sequence identified using
```

```
molecular biology techniques.

<400> SEQUENCE: 50
gacatccaga tgacccagtc tccatcctcc ctgtctgcat ctgtaggaga ccgtgtcacc      60
atcacttgcc gggcaagtca ggatatttac ctgaatttag actggtatca gcagaaacca     120
gggaaagccc ctaagctcct gatcaaattt ggttccgagt tgcaaagtgg tgtcccatca     180
cgtttcagtg gcagtggata tgggacagat ttcactctca ccatcagcaa tctgcaacct     240
gaagatttcg ctacgtacta ctgtcaaccg tcttttttact tcccttatac gttcggccaa     300
gggaccaagg tggaaatcaa atggg                                           325

<210> SEQ ID NO 51
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 51
gacatccaga tgacccagtc tccatcctcc ctgtctgcat ctgtaggaga ccgtgtcacc      60
atcacttgcc gggcaagtca ggatatttac ctgaatttag actggtatca gcagaaacca     120
gggaaagccc ctaagctcct gatcatttat ggttccgagt tgcaaagtgg tgtcccacca     180
cgtttcagtg gcagtggata tgggacagat ttcactctca ccatcagcag tctgcaacct     240
gaagattccg ctacgtacta ctgtcaaccg tcttttttact tcccttatac gttcggccaa     300
gggaccaagg tggaaatcaa acggg                                           325

<210> SEQ ID NO 52
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 52
gacatccaga tgacccagtc tccatcctcc ctgtctgcat ctgtaggaga ccgtgtcacc      60
atcacttgcc gggcaagtca ggatatatac ctgaatttag actggtatca gcagaaacca     120
gggaaagccc ctaagctcct gatcaattt ggttccgagt tgcaaagtgg tgtcccacca     180
cgtttcagtg gcagtggata tgggacagat ttcactctca ccatcagcag tctgcaacct     240
gaagatttcg ctacgtacta ctgtcaaccg tcttttttact tcccttatac gttcggccaa     300
gggaccaagg tggaaatcaa acagg                                           325

<210> SEQ ID NO 53
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 53
gacatccaga tgacccagtc tccatcctcc ctgtctgcat ctgtaggaga ccgtgtcacc      60
atcacttgcc gggcaagtca ggatatttac ctgaatttag actggtatca gcagaaacca     120
gggaaagccc ctaagctcct gatcaattt ggttccgagt tgcaaagtgg tgtcccatca     180
```
cgtttcagtg gcagtggata tgggacagat ttcgctctca ccatcagcag tctgcaacct    240
gaagattccg ctacgtacta ctgtcaaccg tcttttttact tcccatatac gttcggccaa    300
gggaccaagg tggaaatcaa acagg                                           325

<210> SEQ ID NO 54
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 54
gacatccaga tgacccagtc tccatcctcc ctgtctgcat ctgtaggaga ccgtgtcact     60
atcacttgcc gggcaagtca ggatatttac ctgaatttag actggtatca gcagaaacca    120
gggaaagccc ctaagctcct gatcaatttt ggttccgagt tgcaaagtgg tgtcccatca    180
cgtttcagtg gcagtggata tgggacagat ttcactctca ccatcagcag tctgcaacct    240
gaagatgtcg ctacgtacta ctgtcaaccg tcttttttact tcccttatac gttcggccaa    300
gggaccaagg tggaaatcaa acggg                                           325

<210> SEQ ID NO 55
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 55
gacatccaga tgacccagtc tccatcctcc ctgtctgcat ctgtaggaga ccgtgtcacc     60
atcacttgcc gggcaagtca ggatatttac ctgaatttag actggtatca gcagaaacca    120
gggaaagccc ctaagctcct gatcaatttt ggttccgagt tgcaaagtgg tgtcccatca    180
cgtttcagtg gcagtggata tgggacagat ttcactctca ccatcagcag tctgcaacct    240
gaagacttcg ctacgtacta ctgtcaaccg tcttttttact tcccatatac gtttggccaa    300
gggaccaagg tggaaatcaa acagg                                           325

<210> SEQ ID NO 56
<211> LENGTH: 325
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 56
gacatccaaa tgcccagtc tccatcctcc ctgtctgcat ctgtaggaga ccgtgtcacc      60
atcacttgcc gggcaagtca ggatatttac ctgaatttgg actggtatca gcagaaacca    120
gggaaagccc ctaagctcct gatcagtttt ggttccgagt tgcaaagtgg tgtcccatca    180
cgtttcagtg gcagtggata tgggacagat ttcactctca ccatcagcag tctgcaacct    240
gaagattccg ctacgtacta ctgtcagccg tcttttttact tcccttatac gttcggccaa    300
gggaccaagg tggaaatcaa acagg                                           325

<210> SEQ ID NO 57
<211> LENGTH: 325
<212> TYPE: DNA

<213> ORGANISM: Artificial Sequence
<220> FEATURE:
<223> OTHER INFORMATION: Nucleic acid sequence identified using
      molecular biology techniques.

<400> SEQUENCE: 57
gacatccaga tgacccagtc accatcctcc ctgtctgcat ctgtaggaga ccgtgtcacc    60
atcacttgcc gggcaagtca ggacatttac ctgaatttag actggtatca gcagaaacca   120
gggaaagccc ctaagctcct gatcaatttt ggttccgagt tgcaaagtgg tgtcccatca   180
cgtttcagtg gcagtggata tgggacagat ttcactctca ccatcagcag tctgcaacct   240
gaagatttcg ctacgtacta ctgtcaaccg tcttttttact tcccttatac gttcggccaa   300
gggaccaagg tggaaatcaa acggg                                         325

<210> SEQ ID NO 58
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 58
gacatccaga tgacccagtc tccatcctcc ctgtctgcgt ctgtaggaga ccgtgtcacc    60
atcacttgcc gggcaagtca ggatatttac ctgaatttag actggtatca gcagaaacca   120
gggaaagccc ctaagctcct gatcaatttt ggttccgagt tgcaaagtgg tgtcccatca   180
cgtttcagtg gcagtggata tgggacagat ttcacactca ccatcagcag tctgcaacct   240
gaagatttcg ctacgtacta ctgtcaaccg tcttttttact tcccttatac gttcggccaa   300
gggaccaagg tggaaatcaa actg                                          324

<210> SEQ ID NO 59
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 59
gacatccaga taacccagtc tccatcctcc ctgtctgcat ctgtaggaga ccgtgtcacc    60
atcacttgcc gggcaagtca ggatatttac ctgaatttag actggtatca gcagaaacca   120
gggaaagccc ctaagctcct gatcaatttt ggttccgagt tgcaaagtgg tgtcccatca   180
cgtttcagtg gcagtggata tgggacagat ttcactctca ccatcagcag tctgcaacct   240
gaagatttcg ctacgtacta ctgtcaaccg tcttttttact tcccttatac gttcggccaa   300
gggaccaagg tggaaatcaa accg                                          324

<210> SEQ ID NO 60
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 60
gacatccaga tgacccagtc tccatcctcc ctgtctgcat ctgtaggaga ccgtgtcacc    60
atcacttgcc gggcaagtca ggatatttac ctgaatttag actggtatca gcagaaacca   120

```
gggaaagccc ctaagctcct gatcaattt ggttccgagt tgcaaagtgg tgtcccatca    180
cgtttcagtg gcagtggata tgggacagat ttcactctca ccatcagcag tctgcaacct    240
gaagatttcg ctacgtacta ctgtcaaccg tcttttact acccttatac gttcggccaa    300
gggaccaagg tggaaatcaa acag                                            324
```

<210> SEQ ID NO 61
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 61

```
gacatccaga tgacacagtc tccatcctcc ctgtctgcat ctgtaggaga ccgtgtcacc     60
atctcttgcc gggcaagtca ggatatttac ctgaatttag actggtatca gcagaaacca    120
gggaaagccc ctaagctcct gatcagtttt ggttccgagt tgcaaagtgg tgttccttca    180
cgtttcagtg gcagtggata tgggacagat ttcactctca ccatcagcag tctgcagcct    240
gaagattccg ctacgtacta ctgtcaaccg tcttttact acccttatac gttcggccaa    300
gggaccaagg tggaaatcaa acgg                                            324
```

<210> SEQ ID NO 62
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 62

```
gacatccaga tgacccagtc tccatcctcc ctgtctgcat ctgtaggaga ccgtgtcacc     60
atcacttgcc gggcaagtca ggatatttac ctgaatttag actggtatca gcagaaacca    120
gggaaagccc ctaagctcct gatcaattt ggttccgagt tgcaaagtgg tgtcccatca    180
cgtttcagtg gcagtggata tgggacagat ttcactctca ccatcagcag tctgcaacct    240
gaagatttcg ctacgtacta ctgtcaaccg tcttttact acccttatac gttcggccaa    300
gggaccaagg tggaaatcaa acgg                                            324
```

<210> SEQ ID NO 63
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 63

```
gacatccaga tgacccagtc tccatcctcc ctgtctgcat ctgtaggaga ccgtgtcacc     60
atcacttgcc gggcaagtca ggatatttac ctgaatttag actggtatca gcagaaacca    120
gggaaagccc ctaagctcct gatcaattt ggttccgagt tgcaaagtgg agtcccatca    180
cgtttcagtg gcagtggata tgggacagat ttcactctca ccatcagcag tctgcaacct    240
gaagattccg ctacgtacta ctgtcaaccg tcttttact acccttatac gttcggccaa    300
gggaccaagg tggaaatcaa tcgg                                            324
```

<210> SEQ ID NO 64
<211> LENGTH: 324
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 64

| gacatccaga tgacccagtc tccatcctcc ctgtctgcat atgtaggaga ccgtgtcacc | 60 |
| atcacttgcc gggcaagtca ggatatttac ctgaatttag actggtatca gcagaaacca | 120 |
| gggaaagccc ctaagctcct gatcagtttt ggttccgagt tgcaaagtgg tgtcccatca | 180 |
| cgtttcagtg gcagtggata tgggacagat ttcactctca ccatcagcag tctgcaacct | 240 |
| gaagatttcg gtacgtacta ctgtcaaccg tctttttact tcccttatac gttcggccaa | 300 |
| gggaccaagg tggaaatcaa acgg | 324 |

<210> SEQ ID NO 65
<211> LENGTH: 324
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 65

| gacatccaga tgacccagtc tccatcctcc ctgtctgcat ctgtaggaga ccgtgtcacc | 60 |
| atcacttgtc gggcaagtca ggatatttac ctgaatttag actggtatca gcagaaacca | 120 |
| gggaaagccc ctaagctcct gatcaatttt ggttccgagt tgcaaagtgg tgtcccatca | 180 |
| cgtttcagtg gcagtggata tgggacagat ttcactctca ccatcagcag tctgcaacct | 240 |
| gaagatttcg gtacgtacta ctgtcaaccg tctttttact tcccttatac gttcggccaa | 300 |
| gggaccaagg tggaaatcaa acgg | 324 |

<210> SEQ ID NO 66
<211> LENGTH: 324
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 66

| gacatccaga tgacccagtc tccgtcctcc ctgtctgcat ctgtaggaga ccttgtcacc | 60 |
| atcacttgcc gggcaagtca ggatatttac ctgaatttag actggtatca gcagaaacca | 120 |
| gggaaagccc ctaagctcct gatcaattta ggttccgagt tgcaaagtgg tgtcccatca | 180 |
| cgtttcagtg gcagtggata tgggacagat ttcactctca ccatcagcag tctgcaacct | 240 |
| gaagatttcg ctacgtacta ctgtcaaccg tctttttact tcccttatac gttcggccaa | 300 |
| gggaccaagg tggaaatcaa acgt | 324 |

<210> SEQ ID NO 67
<211> LENGTH: 324
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 67

```
gacatcctga tgacccagtc tccatcctcc ctgtctgcat ctgtaggaga ccgtgtcacc    60
atcacttgcc gggcaagtca ggatatttac ctgaatttag actggtatca gcagaaacca   120
gggaaggccc ctaagctcct gatcaatctt ggttccgagt tgcaaagtgg tgtcccatca   180
cgtttcagtg gcagtggata tgggacagat ttcactctca ccatcagcag tctgcaacct   240
gaagatgtcg ctacgtacta ctgtcaaccg tcttttttact tcccttatac gttcggccaa   300
gggaccaagg tggaaatcaa acgg                                          324

<210> SEQ ID NO 68
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 68
gaggtgcagc tgttggagtc tgggggaggc ttggtacagc ctggggggtc cctgcgtctc    60
tcctgtgcag cctccggatt cacctttaag gcttatccga tgatgtgggt ccgccaggct   120
ccagggaagg gtctagagtg ggtctcagag atttcgcctt cgggttctta tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatcct   300
cggaagtttg actactgggg tcagggaacc ctggtcaccg tctcgagc                348

<210> SEQ ID NO 69
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 69
gaggtgcagc tgttggagtc tgggggaggc ttggtacagc ctggggggtc cctgcgtctc    60
tcctgtgcag cctccggatt cacctttaag gcttatccga tgatgtgggt ccgccaggct   120
ccagggaagg gtccagagtg ggtctcagag atttcgcctt cgggttctta tacatactac   180
gcagactccg tgaagggccg gttcaccatc tcccgtgaca attccaagaa cacgctgtat   240
ctgcaaatga acagcctgcg tgccgaggac accgcggtat attactgtgc gaaagatcct   300
cggaagtttg actactgggg tcagggaacc ctggtcaccg tctcgagc                348

<210> SEQ ID NO 70
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 70
gaggtgcagc tgttggtgtc tgggggaggc ttggtacagc ctggggggtc cctgcgtctc    60
tcctgtgcag cctccggatt cacctttaag gcttatccga tgatgtgggt ccgccaggct   120
ccagggaagg gtccagagtg ggtctcagag atttcgcctt cgggttctta tacatactac   180
gcagactccg tgaagggccg gttcaccatc tcccgcgaca attccaagaa cgcgctgtat   240
ctgcaaatga acagcctgcg tgcagaggac accgcggtat attactgtgc gaaagatcct   300
```
cggaagtttg actactgggg tcagggagcc ctggtcaccg tctcgagc    348

<210> SEQ ID NO 71
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 71
gaggtgcagc tgttggtgtc tgggggaggc ttggtacagc ctgggggtc cctgcgtctc    60
tcctgtgcag cctccggatt cacctttaag gcttatccga tgatgtgggt ccgccaggct    120
ccagggaagg gtctagagtg gatctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc aaaagatcct    300
cggaagtttg actactgggg tcagggaacc ctggtcaccg tctcgagc    348

<210> SEQ ID NO 72
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 72
gaggtgcagc tgctggtgtc tgggggaggc ttggtacagc ctgggggtc cctgcgtctc    60
tcctgtgcag cctccggatt cacctttaag gcttatccga tgatgtgggt ccgccaggct    120
ccagggaagg gtctagagtg ggtctcagag atttcgcctt cgggttcata tacatactat    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtttg aatactgggg tcagggaacc ctggtcaccg tctcgagc    348

<210> SEQ ID NO 73
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 73
gaggtgcagc tgttggtgtc tgggggaggc ttggtacagc ctgggggtc cctgcgtctc    60
tcctgtgcag cctccggatt cacctttaag gcttatccga tgatgtgggt ccgccaggct    120
ccagggaagg gtctagagtg ggtctcagag atttcgcctt cgggttctta tacatactac    180
gcggactccg tgaagggccg gttcaccatc tcccgcgaca attccaagaa cacgctgtat    240
ctgcaaatga acagcctgcg tgccgaggac accgcggtat attactgtgc gaatgatcct    300
cggaagtttg actactgggg tcagggaacc ctggtcaccg tctcgagc    348

<210> SEQ ID NO 74
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 74

```
gaggtgcagc tgttggagtc tgggggaggc ttggtacagc ctggggggtc cctgcgtctc      60
tcctgtgcag cctccggatt cacatttaag gcttatccga tgatgtgggt ccgccaggct     120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acggcctgcg tgccgaggac accgcggtat attactgtgc gaacgatcct    300
cggaagattg actactgggg tcagggaacc ctggtcaccg tctcgagc                 348
```

<210> SEQ ID NO 75
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 75

```
gaggtgcagc tgttggtgtc tgggggaggc ttggtacagc ctggggggtc cctgcgtctc      60
tcctgtgcag cctccggatt caccttaag gcttatccga tgatgtgggt ccgccaggct     120
ccagggaagg gtctagagtg ggtctcagag atttcgcctt cgggttctta tacatactac    180
gcatactccg tgaagggccg gttcaccatc tcccgcgaca attccaagaa cacgctgtat    240
ctgcaaatga acagcctgca tgccgaggac accgcggtat attactgtgc gaaagatcct    300
cggaagttag actactgggg tcagggaacc ctggtcaccg tctcgagc                 348
```

<210> SEQ ID NO 76
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 76

```
gaggtgcagc tgttggagtc tgggggaggc ttggtacagc cagggggtc cctgcgtctc       60 tcctgtgctg cctccggatt caccttaag gcttatccga tgatgtgggt ccgccaggct     120
ccagggaaga gtctagagtg ggtctcagag atttcgcctt cgggttctta tacatactac    180
gcagactccg tgaagggccg gttcacaatc tcccgcgaca attccaagaa cacgctgtat    240
ctgcaaatga acagcctgcg tgccgaggac accgcggtat attactgtgc gaaagatcct    300
cggaagattg actactgggg tcagggaacc ctggtcaccg tctcgagc                 348
```

<210> SEQ ID NO 77
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 77

```
gaggtgcagc tggtggagtc tgggggaggc ttggtacagc ctggggggtc cctgcgtctc      60
tcctgtgcag cctccggatt caccttaag gcttatccga tgatgtgggt ccgccaggct     120
ccagggaagg gtctagagtg ggtctcagag atttcgcctt cgggttctta tacatactac    180
gcagagtccg tgaagggccg gttcaccatc tcccgcgaca attccaagaa cacgctgtat    240
```

```
ctgcaaatga acagcctgcg tgccgaggac accgcggtat attactgtac gaaagatcct      300
cggaagtttg actactgggg tcagggaacc ctggtcaccg tctcgagc                  348
```

<210> SEQ ID NO 78
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 78

```
gaggtgcagt tgttggtgtc tgggggaggc ttggtacagc ctgggggtc cctgcgtctc       60 tcctgtgcag cctccggatt cacctttaag gcttatccga tgatgtgggt ccgccaggct     120
ccagggaagg gtctagagtg ggtctcagag atttcgcctt cgggttctta tacatactac    180
gcagactccg tgaagggccg gttcaccatt tcccgcgaca attccaagaa cacgctgtat    240
ctgcaaatga acagcctgcg tgccgaggac accgcggtat attactgtgc gaaagatcct    300
cggaagtttg actactgggg tcagggaacc ctggtcaccg tctcgagc                  348
```

<210> SEQ ID NO 79
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 79

```
gaggtgcagc tgttggagtc tgggggaggc ttggtacagc ctgggggtc cctgcgtctc       60 tcctgtgcag cctccggatt cacctttaag gcttatccga tgatgtgggt ccgccaggct     120
ccagggaagg gtctagagtg ggtctcagag atttcgcctt cgggttctta tacatactac    180
gcaaactccg tgaagggtcg gttcaccatc tcccgcgaca attccaagaa cacgctgtat    240
ctgcaaatga acagcctgcg tgccgaggac accgcggtat attactgtgc gaaagatcct    300
cggaagattg actactgggg tcagggaacc ctggtcaccg tctcgagc                  348
```

<210> SEQ ID NO 80
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 80

```
gaggtgcagc tgttggagtc tgggggaggc ttggtacagc ctgggggtc cctgcgtctc       60 tcctgtgcag cctccggatt cacctttaag gcttatccga tgatgtgggt ccgccaggct     120
ccagggaagg gtctagagtg ggtctcagag atttcgcctt cgggttctta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcct    300
cggaagtctg actactgggg tcagggaacc ctggtcaccg tctcgagc                  348
```

<210> SEQ ID NO 81
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 81

```
gaggtgcagc tgttggagtc tggggggaggc ttggtacagc ctgggggggtc cctgcgtctc    60
tcctgtgcag cctccggatt cacctttaag gcttatccga tgatgtgggt ccgccaggct   120
ccagggaagg gtctagagtg ggtctcagag atctcgcctt cgggttctta tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatcct   300
cggaagattg actactgggg tcagggaacc ctggtcaccg tctcgagc                348
```

<210> SEQ ID NO 82
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 82

```
gaggtgcatc tgttggagtc tggggggaggc ttggtacagc ctgggggggtc cctgcgtctc    60
tcctgtgcag cctccggatt cacctttaag gcttatccga tgatgtgggt ccgccaggct   120
ccagggaagg gtctagagtg ggtctcagag atttcgcctt cgggttctta tacatactac   180
gcaaactccg tgaagggccg gttcaccatc tcccgcgaca attccaagaa cacgctgtat   240
ctgcaaatga acagcctgcg tgccgaggac accgcggtat attactgtgc gaaagatcct   300
cggaagattg actactgggg tcagggaacc ctggtcaccg tctcgagc                348
```

<210> SEQ ID NO 83
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 83

```
gaggtgcagc tgttggagtc tggggggaggc ttggtacagc ctgggggggtc cctgcgtctc    60
tcctgtgcag cctccggatt cacctttaag gcttatccga tgatgtgggt ccgccaggct   120
ccagggaagg gtctagagtg ggtctcagag atttcgcctt cgggttctta tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatcct   300
cggaagttag actactgggg tcagggaacc ctggtcaccg tctcgagc                348
```

<210> SEQ ID NO 84
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 84

```
gaggtgcagc tgttggtgtc tggggggaggc ttggtacagc ctgggggggtc cctgcgtctc    60
tcctgtgcag cctccggatt cacctttaag gcttatccga tgatgtgggt ccgccaggct   120
```

| | |
|---|---|
| ccagggaagg gtctagagtg ggtctcagag atttcgcctt cgggttctta tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtac gaaagatcct | 300 |
| cggaagtttg actactgggg tcagggaacc ctggtcaccg tctcgagc | 348 |

<210> SEQ ID NO 85
<211> LENGTH: 348
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 85

| | |
|---|---|
| gaggtgcagc tgttggtgtc tgggggaggc ttggtacagc ctgggggtc cctgcgtctc | 60 |
| tcctgtgcag cctccggatt cacctttaag gcttatccga tgatgtgggt ccgccaggct | 120 |
| ccagggaagg gtctagagtg ggtttcagag atttcgcctt cgggttctta tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaagatcct | 300 |
| cggaagttag actactgggg tcagggaacc ctggtcaccg tctcgagc | 348 |

<210> SEQ ID NO 86
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 86

| | |
|---|---|
| gacatccaga tgacccagtc tccatcctcc ctgtctgcat ctgtaggaga ccgtgtcacc | 60 |
| atcacttgcc gggcaagtca gtggattggt ccggagttaa gttggtacca gcagaaacca | 120 |
| gggaaagccc ctaagctcct gatctatcat acgtccattt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag tatatgtttc agcctaggac gttcggccaa | 300 |
| gggaccaagg tggaaatcag acgg | 324 |

<210> SEQ ID NO 87
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 87

| | |
|---|---|
| gacatccaga tgacccagtc tccatcctcc ctgtctgcat ctgtaggaga ccgtgtcacc | 60 |
| atcacttgcc gggcaagtca gtggattggt ccggagttaa gttggtacca gcagaaacca | 120 |
| gggaaagccc ctaagcgcct gatctatcat tcgtccattt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag tatatgtttg agcctaggac gttcggccaa | 300 |
| gggaccaagg tggaaatcag acag | 324 |

<210> SEQ ID NO 88

<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 88

```
gacatccaga tgacccagtc tccatcctcc ctgtctgcat ctgtaggaga ccgtgtcacc    60
atcacttgtc gggcaagtca gtggattggt ccggagttaa gatggtacca gaagaaacca   120
gggaaagccc ctaagctcct gatctatcat acgtccattt tgcaaagtgg ggtcccatca   180
cgtttcagtg gcagtggatc tgggacagat ttcactctca ccatcagcag tctgcaacct   240
gaagattttg ctacgtacta ctgtcaacag tatatgtttc agcctaggac gttcggccaa   300
gggaccaagg tggaaatcag acgg                                          324
```

<210> SEQ ID NO 89
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 89

```
gacatccaga tgacccagtc tccatcctcc ctgtctgcat ctgtaggaga ccgtgtcacc    60
atcacttgcc gggcaagtca gtggattggt ccggagttaa gttggtacca gcagaaacca   120
gggaaagccc ctaagcacct gatctatcat acgtccattt tgcaaagtgg ggtcccatca   180
cgtttcagtg gcagtagatc tgggacagat ttcactctca ccatcagcag tctgcaacct   240
gaagattttg ctacgtacta ctgtcaacag tatatgtttc agcctaagac gttcggccaa   300
gggaccaagg tggaaatcag atgg                                          324
```

<210> SEQ ID NO 90
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 90

```
gacatccaga tgacccagtc tccatcctcc ctgtctgcat ctgtaggaga ccgtgtcacc    60
atcacttgcc gggcaagtca gtggattggt cctgagttaa gatggtacca gaagaaacca   120
gggaaagccc ctaagctcct gatctatcat acgtccattt tgcaaagtgg ggtcccatca   180
cgtttcagtg gcagtggata tgggacagat ttcactttca ccatcagcag tctgcaacct   240
gaagattttg ctacgtacta ctgtcaacag tatatgtttc agcctaggac gttcggccca   300
gggaccaagg tggaaattag acgg                                          324
```

<210> SEQ ID NO 91
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 91

```
gacatccaga tgacccagtc tccatcctcc ctgtctgcat ctgtaggaga ccgtgtcacc    60
```

```
atcacttgcc gggcaagtca gtggattggt ccggagttaa gttggtacca gcagaaacca    120
gggaaagccc ctaagctcct gatctatcat acgtccattt tgcgaagtgg ggtcccatct    180
cgtttcagtg gcagtggatc tgggacagat ttcactctca ccatcagcag tctgcaacct    240
gaagattttg ctacgtacta ctgtcaacag tatatgtttc agcctaggac gttcggccaa    300
gggaccaagg tggaaatcag atgg                                           324
```

<210> SEQ ID NO 92
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 92

```
gacatccaga tgacccagtc tccatcctcc ctgtctgcat ctgtaggaga ccgtgtcacc     60
atcacttgcc gggcaagtca gtggattggt ccggagttaa gttggtacca gcagaaacca    120
gggaaagccc ctaagcgcct gatctatcat acgtccattt tacagagtgg ggtcccatca    180
cgtttcagtg gcagtggata tgggacagat ttcactctca ccatcagcag tctgcaacct    240
gcagattttg caacgtacta ctgtcaacag tatatgtttc agcctaggac gttcggccaa    300
gggaccaagg tggaaatcag acag                                           324
```

<210> SEQ ID NO 93
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 93

```
gacatccaga tgacccagtc cccatcctcc ctgtctgcat ctgtaggaga ccgtgtcacc     60
atcacttgcc gggcaagtca gtggattggt ccggagttaa gttggtacca gcagaaacca    120
gggaaagccc ctaagctcct gatctatcat acgtccattt tgcaaagtgg ggtcccatca    180
cgtttcagtg gcagtggatc tgggacagat ttcactctca ccatcagcag tctgcaacct    240
gaagattttg ctacgtacta ctgtcaacag tatatgtttt ggcctaggac gttcggccaa    300
gggaccaagg tggaaatcag acaa                                           324
```

<210> SEQ ID NO 94
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 94

```
gacatccaga tgacccagtc tccatcctcc ctgtccgcat ctgtaggaga ccgtgtcacc     60
atcacttgcc gggcaagtca gtggattggt ccggagttaa gttggtacca gcagaaacca    120
gggaaagctc ctaagctcct gatctatcat acgtccattt tgcaaagtgg ggtcccatca    180
cgtttcagtg gcagtggata tgggacagat ttcactctca ccatcagcag tctgcaactt    240
gaagattttg ctacgtacta ctgtcaacag tatatgtttc tgcctaggac gttcggccaa    300
gggaccaagg tggaaatcag aggg                                           324
```

<210> SEQ ID NO 95
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 95

```
gacatccaga tgacccagtc tccatcctcc ctgtctgcat ctgtaggaga ccgtgtcacc    60
atcacttgcc gggcaagtca gtggattggt ccggagttaa gttggtacca gcagaaacca   120
gggaaagccc ctaagttcct gatctatcat acgtccattt gcaaagtgg ggtcccatca   180
cgtttcagtg gcagtggata tgggacagat ttcactctca ccatcaacag tctgcaacct   240
ggagattttg ctacgtacta ctgtcaacag tatatgtttc agcctaggac gttcggccaa   300
gggaccaagg tggaaatcag acgg                                          324
```

<210> SEQ ID NO 96
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 96

```
gacatccaga tgacccagtc tccatcctcc ctgtctgcat ctgtaggaga ccgtgtcacc    60
atcacttgcc gggcaagtca gtggattggt ccggagttaa gttggtacca gcagaaacca   120
gggaaagccc ctaagctcct gatctatcat acgtccattt gcaaagtgg ggtcccatca   180
cgtttcagtg gcagtggata tgggacagat ttcactctca ccatcagcag tctgcaacct   240
gaagattttg ctacgtacta ctgtcaacag tatatgtatc agcctaggac gttcggccaa   300
gggaccaagg tggaaatcag acag                                          324
```

<210> SEQ ID NO 97
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 97

```
gacatccaga tgacccagtc tccatcctcc ctgtctgcat ctgtaggaga ccgtgtcacc    60
atcacttgcc gggcaagtca gtggattggt ccggagttaa gatggtacca gcagaaacca   120
gggaaagccc ctaagctcct gatctatcat acgtccattt gcaaagtgg ggtcccatca   180
cgtttcagtg gcagtggatc tgggacagat ttcactctca ccatcagcag tctgcaacct   240
gaagattttg ctacgtacta ctgtcaacag tatatgtttc agcctatgac gttcggccaa   300
gggaccaagg tggaaatcag aggg                                          324
```

<210> SEQ ID NO 98
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 98

| | |
|---|---|
| gacatccaga tgacccagtc tccatcctcc ctgtctgcat ctgtaggaga ccgtgtcacc | 60 |
| atcacttgcc gggcaagtca gtggattggt ccggagttaa gatggtacca gaagaaacca | 120 |
| gggaaagccc ctaagctcct gatctatcat acgtccattt tgcaaagtgg ggtcccatca | 180 |
| cgtttcagtg gcagtggatc tgggacagat ttcactctca ccatcagcag tctgcaagct | 240 |
| gaagattctg ctacgtacta ctgtcaacag tatatgtttc agcctaggac gttcggccaa | 300 |
| gggaccaagg tggaaaccag acgg | 324 |

<210> SEQ ID NO 99
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 99

| | |
|---|---|
| gacatccaga tgacccagtc tccatcctcc ctgtctgcat ctgaaggaga ccgtgtcacc | 60 |
| atcacttgcc gggcaagtca gtggattggt ccggagttaa gttggtacca gcagaaacca | 120 |
| cggaaagccc ctaagctcct gatctatcat acgtccattt tgcaaagtgg ggtcccatca | 180 |
| cgtttcactg gcagtggatc tgggacagat ttcactctca ccatcagcag tctgcaacct | 240 |
| gaagattttg ctacgtacta ctgtcaacag tatatgtttc agcctatgac gttcggccaa | 300 |
| gggaccaagg tggaaatcag acgg | 324 |

<210> SEQ ID NO 100
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 100

| | |
|---|---|
| gacatcctga tgacccagtc tccatcctcc ctgtctgcat ctgtaggaga ccgtgtcacc | 60 |
| atcacttgcc gggcaagtca gtggattggt ccggagttac gttggtacca gcataaacca | 120 |
| gggaaagccc ctaagctcct gatctatcat acgtccattt tgcaaagtgg ggtcccatca | 180 |
| cgtttcagtg gcagtggata tgggacagat ttcactctct ccatcagcag tctgcaacct | 240 |
| gaagatttcg ctacgtacta ctgtcaacag tatatgtttc agcctaggac gttcggccaa | 300 |
| gggaccaagg tggaaatcag atgg | 324 |

<210> SEQ ID NO 101
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 101

| | |
|---|---|
| gacatccaga tgacccagtc tccatcctcc ctgtctgcat ctgtaggaga ccgtgtcacc | 60 |
| atcacttgcc gggcaagtca gtggattggt ccggagttaa gttggtacca gcagaaacca | 120 |
| gggaaagccc caaagctcct gatctatcat acgtccattt tgcaaggtgg ggtcccatca | 180 |
| cgtttcagtg gcagtggatc tgggacagat ttcactctca ccatcagcag tctgcaacct | 240 |

```
gaggattttg ctacgtacta ctgtcaacag tatatgtttt ggcctaggac gttcggccaa    300
gggaccaagg tggaaatcag acag                                           324
```

<210> SEQ ID NO 102
<211> LENGTH: 300
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 102

```
gacatccaga tgacccagtc tccatcctcc ctgtctgcat ctgtaggaga ccgtgtcacc    60
atcacttgcc gggcaagtca gtggattggt ccggagttac gttggtacca gcagaaacca   120
gggaaagccc ctaagctcct gatctatcat acgtccattt tgcaaagtgg ggtcccatca   180
cgtttcagtg gcagtggatc tgggacagat ttcactctca ccatcagcag tctgcaacct   240
gaagattttg ctacgtacta ctgtcaacag tatatgtttc agcctatgac gttcggccaa   300
```

<210> SEQ ID NO 103
<211> LENGTH: 108
<212> TYPE: PRT
<213> ORGANISM: Artificial Sequence
<220> FEATURE:
<223> OTHER INFORMATION: Amino acid sequence identified using
      molecular biology techniques.

<400> SEQUENCE: 103

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Arg Asn Ser Phe Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Thr Val Pro Pro
                 85                  90                  95

Thr Phe Gly Gln Gly Thr Lys Val Glu Ile Lys Gln
            100                 105
```

<210> SEQ ID NO 104
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 104

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Arg Asn Ser Pro Leu Gln Ser Gly Val Pro Ser Arg Phe Ser Gly
 50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Ser Ile Pro Pro
                 85                  90                  95

Thr Phe Gly Gln Gly Thr Lys Val Glu Ile Lys Arg
            100                 105
```

<210> SEQ ID NO 105
<211> LENGTH: 108
<212> TYPE: PRT
<213> ORGANISM: Artificial Sequence
<220> FEATURE:
<223> OTHER INFORMATION: Amino acid sequence identified using molecular biology techniques.

<400> SEQUENCE: 105

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Arg Pro Ile Gly Thr Thr
                 20                  25                  30

Leu Ser Trp Tyr Gln Gln Lys Pro Gly Lys Ala Pro Lys Leu Leu Ile
             35                  40                  45

Trp Phe Gly Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Ala Gly Thr His Pro Thr
                 85                  90                  95

Thr Phe Gly Gln Gly Thr Lys Val Glu Ile Lys Arg
            100                 105
```

<210> SEQ ID NO 106
<211> LENGTH: 108
<212> TYPE: PRT
<213> ORGANISM: Artificial Sequence
<220> FEATURE:
<223> OTHER INFORMATION: Amino acid sequence identified using molecular biology techniques.

<400> SEQUENCE: 106

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Lys Tyr Ile Gly Ser Gln
                 20                  25                  30

Leu Asn Trp Tyr Gln Gln Lys Pro Gly Lys Ala Pro Lys Leu Leu Ile
             35                  40                  45

Ala Trp Ala Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Arg Gln Gly Ala Ala Ser Pro Arg
                 85                  90                  95

Thr Phe Gly Gln Gly Thr Lys Val Glu Ile Lys Arg
            100                 105
```

<210> SEQ ID NO 107
<211> LENGTH: 108
<212> TYPE: PRT
<213> ORGANISM: Artificial Sequence

```
<220> FEATURE:
<223> OTHER INFORMATION: Amino acid sequence identified using molecular
      biology techniques.

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Ile Tyr Arg Tyr
            20                  25                  30

Leu Ser Trp Tyr Gln Gln Lys Pro Gly Lys Val Pro Lys Leu Leu Ile
        35                  40                  45

Tyr Asn Ala Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ala His Leu Pro Arg
                85                  90                  95

Thr Phe Gly Gln Gly Thr Lys Val Glu Ile Lys Arg
            100                 105

<210> SEQ ID NO 108
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Ala Ala Leu Pro Arg
                85                  90                  95

Thr Phe Gly Gln Gly Thr Lys Val Glu Ile Lys Arg
            100                 105

<210> SEQ ID NO 109
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ala Thr Tyr
            20                  25                  30

Leu Asn Trp Tyr Gln Gln Lys Pro Gly Lys Ala Pro Lys Leu Leu Ile
        35                  40                  45
```

Tyr Arg Ser Ser Ser Leu Gln Ser Ala Val Pro Arg Phe Ser Gly
            50                  55                  60

Ser Gly Ser Gly Thr Val Phe Thr Leu Thr Ile Ser Ser Leu Gln Pro
 65                  70                  75                  80

Glu Asp Phe Ala Thr Tyr Tyr Cys Gln Gln Thr Tyr Ala Val Pro Pro
                 85                  90                  95

Thr Phe Gly Gln Gly Thr Lys Val Glu Ile Lys Arg
            100                 105

<210> SEQ ID NO 110
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 110

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Asp Thr Gly
                 20                  25                  30

Leu Ala Trp Tyr Gln Gln Lys Pro Gly Lys Ala Pro Arg Leu Leu Ile
             35                  40                  45

Tyr Asn Val Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Ile Gly Asp Pro Val
                 85                  90                  95

Thr Phe Gly Gln Gly Thr Lys Val Glu Ile Lys Arg
            100                 105

<210> SEQ ID NO 111
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 111

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Tyr Ser Trp
                 20                  25                  30

Leu Ala Trp Tyr Gln Gln Arg Pro Gly Lys Ala Pro Lys Leu Leu Ile
             35                  40                  45

Tyr Asn Ala Ser His Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Ile Gly Asp Pro Val
                 85                  90                  95

Thr Phe Gly Gln Gly Thr Lys Val Glu Ile Lys Arg
            100                 105

<210> SEQ ID NO 112
<211> LENGTH: 108

```
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Thr Leu Leu Ile
        35                  40                  45

Tyr Arg Leu Ser Val Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Asn Val Pro Pro
                85                  90                  95

Thr Phe Gly Gln Gly Thr Lys Val Glu Ile Lys Arg
            100                 105

<210> SEQ ID NO 113
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Gln Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Ala Val Pro Pro
                85                  90                  95

Thr Phe Gly Gln Gly Thr Lys Val Glu Ile Lys Arg
            100                 105

<210> SEQ ID NO 114
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

```
                35                  40                  45
Tyr Arg Asn Ser Pro Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Arg Val Pro Pro
                 85                  90                  95

Thr Phe Gly Gln Gly Thr Lys Val Glu Ile Lys Arg
            100                 105
```

<210> SEQ ID NO 115
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 115

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln His Ile Gly Leu Trp
             20                  25                  30

Leu His Trp Tyr Gln Gln Lys Pro Gly Lys Ala Pro Lys Leu Leu Ile
         35                  40                  45

Tyr Arg Ser Ser Leu Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Lys Tyr Asn Leu Pro Tyr
                 85                  90                  95

Thr Ser Gly Gln Gly Thr Lys Val Glu Ile Lys Arg
            100                 105
```

<210> SEQ ID NO 116
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 116

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Phe Arg His
             20                  25                  30

Leu Lys Trp Tyr Gln Gln Lys Pro Gly Lys Ala Pro Lys Leu Leu Ile
         35                  40                  45

Tyr Ala Ala Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Ala Leu Tyr Pro Lys
                 85                  90                  95

Thr Phe Gly Gln Gly Thr Lys Val Glu Ile Lys Arg
            100                 105
```

```
<210> SEQ ID NO 117
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ile Lys His
            20                  25                  30

Leu Lys Trp Tyr Gln Gln Lys Pro Gly Lys Ala Pro Lys Leu Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Arg Trp Pro Gln
                85                  90                  95

Thr Phe Gly Gln Gly Thr Lys Val Glu Ile Lys Arg
            100                 105

<210> SEQ ID NO 118
<211> LENGTH: 108
<212> TYPE: PRT
<213> ORGANISM: 'Artificial Sequence
<220> FEATURE:
<223> OTHER INFORMATION: Amino acid sequence identified using molecular
      biology techniques.

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Tyr His
            20                  25                  30

Leu Lys Trp Tyr Gln Gln Lys Pro Gly Lys Ala Pro Lys Leu Leu Ile
        35                  40                  45

Tyr Lys Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Arg Lys Val Pro Arg
                85                  90                  95

Thr Phe Gly Gln Gly Thr Lys Val Glu Ile Lys Arg
            100                 105

<210> SEQ ID NO 119
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 119

Asp Ile Gln Thr Thr Gln Ser Pro Ser Ser Leu Ser Ala Ser Val Gly
1               5                   10                  15

Asp Arg Val Thr Ile Thr Cys Arg Ala Ser Gln Tyr Ile Gly Arg Tyr
            20                  25                  30
```

```
Leu Arg Trp Tyr Gln Gln Lys Pro Gly Lys Ala Pro Lys Leu Leu Ile
            35                  40                  45

Tyr Asp Ser Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Tyr Arg Met Pro Tyr
                 85                  90                  95

Thr Phe Gly Gln Gly Thr Arg Val Glu Ile Lys Arg
                100                 105
```

<210> SEQ ID NO 120
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 120

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln His Ile His Arg Glu
             20                  25                  30

Leu Arg Trp Tyr Gln Gln Lys Pro Gly Lys Ala Pro Lys Leu Leu Ile
            35                  40                  45

Tyr Gln Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Lys Tyr Leu Pro Pro Tyr
                 85                  90                  95

Thr Phe Gly Gln Gly Thr Lys Val Glu Ile Lys Arg
                100                 105
```

<210> SEQ ID NO 121
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 121

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln His Ile His Arg Glu
             20                  25                  30

Leu Arg Trp Tyr Gln Gln Lys Pro Gly Lys Ala Pro Lys Leu Leu Ile
            35                  40                  45

Tyr Gln Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Tyr Arg Val Pro Tyr
                 85                  90                  95

Thr Phe Gly Gln Gly Thr Lys Val Glu Ile Lys Arg
                100                 105
```

<210> SEQ ID NO 122
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Arg
            20                  25                  30

Leu Lys Trp Tyr Gln Gln Lys Pro Gly Ala Ala Pro Arg Leu Leu Ile
        35                  40                  45

Tyr Arg Thr Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Ser Gln Trp Pro His
                85                  90                  95

Thr Phe Gly Gln Gly Thr Lys Val Glu Ile Lys Arg
            100                 105

<210> SEQ ID NO 123
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Lys Asn
            20                  25                  30

Leu Arg Trp Tyr Gln Gln Lys Pro Gly Lys Ala Pro Lys Leu Leu Ile
        35                  40                  45

Tyr Asn Ser Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Ser Pro Tyr
                85                  90                  95

Thr Phe Gly Gln Gly Thr Lys Val Glu Ile Lys Arg
            100                 105

<210> SEQ ID NO 124
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Asn Asn
            20                  25                  30

Leu Arg Trp Tyr Gln Gln Lys Pro Gly Lys Ala Pro Lys Leu Leu Ile
        35                  40                  45

Tyr Asn Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Trp Arg Ala Pro Tyr
                85                  90                  95

Thr Phe Gly Gln Gly Thr Lys Val Glu Ile Lys Arg
            100                 105

<210> SEQ ID NO 125
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Tyr Lys Ser
            20                  25                  30

Leu Gly Trp Tyr Gln Gln Lys Pro Gly Lys Ala Pro Lys Leu Leu Ile
        35                  40                  45

Tyr Gln Ser Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Gln Met Pro Arg
                85                  90                  95

Thr Phe Gly Gln Gly Thr Lys Val Glu Ile Lys Arg
            100                 105

<210> SEQ ID NO 126
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Tyr Arg His
            20                  25                  30

Leu Arg Trp Tyr Gln Gln Lys Pro Gly Lys Ala Pro Lys Leu Leu Ile
        35                  40                  45

Tyr Asp Ala Ser Arg Leu Gln Ser Gly Val Pro Thr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr His Asn Pro Pro Lys
                85                  90                  95

Thr Phe Gly Gln Gly Thr Lys Val Glu Ile Lys Arg
            100                 105

<210> SEQ ID NO 127
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 127

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Tyr Ile Gly Arg Tyr
            20                  25                  30

Leu Arg Trp Tyr Gln Gln Lys Pro Gly Lys Ala Pro Lys Leu Leu Ile
        35                  40                  45

Tyr Asp Ser Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Met Gln Pro Phe
                85                  90                  95

Thr Phe Gly Gln Gly Thr Lys Val Glu Ile Lys Arg
            100                 105

<210> SEQ ID NO 128
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 128

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Arg Tyr
            20                  25                  30

Leu Arg Trp Tyr Gln Gln Lys Pro Gly Lys Ala Pro Lys Leu Leu Ile
        35                  40                  45

Tyr Asn Gly Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Gln Pro Tyr
                85                  90                  95

Thr Phe Gly Gln Gly Thr Lys Val Glu Ile Lys Arg
            100                 105

<210> SEQ ID NO 129
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 129

Asp Ile Gln Met Thr Gln Ser Pro Ser Ser Leu Ser Ala Ser Val Gly

```
                1               5                   10                  15
Asp Arg Val Thr Ile Thr Cys Arg Ala Ser Gln Tyr Ile Gly Arg Tyr
                            20                  25                  30

Leu Arg Trp Tyr Gln Gln Lys Pro Gly Lys Ala Pro Lys Leu Leu Ile
                35                  40                  45

Tyr Asp Ser Ser Val Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Ser Pro Tyr
                        85                  90                  95

Thr Phe Gly Gln Gly Thr Lys Val Glu Ile Lys Arg
                100                 105

<210> SEQ ID NO 130
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser Arg Gln
                    20                  25                  30

Leu Arg Trp Tyr Gln Gln Lys Pro Gly Lys Ala Pro Arg Leu Leu Ile
                35                  40                  45

Tyr Gly Ala Ser Val Leu Gln Ser Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ile Thr Pro Tyr
                        85                  90                  95

Thr Phe Gly Gln Gly Thr Lys Val Glu Val Lys Arg
                100                 105

<210> SEQ ID NO 131
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile His Arg Gln
                    20                  25                  30

Leu Lys Trp Tyr Gln Gln Lys Pro Gly Lys Ala Pro Lys Leu Leu Ile
                35                  40                  45

Tyr Tyr Ala Ser Ile Leu Gln Ser Gly Val Pro Ser Arg Phe Ser Gly
        50                  55                  60

Ser Gly Ser Gly Thr Asp Tyr Gln Gln Lys Pro Gly Lys Ala Pro Lys
65                  70                  75                  80

Leu Leu Ile Tyr Tyr Ala Ser Ile Leu Gln Ser Gly Val Pro Ser Arg
```

-continued

```
                85                  90                  95
Phe Ser Gly Ser Gly Ser Gly Thr Asp Ile Lys Arg
            100                 105

<210> SEQ ID NO 132
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Asp Tyr
            20                  25                  30

Asn Met Ser Trp Val Arg Gln Ala Pro Gly Lys Gly Leu Glu Trp Val
        35                  40                  45

Ser Thr Ile Thr His Thr Gly Gly Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asn Pro Ser Tyr Gln Phe Asp Tyr Trp Gly Gln Gly Thr
            100                 105                 110

Leu Val Thr Val Ser Ser
        115

<210> SEQ ID NO 133
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Leu Tyr
            20                  25                  30

Asp Met Ser Trp Val Arg Gln Ala Pro Gly Lys Gly Leu Glu Trp Val
        35                  40                  45

Ser Ser Ile Val Asn Ser Gly Val Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asn Gln Ser Tyr His Trp Asp Phe Asp Tyr Trp Gly Gln
            100                 105                 110

Gly Thr Leu Val Thr Val Ser Ser
        115                 120

<210> SEQ ID NO 134
<211> LENGTH: 123
<212> TYPE: PRT
```

<213> ORGANISM: Artificial Sequence
<220> FEATURE:
<223> OTHER INFORMATION: Amino acid sequence identified using molecular
      biology techniques.

<400> SEQUENCE: 134

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Lys Tyr
             20                  25                  30

Trp Met Ser Trp Val Arg Gln Ala Pro Gly Lys Gly Leu Glu Trp Val
         35                  40                  45

Ser Ser Ile Asp Phe Met Gly Pro His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Arg Thr Ser Met Leu Pro Met Lys Gly Lys Phe Asp Tyr
            100                 105                 110

Trp Gly Gln Gly Thr Leu Val Thr Val Ser Ser
        115                 120
```

<210> SEQ ID NO 135
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 135

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe His Arg Tyr
             20                  25                  30

Ser Met Ser Trp Val Arg Gln Ala Pro Gly Lys Gly Leu Glu Trp Val
         35                  40                  45

Ser Thr Ile Leu Pro Gly Gly Asp Val Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Thr Pro Asp Tyr Met Phe Asp Tyr Trp Gly Gln Gly Thr
            100                 105                 110

Leu Val Thr Val Ser Ser
        115
```

<210> SEQ ID NO 136
<211> LENGTH: 117
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 136

```
Glu Val Gln Leu Leu Glu Ser Gly Gly Gly Leu Val Gln Pro Gly Gly
 1               5                  10                  15
```

```
Ser Leu Arg Leu Ser Cys Ala Ala Ser Gly Phe Thr Phe Trp Lys Tyr
            20                  25                  30

Asn Met Ala Trp Val Arg Gln Ala Pro Gly Lys Gly Leu Glu Trp Val
        35                  40                  45

Ser Thr Ile Leu Gly Glu Gly Asn Asn Thr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Thr Met Asp Tyr Lys Phe Asp Tyr Trp Gly Gln Gly Thr Leu
            100                 105                 110

Val Thr Val Ser Ser
            115

<210> SEQ ID NO 137
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 137

Glu Val Gln Leu Leu Glu Ser Gly Gly Gly Leu Val Gln Pro Gly Gly
 1               5                  10                  15

Ser Leu Arg Leu Ser Cys Thr Ala Ser Gly Phe Thr Phe Asp Glu Tyr
            20                  25                  30

Asn Met Ser Trp Val Arg Gln Ala Pro Gly Lys Gly Leu Glu Trp Val
        35                  40                  45

Ser Thr Ile Leu Pro His Gly Asp Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Asp Pro Leu Tyr Arg Phe Asp Tyr Trp Gly Gln Gly Thr
            100                 105                 110

Leu Val Thr Val Ser Ser
            115

<210> SEQ ID NO 138
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 138

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Arg Met Ser Trp Val Arg Gln Ala Pro Gly Lys Gly Leu Glu Trp Val
        35                  40                  45

Ser Thr Ile Ile Ser Asn Gly Lys Phe Thr Tyr Tyr Ala Asp Ser Val
 50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Asp Trp Met Tyr Met Phe Asp Tyr Trp Gly Gln Gly Thr
            100                 105                 110

Leu Val Thr Val Ser Ser
            115

<210> SEQ ID NO 139
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 139

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Thr Tyr
                 20                  25                  30

Thr Met Ala Trp Val Arg Gln Ala Pro Gly Lys Gly Leu Glu Trp Val
             35                  40                  45

Ser Ser Ile Thr Ser Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Asn Ser Leu Tyr Lys Phe Asp Tyr Trp Gly Gln Gly Thr
            100                 105                 110

Leu Val Thr Val Ser Ser
            115

<210> SEQ ID NO 140
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 119
<223> OTHER INFORMATION: Xaa = Any Amino Acid

<400> SEQUENCE: 140

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Pro Thr
                 20                  25                  30

Asn Met Ser Trp Val Arg Gln Ala Pro Gly Lys Gly Leu Glu Trp Val
             35                  40                  45

Ser Thr Ile Thr Gly Thr Gly Ala Ala Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

-continued

```
                85                  90                  95
Ala Lys Gln Asn Ser Arg Tyr Arg Phe Asp Tyr Trp Gly Gln Gly Thr
            100                 105                 110

Leu Val Thr Val Ser Ser Xaa
        115

<210> SEQ ID NO 141
<211> LENGTH: 117
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 117
<223> OTHER INFORMATION: Xaa = Any Amino Acid

<400> SEQUENCE: 141

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
             20                  25                  30

Thr Met Ser Trp Val Arg Gln Ala Pro Gly Lys Gly Leu Glu Trp Val
         35                  40                  45

Ser Thr Ile Ser Pro Phe Gly Ser Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Gly Lys Asp Phe Asp Tyr Trp Gly Gln Gly Thr Leu Val
            100                 105                 110

Thr Val Ser Ser Xaa
        115

<210> SEQ ID NO 142
<211> LENGTH: 123
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 123
<223> OTHER INFORMATION: Xaa = Any Amino Acid

<400> SEQUENCE: 142

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
             20                  25                  30

Thr Met Ser Trp Val Arg Gln Ala Pro Gly Lys Gly Leu Glu Trp Val
         35                  40                  45

Ser Thr Ile Ser Pro Phe Gly Ser Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Lys Ser Asp Val Leu Lys Thr Gly Leu Asp Gly Phe Asp Tyr Trp
            100                 105                 110

Gly Gln Gly Thr Leu Val Thr Val Ser Ser Xaa
        115                 120

<210> SEQ ID NO 143
<211> LENGTH: 121
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 121
<223> OTHER INFORMATION: Xaa = Any Amino Acid

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Ala Tyr
            20                  25                  30

Gln Met Ala Trp Val Arg Gln Ala Pro Gly Lys Gly Leu Glu Trp Val
        35                  40                  45

Ser Thr Ile His Gln Thr Gly Phe Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Ser Met Arg Pro Tyr Lys Phe Asp Tyr Trp Gly Gln
            100                 105                 110

Gly Thr Leu Val Thr Val Ser Ser Xaa
        115                 120

<210> SEQ ID NO 144
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 144

Gly Gly Gly Gly Ser
1               5

<210> SEQ ID NO 145
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 118
<223> OTHER INFORMATION: Xaa = Any Amino Acid

<400> SEQUENCE: 145

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
```

```
                    20                  25                  30

Thr Met Ser Trp Val Arg Gln Ala Pro Gly Lys Gly Leu Glu Trp Val
            35                  40                  45

Ser Thr Ile Ser Pro Phe Gly Ser Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Asn Leu Glu Pro Phe Asp Tyr Trp Gly Gln Gly Thr Leu
            100                 105                 110

Val Thr Val Ser Ser Xaa
        115

<210> SEQ ID NO 146
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 119
<223> OTHER INFORMATION: Xaa = Any Amino Acid

<400> SEQUENCE: 146

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
            35                  40                  45

Ser Thr Ile Ser Pro Phe Gly Ser Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Lys Thr Gly Pro Ser Ser Phe Asp Tyr Trp Gly Gln Gly Thr
            100                 105                 110

Leu Val Thr Val Ser Ser Xaa
        115

<210> SEQ ID NO 147
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 118
<223> OTHER INFORMATION: Xaa = Any Amino Acid

<400> SEQUENCE: 147

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
            20                  25                  30
```

```
Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Leu Ser Asn Gly Phe Asp Tyr Trp Gly Gln Gly Thr Leu
            100                 105                 110

Val Thr Val Ser Ser Xaa
        115

<210> SEQ ID NO 148
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 119
<223> OTHER INFORMATION: Xaa = Any Amino Acid

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Val Lys Asp Asn Thr Phe Asp Tyr Trp Gly Gln Gly Thr
            100                 105                 110

Leu Val Thr Val Ser Ser Xaa
        115

<210> SEQ ID NO 149
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 119
<223> OTHER INFORMATION: Xaa = Any Amino Acid

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
            20                  25                  30
```

```
Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Lys Asn Thr Gly Gly Lys Gln Phe Asp Tyr Trp Gly Gln Gly Thr
            100                 105                 110

Leu Val Thr Val Ser Ser Xaa
        115
```

<210> SEQ ID NO 150
<211> LENGTH: 121
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 121
<223> OTHER INFORMATION: Xaa = Any Amino Acid

<400> SEQUENCE: 150

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Lys Arg Thr Glu Asn Arg Gly Val Ser Phe Asp Tyr Trp Gly Gln
            100                 105                 110

Gly Thr Leu Val Thr Val Ser Ser Xaa
        115                 120
```

<210> SEQ ID NO 151
<211> LENGTH: 121
<212> TYPE: PRT
<213> ORGANISM: Artificial Sequence
<220> FEATURE:
<223> OTHER INFORMATION: Amino acid sequence identified using molecular
      biology techniques.
<220> FEATURE:
<221> NAME/KEY: VARIANT
<222> LOCATION: 121
<223> OTHER INFORMATION: Xaa = Any Amino Acid

<400> SEQUENCE: 151

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Lys Asp Tyr
            20                  25                  30

Asp Met Thr Trp Val Arg Gln Ala Pro Gly Lys Gly Leu Glu Trp Val
```

```
                35                  40                  45
Ser Met Ile Ser Ser Ser Gly Leu Trp Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Phe Arg Leu Phe Pro Arg Thr Phe Asp Tyr Trp Gly Gln
            100                 105                 110

Gly Thr Leu Val Thr Val Ser Ser Xaa
        115                 120
```

<210> SEQ ID NO 152
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 152

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Pro Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Ser Val Pro Pro
                 85                  90                  95

Thr Phe Gly Gln Gly Thr Lys Val Glu Ile Lys Arg
            100                 105
```

<210> SEQ ID NO 153
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 153

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser Pro Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Arg Ile Pro Pro
                 85                  90                  95

Thr Phe Gly Gln Gly Thr Lys Val Glu Ile Lys Arg
```

<210> SEQ ID NO 154
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Lys Ser
            20                  25                  30

Leu Lys Trp Tyr Gln Gln Lys Pro Gly Lys Ala Pro Lys Leu Leu Ile
        35                  40                  45

Tyr Asn Ala Ser Tyr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Tyr Trp Pro Val
                85                  90                  95

Thr Phe Gly Gln Gly Thr Lys Val Glu Ile Lys Arg
            100                 105

<210> SEQ ID NO 155
<211> LENGTH: 107
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Tyr His
            20                  25                  30

Leu Lys Trp Tyr Gln Gln Lys Pro Gly Lys Ala Pro Lys Leu Leu Ile
        35                  40                  45

Tyr Lys Ser Thr Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Val Arg Lys Val Pro Arg Thr
                85                  90                  95

Phe Gly Gln Gly Thr Lys Val Glu Ile Lys Arg
            100                 105

<210> SEQ ID NO 156
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 156

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Arg Arg Tyr
            20                  25                  30

Leu Lys Trp Tyr Gln Gln Lys Pro Gly Lys Ala Pro Lys Leu Leu Ile
        35                  40                  45

Tyr Gln Ala Ser Val Leu Gln Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Leu Tyr Pro Pro Ile
                85                  90                  95

Thr Phe Gly Gln Gly Thr Lys Val Glu Ile Lys Arg
            100                 105
```

<210> SEQ ID NO 157
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 157

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Asn Trp
            20                  25                  30

Leu Lys Trp Tyr Gln Gln Lys Pro Gly Lys Ala Pro Lys Leu Leu Ile
        35                  40                  45

Tyr Arg Ala Ser Ser Leu Gln Ser Gly Val Pro Ser Arg Phe Ser Gly
50                  55                      60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Val Val Ile Pro Arg
                85                  90                  95

Thr Phe Gly Gln Gly Thr Lys Val Glu Ile Lys Arg
            100                 105
```

<210> SEQ ID NO 158
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 158

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Leu Trp His
            20                  25                  30

Leu Arg Trp Tyr Gln Gln Lys Pro Gly Lys Ala Pro Lys Leu Leu Ile
        35                  40                  45

Tyr His Ala Ser Leu Leu Gln Ser Gly Val Pro Ser Arg Phe Ser Gly
50                  55                      60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Val Tyr Pro Lys
                85                  90                  95
```

```
Thr Phe Gly Gln Gly Thr Lys Val Glu Ile Lys Arg
            100                 105
```

<210> SEQ ID NO 159
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 159

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Phe Arg Tyr
             20                  25                  30

Leu Ala Trp Tyr Gln Gln Lys Pro Gly Lys Ala Pro Lys Leu Leu Ile
         35                  40                  45

Tyr His Ala Ser His Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Leu Leu Tyr Pro Lys
                 85                  90                  95

Thr Phe Gly Gln Gly Thr Lys Val Glu Ile Lys Arg
            100                 105
```

<210> SEQ ID NO 160
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 160

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Phe Tyr His
             20                  25                  30

Leu Ala Trp Tyr Gln Gln Lys Pro Gly Lys Ala Pro Lys Leu Leu Ile
         35                  40                  45

Tyr Pro Ala Ser Lys Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Ala Arg Trp Pro Arg
                 85                  90                  95

Thr Phe Gly Gln Gly Thr Lys Val Glu Ile Lys Arg
            100                 105
```

<210> SEQ ID NO 161
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ile Trp His
            20                  25                  30

Leu Asn Trp Tyr Gln Gln Lys Pro Gly Lys Ala Pro Lys Leu Leu Ile
            35                  40                  45

Tyr Arg Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ala Arg Val Pro Arg
                85                  90                  95

Thr Phe Gly Gln Gly Thr Lys Val Glu Ile Lys Arg
            100                 105

<210> SEQ ID NO 162
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Arg Tyr
            20                  25                  30

Leu Arg Trp Tyr Gln Gln Lys Pro Gly Lys Ala Pro Lys Leu Leu Ile
            35                  40                  45

Tyr Lys Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Gly Tyr Pro Arg
                85                  90                  95

Thr Phe Gly Gln Gly Thr Lys Val Glu Ile Lys Arg
            100                 105

<210> SEQ ID NO 163
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Leu Lys Tyr
            20                  25                  30

Leu Lys Trp Tyr Gln Gln Lys Pro Gly Lys Ala Pro Lys Leu Leu Ile
            35                  40                  45

Tyr Asn Ala Ser His Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Thr Tyr Tyr Pro Ile
                85                  90                  95

Thr Phe Gly Gln Gly Thr Lys Val Glu Ile Lys Arg
            100                 105

<210> SEQ ID NO 164
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Leu Arg Tyr
            20                  25                  30

Leu Arg Trp Tyr Gln Gln Lys Pro Gly Lys Ala Pro Lys Leu Leu Ile
        35                  40                  45

Tyr Lys Ala Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu Tyr Tyr Pro Gln
                85                  90                  95

Thr Phe Gly Gln Gly Thr Lys Val Glu Ile Lys Arg
            100                 105

<210> SEQ ID NO 165
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Leu Arg Ser
            20                  25                  30

Leu Lys Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Tyr Trp Pro Ala
                85                  90                  95

Thr Phe Gly Gln Gly Thr Lys Val Glu Ile Lys Arg
            100                 105

<210> SEQ ID NO 166
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Arg His
            20                  25                  30

Leu Lys Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ala Leu Tyr Pro Lys
                85                  90                  95

Thr Phe Gly Gln Gly Thr Lys Val Glu Ile Lys Arg
            100                 105

<210> SEQ ID NO 167
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Lys Tyr
            20                  25                  30

Leu Arg Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Leu Phe Trp Pro Arg
                85                  90                  95

Thr Phe Gly Gln Gly Thr Lys Val Glu Ile Lys Arg
            100                 105

<210> SEQ ID NO 168
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro

```
                 65                  70                  75                  80

Glu Asp Phe Ala Thr Tyr Tyr Cys Gln Gln Met Leu Phe Tyr Pro Lys
                 85                  90                  95

Thr Phe Gly Gln Gly Thr Lys Val Glu Ile Lys Arg
            100                 105
```

<210> SEQ ID NO 169
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 169

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ile Lys His
                 20                  25                  30

Leu Lys Trp Tyr Gln Gln Lys Pro Gly Lys Ala Pro Lys Leu Leu Ile
             35                  40                  45

Tyr Gly Ala Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ala Arg Trp Pro Gln
                 85                  90                  95

Thr Phe Gly Gln Gly Thr Lys Val Glu Ile Lys Arg
            100                 105
```

<210> SEQ ID NO 170
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 170

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Tyr Tyr His
                 20                  25                  30

Leu Lys Trp Tyr Gln Gln Lys Pro Gly Lys Ala Pro Lys Leu Leu Ile
             35                  40                  45

Tyr Lys Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Arg Lys Val Pro Arg
                 85                  90                  95

Thr Phe Gly Gln Gly Thr Lys Val Glu Ile Lys Arg
            100                 105
```

<210> SEQ ID NO 171
<211> LENGTH: 108
<212> TYPE: PRT
<213> ORGANISM: Artificial Sequence
<220> FEATURE:
<223> OTHER INFORMATION: Amino acid sequence identified using molecular -continued biology techniques.

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Lys His
            20                  25                  30

Leu Lys Trp Tyr Gln Gln Lys Pro Gly Lys Ala Pro Lys Leu Leu Ile
        35                  40                  45

Tyr Asn Ala Ser His Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Gly Arg Tyr Pro Lys
                85                  90                  95

Thr Phe Gly Gln Gly Thr Lys Val Glu Ile Lys Arg
            100                 105

<210> SEQ ID NO 172
<211> LENGTH: 108
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Lys Ser
            20                  25                  30

Leu Lys Trp Tyr Gln Gln Lys Pro Gly Lys Ala Pro Lys Leu Leu Ile
        35                  40                  45

Tyr Asn Ala Ser Tyr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Tyr Trp Pro Val
                85                  90                  95

Thr Phe Gly Gln Gly Thr Lys Val Glu Ile Lys Arg
            100                 105

<210> SEQ ID NO 173
<211> LENGTH: 116
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Val Tyr
            20                  25                  30

Gln Met Asp Trp Val Arg Gln Ala Pro Gly Lys Gly Leu Glu Trp Val
        35                  40                  45

Ser Ser Ile Ser Ala Phe Gly Ala Lys Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Lys Phe Asp Tyr Trp Gly Gln Gly Thr Leu Val
            100                 105                 110

Thr Val Ser Ser
        115

<210> SEQ ID NO 174
<211> LENGTH: 120
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Ser Tyr
            20                  25                  30

Gln Met Thr Trp Val Arg Gln Ala Pro Gly Lys Gly Leu Glu Trp Val
        35                  40                  45

Ser Ser Ile Ser Ser Phe Gly Ser Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Asp His Asn Tyr Ser Leu Phe Asp Tyr Trp Gly Gln
            100                 105                 110

Gly Thr Leu Val Thr Val Ser Ser
        115                 120

<210> SEQ ID NO 175
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 175
gacatccaga tgacccagtc tccatcctcc ctgtctgcat ctgtaggaga ccgtgtcacc        60
atcacttgcc gggcaagtca gagcattagc agctatttaa attggtacca gcagaaacca      120
gggaaagccc ctaagctcct gatctatcgg aattcctttt tgcaaagtgg ggtcccatca      180
cgtttcagtg gcagtggatc tgggacagat ttcactctca ccatcagcag tctgcaaccc      240
gaagattttg ctacgtacta ctgtcaacag acgtatactg ttcctcctac gtttggccaa      300
gggaccaagg tggaaatcaa acag                                              324

<210> SEQ ID NO 176
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 176

```
gacatccaga tgacccagtc tccaccctcc ctgtccgcat ctgtaggaga ccgtgtcacc    60
atcacttgcc gggcaagtca gagcattagc agctatttaa attggtatca gcagaaacca   120
gggaaagccc ctaagctcct gatctatcgg aattcccctt tgcaaagtgg ggtcccatca   180
cggttcagtg gcagtggatc tgggacagat ttcactctca ccatcagcag tctgcaacct   240
gaagattttg ctacgtacta ctgtcaacag acttattcga ttcctcctac gttcggccaa   300
gggaccaagg tggaaatcaa acgg                                          324
```

<210> SEQ ID NO 177
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 177

```
gacatccaga tgacccagtc tccatcctcc ctgtctgcat ctgtaggaga ccgtgtcacc    60
atcacttgcc gggcaagtcg tccgattggg acgacgttaa gttggtacca gcagaaacca   120
gggaaagccc ctaagctcct gatctggttt ggttcccggt tgcaaagtgg ggtcccatca   180
cgtttcagtg gcagtggatc tgggacagat ttcactctca ccatcagcag tctgcaacct   240
gaagattttg ctacgtacta ctgtgcgcag gctgggacgc atcctacgac gttcggccaa   300
gggaccaagg tggaaatcaa acgg                                          324
```

<210> SEQ ID NO 178
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 178

```
gacatccaga tgacccagtc tccatcctcc ctgtctgcat ctgtaggaga ccgtgtcacc    60
atcacttgcc gggcaagtaa gtatattggt tcgcagttaa attggtacca gcagaaacca   120
gggaaagccc ctaagctcct gatcgcttgg gcgtccgttt tgcaaagtgg ggtcccatca   180
cgtttcagtg gcagtggatc tgggacagat ttcactctca ccatcagcag tctgcaacct   240
gaagattttg ctacgtacta ctgtcgtcag ggtgctgcgt cgcctcggac gttcggccaa   300
gggaccaagg tggaaatcaa acgg                                          324
```

<210> SEQ ID NO 179
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 179

```
gacattcaga tgacccagtc tccatcctcc ctgtctgcat ctgtaggaga ccgtgtcacc    60
atcacttgcc gggcaagtca gtttatttat cggtatttat cgtggtatca gcagaaacca   120
gggaaagtcc ctaagctcct gatctataat gcgtccatt tgcaaagtgg ggtcccatca   180
cgtttcagtg gcagtggatc tgggacagat ttcactctca ccatcagcag tctgcaacct   240
```

```
gaagattttg ctacgtacta ctgtcaacag catgctcatt tgcctcgtac gttcggccaa    300
gggaccaagg tggaaatcaa acgg                                           324

<210> SEQ ID NO 180
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 180
gacatccaga tgacccagtc tccatcctcc ctgtctgcat ctgtaggaga ccgtgtcacc    60
atcacttgcc gggcaagtca gaagattgct acttatttaa attggtatca gcagaaacca    120
gggaaagccc ctaagctcct gatctatagg tcttcctctt tgcaaagcgc ggtcccatca    180
cgtttcagtg gcagtggatc tgggacagtt ttcacactca ccatcagcag tctgcaacct    240
gaagattttg ctacgtacta ctgtcaacag acgtatgctg ttcctcctac gttcggccaa    300
gggaccaagg tggaaatcaa acgg                                           324

<210> SEQ ID NO 181
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 181
gacatccaga tgacccagtc tccatcctcc ctgtctgcat ctgtaggaga ccgtgtcacc    60
atcacttgcc gggcaagtca gtggattgat actgggttag cgtggtacca gcagaaacca    120
gggaaagccc ctaggctcct gatctataat gtgtccaggt tgcaaagtgg ggtcccatca    180
cgtttcagtg gcagtggatc tgggacagat ttcactctca ccatcagcag tctgcaacct    240
gaagattttg ctacgtacta ctgtcaacag tattggggta gtcctacgac gttcggccaa    300
gggaccaagg tggaaatcaa acgg                                           324

<210> SEQ ID NO 182
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 182
gacatccaga tgacccagtc tccatcctcc ctgtctgcat ctgtaggaga ccgtgtcacc    60
atcacttgcc gggcaagtca ggagatttat tcgtggttag cgtggtacca gcagagacca    120
gggaaagccc ctaagctcct gatctataat gcttcccatt tgcaaagtgg ggtcccatca    180
cgtttcagtg gcagtggatc tgggacagat ttcactctca ccatcagcag tctgcaacct    240
gaagattttg ctacgtacta ctgtcaacag gtgattggtg atcctgttac gttcggccaa    300
gggaccaagg tggaaatcaa acgg                                           324

<210> SEQ ID NO 183
<211> LENGTH: 324
<212> TYPE: DNA
<213> ORGANISM: Artificial Sequence
```

<220> FEATURE:
<223> OTHER INFORMATION: Nucleic acid sequence identified using
molecular biology techniques.

<400> SEQUENCE: 183

| gacatccaga tgacccagtc tccatcctcc ctgtctgcat ctgtaggaga ccgtgtcacc | 60 |
| atcacttgcc gggcaagtca gagcattagc agctatttaa attggtacca gcagaaacca | 120 |
| gggaaagccc ctacgctcct gatctatcgg ttgtccgtgt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag acttataatg ttcctcctac gttcggccaa | 300 |
| gggaccaagg tggaaatcaa acgg | 324 |

<210> SEQ ID NO 184
<211> LENGTH: 324
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 184

| gacatccaga tgacccagtc tccatcctcc ctgtctgcat ctgtaggaga ccgtgtcacc | 60 |
| atcacttgcc gggcaagtca gagcattagc agctatctaa attggtacca gcagaaacca | 120 |
| gggaaagccc ctaagctcct gatctatagg aattcccagt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag acttttgcgg ttcctcctac gttcggccaa | 300 |
| gggaccaagg tggagatcaa acgg | 324 |

<210> SEQ ID NO 185
<211> LENGTH: 324
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 185

| gacatccaga tgacccagtc tccatcctcc ctgtctgcat ctgtaggaga ccgtgtcacc | 60 |
| atcacttgcc gggcaagtca gagcattagc agctatttaa attggtatca gcagaaacca | 120 |
| gggaaagccc ctaagctcct gatctatcgg aattcccctt tgcaaagtgg ggtcccatca | 180 |
| cgtttcagtg gcagtggatc tgggacagat ttcactctca ccatcagcag tctgcaacct | 240 |
| gaagattttg ctacgtacta ctgtcaacag acgtataggg tgcctcctac gttcggccaa | 300 |
| gggaccaagg tggaaatcaa acgg | 324 |

<210> SEQ ID NO 186
<211> LENGTH: 324
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 186

| gacatccaga tgacccagtc tccatcctcc ctgtctgcat ctgtaggaga ccgtgtcacc | 60 |
| atcacttgcc gggcaagtca gcatattggg ttgtggttac attggtatca gcagaaacca | 120 |

```
gggaaagccc ctaagctcct gatctatagg tcttccttgt tgcaaagtgg ggtcccatca    180
cgtttcagtg gcagtggatc tgggacagat ttcactctca ccatcagcag tctgcaacct    240
gaagattttg ctacgtacta ctgtcaacag aagtataatt tgccttatac gtccggccaa    300
gggaccaagg tggaaatcaa acgg                                            324
```

<210> SEQ ID NO 187
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 187

```
gacatccaga tgacccagtc tccatcctcc ctgtctgcat ctgtaggaga ccgtgtcacc     60
atcacttgcc gggcaagtca gagcattttt cggcatttaa agtggtacca gcagaaacca    120
gggaaagccc ctaagctcct gatctatgcg gcatcccgtt tgcaaagtgg ggtcccatca    180
cgtttcagtg gcagtggatc tgggacagat ttcactctca ccatcagcag tctgcaacct    240
gaagattttg ctacgtacta ctgtcaacag gttgcgctgt atcctaagac gttcggccaa    300
gggaccaagg tggaaatcaa acgg                                            324
```

<210> SEQ ID NO 188
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 188

```
gacatccaga tgacccagtc tccatcctcc ctgtctgcat ctgtaggaga ccgtgtcacc     60
atcacttgcc gggcaagtca gagcattatt aagcatttaa agtggtacca gcagaaacca    120
gggaaagccc ctaagctcct gatctatggt gcatcccggt tgcaaagtgg ggtcccatca    180
cgtttcagtg gcagtggatc tgggacagat ttcactctca ccatcagcag tctgcaacct    240
gaagattttg ctacgtacta ctgtcaacag ggggctcggt ggcctcagac gttcggccaa    300
gggaccaagg tggaaatcaa acgg                                            324
```

<210> SEQ ID NO 189
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 189

```
gacatccaga tgacccagtc tccatcctcc ctgtctgcat ctgtaggaga ccgtgtcacc     60
atcacttgcc gggcaagtca gagcatttat tatcatttaa agtggtacca gcagaaacca    120
gggaaagccc ctaagctcct gatctataag gcatccacgt tgcaaagtgg ggtcccatca    180
cgtttcagtg gcagtggatc tgggacagat ttcactctca ccatcagcag tctgcaacct    240
gaagattttg ctacgtacta ctgtcaacag gttcggaagg tgcctcggac gttcggccaa    300
gggaccaagg tggaaatcaa acgg                                            324
```

<210> SEQ ID NO 190

```
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 190
gacatccaga cgacccagtc tccatcctcc ctgtctgcat ctgtaggaga ccgtgtcacc    60
atcacttgcc gggcaagtca gtatattggt aggtatttac gttggtatca gcagaaacca   120
gggaaagccc ctaagctcct gatctatgat tcttccgtgt tgcaaagtgg ggtcccatca   180
cgtttcagtg gcagtggatc tgggacagat ttcactctca ccatcagcag tctgcaacct   240
gaagattttg ctacgtacta ctgtcaacag cgttatcgta tgccttatac gttcggccaa   300
gggaccaggg tagaaatcaa acgg                                          324

<210> SEQ ID NO 191
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 191
gacatccaga tgacccagtc tccatcctcc ctgtctgcat ctgtaggaga ccgtgtcacc    60
atcacttgcc gggcaagtca gcatattcat agggagttaa ggtggtatca gcagaaacca   120
gggaaagccc ctaagctcct gatctatcag gcgtcccgtt tgcaaagtgg ggtcccatca   180
cgtttcagtg gcagtggatc tgggacagat ttcactctca ccatcagcag tctgcaacct   240
gaagattttg ctacgtacta ctgtcaacag aagtatctgc tccttatac gttcggccaa    300 gggaccaagg tggaaatcaa acgg                                          324

<210> SEQ ID NO 192
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 192
gacatccaga tgacccagtc tccatcctcc ctgtctgcat ctgtaggaga ccgtgtcacc    60
atcacttgcc gggcaagtca gcatattcat agggagttaa ggtggtatca gcagaaacca   120
gggaaagccc ctaagctcct gatctatcag gcgtcccgtt tgcaaagtgg ggtcccatca   180
cgtttcagtg gcagtggatc tgggacagat ttcactctca ccatcagcag tctgcaacct   240
gaagattttg ctacgtacta ctgtcaacag cgttataggg tgccttatac gttcggccaa   300
gggaccaagg tggaaatcaa acgg                                          324

<210> SEQ ID NO 193
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 193
gacatccaga tgacccagtc tccatcctcc ctgtctgcat ctgtaggaga ccgtgtcacc    60
```

```
atcacttgcc gggcaagtca gagtattggg cggaggttaa agtggtacca gcagaaacca      120
ggggcagccc ctaggctcct gatctatcgt acgtcctggt tgcaaagtgg ggtcccatca      180
cgtttcagtg gcagtggatc tgggacagat ttcactctca ccatcagcag tctgcaacct      240
gaagattttg ctacgtacta ctgtcaacag acgtcgcagt ggcctcatac gttcggccaa      300
gggaccaagg tggaaatcaa acgg                                             324
```

<210> SEQ ID NO 194
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 194

```
gacatccaga tgacccagtc tccatcctcc ctgtctgcat ctgtaggaga ccgtgtcacc       60
atcacttgcc gggcaagtca gaagatttat aagaatttac gttggtatca gcagaaacca      120
gggaaagccc ctaagctcct gatctataat tcttccattt tgcaaagtgg ggtcccatca      180
cgtttcagtg gcagtggatc tgggacagat ttcactctca ccatcagcag tctgcaacct      240
gaagattttg ctacgtacta ctgtcaacag aggtatctgt cgccttatac gttcggccaa      300
gggaccaagg tggaaatcaa acgg                                             324
```

<210> SEQ ID NO 195
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 195

```
gacatccaga tgacccagtc tccatcctcc ctgtctgcat ctgtaggaga ccgtgtcacc       60
atcacttgcc gggcaagtca gaagatttat aataatttaa ggtggtacca gcagaaacca      120
gggaaagccc ctaagctcct gatctataat acttccattt tgcaaagtgg ggtcccatca      180
cgtttcagtg gcagtggatc tgggacagat ttcactctca ccatcagcag tctgcaacct      240
gaagattttg ctacgtacta ctgtcaacag cgatggcgtg cgccttatac gttcggccaa      300
gggaccaagg tggaaatcaa acgg                                             324
```

<210> SEQ ID NO 196
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 196

```
gacattcaga tgacccagtc tccatcctcc ctgtctgcat ctgtaggaga ccgtgtcacc       60
atcacttgcc gggcaagtca gtggatttat aagtcgttag ggtggtacca gcagaaacca      120
gggaaagccc ctaagctcct gatctatcag tcttctttgt tgcaaagtgg ggtcccatca      180
cgtttcagtg gcagtggatc tgggacagat ttcactctca ccatcagcag tctgcaacct      240
gaagattttg ctacgtacta ctgtcaacag tatcatcaga tgcctcggac gttcggccaa      300
gggaccaagg tggaaatcaa acgg                                             324
```

<210> SEQ ID NO 197
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 197
gacatccaga tgacccagtc tccatcctcc ctatctgcat ctgtaggaga ccgtgtcacc      60
atcacttgcc gggcaagtca gtggatttat aggcatttaa ggtggtacca gcagaaacca     120
gggaaagccc ctaagctcct gatctatgat gcgtccaggt tgcaaagtgg ggtcccaaca     180
cgtttcagtg gcagtggatc tgggacagat ttcactctca ccatcagcag tctgcaacct     240
gaagattttg ctacgtacta ctgtcaacag actcataatc ctcctaagac gttcggccaa     300
gggaccaagg tggaaatcaa acgg                                            324

<210> SEQ ID NO 198
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 198
gacatccaga tgacccagtc tccatcctcc ctgtctgcat ctgtaggaga ccgtgtcacc      60
atcacttgcc gggcaagtca gtatattggt aggtatttac gttggtatca gcagaaacca     120
gggaaagccc ctaagctcct gatctatgat tcttccgtgt tgcaaagtgg ggtcccatca     180
cgtttcagtg gcagtggatc tgggacagat ttcactctca ccatcagcag tctgcaacct     240
gaagattttg ctacgtacta ctgtcaacag aggtatatgc agccttttac gttcggccaa     300
gggaccaagg tggaaatcaa acgg                                            324

<210> SEQ ID NO 199
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 199
gacatccaga tgacccagtc tccatcctcc ctgtccgcat ctgtaggaga ccgtgtcacc      60
atcacttgcc gggcaagtca gtggattggt cggtatttac ggtggtacca gcagaaacca     120
gggaaagccc ctaagctcct gatctataat gggtcccagt tgcaaagtgg ggtcccatca     180
cgtttcagtg gcagtggatc tgggacagat ttcactctca ccatcagcag tctgcaacct     240
gaagattttg ctacgtacta ctgtcaacag cggtatcttc agccttatac gttcggccaa     300
gggaccaagg tggaaatcaa acgg                                            324

<210> SEQ ID NO 200
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

```
<400> SEQUENCE: 200
gacatccaga tgacccagtc tccatcctcc ctgtctgcat ctgtaggaga ccgtgtcacc      60
atcacttgcc gggcaagtca gtatattggt aggtatttac gttggtatca gcagaaacca     120
gggaaagccc ctaagctcct gatctatgat tcttccgtgt tgcaaagtgg ggtcccatca     180
cgtttcagtg gcagtggatc tgggacagat ttcactctca ccatcagcag tctgcaacct    240
gaagattttg ctacgtacta ctgtcaacag cgttattctt cgccttatac gttcggccaa    300
gggaccaagg tggaaatcaa gcgg                                            324

<210> SEQ ID NO 201
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 201
gacatccaga tgacccagtc tccatcctcc ctgtctgcat ctgtaggaga ccgtgtcacc      60
atcacttgcc gggcaagtca gtatatttcg cgtcagttaa ggtggtacca gcagaaacca    120
gggaaagccc ctaggctcct gatctatggg gcgtccgttt tgcaaagcgg gatcccatca    180
cgtttcagtg gcagtggatc tgggacagat ttcactctca ccatcagcag tctgcaacct    240
gaagattttg ctacgtacta ctgtcaacag aggtatatta ctccttatac gttcggccaa    300
gggaccaagg tggaagtcaa acgg                                            324

<210> SEQ ID NO 202
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 202
gacatccaga tgacccagtc tccatcctcc ctgtctgcat ctgtaggaga ccgtgtcacc      60
atcacttgcc gggcaagtca gtggattcat aggcagttaa agtggtacca gcagaaacca    120
gggaaagccc ctaagctcct gatctattat gcttccattt tgcaaagtgg ggtcccatca    180
cgtttcagtg gcagtggatc tgggacagat ttcactctca ccatcagcag tctgcaacct    240
gaagattttg ctacgtacta ctgtcaacag acgttttcta agccttctac gttcggccaa    300
gggaccaagg tggaaatcaa acgg                                            324

<210> SEQ ID NO 203
<211> LENGTH: 354
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 203
gaggtgcagc tgttggagtc tgggggaggc ttggtacagc ctgggggtc cctgcgtctc      60 tcctgtgcag cctccggatt caccttttat gattataata tgtcttgggt ccgccaggct    120
ccagggaagg gtctagagtg gtctcaact attacgcata cggtggggt tacatactac    180 gcagactccg tgaagggccg gttcaccatc tcccgcgaca attccaagaa cacgctgtat    240
```

```
ctgcaaatga acagcctgcg tgccgaggat accgcggtat attactgtgc gaaacagaat    300
ccttcttatc agtttgacta ctggggtcag ggaaccctgg tcaccgtctc gagc          354
```

<210> SEQ ID NO 204
<211> LENGTH: 360
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 204

```
gaggtgcagc tgttggagtc tgggggaggc ttggtacagc ctgggggtc  cctgcgtctc     60 tcctgtgcag cctccggatt cacctttgat ctttatgata tgtcgtgggt ccgccaggct    120
ccagggaagg gtctagagtg ggtctcatcg attgttaatt cgggtgttag gacatactac    180
gcagactccg tgaagggccg gttcaccatc tcccgcgaca attccaagaa cacgctgtat    240
ctgcaaatga acagcctgcg tgccgaggac accgcggtat attactgtgc gaaacttaat    300
cagagttatc attgggattt tgactactgg ggtcagggaa ccctggtcac cgtctcgagc    360
```

<210> SEQ ID NO 205
<211> LENGTH: 369
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 205

```
gaggtgcagc tgttggagtc tgggggaggc ttggtacagc ctgggggtc  cctgcgtctc     60 tcctgtgcag cctccggatt cacctttcg  aagtattgga tgtcgtgggt ccgccaggct    120
ccagggaagg gtctagagtg ggtctcatct attgattta  tgggtccgca tacatactac    180
gcagactccg tgaagggccg gttcaccatc tcccgcgaca attccaagaa cacgctgtat    240
ctgcaaatga acagcctgcg tgccgaggat accgcggtat attactgtgc gaaagggagg    300
acgtcgatgt tgccgatgaa ggggaagttt gactactggg gtcagggaac cctggtcacc    360
gtctcgagc                                                             369
```

<210> SEQ ID NO 206
<211> LENGTH: 354
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 206

```
gaggtgcagc tgttggagtc tgggggaggc ttggtacagc ctgggggtc  cctgcgtctc     60 tcctgtgcag cctccggatt cacctttcat cgttattcga tgtcttgggt ccgccaggct    120
ccagggaagg gtctagagtg ggtctcaacg attttgcctg tggtgatgt  tacatactac    180 gcagactccg tgaagggccg gttcaccatc tcccgcgaca attccaagaa cacgctgtat    240
ctgcaaatga acagcctgcg tgccgaggat accgcggtat attactgtgc gaaacagacg    300
cctgattata tgtttgacta ctggggtcag ggaaccctgg tcaccgtctc gagc          354
```

<210> SEQ ID NO 207
<211> LENGTH: 351
<212> TYPE: DNA

<213> ORGANISM: Artificial Sequence
<220> FEATURE:
<223> OTHER INFORMATION: Nucleic acid sequence identified using
      molecular biology techniques.

<400> SEQUENCE: 207

| gaggtgcagc tgttggagtc tgggggaggc ttggtacagc ctgggggtc cctgcgtctc | 60 |
| tcctgtgcag cctccggatt caccttttgg aagtataata tggcgtgggt ccgccaggct | 120 |
| ccagggaagg gtctagagtg gtctcaact attcttggtg agggtaataa tacatactac | 180 |
| gcagactccg tgaagggccg gttcaccatc tcccgcgaca attccaagaa cacgctgtat | 240 |
| ctgcaaatga acagcctgcg tgccgaggat accgcggtat attactgtgc gaaaacgatg | 300 |
| gattataagt ttgactactg gggtcaggga accctggtca ccgtctcgag c | 351 |

<210> SEQ ID NO 208
<211> LENGTH: 354
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 208

| gaggtgcagc tgttggagtc tgggggaggc ttggtacagc ctgggggtc cctgcgtctc | 60 |
| tcctgtacag cctccggatt caccttttgat gagtataata tgtcttgggt ccgccaggct | 120 |
| ccagggaagg gtctagagtg gtctcaacg attctgccgc atggtgatcg gacatactac | 180 |
| gcagactccg tgaagggccg gttcaccatc tcccgcgaca attccaagaa cacgctgtat | 240 |
| ctgcaaatga acagcctgcg tgccgaggat accgcggtat attactgtgc gaaacaggat | 300 |
| cctttgtata ggtttgacta ctggggtcag ggaaccctgg tcaccgtctc gagc | 354 |

<210> SEQ ID NO 209
<211> LENGTH: 354
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 209

| gaggtgcagc tgttggagtc tgggggaggc ttggtacagc ctgggggtc cctgcgtctc | 60 |
| tcctgtgcag cctccggatt caccttttcg gattatcgga tgagttgggt ccgccaggct | 120 |
| ccagggaagg gtctagagtg gtctcaacg attatttcga atggtaagtt tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaacaggat | 300 |
| tggatgtata tgtttgacta ctggggtcag ggaaccctgg tcaccgtctc gagc | 354 |

<210> SEQ ID NO 210
<211> LENGTH: 354
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 210

| gaggtgcagc tgttggagtc tgggggaggc ttggtacagc ctgggggtc cctgcgtctc | 60 |
| tcctgtgcag cctccggatt caccttttcgg acgtatacta tggcttgggt ccgccaggcc | 120 |

```
ccagggaagg gtctagagtg ggtctcatcg attactagta gtggttcttc tacatactac    180
gcagactccg tgaagggccg gttcaccatc tcccgcgaca attccaagaa cacgctgtat    240
ctgcaaatga acagcctgcg tgccgaggat accgcggtat attactgtgc gaaagtgaat    300
tctttgtata agtttgacta ctggggtcag ggaaccctgg tcaccgtctc gagc          354
```

<210> SEQ ID NO 211
<211> LENGTH: 355
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 211

```
gaggtgcagc tgttggagtc tgggggaggc ttggtacagc ctgggggtc cctgcgtctc      60 tcctgtgcag cctccggatt cacctttcgg ccgactaata tgtcgtgggt ccgccaggct    120
ccagggaagg gtctagagtg gtctcaact attactggta ctggtgctgc gacatactac    180
gcagactccg tgaagggccg gttcaccatc tcccgcgaca attccaagaa cacgctgtat    240
ctgcaaatga acagcctgcg tgccgaggac accgcggtat attactgtgc gaaacagaat    300
tctcgttata ggtttgacta ctggggtcag ggaaccctgg tcaccgtctc gagcg         355
```

<210> SEQ ID NO 212
<211> LENGTH: 349
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 212

```
gaggtgcagc tgttggagtc tgggggaggc ttggtacagc ctgggggtc cctgcgtctc      60 tcctgtgcag cctccggatt caccttttgg ccgtatacga tgagttgggt ccgccaggct    120
ccagggaagg gtctagagtg gtctcaacg atttcgccgt ttggttcgac tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaggggggg  300 aaggattttg actactgggg tcagggaacc ctggtcaccg tctcgagcg                349
```

<210> SEQ ID NO 213
<211> LENGTH: 367
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 213

```
gaggtgcagc tgttggagtc tgggggaggc ttggtacagc ctgggggtc cctgcgtctc      60 tcctgtgcag cctccggatt cacctttgg ccgtatacga tgagttgggt ccgccaggct    120
ccagggaagg gtctagagtg gtctcaacg atttcgccgt ttggttcgac tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaagtgat    300
gttcttaaga cgggtctgga tggttttgac tactggggtc agggaaccct ggtcaccgtc    360
tcgagcg                                                                367
```

<210> SEQ ID NO 214
<211> LENGTH: 361
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 214
gaggtgcagc tgttggagtc tgggggaggc ttggtacagc ctgggggtc cctgcgtctc      60 tcctgtgcag cctccggatt cacctttatg gcgtatcaga tggcttgggt ccgccaggct     120
ccagggaagg gtctagagtg ggtctcaact attcatcaga cgggttttc tacatactac     180 gcagactccg tgaagggccg gttcaccatc tcccgcgaca attccaagaa cacgctgtat     240
ctgcaaatga acagcctgcg tgccgaggat accgcggtat attactgtgc gaaagtgcgt     300
tctatgcgtc cttataagtt tgactactgg ggtcagggaa ccctggtcac cgtctcgagc     360
g                                                                    361

<210> SEQ ID NO 215
<211> LENGTH: 352
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 215
gaggtgcagc tgttggagtc tgggggaggc ttggtacagc ctgggggtc cctgcgtctc      60 tcctgtgcag cctccggatt caccttttgg ccgtatacga tgagttgggt ccgccaggct    120
ccagggaagg gtctagagtg ggtctcaacg atttcgccgt ttggttcgac tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaggtaat    300
cttgagccgt ttgactactg ggtcaggga accctggtca ccgtctcgag cg             352

<210> SEQ ID NO 216
<211> LENGTH: 355
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 216
gaggtgcagc tgttggagtc tgggggaggc ttggtacagc ctgggggtc cctgcgtctc      60 tcctgtgcag cctccggatt caccttttgg ccgtatacga tgagttgggt ccgccaggct    120
ccagggaagg gtctagagtg ggtctcaacg atttcgccgt ttggttcgac tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaaagacg    300
ggtccgtcgt cgtttgacta ctggggtcag ggaaccctgg tcaccgtctc gagcg         355

<210> SEQ ID NO 217
<211> LENGTH: 352
<212> TYPE: DNA
<213> ORGANISM: Artificial Sequence
<220> FEATURE:
<223> OTHER INFORMATION: Nucleic acid sequence identified using

<400> SEQUENCE: 217

```
gaggtgcagc tgttggagtc tgggggaggt ttggtacagc ctggggggtc cctgcgtctc    60
tcctgtgcag cctccggatt cacctttggg ccgtatacga tgagttgggt ccgccaggct   120
ccagggaagg gtctagagtg gtctcaacg atttcgccgt ttggttcgac tacatactac   180
gcagactccg tgaagggccg gttcaccatc tcccgcgaca attccaagaa cacgctgtat   240
ctgcaaatga acagcctgcg tgccgaggat accgcggtat attactgtgc gaaaaagctt   300
agtaatggtt ttgactactg gggtcaggga accctggtca ccgtctcgag cg           352
```

<210> SEQ ID NO 218
<211> LENGTH: 355
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 218

```
gaggtgcagc tgttggagtc tgggggaggc ttggtacagc ctggggggtc cctgcgtctc    60
tcctgtgcag cctccggatt cacctttggg ccgtatacga tgagttgggt ccgccaggct   120
ccagggaagg gtctagagtg gtctcaacg atttcgccgt ttggttcgac tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagtggtt   300
aaggataata cgtttgacta ctggggtcag ggaaccctgg tcaccgtctc gagcg        355
```

<210> SEQ ID NO 219
<211> LENGTH: 355
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 219

```
gaggtgcagc tgttggagtc tgggggaggc ttggtacagc ctggggggtc cctgcgtctc    60
tcctgtgcag cctccggatt cacctttggg ccgtatacga tgagttgggt ccgccaggct   120
ccagggaagg gtctagagtg gtctcaacg atttcgccgt ttggttcgac tacatactac   180
gcagactccg tgaagggccg gttcaccatt tcccgcgaca attccaagaa cacgctgtat   240
ctgcaaatga acagcctgcg tgccgaggac accgcggtat attactgtgc gaaaaatact   300
gggggtaagc agtttgacta ctggggtcag ggaaccctgg tcaccgtctc gagcg        355
```

<210> SEQ ID NO 220
<211> LENGTH: 361
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 220

```
gaggtgcagc tgttggagtc tgggggaggc ttggtacagc ctggggggtc cctgcgtctc    60
tcctgtgcag cctccggatt cacctttggg ccgtatacga tgagttgggt ccgccaggct   120
ccagggaagg gtctagagtg gtctcaacg atttcgccgt ttggttcgac tacatactac   180
```

```
gcagactccg tgaagggccg gttcaccatc tcccgcgaca attccaagaa cacgctgtat    240
ctgcaaatga acagcctgcg tgccgaggac accgcggtat attactgtgc gaaaaggact    300
gagaataggg gggtttcttt tgactactgg ggtcaggaa ccctggtcac cgtctcgagc    360
g                                                                    361
```

<210> SEQ ID NO 221
<211> LENGTH: 361
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 221

```
gaggtgcagc tgttggagtc tgggggaggc ttggtacagc ctgggggtc cctgcgtctc     60 tcctgtgcag cctccggatt caccttaag gattatgata tgacttgggt ccgccaggct    120
ccagggaagg gtctagagtg ggtctcaatg atttcttcgt cgggtctttg acatactac    180 gcagactccg tgaagggccg gttcaccatc tcccgcgaca attccaagaa cacgctgtat    240
ctgcaaatga acagcctgcg tgccgaggac accgcggtat attactgtgc gaaaggtttt    300
aggctgtttc ctcggacttt tgactactgg ggtcagggaa ccctggtcac cgtctcgagc    360
g                                                                    361
```

<210> SEQ ID NO 222
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 222

Gly Gly Gly Gly Ser
 1               5

<210> SEQ ID NO 223
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 223

```
gaggttcaat tgttggaatc cggtggtgga ttggttcaac ctggtggttc tttgagattg     60
tcctgtgctg cttccggttt tactttcgct cacgagacta tggtttgggt tagacaggct    120
ccaggtaaag gattggaatg gtttcccac attccaccag atggtcaaga tccattctac    180
gctgactccg ttaagggaag attcactatc tccagagaca actccaagaa cactttgtac    240
ttgcagatga actccttgag agctgaggat actgctgttt accactgtgc tttgttgcca    300
aagagaggac cttggtttga ttactgggga cagggaactt tggttactgt ttcttcc       357
```

<210> SEQ ID NO 224
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 225
<211> LENGTH: 363
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 225
gaggttcaat tgttggaatc cggtggtgga ttggttcaac tggtggttc tttgagattg      60 tcctgtgctg cttccggttt tactttcgct cacgagacta tggtttgggt tagacaggct    120
ccaggtaaag gattggaatg ggtttcccac attccaccag atggtcaaga tccattctac    180
gctgactccg ttaagggaag attcactatc tccagagaca actccaagaa cactttgtac    240
ttgcagatga actccttgag agctgaggat actgctgttt accactgtgc tttgttgcca    300
aagagaggac cttggtttga ttactgggga cagggaactt tggttactgt tcttcctaa     360 tga                                                                   363

<210> SEQ ID NO 226
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 226
gaggtgcagc tgttggagtc tgggggaggc ttggtacagc ctgggggtc cctgcgtctc      60 tcctgtgcag cctccggatt cacctttgcg catgagacga tggtgtgggt ccgccaggca    120
ccagggaagg gtctagagtg gtctcacat attccccccgg atggtcagga tcccttctac    180
gcagactccg tgaagggccg gttcaccatc tcccgcgaca attccaagaa cacgctatat    240
ctgcaaatga acagcctgcg tgccgaggac acagcggtat atcactgtgc gctgcttcct    300 aagaggggc cttggtttga ctactggggt cagggaaccc tggtcaccgt ctcgagc        357

<210> SEQ ID NO 227
<211> LENGTH: 11
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 227
tccaagaaca c                                                          11

<210> SEQ ID NO 228
<211> LENGTH: 11
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 228
ccttggtttg a                                                          11

<210> SEQ ID NO 229
<211> LENGTH: 366
<212> TYPE: DNA
<213> ORGANISM: Artificial Sequence
<220> FEATURE:
<223> OTHER INFORMATION: Nucleic acid sequence identified using
molecular biology techniques.

<400> SEQUENCE: 229
gagaaaagag aggttcaatt gcttgaatct ggaggaggtt tggtccagcc aggagggtcc      60
cttcgactaa gttgtgctgc cagtgggttt acgtttgctc atgaaactat ggtatgggtc     120
cgacaggcac ctggtaaagg tcttgaatgg gtttcacata tccctccaga cggtcaagac     180 ccatttacg ctgattccgt gaaaggcaga tttacaattt cacgagataa ttctaaaaac      240
accttgtact acaaatgaa ctcattgaga gctgaggaca ctgcagttta tcactgcgct      300
ttactaccaa aacgtggacc ttggtttgat tattggggcc aaggtacgtt agtgactgtt     360
agttct                                                                366

<210> SEQ ID NO 230
<211> LENGTH: 122
<212> TYPE: PRT
<213> ORGANISM: Artificial Sequence
<220> FEATURE:
<223> OTHER INFORMATION: Amino acid sequence identified using molecular
biology techniques.

<400> SEQUENCE: 230

Glu Lys Arg Glu Val Gln Leu Leu Glu Ser Gly Gly Gly Leu Val Gln
 1               5                  10                  15

Pro Gly Gly Ser Leu Arg Leu Ser Cys Ala Ala Ser Gly Phe Thr Phe
            20                  25                  30

Ala His Glu Thr Met Val Trp Val Arg Gln Ala Pro Gly Lys Gly Leu
        35                  40                  45

Glu Trp Val Ser His Ile Pro Pro Asp Gly Gln Asp Pro Phe Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr His Cys Ala Leu Leu Pro Lys Arg Gly Pro Trp Phe Asp Tyr Trp
            100                 105                 110

Gly Gln Gly Thr Leu Val Thr Val Ser Ser

<210> SEQ ID NO 231
<211> LENGTH: 357
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 231
gaggtgcagc tgttggagtc tgggggaggc ttggtacagc ctggggggtc cctgcgtctc    60
tcctgtgcag cctccggatt cacctttgcg catgagacga tggtgtgggt ccgccaggca   120
ccagggaagg gtctagagtg gtctcacat attcccccgg atggtcagga tcccttctac    180
gcagactccg tgaagggccg gttcaccatc tcccgcgaca attccaagaa cacgctatat   240
ctgcaaatga acagcctgcg tgccgaggac acagcggtat atcactgtgc gctgcttcct   300 aagaggggc cttggtttga ctactgggt cagggaaccc tggtcaccgt ctcgagc       357

<210> SEQ ID NO 232
<211> LENGTH: 366
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 232
gagaaaagag aggttcaatt gcttgaatct ggaggaggtt tggtccagcc aggagggtcc    60
cttcgactaa gttgtgctgc cagtgggttt acgtttgctc atgaaactat ggtatgggtc   120
cgacaggcac ctggtaaagg tcttgaatgg gtttcacata tccctccaga cggtcaagac   180 ccatttacg ctgattccgt gaaaggcaga tttacaattt cacgagataa ttctaaaaac    240
accttgtact tacaaatgaa ctcattgaga gctgaggaca ctgcagttta tcactgcgct   300
ttactaccaa aacgtggacc ttggtttgat tattggggcc aaggtacgtt agtgactgtt   360
agttct                                                              366

<210> SEQ ID NO 233
<211> LENGTH: 11
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 233
ccttggtttg a                                                         11

<210> SEQ ID NO 234
<211> LENGTH: 357
<212> TYPE: DNA
<213> ORGANISM: Artificial Sequence
<220> FEATURE:
<223> OTHER INFORMATION: Nucleic acid sequence identified using
    molecular biology techniques.

<400> SEQUENCE: 234
gaagtgcagc ttcttgaaag tggtggaggg ctagtgcagc caggggatc tttaagatta    60 tcatgcgctg ccagtggatt tactttgct cacgagacga tggtctgggt gagacaagct   120
cctggaaaag gtttagagtg ggtttctcac attccacctg atggtcaaga tccttctac     180

```
gcagattccg tcaaaggaag atttactatc tccagagata atagtaaaaa cactttgtac      240
ctacagatga actcacttag agccgaagat accgctgtgt accactgcgc cttgttgcca      300
aagagaggtc cttggttcga ttactggggt cagggtactc tggttacagt ctcatct         357
```

<210> SEQ ID NO 235
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 235

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala His Glu
             20                  25                  30

Thr Met Val Trp Val Arg Gln Ala Pro Gly Lys Gly Leu Glu Trp Val
         35                  40                  45

Ser His Ile Pro Pro Asp Gly Gln Asp Pro Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr His Cys
                 85                  90                  95

Ala Leu Leu Pro Lys Arg Gly Pro Trp Phe Asp Tyr Trp Gly Gln Gly
            100                 105                 110

Thr Leu Val Thr Val Ser Ser
        115
```

<210> SEQ ID NO 236
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 236

```
gaggtgcagc tgttggagtc tgggggaggc ttggtacagc ctggggggtc cctgcgtctc      60
tcctgtgcag cctccggatt cacctttgcg catgagacga tggtgtgggt ccgccaggca     120
ccagggaagg gtctagagtg gtctcacat attccccgg atggtcagga tcccttctac       180
gcagactccg tgaagggccg gttcaccatc tcccgcgaca attccaagaa cacgctatat     240
ctgcaaatga acagcctgcg tgccgaggac acagcggtat atcactgtgc gctgcttcct     300
aagagggggc cttggtttga ctactggggt cagggaaccc tggtcaccgt ctcgagc        357
```

<210> SEQ ID NO 237
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 237

```
gaagtgcagc ttcttgaaag tggtggaggg ctagtgcagc caggggggatc tttaagatta    60 tcatgcgctg ccagtggatt tactttttgct cacgagacga tggtctgggt gagacaagct   120
```

```
cctggaaaag gtttagagtg ggtttctcac attccacctg atggtcaaga tcctttctac    180
gcagattccg tcaaaggaag atttactatc tccagagata atagtaaaaa cactttgtac    240
ctacagatga actcacttag agccgaagat accgctgtgt accactgcgc cttgttgcca    300
aagagaggtc cttggttcga ttactggggt cagggtactc tggttacagt ctcatct      357
```

<210> SEQ ID NO 238
<211> LENGTH: 10
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 238

```
tagagtgggt                                                            10
```

<210> SEQ ID NO 239
<211> LENGTH: 11
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 239

```
ttctacgcag a                                                          11
```

<210> SEQ ID NO 240
<211> LENGTH: 14
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 240

```
tactggggtc aggg                                                       14
```

<210> SEQ ID NO 241
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 241

```
gaagtacaac tgctggagag cggtggcggc ctggttcaac cgggtggttc cctgcgcctg    60
tcctgtgcgg catctggttt caccttcgca cacgaaacca tggtgtgggt cgccaagct    120 ccgggcaaag gcctggaatg ggtaagccac attcctccag atggccagga cccattctat    180
gcggattccg ttaagggtcg ctttaccatt tctcgtgata actccaaaaa caccctgtac    240
ctgcagatga actccctgcg cgccgaggat actgcggtgt accattgtgc gctgctgcct    300
aaacgtggcc cgtggttcga ttactggggt cagggtactc tggtcaccgt aagcagc      357
```

<210> SEQ ID NO 242
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 243
<211> LENGTH: 407
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 243
gaggtgcagc tgttggagtc tgggggaggc ttggtacagc ctgggggtc cctgcgtctc      60 tcctgtgcag cctccggatt cacctttgcg catgagacga tggtgtgggt ccgccaggca    120
ccagggaagg gtctagagtg gtctcacat attccccgg atggtcagga tcccttctac      180
gcagactccg tgaagggccg gttcaccatc tcccgcgaca attccaagaa cacgctatat    240
ctgcaaatga acagcctgcg tgccgaggac acagcggtat atcactgtgc gctgcttcct    300 aagaggggc cttggtttga ctactgggt cagggaaccc tggtcaccgt aagagggggc      360
cttggtttga ctactgggt cagggaaccc tggtcaccgt ctcgagc                   407

<210> SEQ ID NO 244
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 244
gaagtacaac tgctggagag cggtggcggc ctggttcaac cgggtggttc cctgcgcctg     60
tcctgtgcgg catctggttt caccttcgca cacgaaacca tggtgtgggt tcgccaagct    120
ccgggcaaag gcctggaatg gtaagccac attcctccag atggccagga cccattctat     180
gcggattccg ttaagggtcg ctttaccatt tctcgtgata actccaaaaa cacccctgtac    240 ctgcagatga actccctgcg cgccgaggat actgcggtgt accattgtgc gctgctgcct    300
aaacgtggcc cgtggttcga ttactgggt cagggtactc tggtcaccgt aagcagc        357

<210> SEQ ID NO 245
<211> LENGTH: 10
<212> TYPE: DNA

<213> ORGANISM: Artificial Sequence
<220> FEATURE:
<223> OTHER INFORMATION: Nucleic acid sequence identified using molecular biology techniques.

<400> SEQUENCE: 245
tggtgtgggt                                                        10

<210> SEQ ID NO 246
<211> LENGTH: 11
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 246
tgtgcgctgc t                                                      11

<210> SEQ ID NO 247
<211> LENGTH: 14
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 247
tactggggtc aggg                                                   14

<210> SEQ ID NO 248
<211> LENGTH: 11
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 248
ctggtcaccg t                                                      11

<210> SEQ ID NO 249
<211> LENGTH: 357
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 249
gaggttcaac tgctggaatc tgtggtggt ctggtacaac cgggtggttc cctgcgtctg      60
agctgtgcag cctctggttt caccttcgct catgagacca tggtttgggt acgccaggct    120
ccgggtaaag gcctggagtg ggtaagccat atccctcctg atggtcagga cccgttctat    180
gctgattccg tcaaaggccg ttttaccatt tctcgtgaca acagcaaaaa cactctgtac    240
ctgcaaatga actccctgcg tgcagaagac acggcggttt atcactgtgc actgctgcca    300
aaacgcggcc cttggttcga ctactggggc cagggtactc tggtcactgt atcttct       357

<210> SEQ ID NO 250
<211> LENGTH: 119
<212> TYPE: PRT
<213> ORGANISM: Artificial Sequence
<220> FEATURE:
<223> OTHER INFORMATION: Amino acid sequence identified using molecular biology techniques.

<400> SEQUENCE: 250

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ala His Glu
            20                  25                  30
Thr Met Val Trp Val Arg Gln Ala Pro Gly Lys Gly Leu Glu Trp Val
        35                  40                  45
Ser His Ile Pro Pro Asp Gly Gln Asp Pro Phe Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr His Cys
                85                  90                  95
Ala Leu Leu Pro Lys Arg Gly Pro Trp Phe Asp Tyr Trp Gly Gln Gly
            100                 105                 110
Thr Leu Val Thr Val Ser Ser
        115

<210> SEQ ID NO 251
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 251
gaggtgcagc tgttggagtc tgggggaggc ttggtacagc ctgggggggtc cctgcgtctc    60
tcctgtgcag cctccggatt cacctttgcg catgagacga tggtgtgggt ccgccaggca   120
ccagggaagg gtctagagtg gtctcacat attccccccgg atggtcagga tcccttctac   180
gcagactccg tgaagggccg gttcaccatc tcccgcgaca attccaagaa cacgctatat   240
ctgcaaatga acagcctgcg tgccgaggac acagcggtat atcactgtgc gctgcttcct   300
aagagggggc cttggtttga ctactggggt cagggaaccc tggtcaccgt ctcgagc     357

<210> SEQ ID NO 252
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 252
gaggttcaac tgctggaatc tgtggtggt ctggtacaac cgggtggttc cctgcgtctg    60
agctgtgcag cctctggttt cacctttcgct catgagacca tggtttgggt acgccaggct   120
ccgggtaaag gcctggagtg gtaagccat atccctcctg atggtcagga cccgttctat   180
gctgattccg tcaaaggccg tttaccatt tctcgtgaca acagcaaaaa cactctgtac   240
ctgcaaatga actccctgcg tgcagaagac acggcggttt atcactgtgc actgctgcca   300
aaacgcggcc cttggttcga ctactggggc cagggtactc tggtcactgt atcttct     357

<210> SEQ ID NO 253
<211> LENGTH: 12
<212> TYPE: DNA
<213> ORGANISM: Artificial Sequence
<220> FEATURE:

```
<223> OTHER INFORMATION: Nucleic acid sequence identified using
      molecular biology techniques.

<400> SEQUENCE: 253
ctgtgcagcc tc                                                          12

<210> SEQ ID NO 254
<211> LENGTH: 11
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 254
gatggtcagg a                                                           11

<210> SEQ ID NO 255
<211> LENGTH: 10
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 255
ctgcaaatga                                                             10

<210> SEQ ID NO 256
<211> LENGTH: 11
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 256
tatcactgtg c                                                           11

<210> SEQ ID NO 257
<211> LENGTH: 11
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 257
gactactggg g                                                           11

<210> SEQ ID NO 258
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 258

Gly Gly Gly Gly Ser
 1               5

<210> SEQ ID NO 259
<211> LENGTH: 5
<212> TYPE: PRT
<213> ORGANISM: Artificial Sequence
<220> FEATURE:
```

<223> OTHER INFORMATION: Amino acid sequence identified using molecular
      biology techniques.

<400> SEQUENCE: 259

Glu Val Gln Leu Leu
 1               5

<210> SEQ ID NO 260
<211> LENGTH: 31
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 260

Glu Val Gln Gly Gln Gly Thr Leu Val Thr Val Ser Ser Ala Ser Thr
 1               5                  10                  15

His Thr Cys Pro Pro Cys Pro Ala Pro Glu Leu Leu Gly Gly Pro
            20                  25                  30

<210> SEQ ID NO 261
<211> LENGTH: 35
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 261

Asp Ile Gln Gly Gln Gly Thr Lys Val Glu Ile Lys Arg Thr Val Ala
 1               5                  10                  15

Ala Pro Ser Thr His Thr Cys Pro Pro Cys Pro Ala Pro Glu Leu Leu
            20                  25                  30

Gly Gly Pro
        35

<210> SEQ ID NO 262
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 262
gaggtgcagc tgttggagtc tggggggaggc ttggtacagc ctggggggtc cctgcgtctc      60
tcctgtgcag cctccggatt cacctttgcg catgagacga tggtgtgggt ccgccaggct     120
ccagggaagg gtctagagtg gtctcacat attccccgg ttggtcagga tcccttctac       180
gcagactccg tgaagggccg gttcaccatc tcccgcgaca attccaagaa cacgctatat     240
ctgcaaatga acagcctgcg tgccgaggac acagcggtat attactgtgc gctgcttcct     300
aagagggggc cttggtttga ctactggggt cagggaaccc tggtcaccgt ctcgagc        357

<210> SEQ ID NO 263
<211> LENGTH: 324
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 263

```
gacatccaga tgacccagtc tccatcctcc ctgtctgcat ctgtaggaga ccgtgtcacc      60
atcacttgcc gggcaagtca gtggattggg tctcagttat cttggtacca gcagaaacca     120
gggaaagccc ctaagctcct gatcatgtgg cgttcctcgt tgcaaagtgg ggtcccatca     180
cgtttcagtg gcagtggatc tgggacagat ttcactctca ccatcagcag tctgcaacct     240
gaagattttg ctacgtacta ctgtgctcag ggtgcggcgt tgcctaggac gttcggccaa     300
gggaccaagg tggaaatcaa acgg                                            324
```

<210> SEQ ID NO 264
<211> LENGTH: 343
<212> TYPE: PRT
<213> ORGANISM: AArtificial Sequence
<220> FEATURE:
<223> OTHER INFORMATION: Amino acid sequence identified using molecular
      biology techniques.

<400> SEQUENCE: 264

```
Glu Val Gln Leu Leu Val Ser Gly Gly Gly Leu Val Gln Pro Gly Gly
 1               5                  10                  15

Ser Leu Arg Leu Ser Cys Ala Ala Ser Gly Phe Thr Phe Lys Ala Tyr
            20                  25                  30

Pro Met Met Trp Val Arg Gln Ala Pro Gly Lys Gly Leu Glu Trp Val
        35                  40                  45

Ser Glu Ile Ser Pro Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Arg Lys Leu Asp Tyr Trp Gly Gln Gly Thr Leu Val
            100                 105                 110

Thr Val Ser Ser Ala Ser Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300
```

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
            325                 330                 335

Leu Ser Leu Ser Pro Gly Lys
            340

<210> SEQ ID NO 265
<211> LENGTH: 225
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 265

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 266
<211> LENGTH: 1030
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 266
gaggtgcagc tgttggtgtc tgggggaggc ttggtacagc ctggggggtc cctgcgtctc      60

```
                                         -continued
tcctgtgcag cctccggatt caccttaag gcttatccga tgatgtgggt ccgccaggct    120
ccagggaagg gtctagagtg ggtttcagag atttcgcctt cgggttctta tacatactac    180
gcagactccg tgaagggccg gttcaccatc tcccgcgaca attccaagaa cacgctgtat    240
ctgcaaatga acagcctgcg tgccgaggaa caccgcggta tattactgtg cgaaagatcc    300
tcggaagtta gactactggg gtcagggaac cctggtcacc gtctcgagcg ctagcaccca    360
cacctgcccc ccctgccctg cccccgagct gctgggcgga cctagcgtgt tcctgttccc    420
ccccaagcct aaggacaccc tgatgatcag caggacccc gaagtgacct gcgtggtggt    480
ggatgtgagc cacgaggacc ctgaagtgaa gttcaactgg tacgtggacg gcgtggaagt    540
gcacaacgcc aagaccaagc ccagagagga gcagtacaac agcacctacc gcgtggtgtc    600
tgtgctgacc gtgctgcacc aggattggct gaacggcaag gagtacaagt gcaaagtgag    660
caacaaggcc ctgcctgccc ctatcgagaa aaccatcagc aaggccaagg gccagcctag    720
agagccccag gtctacaccc tgcctccctc cagagatgag ctgaccaaga accaggtgtc    780
cctgacctgt ctggtgaagg gcttctaccc cagcgacatc gccgtggagt gggagagcaa    840
cggccagccc gagaacaact acaagaccac cccccctgtg ctggacagcg atggcagctt    900
cttcctgtac tccaagctga ccgtggacaa gagcagatgg cagcagggca acgtgttcag    960
ctgcagcgtg atgcacgagg ccgtgcacaa tcactacacc cagaagagtc tgagcctgtc   1020
ccctggcaag                                                          1030
```